(12) United States Patent
Steelman

(10) Patent No.: US 11,401,558 B2
(45) Date of Patent: Aug. 2, 2022

(54) METHODS, COMPOSITIONS, KITS AND DEVICES FOR RAPID ANALYSIS OF BIOLOGICAL MARKERS

(71) Applicant: CLEAR GENE, INC., San Carlos, CA (US)

(72) Inventor: Brandon Steelman, Moss Beach, CA (US)

(73) Assignee: CLEAR GENE, INC., San Carlos, CA (US)

(*) Notice: Subject to any disclaimer, the term of this patent is extended or adjusted under 35 U.S.C. 154(b) by 178 days.

(21) Appl. No.: 16/061,517

(22) PCT Filed: Dec. 16, 2016

(86) PCT No.: PCT/US2016/067381
§ 371 (c)(1),
(2) Date: Jun. 12, 2018

(87) PCT Pub. No.: WO2017/106790
PCT Pub. Date: Jun. 22, 2017

(65) Prior Publication Data
US 2020/0181710 A1    Jun. 11, 2020

Related U.S. Application Data

(60) Provisional application No. 62/387,526, filed on Dec. 23, 2015, provisional application No. 62/269,904, filed on Dec. 18, 2015.

(51) Int. Cl.
*C12Q 1/00* (2006.01)
*C12Q 1/6886* (2018.01)
(Continued)

(52) U.S. Cl.
CPC .......... *C12Q 1/6886* (2013.01); *A61B 5/4288* (2013.01); *A61B 10/02* (2013.01);
(Continued)

(58) Field of Classification Search
None
See application file for complete search history.

(56) References Cited

U.S. PATENT DOCUMENTS 5,122,284 A    6/1992    Braynin et al.
5,304,487 A    4/1994    Wilding et al.
(Continued)

FOREIGN PATENT DOCUMENTS

EP    1312682 A1    5/2003
EP    1420069 A1    5/2004
(Continued)

OTHER PUBLICATIONS

Aha et al. Instance-Based Learning Algorithms Machine Learning 1991 vol. 6: pp. 37-66.
(Continued)

*Primary Examiner* — Jyoti Nagpaul
(74) *Attorney, Agent, or Firm* — Wilson Sonsini Goodrich & Rosati

(57) ABSTRACT

Provided herein are kits, devices and methods for rapid analysis of biological samples. In particular, kits, devices and methods described herein can be applied to rapid nucleic acid analysis of solid tissue samples.

39 Claims, 27 Drawing Sheets
Specification includes a Sequence Listing.

(51) Int. Cl.
*A61B 5/00* (2006.01)
*A61B 10/02* (2006.01)
*C12N 15/10* (2006.01)
*A61B 17/00* (2006.01)
*B01L 3/00* (2006.01)
*A61M 1/00* (2006.01)

(52) U.S. Cl.
CPC ............ *A61B 17/00* (2013.01); *A61M 1/0001* (2013.01); *B01L 3/502707* (2013.01); *C12N 15/1003* (2013.01); *C12N 15/1096* (2013.01); *A61B 2010/0216* (2013.01); *C12Q 2600/112* (2013.01); *C12Q 2600/158* (2013.01)

(56) References Cited

U.S. PATENT DOCUMENTS

| | | |
|---|---|---|
| 5,496,562 A | 3/1996 | Burgoyne |
| 5,756,126 A | 5/1998 | Burgoyne |
| 5,763,181 A | 6/1998 | Han et al. |
| 6,030,581 A | 2/2000 | Virtanen |
| 6,197,595 B1 | 3/2001 | Anderson et al. |
| 6,664,379 B1 | 12/2003 | Kudlicki et al. |
| 6,682,889 B1 | 1/2004 | Wang et al. |
| 7,001,724 B1 | 2/2006 | Greenfield et al. |
| 7,112,406 B2 | 9/2006 | Behlke et al. |
| 7,135,291 B2 | 11/2006 | Sagawa et al. |
| 7,208,313 B2 | 4/2007 | McCart et al. |
| 8,202,697 B2 | 6/2012 | Holmes |
| 8,319,398 B2 | 11/2012 | Vivek et al. |
| 8,506,947 B2 | 8/2013 | McCart et al. |
| 8,647,742 B2 | 2/2014 | Dendukuri et al. |
| 8,911,948 B2 | 12/2014 | Walder et al. |
| 9,434,988 B2 | 9/2016 | Behlke et al. |
| 9,984,201 B2 | 5/2018 | Zhang et al. |
| 11,060,149 B2 | 7/2021 | Steelman |
| 2001/0018513 A1 | 8/2001 | Baker |
| 2001/0051344 A1 | 12/2001 | Shalon et al. |
| 2003/0031681 A1 | 2/2003 | McCart et al. |
| 2003/0190602 A1 | 10/2003 | Pressman et al. |
| 2006/0166231 A1 | 7/2006 | Baker et al. |
| 2006/0246575 A1 | 11/2006 | Lancaster et al. |
| 2007/0031867 A1 | 2/2007 | Hoon et al. |
| 2007/0077582 A1 | 4/2007 | Slepnev |
| 2007/0154458 A1 | 7/2007 | McCart et al. |
| 2007/0213939 A1 | 9/2007 | Liew et al. |
| 2008/0068643 A1 | 3/2008 | Yasunaga |
| 2008/0305528 A1 | 12/2008 | Baker |
| 2010/0047130 A1 | 2/2010 | Ong et al. |
| 2010/0240123 A1 | 9/2010 | Belgrader |
| 2010/0256465 A1 | 10/2010 | Bernstein et al. |
| 2011/0091987 A1 | 4/2011 | Weissleder et al. |
| 2011/0123990 A1 | 5/2011 | Baker et al. |
| 2011/0151435 A1 | 6/2011 | Mehra et al. |
| 2012/0123205 A1 | 5/2012 | Nie et al. |
| 2012/0308484 A1 | 12/2012 | Szalay et al. |
| 2013/0040852 A1 | 2/2013 | Anastassiou et al. |
| 2013/0137107 A1 | 5/2013 | Ko et al. |
| 2013/0209473 A1 | 8/2013 | De et al. |
| 2013/0274136 A1 | 10/2013 | McDevitt et al. |
| 2013/0280706 A1 | 10/2013 | Judice |
| 2013/0295580 A1 | 11/2013 | McDevitt et al. |
| 2013/0295581 A1 | 11/2013 | Chapman et al. |
| 2013/0332083 A1 | 12/2013 | Van |
| 2013/0337462 A1 | 12/2013 | Mergemeier |
| 2014/0031254 A1 | 1/2014 | Pestova et al. |
| 2014/0243239 A1 | 8/2014 | Johnson et al. |
| 2014/0329704 A1 | 11/2014 | Melton et al. |
| 2015/0299797 A1 | 10/2015 | Bild et al. |
| 2015/0307947 A1 | 10/2015 | Basu et al. |
| 2015/0366835 A1 | 12/2015 | Pogue-Geile et al. |
| 2016/0097102 A1 | 4/2016 | Suh et al. |
| 2016/0146818 A1 | 5/2016 | Goodison et al. |
| 2016/0153053 A1 | 6/2016 | Skog et al. |
| 2016/0258960 A1 | 9/2016 | Kruk |
| 2017/0218455 A1 | 8/2017 | Steelman |
| 2018/0371553 A1 | 12/2018 | Steelman et al. |

FOREIGN PATENT DOCUMENTS

| | | |
|---|---|---|
| EP | 2028270 B1 | 2/2012 |
| EP | 2032722 B1 | 8/2013 |
| GB | 2513275 A | 10/2014 |
| WO | WO-2008043987 A2 | 4/2008 |
| WO | WO-2008043987 A3 | 9/2008 |
| WO | WO-2010009074 A2 | 1/2010 |
| WO | WO-2012001607 A1 | 1/2012 |
| WO | WO-2013010134 A2 | 1/2013 |
| WO | WO-2013025952 A2 | 2/2013 |
| WO | WO 2014/093934 * | 6/2014 |
| WO | WO-2014093934 A1 | 6/2014 |
| WO | WO-2015171741 A1 | 11/2015 |
| WO | WO-2015195949 A2 | 12/2015 |
| WO | WO-2015195949 A3 | 2/2016 |
| WO | WO-2016115530 A1 | 7/2016 |
| WO | WO-2017106790 A1 | 6/2017 |
| WO | WO-2019245587 A1 | 12/2019 |

OTHER PUBLICATIONS

Amancio et al. A Systematic Comparison of Supervised Classifiers. PLoS One 2014 vol. 9: e94137.

Ausubel, et al. Current Protocols in Molecular Biology (1987).

Bakhshandeh, et al. Use of imprint cytology for assessment of surgical margins in lumpectomy specimens of breast cancer patients. Diagn Cytopathol. Oct. 2007; 35(10) :656-9.

Bastien, et al. PAM50 breast cancer subtyping by RT-qPCR and concordance with standard clinical molecular markers. BMC Med Genomics. Oct. 4, 2012;5:44. PMCID: PMC3487945.

Bignotti, et al. Gene expression profile of ovarian serous papillary carcinomas: identification of metastasis-associated genes. Am J Obstet Gynecol. Mar. 2007;196(3):245.e1-11.

Boldisen, et al. Importance of margin width in breast-conserving treatment of early breast cancer. J Surg Oncol. May 2016;113(6):609-15. PMID: 26991020.

Buchholz, et al. Margins for breast-conserving surgery with whole-breast irradiation in stage I and II invasive breast cancer: American Society of Clinical Oncology endorsement of the Society of Surgical Oncology/American Society for Radiation Oncology consensus guideline. J Clin Oncol. May 10, 2014;32(14):1502-6. PMID: 24711553.

Castano-Alvarez, et al. Electroactive intercalators for DNA analysis on microchip electrophoresis. Electrophoresis. Dec. 2007;28(24):4679-89.

Chagpar, et al. A Randomized, Controlled Trial of Cavity Shave Margins in Breast Cancer. N Engl J Med. Aug. 6, 2015;373(6):503-10.

Cooney, et al. A plastic, disposable microfluidic flow cell for coupled on-chip PCR and microarray detection of infectious agents. Biomed Microdevices. Feb. 2012;14(1):45-53. doi: 10.1007/s10544-011-9584-9.

Cortazar, et al. Pathological complete response and long-term clinical benefit in breast cancer: the CTNeoBC pooled analysis. Lancet. Jul. 12, 2014;384(9938):164-72. doi: 10.1016/S0140-6736(13)62422-8. Epub Feb. 14, 2014.

Cox, et al. Touch Preparation Cytology of Breast Lumpectomy Margins with Histologic Correlation. Arch Surg. 1991. vol. 126, pp. 490-493.

Crawley. Statistics: An Introduction Using R, (John Wiley and Sons, Ltd, 2005).

Creager, et al. Intraoperative evaluation of lumpectomy margins by imprint cytology with histologic correlation: a community hospital experience. Archives of Pathology & Laboratory Medicine. 2002. vol. 126, No. 7, pp. 846-848.

Cserni, et al. Discrepancies in current practice of pathological evaluation of sentinel lymph nodes in breast cancer. Results of a

(56) References Cited

OTHER PUBLICATIONS questionnaire based survey by the European Working Group for Breast Screening Pathology. J Clin Pathol. Jul. 2004;57(7):695-701. PMCID: PMC1770358.

Cserni, G. Complete sectioning of axillary sentinel nodes in patients with breast cancer. Analysis of two different step sectioning and immunohistochemistry protocols in 246 patients. J Clin Pathol. Dec. 2002;55(12):926-31. PMID: 12461060.

Cserni, G. Metastases in axillary sentinel lymph nodes in breast cancer as detected by intensive histopathological work up. J Clin Pathol. Dec. 1999;52(12):922-4. PMID: 10711258.

Dabbs, D. J. Breast Pathology. Elsevier Health Sciences, Nov. 4, 2016, p. 107.

Defever, et al. Real-time electrochemical PCR with a DNA intercalating redox probe. Anal Chem. Mar. 1, 2011;83(5):1815-21. doi: 10.1021/ac1033374. Epub Jan. 31, 2011.

Dhage, et al. A genomic ruler to assess oncogenic transition between breast tumor and stroma. PLoS One. 2018; 13(10): e0205602.

D'halluin F, et al. Intra-operative touch preparation cytology following lumpectomy for breast cancer: a series of 400 procedures. Breast. Aug. 2009.;18(4):248-53.

Dibiase, et al. Influence of radiation dose on positive surgical margins in women undergoing breast conservation therapy. Int J Radiat Oncol Biol Phys. Jul. 1, 2002;53(3):680-6. PMID: 12062612.

Dogan, et al. Use of touch imprint cytology as a simple method to enrich tumor cells for molecular analysis. Cancer cytopathology 121.7 (2013): 354-360.

EP 15809388.0 Extended European Search Report and Search Opinion dated Dec. 21, 2017.

EP15809388 The extended European Search Report dated Dec. 21, 2017.

EP16876870.3 The Extended European Search Report dated Apr. 23, 2019.

Ferrario, et al. Prospective of Using Nano-Structured High Performances Sensors Based on Polymer Nano-Imprinting Technology for Chemical and Biomedical Applications. Sensors and Biosensors 54; 2010, pp. 197-200.

Freshney, et al. Culture of Animal Cells: A Manual of Basic Technique and Specialized Applications, 6th Edition. 2010.

Gage, et al. Pathologic margin involvement and the risk of recurrence in patients treated with breast-conserving therapy. Cancer. Nov. 1, 1996;78(9):1921-8.

Gansen, et al. Digital LAMP in a sample self-digitization (SD) chip. Lab Chip. Jun. 21, 2012;12(12):2247-54. doi: 10.1039/c2lc21247a. Epub Mar. 7, 2012.

Genbank Accession NM_080282: Homo sapiens ATP-Binding Cassette, Sub-Family A (ABC1) Member 10 mRNA. Feb. 26, 2014; pp. 1-7.

Gill, et al. Nucleic acid isothermal amplification technologies: a review. Nucleosides Nucleotides Nucleic Acids. Mar. 2008;27(3):224-43. doi: 10.1080/15257770701845204.

Gradishar, et al. Invasive Breast Cancer Version 1.2016. National Comprehensive Cancer Network (NCCN). NCCN Clinical Practice Guidelines in Oncology (NCCN Guidelines). 2016.

Hastie, et al. Elements Of Statistical Learning, 2nd edition (2009).

Hayashi, et al. Paired Box 5 Methylation Detection by Droplet Digital PCR for Ultra-Sensitive Deep Surgical Margins Analysis of Head and Neck Squamous Cell Carcinoma. Cancer Prev Res, Aug. 24, 2015 (Aug. 24, 2015), vol. 8, pp. 1017-1026.

Horvath, et al. Novel insights into breast cancer genetic variance through RNA sequencing. Scientific reports 3 (2013).

Houssami, et al. Meta-analysis of the impact of surgical margins on local recurrence in women with early-stage invasive breast cancer treated with breast-conserving therapy. Eur J Cancer. Dec. 2010;46(18):3219-32. PMID: 20817513.

Houssami, et al. The association of surgical margins and local recurrence in women with early-stage invasive breast cancer treated with breast-conserving therapy: a meta-analysis. Ann Surg Oncol. Mar. 2014;21(3):717-30. PMID: 24473640.

Huan, et al. Micro-NMR for Rapid Molecular Analysis of Human Tumor Samples. Sci Transl Med. Feb. 23, 2011; 3(71): 71ra16. doi:10.1126/scitranslmed.3002048.

Huang, et al. fM to aM nucleic acid amplification for molecular diagnostics in a non-stick-coated metal microfluidic bioreactor. Scientific Reports 4, Article No. 7344. Dec. 2014.).

International search report and written opinion dated Dec. 8, 2015 for PCT Application No. PCT/US15/36480.

Invitrogen. ChargeSwitch® Forensic DNA Purification Kits: For purification of genomic DNA from forensic samples. Version A. Jan. 3, 2005.

Johnson & Johnson. Instructions for Use for GeneSearch Breast Lymph Node (BLN)Test Kit and GeneSearch RNA Sample Preparation Kit. Apr. 28, 2006. Available at http://www.fda.gov/ohrms/dockets/ac/06/briefing/2006-4249b1_02.pdf. Accessed Feb. 2, 2017.

Kale, et al. Cross-Validation and Mean-Square Stability. Symposium on Innovations in Computer Science. Jan. 7, 2011.).

Kim, et al. Ultrafast colorimetric detection of nucleic acids based on the inhibition of the oxidase activity of cerium oxide nanoparticles. Chem. Commun., 2014,50, 9577-9580.

Kinkaid, et al. Can touch imprint cytology replace fine needle aspiration within current clinical practice? Breast Cancer Research 2010, 12(3):P14. doi:10.1186/bcr2667.

Kivlehan, et al. Real-time electrochemical monitoring of isothermal helicase-dependent amplification of nucleic acids.Analyst. Sep. 21, 2011;136(18):3635-42. doi: 10.1039/c1an15289k. Epub Jul. 27, 2011.

Klimberg VS, et al. Use of touch preps for diagnosis and evaluation of surgical margins in breast cancer. Ann Surg Oncol. 1998;5: 220-226.

Koboldt, et al. Comprehensive molecular portraits of human breast tumours. Nature 2012 vol. 490, pp. 61-70.

Lalkhen, et al. Clinical Tests: Sensitivity and Specificity. Continuing Education in Anaesthesia Critical Care and Pain. 2008;8(6):221-3. doi: 10.1093/bjaceaccp/mkn041.

Liu, et al. A low-cost microfluidic chip for rapid genotyping of malaria-transmitting mosquitoes. PLoS One. 2012;7(8):e42222. doi: 10.1371/journal.pone.0042222. Epub Aug. 3, 2012.

McPherson, et al. PCR 2: A Practical Approach (1995).

Meric, et al. Positive surgical margins and ipsilateral breast tumor recurrence predict disease-specific survival after breast-conserving therapy. Cancer. Feb. 15, 2003;97(4):926-33. PMID: 12569592.

Moran, et al. Society of Surgical Oncology—American Society for Radiation Oncology consensus guideline on margins for breast-conserving surgery with whole-breast irradiation in stages I and II invasive breast cancer.Int J Radiat Oncol Biol Phys. Mar. 1, 2014;88(3):553-64. doi: 10.1016/j.ijrobp.2013.11.012.

Narrandes, et al. Gene Expression Detection Assay for Cancer Clinical Use. J Cancer. 2018; 9(13): 2249-2265.

Neuzil, et al. Ultra fast miniaturized real-time PCR: 40 cycles in less than six minutes. Nucleic Acids Research, 2006, vol. 34, No. 11 e77.

Noguchi, et al. Detection of Breast Cancer Micrometastases in Axillary Lymph Nodes by Means of Reverse Transcriptase-Polymerase Chain Reaction. American Journal of Pathology, vol. 148, No. 2, Feb. 1996.

Notomi, et al. Loop-mediated isothermal amplification of DNA. Nucleic Acids Res. Jun. 15, 2000;28(12):E63.

Park, et al. Advances in microfluidic PCR for point-of-care infectious disease diagnostics. Biotechnology advances 29.6 (2011): 830-839.

Parker, et al. Supervised risk predictor of breast cancer based on intrinsic subtypes. J Clin Oncol. Mar. 10, 2009;27(8):1160-7.

PCT/US2016/067381 International Search Report and Written Opinion dated Apr. 3, 2017.

PCT/US2018/039163 International Search Report and Written Opinion dated Nov. 19, 2018.

Pearch, et al. Tumour sampling method can significantly influence gene expression profiles derived from neoadjuvant window studies. Sci Rep. 2016; 6: 29434.

Prowell, et al. Pathological complete response and accelerated drug approval in early breast cancer. N Engl J Med. Jun. 28, 2012;366(26):2438-41. doi: 10.1056/NEJMp1205737. Epub May 30, 2012.

(56) References Cited

OTHER PUBLICATIONS

Radmacher, et al. (2003). Pitfalls in the Use of DNA Microarray Data for Diagnostic and Prognostic Classification. Journal of the National Cancer Institute, 95(1), 14-18.
Rose, et al. Perils of the Pathologic Complete Response. J Clin Oncol. Nov. 20, 2016;34(33):3959-3962. doi: 10.1200/JCO.2016. 68.1718. Epub Oct. 31, 2016. PMID: 27551115.
Sambrook, et al. Molecular cloning: a laboratory manual, 4th edition (2012).
Sharma, et al. High-Throughput Ultrasonic DNA Shearing for NGS Sample Preparation.
Singletary, SE. Surgical margins in patients with early-stage breast cancer treated with breast conservation therapy. Am J Surg. Nov. 2002;184(5):383-93. PMID: 12433599.
Steelman, B. Trump: polls right, models wrong. Nature. Nov. 30, 2016;540(7631):39. PMID: 27905426.
Tan, et al. Quantitative methylation analyses of resection margins predict local recurrences and disease-specific deaths in patients with head and neck squamous cell carcinomas. Br J Cancer. Jul. 22, 2008; 99(2): 357-363.
Tang, et al. Lumpectomy specimen margins are not reliable in predicting residual disease in breast conserving surgery. Am J Surg. Jul. 2015;210(1):93-8. PMID: 25613784 .
Tanner et al. Loop-mediated isothermal amplification for detection of nucleic acids. Current Protocols in Molecular Biology 15.14.1-15.14.14, Jan. 2014.
The American Society of Breast Surgeons. Position Statement on Breast Cancer Lumpectomy Margins. Approved Jan. 16, 2013. Last accessed May 22, 2016. Available at: https://www.breastsurgeons.org/new_layout/about/statements/PDF_Statements/Lumpectomy_Margins.pdf.
Treseler, et al. Pathologic analysis of the sentinel lymph node. Surg Clin North Am. Dec. 2000;80(6):1695-719. PMID: 11140868.
U.S. Department of Health and Human Services, Food and Drug Administration, Center for Drug Evaluation and Research. Guidance for Industry: Pathological Complete Response in Neoadjuvant Treatment of High-Risk Early-Stage Breast Cancer: Use as an Endpoint to Support Accelerated Approval. Oct. 2014. https://www.fda.gov/downloads/Drugs/GuidanceComplianceRegulatoryInformation/Guidances/UCM305501.pdf.
U.S. Department of Health and Human Services, Food and Drug Administration. BLA Approval Letter to Genetech, Inc. Dated Jun. 8, 2012. Available at: https://www.accessdata.fda.gov/drugsatfda_docs/appletter/2012/125409Orig1s000ltr.pdf.
U.S. Appl. No. 15/317,068 Office Action dated Jul. 31, 2019.
U.S. Appl. No. 15/317,068 Restriction Requirement Office Action dated May 14, 2019 (with reference).
Valdes, et al. Intra-operative touch preparation cytology; does it have a role in re-excision lumpectomy? Ann Surg Oncol. Mar. 2007; 14(3):1045-50.
Van Diest, P.J. Histopathological workup of sentinel lymph nodes: how much is enough? J Clin Pathol. Dec. 1999;52(12):871-3. PMID: 10711247.
Viale, et al. Intraoperative examination of axillary sentinel lymph nodes in breast carcinoma patients. Cancer. Jun. 1, 1999;85(11):2433-8. PMID: 10357414 .
Vivek, et al. Novel Acoustic-Wave Micromixer device for mixing, solubilization, and isothermal thawing of microplates.
Voogd, et al. Differences in risk factors for local and distant recurrence after breast-conserving therapy or mastectomy for stage I and II breast cancer: pooled results of two large European randomized trials. J Clin Oncol. Mar. 15, 2001;19(6):1688-97.
Wang, et al. Distinct molecular mechanisms underlying clinically relevant subtypes of breast cancer: gene expression analyses across three different platforms. BMC Genomics 2006 vol. 7, p. 127.
Weaver, D. L. Pathology evaluation of sentinel lymph nodes in breast cancer: protocol recommendations and rationale. Modern Pathology (2010) 23, S26-S32; doi:10.1038/modpathol.2010.36.
Wei et al., DNA diagnostics: Nanotechnology-enhanced electrochemical detection of nucleic acids, Pediatric Research (2010) 67, 458-468.
Westin et al. Anchored multiplex amplification on a microelectronic chip array. 2000, Nature Biotechnology, 18, 199-202.
Wick, MR, MD et al. Diagnostic Histochemistry, Chapter 1: Tissue Procurement, Processing, and Staining Techniques. Aug. 2008; pp. 1-10; ISBN: 9780521874106; figure 1.3, p. 10, paragraph 4; p. 4, paragraph 2, p. 2, paragraph 2.
Witten, et al. Data Mining: Practical Machine Learning Tools and Techniques, 3rd edition (2011).
Yared, et al. Recommendations for sentinel lymph node processing in breast cancer. Am J Surg Pathol. Mar. 2002;26(3):377-82. PMID: 11859211.
Zhang, et al. Insights into the distinct roles of MMP-11 in tumor biology and future therapeutics (Review). Int J Oncol. May 2016;48(5):1783-93. doi: 10.3892/ijo.2016.3400. Epub Feb. 18, 2016.
U.S. Appl. No. 15/317,068 Office Action dated Dec. 9, 2019.
Cobb, et al. Sepsis Gene Expression Profiling: Murine Splenic Compared With Hepatic Responses Determined by Using Complementary DNA Microarrays. Crit Care Med.Dec. 2002;30(12):2711-21.
Lucentini, J. Gene Association Studies Typically Wrong. The Scientist, 18(24):20 (2004).
Pedersen, et al. Differential effect of surgical manipulation on gene expression in normal breast tissue and breast tumor tissue. Mol Med. 2018; 24: 57, pp. 1-8.
Pedersen, et al. Supplement—Differential effect of surgical manipulation on gene expression in normal breast tissue and breast tumor tissue. Mol Med. 2018; 24: 57, p. 1.
U.S. Appl. No. 15/317,068 Office Action dated Jun. 23, 2020.
U.S. Appl. No. 16/016,460 Office Action dated Apr. 1, 2020.
U.S. Appl. No. 16/016,460 Office Action dated Dec. 3, 2020.
Bellahcène, A. and V. Castronovo. Expression of bone matrix proteins in human breast cancer: potential roles in microcalcification formation and in the genes is of bone metastases. Bulletin du cancer vol. 84,1 (1997): 17-24.
Co-pending U.S.Appl. No. 202117328979, inventor Steelman; Brandon, filed May 24, 2021.
EP18923183 extended European Search Report dated Dec. 20, 2021.
EP20202815 extended European Search Report dated Apr. 23, 2021.
Giussani, Marta et al. Extracellular matrix proteins as diagnostic markers of breast carcinoma. Journal of cellular physiology vol. 233,8 (2018): 6280-6290. doi:10.1002/jcp.26513.
Koga, Takaomi et al. Identification of MGB1 as a marker in the differential diagnosis oflung tumors in patients with a history of breast cancer by analysis of publicly available SAGE data. The Journal of moleculardiagnostics: JMD vol.6,2 (2004): 90-5. doi:10.1016/S1525-1578(10)60495-3.
Krishnamurthy et al. Intraoperative Evaluation of Axillary Sentinel Lymph Nodes in Breast Cancer, Breast Diseases: A Year Book Quarterly, Mosby, St. Louis, MO, US, vol. 19, No. 3, Jan. 1, 2008 (Jan. 1, 2008), pp. 211-217, XP026032607, ISSN: 1043-321X, Doi: 10.1016/S1043-321X (09)79246-X.
Maitra, A et al. Enrichment of epithelial cells for molecular studies. Nature medicine vol.5,4(1999): 459-63. doi:10.1038/7458.
Mangia, Anita et al. Touch imprint cytology in tumortissue banks for the confirmation of neoplastic cellularity and for DNA extraction. Archives of pathology & laboratory medicine vol. 132,6 (2008): 974-8. doi:10.5858/2008-132-974-TICITT.
Tamiolakis, D. et al. Bilateral metastatic rhabdomyosarcoma to the breast in an adolescentfemale: touch imprint cytology and implication of MyoD1 nuclear antigen. Onkologievol. 27,5 (2004): 469-71. doi:10.1159/000080367.
U.S. Appl. No. 15/317,068 Notice of Allowance dated Feb. 24, 2021.
U.S. Appl. No. 16/016,460 Office Action dated Sep. 23, 2021.
Wang, Yong-sheng et al. GeneSearch™ BLN Assay could replace frozen section and touch imprint cytology for intra-operative assess-

(56) References Cited

OTHER PUBLICATIONS ment of breast sentinel lymph nodes. Breast cancer (Tokyo, Japan) vol. 21,5 (2014): 583-9. doi:10.1007/s12282-012-0437-z.

* cited by examiner

FIG. 20A
FIG. 20B
FIG. 20C
FIG. 20D
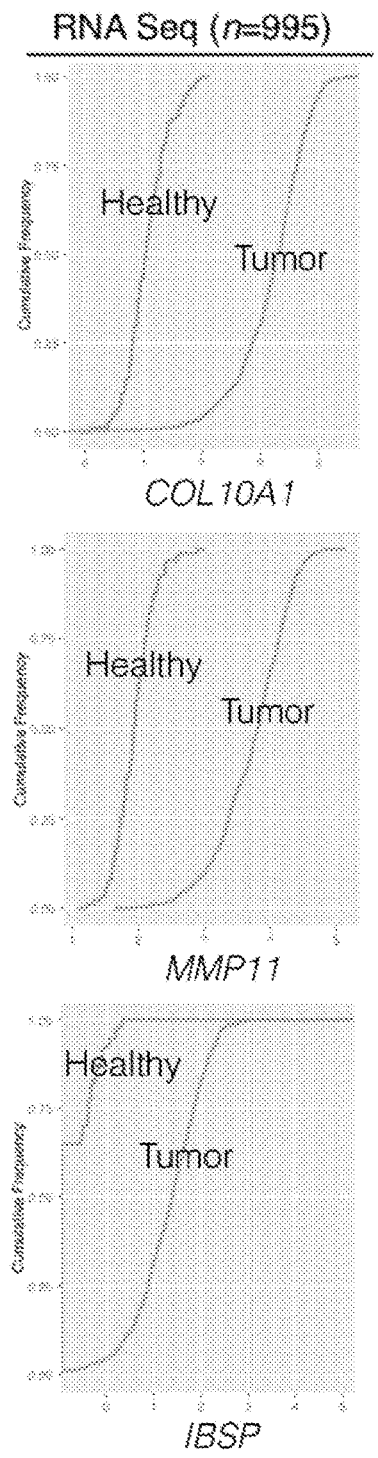
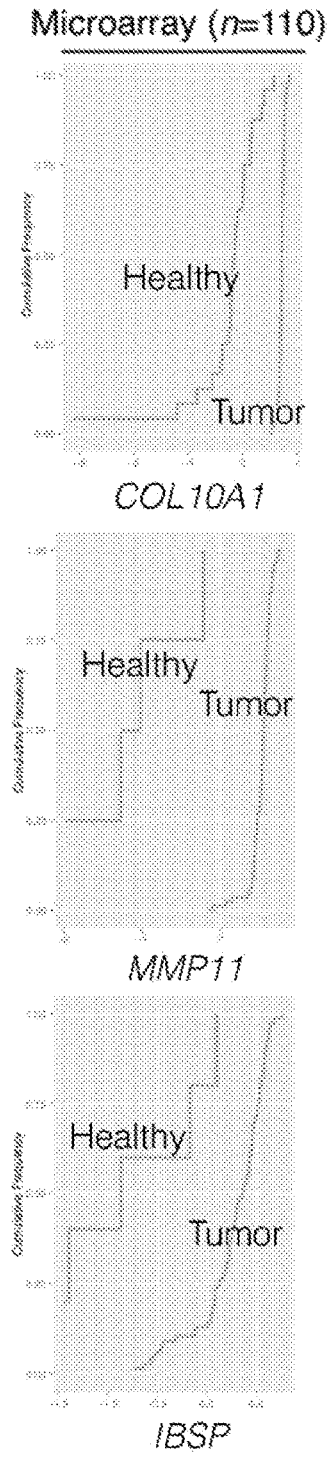
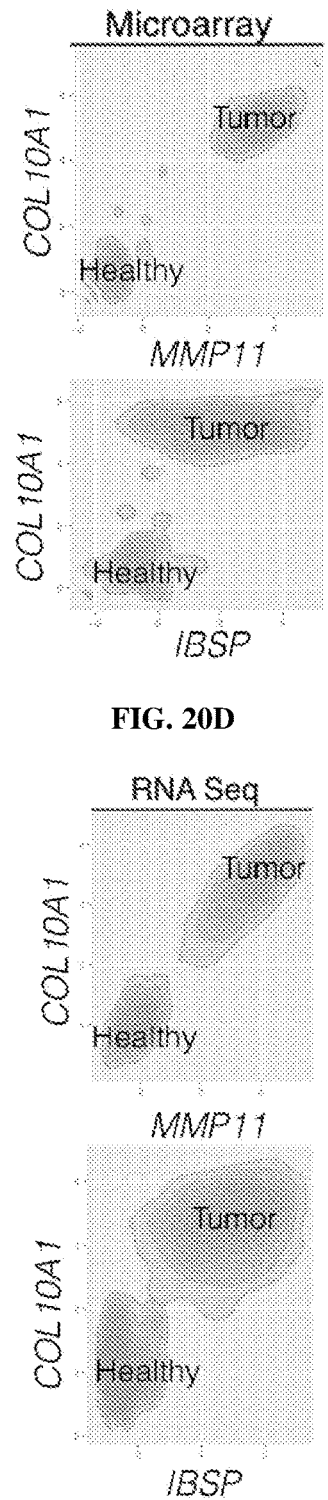
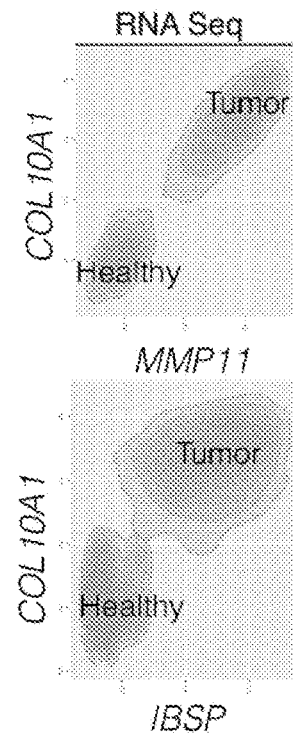

FIG. 24

SEQUENCE LISTING

<160> NUMBER OF SEQ ID NOS: 55

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tccttgaact tggtctcc                                                    19

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagttcataa aggaattgat agc                                              23

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tccttgaact tggtctcc                                                    19

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagttcataa aggaattgat agc                                              23

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atccccagtc tgtgaaattg ggcaaaatgc tgggattata gatgt                45

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcagcagaaa gattattaac ttgggcagtt ggtaagtaaa tggaaga              47

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agaaccagag gccaggcgag                                            20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tccttgaact ttggtctcc                                             19

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagttcataa aggaattgat agc                                        23

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
accgcatcga atgcatgtct cgggaaatgc tgggattata gatgt                45

```
<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggattccgct ccagacttct cggggttggt aagtaaatgg aaga              44

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 12
tccttgaact ttggtctccc aaaac                                   25

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 13
cagttcataa aggaattgat agcacagtc                               29

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 14
accgcatcga atgcatgtct cgggaaatgc tgggattata gatgtcagcc g       51

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 15
ggattccgct ccagacttct cggggttggt aagtaaatgg aagaatagga         50

<210> SEQ ID NO 16
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tccttgaact ttggtctycc atttacttac caaccccgag aagtctctgg agcggaatcc    60

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tccttgaact ttggtctcc                                                  19

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tcttccattt acttaccaac cccgagaagt ctggagcgga atcc                      44

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tccttgaact ttggtctcc                                                  19

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cagttcataa aggaattgat agc                                             23

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atccccagtc tgtgaaattg ggcaaaatgc tgggattata gatgt                     45

<210> SEQ ID NO 22
<211> LENGTH: 47
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gcagcagaaa gattattaac ttgggcagtt ggtaagtaaa tggaaga                        47

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agaaccagag gccaggcgag                                                      20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aggcagatag gcttagactc aa                                                   22

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
accgcatcga atgcatgtct cgggaaatgc tgggattata gatgt                          45

<210> SEQ ID NO 26
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggattccgct ccagacttct cggggttggt aagtaaatgg aaga                           44

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tccttgaact ttggtctcc                                                       19

<210> SEQ ID NO 28
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 28
cagttcataa aggaattgat agc                                          23

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 29
accgcatcga atgcatgtct cgggaaatgc tgggattata gatgtcagcc g            51

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 30
ggattccgct ccagacttct cggggttggt aagtaaatgg aagaatagga              50

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 31
tccttgaact ttggtctccc aaaac                                        25

<210> SEQ ID NO 32
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 32
cagttcataa aggaattgat agcacagtc                                    29

<210> SEQ ID NO 33
<211> LENGTH: 23
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 33
cacagggtat acagggttag ctg                                              23

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttctgcttc gctttcttcg                                                  20

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggccactgac tggagagg                                                    18

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gcgcaggaag taggcatag                                                   19

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
taggtgcctg catctgtctg                                                  20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agaatacccc tccccatttg                                                  20

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cccaacacca agacacagtt c                                              21

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtagcctggt tttcctggtg                                                20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
taccccaccc tacaaaatgc                                                20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgttgctgct cacttttcag                                                20

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gccatagaag ctccattagc ac                                             22

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tttcctaacc cagctccatc                                                20

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 45
ggtgactgat tacatcgcag ag                                         22

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gccttctgga ttttgcacag                                            20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cttggacaca aaaccgatcc                                            20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aaaggccttc cttcaactgg                                            20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ttgtaggggt tctggtgatg                                            20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tgacggcaat attgatgagg                                            20

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 51
agcagcctca ctcttaactt cg                                              22

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaacactgat tcggctctcc                                                 20

<210> SEQ ID NO 53
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ttcccgagac atg                                                        13

<210> SEQ ID NO 54
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
catgtctcgg gaa                                                        13

<210> SEQ ID NO 55
<211> LENGTH: 472
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55
cacagggtat acagggttag ctgtttggcc actgactgga gaggttttag gtgcctgcat     60
ctgtctgttt cccaacacca agacacagtt cttttacccc accctacaaa atgctttgcc    120
atagaagctc cattagcact tggtgactg attacatcgc agagtttctt ggacacaaaa     180
ccgatccttt ttgtaggggt tctggtgatg tttagcagcc tcactcttaa cttcgtttcg    240
aagaaagcga agcagaagtt tctatgccta cttcctgcgc tttcaaatgg ggagggtat     300 tcttttcacc aggaaaacca ggctactttc tgaaaagtga gcagcaacgt ttgatggagc    360
tgggttagga aatttctgtg caaaatccag aaggctttcc agttgaagga aggccttttt    420
tcctcatcaa tattgccgtc atttggagag ccgaatcagt gtttgcggcc gc            472
```

METHODS, COMPOSITIONS, KITS AND DEVICES FOR RAPID ANALYSIS OF BIOLOGICAL MARKERS

CROSS-REFERENCE

This application is a national stage entry of PCT application Ser. No. PCT/US2016/067381, filed Dec. 16, 2016; which claims the benefit of U.S. provisional application Ser. No. 62/269,904, filed Dec. 18, 2015; and U.S. provisional application Ser. No. 62/387,526, filed Dec. 23, 2015; which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 3, 2019, is named 45901_702_831_SL.txt and is 14,046 bytes in size.

BACKGROUND

Complete surgical excision is often a prerequisite for curing many solid tumors. One of the most important questions in treating a solid tumor is therefore whether the surgical procedure successfully removed the entire tumor. Contemporary methods rely on microscopy, which is not ideally suited for detecting malignant cells along the surface of a surgical specimen. Little progress has been made in the microscopic detection of positive surgical margins over the past 100 years, and a study in 2015 found that conventional techniques have a sensitivity of 50.9% when used to detect positive margins. Contemporary analytical methods face the challenge of sensitivity, accuracy and efficiency. Inaccurate analysis of surgical specimen often places patients at high health risk such as recurrence of a disease and disease-specific mortality, as well as heavy financial burden for additional medical treatments. There remains an urgent need to develop a post-operative test that is economical and returns reliable results for determining the success of a surgical procedure at a treatable stage. Genomics provides an opportunity to identify biomarkers that can be used to detect positive margins, which consist of rare malignant cells on the surface of a surgical specimen. Nucleic acid signatures of cells from the surface of a surgical specimen therefore has the potential to improve detection of positive margins, which could improve clinical outcomes and reduce healthcare costs.

Accordingly, disclosed herein are methods, systems compositions, and kits for post-operative test that performs complex multivariate analysis of nucleic acids of a surgical specimen.

SUMMARY

Disclosed herein are methods, systems, devices, compositions and kits for analyzing nucleic acids from solid tumors during or after an operation.

Methods, systems and kits disclosed herein may be used for postoperative analysis of a surgical specimen. The methods, systems and kits may be used for evaluating the success of a surgical procedure and/or to detect the presence of residual tissues. The methods, systems and kits may be used for coordinated intraoperative and routine margin analysis. The methods, systems and kits may be used during breast conservation surgery (BCS) on previously diagnosed invasive breast cancer. Methods, systems and kits may be used for a subject previously diagnosed for breast carcinoma (e.g. DCIS) that is not invasive breast cancer, but has a risk of becoming invasive cancer, or has a risk of recurrence.

Disclosed herein are kits comprising devices and reagents to analyze cellular specimens using the devices and methods disclosed herein. The kit comprises (a) a sample acquisition device for collecting a biological sample; (b) a set of reagents for analyzing nucleic acid molecules of the biological sample; (c) a set of instructions for analyzing the nucleic acid molecules of (b), and (d) a set of reagents for storing the biological sample prior to the analyzing in (b) and (c). The kit may comprise (e) primers and probes to detect a panel of nucleic acids, (0 oligonucleotides to prime cDNA synthesis, (g) primers and probes to detect endogenous references, (h) primers and probes to detect endogenous controls, (i) primers and probes to detect exogenous controls, (j) a sample acquisition device to collect the surgical specimen, (k) a set of instruction for performing test on the surgical specimen, (1) a platform for analyzing the test result, and (m) a set of instructions for analyzing the test result. The kit may comprise synthetic exogenous controls to test key steps of the workflow. Controls may comprise synthetic DNA to verify and calibrate the amplification of DNA. Controls may comprise synthetic RNA to verify and calibrate cDNA synthesis and subsequent amplification. The kit may comprise negative controls to ensure that amplification is not the result of cross-over contamination. The kit may comprise a sample acquisition device. The sample acquisition device may comprise a slide with a functionalized surface coating that is used to obtain biologic material from the surface of a surgical specimen. The kit may comprise analyte-specific reagents. The analyte-specific reagents may be nucleic acid primers and/or probes to detect the panel of target and control nucleic acids. The kits may comprise a standard. The kits may comprise a control. The control may be utilized to detect and/or confirm the presence of a control cellular material, a control nucleic acid or a control analyte. The control nucleic acid may be an amplified nucleic acid. The control nucleic acid may be a synthetic nucleic acid. The control nucleic acid may be an exogenous nucleic acid. The control nucleic acid may comprise a nucleic acid selected from genomic DNA, mitochondrial DNA, chloroplast DNA, microbial DNA, cDNA, messenger RNA, ribosomal RNA, micro RNA, an amplicon thereof, and a combination thereof. The control nucleic acid may encode pre-determined internal reference genes against which the target nucleic acid(s) are compared to obtain a normalization ratio. The kit may comprise a plurality of control nucleic acids. The control nucleic acids may comprise a control nucleic acid signature. The control nucleic acid signature may indicate a cell type. The cell type may be cells of epithelial origin. The cell type may be cells of breast tissue origin. The cell type may be an adipocyte or pre-adipocyte. Presence of only an adipocyte signature in the cellular specimen may exclude malignancy. The cell type may be a vascular cell type. The control may be a control for obtaining the cellular specimen. The method may be a control for homogenizing and/or lysing the cellular specimen. The control may be for amplifying the nucleic acids of the cellular specimen. The control may be for cDNA synthesis. The control may be for nucleic acid sequencing.

Disclosed herein are systems for determining success of a surgical procedure for removing a tumor from a subject, said system comprising: a) a kit comprising a sample acquisition device comprising a sample collection unit for collecting a biological sample from said subject, wherein said biological sample is collected from the surface of a surgical specimen; a set of reagents for processing said biological sample, and a set of instructions for detecting a pattern of expression of at least one biomarker associated with a cancer in said biological sample; and b) a platform for analyzing said biological sample for detecting a presence or absence of a positive surgical margin in said biological sample; wherein said pattern of expression of said at least one biomarker determines a presence or absence of a positive surgical margin in said biological sample, thereby determining a likelihood of success of said surgical procedure for removing said tumor. The sample collection unit may comprise a coated surface. The coated surface may be selected from a slide, a plate, tube, a chip and a paper. The sample collection unit may comprise a nitrocellulose membrane. The sample collection unit may comprise a receptacle containing a reagent for collecting said biological sample. Collecting the biological sample may comprise an imprint cytology method. Collecting the biological sample may comprise a touch-prep method. Collecting the biological sample may comprise a brush biopsy method. Analysis of the biological sample may be performed after said surgical procedure. Analysis of the biological sample may be performed during said surgical procedure. The likelihood of success of said surgical procedure for removing said tumor may be determined by an absence of a cancer remission in said subject within 5 years of said surgical procedure. The likelihood of success of said surgical procedure for removing said tumor may be determined by reduction of a risk of a cancer remission in said subject within 5 years of the surgical procedure by at least 70%. In some cases, when no positive surgical margin is detected in said subject, said subject may have a 70% likelihood of no cancer remission within 5 years of the surgical procedure. The biological sample may comprise at least 20% of the surface of a surgical specimen. The systems may comprise a kit that comprises a set of reagents for extracting nucleic acid molecules from said biological sample. The nucleic acid molecules may comprise RNA, mRNA, spliced RNA, non-spliced RNA, DNA, or combinations thereof. The systems may comprise a kit that comprises a set of reagents for synthesizing cDNA from said biological sample. The reagents may be for preserving or storing said biological sample. The reagents may be for shipping said biological sample. The systems may comprise a kit that comprises at least one pair of primers for amplifying said at least one biomarker. The primers for amplifying a biomarker may be selected from SEQ ID NO. 33-SEQ ID NO. 52. The primers may be selected from amplifying a biomarker may have at least 90% homology over 12 nucleotides of a primer selected from SEQ ID NO. 33-SEQ ID NO. 52. The systems may comprise a kit that comprises instructions for detecting a pattern of expression of at least one biomarker associated with a cancer in said biological sample comprise instructions for detecting a pattern of expression of said at least one biomarker associate with a cancer in said biological sample. The systems may be configured to further detect a pattern of expression of a second biomarker associated with a cancer in said biological sample, wherein a combination of an increase of said at least one biomarker and said second biomarker indicates a presence or absence of positive surgical margin in said biological sample. The at least one biomarker associated with a cancer in said biological sample may be a biomarker associated with a gene or a partial thereof selected from the group consisting of ACTR3B, ALK, ANLN, AURKA, BAG1, Bcl2, BCL2, BCR-Abl, BIRC5, BLVRA, BRAF, c-KIT Cathepsin L2, CCNB1, CCNE1, CD20 antigen, CD30, CD68, CDC20, CDC6, CDH3, CENPF, CEP55, CXXC5, Cyclin B1, EGFR, ER, ERBB2, ESR1, EXO1, FGFR4, FIP1L-PDGFRalpha, FOXA1, FOXC1, GPR160, GRB7, GSTM1, HOXB13, IL17BR, Ki-67, KIF2C, KRAS, KRT14, KRT17, KRT5, MAPT, MDM2, MELK, MIA, MKI67, MLPH, MMP11, MYBL2, MYC, NAT1, NDC80, NUF2, ORC6L, PDGFR, PGR, PHGDH, PML/RAR alpha, PR, PTTG1, RRM2, SCUBE2, SFRP1, SLC39A6, STK15, Stromelysin 3 (MMP11), Survivin, TMEM45B, TPMT, TYMS, UBE2C, UBE2T, UGT1A1, ABCA10, ABCA9, ADAM33, ADAMTS5, ANGPT1, ANKRD29, ARHGAP20, ARMCX5GPRASP2, ASB1, CA4, CACHD1, CAPN11, CAV1, CAV2, CAV3, CBX7, CCNE2, CD300LG, CDC14B, CDC42SE1, CENPF, CEP68, CFL2, CHL1, CLIP4, CNTNAP3, COL10A1, COL11A1, CRIM1, CXCL3, DAB2IP, DMD, DPYSL2, DST, EEPD1, ENTPD7, ERCC6L, EZH1, F10, FAM126A, FBXO31, FGF1, FIGF, FMO2, FXYD1, GIPC2, GLYAT, GPR17, GPRASP1, GPRASP2, HAGL, HAND2-AS1, HLF, HMMR, HOXA2, HOXA4, HOXA5, IGSF10, INHBA, IL11RA, ITM2A, JADE1, JUN, KIAA0101, KIF4A, KLHL29, LCAT, LGI4, LIFR, LIMS2, LRIG3, LRRC2, LRRC3B, MAMDC2, MATN2, MICU3, MIR99AHG, MME, MMP11, NECAB1, NEK2, NKAPL, NPHP3, NR3C1, NR3C2, NUF2, PAMR1, PAFAH1B3, PAQR4, PARK2, PEAR1, PGM5, PKMYT1, PLEKHM3, PLSCR4, POU6F1, PPAP2B, PPP1R12B, PRCD, PRX, PYCR1, RAPGEF3, RBMS2, SCN4B, SDPR, SLC35A2, SH3BGRL2, SPRY2, STAT5B, SYN2, TK1, TMEM220, TMEM255A, TMOD1, TPM3, TPX2, TSHZ2, TSLP, TSTA3, TTC28, WISP1, USHBP1, USP44, IBSP, CST1, ZWINT, and combinations thereof. The at least one biomarker associated with a cancer in said biological sample may be a biomarker associated with a gene or a partial thereof selected from the group consisting of COL10A1, MMP11, IBSP, CST1, and combinations thereof. The biomarker associated with a cancer may be a biomarker associated with a cancer selected from the group consisting of breast cancer, prostate cancer, colon cancer, lung cancer, liver cancer, brain cancer, skin cancer, testicular cancer, oral cancer, pancreatic cancer, stomach cancer, cervical cancer, uterine cancer, endometrial cancer, and ovarian cancer. The biomarker associated with a cancer may be a biomarker associated with breast cancer. The platform for analyzing said biological sample may be a platform selected from the group consisting of a device for performing polymerase chain reaction (PCR), quantitative PCR (QPCR), next generation sequencing, RNAseq, digital PCR (dPCR), digital droplet PCR (ddPCR), isothermal amplification, endoribonucleotide strand displacement assay (ERiN SDA), microarray, and combinations thereof. The platform for analyzing said biological sample may comprise a device for performing RNAseq. The platform for analyzing said biological sample may comprise a device for performing quantitative (QPCR). A presence of said positive surgical margins in said biological sample may indicate incomplete removal of said tumor from said subject. An absence of positive surgical margin in said biological sample may indicate complete removal of said tumor from said subject. The pattern of expression of said at least one biomarker may have at least 60% sensitivity for determining success of said surgical procedure for removing said tumor. The systems may be configured to further comprise communicating with a physician or surgeon for additional surgical procedures. The systems may be configured to further comprise communicating with a physician or surgeon for prescription of chemotherapy, radiotherapy, trastuzumab, endocrine therapy, or combinations thereof.

Disclosed herein are methods for determining success of a surgical procedure for removing a tumor from a subject, said methods comprising: a) collecting a biological sample from said subject, wherein said biological sample is collected from the surface of a surgical specimen; b) bringing said biological sample in proximity to a sample collection unit, thereby contacting said biological sample with said sample collection unit and collecting said biological sample; and c) detecting a pattern of expression of at least one biomarker associated with a cancer in said biological sample for detecting a presence or absence of a positive surgical margin of said tumor; wherein said pattern of expression of said at least one biomarker determines a presence or absence of a positive surgical margin of said tumor, thereby determining a likelihood of success of said surgical procedure for removing said tumor. The sample collection unit may comprise a coated surface. The coated surface may be selected from a slide, a plate, tube, a chip and a paper. The sample collection unit may comprise a nitrocellulose membrane. The sample collection unit may comprise a receptacle containing a reagent for collecting said biological sample. Collecting said biological sample may comprise an imprint cytology method. Collecting said biological sample may comprise a touch-prep method. Collecting said biological sample may comprise a brush biopsy method. Detecting a pattern of expression of at least one biomarker associated with a cancer in said biological sample may be performed after said surgical procedure. Detecting a pattern of expression of at least one biomarker associated with a cancer in said biological sample may be performed during said surgical procedure. The likelihood of success of said surgical procedure for removing said tumor may be determined by an absence of a cancer remission in said subject within 5 years of said surgical procedure. The likelihood of success of said surgical procedure for removing said tumor may be determined by a reduction of a risk of a cancer remission in said subject within 5 years of said surgical procedure. In some cases, when no positive surgical margin is detected, said subject may have a 70% likelihood of no cancer remission within 5 years of said surgical procedure. The biological sample may comprise at least 20% of the surface of a surgical specimen. The methods may further comprise extracting nucleic acid molecules from said biological sample. The nucleic acid molecules may comprise RNA, mRNA, spliced RNA, non-spliced RNA, DNA, or combinations thereof. The methods may further comprise synthesizing cDNA from said biological sample. The methods may further comprise preserving or storing said biological sample. The methods may further comprise shipping said biological sample. The methods may further comprise amplifying said at least one biomarker with at least one pair of primers. The at least one pair of primers may be selected from SEQ ID NO. 33-SEQ ID NO. 52. The at least one pair of primers may have at least 90% homology over 12 nucleotides of a primer selected from SEQ ID NO. 33-SEQ ID NO. 52. The methods may further comprise measuring a pattern of expression of a second biomarker associated with a cancer in said biological sample, wherein a combination of an increase of said at least one biomarker and said second biomarker indicates a presence or absence of positive surgical margin in said biological sample. The at least one biomarker associated with a cancer in said biological sample may be a biomarker associated with a gene or a partial thereof selected from the group consisting of ACTR3B, ALK, ANLN, AURKA, BAG1, Bcl2, BCL2, BCR-Abl, BIRC5, BLVRA, BRAF, c-KIT Cathepsin L2, CCNB1, CCNE1, CD20 antigen, CD30, CD68, CDC20, CDC6, CDH3, CENPF, CEP55, CXXC5, Cyclin B1, EGFR, ER, ERBB2, ESR1, EXO1, FGFR4, FIP1L-PDGFRalpha, FOXA1, FOXC1, GPR160, GRB7, GSTM1, HOXB13, IL17BR, Ki-67, KIF2C, KRAS, KRT14, KRT17, KRT5, MAPT, MDM2, MELK, MIA, MKI67, MLPH, MMP11, MYBL2, MYC, NAT1, NDC80, NUF2, ORC6L, PDGFR, PGR, PHGDH, PML/RAR alpha, PR, PTTG1, RRM2, SCUBE2, SFRP1, SLC39A6, STK15, Stromelysin 3, Survivin, TMEM45B, TPMT, TYMS, UBE2C, UBE2T, UGT1A1, ABCA10, ABCA9, ADAM33, ADAMTS5, ANGPT1, ANKRD29, ARHGAP20, ARMCX5GPRASP2, ASB1, CA4, CACHD1, CAPN11, CAV1, CAV2, CAV3, CBX7, CCNE2, CD300LG, CDC14B, CDC42SE1, CENPF, CEP68, CFL2, CHL1, CLIP4, CNTNAP3, COL10A1, COL11A1, CRIM1, CXCL3, DAB2IP, DMD, DPYSL2, DST, EEPD1, ENTPD7, ERCC6L, EZH1, F10, FAM126A, FBXO31, FGF1, FIGF, FMO2, FXYD1, GIPC2, GLYAT, GPR17, GPRASP1, GPRASP2, HAGL, HAND2-AS1, HLF, HMMR, HOXA2, HOXA4, HOXA5, IGSF10, INHBA, IL11RA, ITM2A, JADE', JUN, KIAA0101, KIF4A, KLHL29, LCAT, LGI4, LIFR, LIMS2, LRIG3, LRRC2, LRRC3B, MAMDC2, MATN2, MICU3, MIR99AHG, MME, MMP11, NECAB1, NEK2, NKAPL, NPHP3, NR3C1, NR3C2, NUF2, PAMR1, PAFAH1B3, PAQR4, PARK2, PEAR1, PGM5, PKMYT1, PLEKHM3, PLSCR4, POU6F1, PPAP2B, PPP1R12B, PRCD, PRX, PYCR1, RAPGEF3, RBMS2, SCN4B, SDPR, SLC35A2, SH3BGRL2, SPRY2, STAT5B, SYN2, TK1, TMEM220, TMEM255A, TMOD1, TPM3, TPX2, TSHZ2, TSLP, TSTA3, TTC28, WISP1, USHBP1, USP44, IBSP, CST1, ZWINT, and combinations thereof. The at least one biomarker associated with a cancer in said biological sample may be a biomarker associated with a gene or a partial thereof selected from the group consisting of COL10A1, MMP11, IBSP, CST1, and combinations thereof. The biomarker associated with a cancer may be a biomarker associated with a cancer selected from the group consisting of breast cancer, prostate cancer, colon cancer, lung cancer, liver cancer, brain cancer, skin cancer, testicular cancer, oral cancer, pancreatic cancer, stomach cancer, cervical cancer, uterine cancer, endometrial cancer, and ovarian cancer. The biomarker associated with a cancer may be a biomarker associated with breast cancer. Detecting a pattern of expression of said at least one biomarker may be an analysis selected from the group consisting of performing polymerase chain reaction (PCR), quantitative PCR (QPCR), next generation sequencing, RNAseq, digital PCR (dPCR), digital droplet PCR (ddPCR), isothermal amplification, endoribonucleotide strand displacement assay (ERiN SDA), microarray, and combinations thereof. Detecting a pattern of expression of said at least one biomarker may comprises performing RNAseq. Detecting a pattern of expression of said at least one biomarker may comprises performing quantitative PCR (QPCR). A presence of said positive surgical margin in said biological sample may indicate incomplete removal of said tumor from said subject. An absence of said positive surgical margin in said biological sample may indicate complete removal of said tumor from said subject. The methods may further comprise comparing said pattern of expression of said at least one biomarker in said biological sample with a pattern of expression of said at least one biomarker in a control sample. The pattern of expression of said at least one biomarker may have at least 60% sensitivity for determining success of said surgical procedure for removing said tumor. The methods may further comprise communicating with a physician or surgeon for additional surgical procedures. The methods may further comprise communicating with a physician or surgeon for prescription of chemotherapy, radiotherapy, trastuzumab, endocrine therapy, or combinations thereof.

Disclosed are kits for analyzing a biological sample removed from a tumor of a subject, said kit comprising a) a sample acquisition device for collecting said biological sample during a surgical procedure for removing said tumor from said subject, wherein said biological sample is collected from the surface of a surgical specimen; b) a set of reagents for processing a nucleic acid molecule of said biological sample; c) sets of primers or probes for detecting a pattern of expression of at least one biomarker in said biological sample; and d) a set of instructions for analyzing said biological sample to detect a presence or absence of a positive surgical margin in said biological sample, thereby determining a likelihood of success of said surgical procedure for removing said tumor from said subject.

Disclosed are methods for detecting a presence of a tumor cell in an aspirate fluid collected from a subject, said method comprising: a) collecting an aspirate fluid from a breast, and b) detecting a pattern of expression of a combination of at least three biomarkers associated with a cancer selected from a group consisting of COL10A1, MMP11, IBSP and CST1, wherein said pattern of expression of said combination of at least three biomarkers indicates a presence or absence of said tumor cell in said subject. The aspirate fluid may comprise nipple aspirate fluid. The aspirate fluid may comprise ductal lavage aspirates from a breast. Collecting of the aspirate fluid from a breast may comprise needle aspiration. The methods may further comprise extracting nucleic acid molecules from said aspirate fluid. The nucleic acid molecules may comprise RNA, mRNA, spliced RNA, non-spliced RNA, DNA, or combinations thereof. The method may further comprise synthesizing cDNA from said aspirate fluid. The methods may further comprise preserving or storing said aspirate fluid. The methods may further comprise shipping said aspirate fluid. The methods may further comprise amplifying said combination of at least three biomarkers with at least one pair of primers. The at least one pair of primers may be selected from SEQ ID NO. 33-SEQ ID NO. 52. The at least one pair of primers may have at least 90% homology over 12 nucleotides of a primer selected from SEQ ID NO. 33-SEQ ID NO. 52. The methods may further comprise measuring a pattern of expression of a fourth biomarker associated with a cancer in said aspirate fluid, wherein a combination of an increase of said combination of at least three biomarkers and said fourth biomarker indicates a presence or absence of positive surgical margin in said aspirate fluid. The fourth biomarkers associated with a cancer may be a biomarker associate with a gene or a partial thereof selected from the group consisting of ACTR3B, ALK, ANLN, AURKA, BAG1, Bcl2, BCL2, BCR-Abl, BIRC5, BLVRA, BRAF, c-KIT Cathepsin L2, CCNB1, CCNE1, CD20 antigen, CD30, CD68, CDC20, CDC6, CDH3, CENPF, CEP55, CXXC5, Cyclin B1, EGFR, ER, ERBB2, ESR1, EXO1, FGFR4, FIP1L-PDGFRalpha, FOXA1, FOXC1, GPR160, GRB7, GSTM1, HOXB13, IL17BR, Ki-67, KIF2C, KRAS, KRT14, KRT17, KRT5, MAPT, MDM2, MELK, MIA, MKI67, MLPH, MMP11, MYBL2, MYC, NAT1, NDC80, NUF2, ORC6L, PDGFR, PGR, PHGDH, PML/RAR alpha, PR, PTTG1, RRM2, SCUBE2, SFRP1, SLC39A6, STK15, Stromelysin 3, Survivin, TMEM45B, TPMT, TYMS, UBE2C, UBE2T, UGT1A1, ABCA10, ABCA9, ADAM33, ADAMTS5, ANGPT1, ANKRD29, ARHGAP20, ARMCX5GPRASP2, ASB1, CA4, CACHD1, CAPN11, CAV1, CAV2, CAV3, CBX7, CCNE2, CD300LG, CDC14B, CDC42SE1, CENPF, CEP68, CFL2, CHL1, CLIP4, CNTNAP3, COL11A1, CRIM1, CXCL3, DAB2IP, DMD, DPYSL2, DST, EEPD1, ENTPD7, ERCC6L, EZH1, F10, FAM126A, FBXO31, FGF1, FIGF, FMO2, FXYD1, GIPC2, GLYAT, GPR17, GPRASP1, GPRASP2, HAGL, HAND2-AS1, HLF, HMMR, HOXA2, HOXA4, HOXA5, IGSF10, INHBA, IL11RA, ITM2A, JADE', JUN, KIAA0101, KIF4A, KLHL29, LCAT, LGI4, LIFR, LIMS2, LRIG3, LRRC2, LRRC3B, MAMDC2, MATN2, MICU3, MIR99AHG, MME, NECAB1, NEK2, NKAPL, NPHP3, NR3C1, NR3C2, NUF2, PAMR1, PAFAH1B3, PAQR4, PARK2, PEARL, PGM5, PKMYT1, PLEKHM3, PLSCR4, POU6F1, PPAP2B, PPP1R12B, PRCD, PRX, PYCR1, RAPGEF3, RBMS2, SCN4B, SDPR, SLC35A2, SH3BGRL2, SPRY2, STAT5B, SYN2, TK1, TMEM220, TMEM255A, TMOD1, TPM3, TPX2, TSHZ2, TSLP, TSTA3, TTC28, WISP1, USHBP1, USP44, ZWINT, and combinations thereof. The combination of at least three biomarkers associated with a cancer may be biomarkers associated with breast cancer. Detecting a pattern of expression of said combination of at least three biomarkers is selected from the group consisting of a device for performing polymerase chain reaction (PCR), quantitative PCR (QPCR), next generation sequencing, RNAseq, digital PCR (dPCR), digital droplet PCR (ddPCR), isothermal amplification, endoribonucleotide strand displacement assay (FRiN SDA), microarray, and combinations thereof. Detecting a pattern of expression of said combination of at least three biomarkers comprises performing RNAseq. Detecting a pattern of expression of said combination of at least three biomarkers comprises performing quantitative PCR (QPCR). A presence of said tumor cell in said aspirate fluid may indicate a presence of a cancer in said subject. An absence of said tumor cell in said aspirate fluid may indicate an absence of a cancer said subject. A presence of said tumor cell in said aspirate fluid may indicate a cancer remission in said subject. An absence of said tumor cell in said aspirate fluid may indicate an absence of a cancer remission in said subject. In some cases, when no tumor cell is detected, said subject may have a 70% likelihood of no cancer remission within 5 years of a surgical procedure. The methods may further comprise comparing said pattern of expression of said combination of at least three biomarkers in said biological sample with a pattern of expression of said combination of at least three biomarkers in a control sample. The methods may further comprise communicating with a physician or surgeon for surgical procedures. The methods may further comprise communicating with a physician or surgeon for prescription of chemotherapy, radiotherapy, trastuzumab, endocrine therapy, or combinations thereof.

Disclosed herein are devices comprising: a sample input unit that receives a cellular specimen comprising a target nucleic acid; a nucleic acid analysis unit that measures a target nucleic acid expression level of the target nucleic acid, wherein measuring the target nucleic acid expression level comprises an isothermal amplification of the target nucleic acid; and a computational unit that interprets the target nucleic acid expression level as an indication of the presence or absence of a condition affecting the cellular specimen, wherein the sample input unit, nucleic acid analysis unit, and computational unit are integrated within the device. The cellular specimen may comprise a cell, wherein the cell possesses a cell wall or cellular membrane that is not disrupted. The cellular specimen may be derived from a lumpectomy, a cancer, a solid tumor, a liquid tumor, a malignant tumor, a benign tumor, a primary tumor, a metastatic tumor, a polyp, a lymph node, an early stage tumor, a localized tumor, and a non-metastatic tumor. The cellular specimen may be derived from a surface of a surgical specimen. The cellular specimen may be derived from at least 50% of the surface of the surgical specimen. The surface of the surgical specimen may be the entire surface of the surgical specimen. The cellular specimen may be derived from a method selected from a touch prep method and a brush biopsy. The cellular specimen may consist essentially of mammalian cells. The device may further comprise a sample collection unit that carries the cellular specimen and is inserted in the sample input unit. The sample collection unit may comprise a surface. The sample collection unit may comprise a slide. The surface may have a coating that promotes adhesion of the cellular specimen to the surface. The coating comprises an agent selected from poly-l-lysine, poly-d-lysine, poly-ornithine, a collagen, a laminin, a fibronectin, a mucopolysacharride, heparin sulfate, hyaluronidate, chondroitin sulfate, and a hydrogel. The sample collection unit may comprise information about a location from which the cellular specimen was derived. The location may be a surface of a surgical specimen selected from an inferior surface, a medial surface, a lateral surface, a proximal surface, a distal surface, and a combination thereof. The device may further comprise a sample preparation unit that releases, isolates and/or purifies the target nucleic acid from the cellular specimen. The sample preparation unit may be capable of disrupting a cell membrane or cell wall of the cellular specimen. Disrupting the cell may comprise a method selected from lysing the cell, sonicating the cell, homogenizing the cell, shaking the cell, vortexing a solution containing the cell, and combinations thereof. The sample preparation unit and/or nucleic acid analysis unit may comprise a microfluidics unit, wherein disrupting the cell occurs in the microfluidics unit. The sample preparation unit and nucleic acid analysis unit may share a common reaction chamber. The nucleic acid analysis unit may comprise an oligonucleotide that binds to the target nucleic acid. The nucleic acid analysis unit may comprise a temperature regulator. The nucleic acid analysis unit may be capable of performing a polymerization reaction of the target nucleic acid or portion thereof. The polymerization reaction may be selected from the isothermal amplification, a reverse transcription reaction, and a combination thereof. The isothermal amplification and reverse transcription reaction may occur in the same reaction container, and wherein the reverse transcription reaction transcribes RNA in the cellular specimen to produce a cDNA, wherein the cDNA is the target nucleic acid. The isothermal amplification may be selected from Loop-mediated Isothermal Amplification (LAMP), Helicase-Dependent Amplification (HDA), Recombinase Polymerase Assay (RPA), Transcription-Mediated Amplification (TMA), Nucleic Acid Sequence-Based Amplification (NASBA), Signal mediated amplification of RNA Technology (SMART), Strand Displacement Amplification (SDA), Rolling Circle Amplification (RCA), Isothermal Multiple Displacement Amplification (IMDA), Single Primer Isothermal Amplification (SPIA), Recombinase Polymerase Assay (RPA), and Self-sustained Sequence Replication (3SR). The isothermal amplification may be an endoribonucleotide strand displacement assay (ERiN SDA). The isothermal amplification may comprise an amplification reaction that produces an amplicon less than about 70 base pairs. The isothermal amplification may comprise an amplification reaction that produces an amplicon in less than about 10 minutes. The isothermal amplification may comprise an amplification reaction that produces an amplicon in less than about 2 minutes. The nucleic acid analysis unit may measure a plurality of target nucleic acid expression levels of a plurality of target nucleic acids. The plurality of target nucleic acids may correspond to a plurality of genetic loci. The plurality of genetic loci may be less than about 10 genetic loci, less than about 7 genetic loci or less than about 4 genetic loci. The plurality of genetic loci may be about 3 genetic loci. The one or more genetic loci of the plurality of genetic loci may correspond to a distinct gene. The plurality of genetic loci may be located in one or more genes selected from the group consisting of ABCA10, ABCA9, ADAM33, ADAMTS5, ANGPT1, ANKRD29, ARHGAP20, ARMCX5GPRASP2, ASB1, CA4, CACHD1, CAPN11, CAV1, CAV2, CAV3, CBX7, CCNE2, CD300LG, CDC14B, CDC42SE1, CENPF, CEP68, CFL2, CHL1, CLIP4, CNTNAP3, COL10A1, COL11A1, CRIM1, CXCL3, DAB2IP, DMD, DPYSL2, DST, EEPD1, ENTPD7, ERCC6L, EZH1, F10, FAM126A, FBXO31, FGF1, FIGF, FMO2, FXYD1, GIPC2, GLYAT, GPR17, GPRASP1, GPRASP2, HAGL, HAND2-AS1, HLF, HMMR, HOXA2, HOXA4, HOXA5, IGSF10, INHBA, IL11RA, ITM2A, JADE', JUN, KIAA0101, KIF4A, KLHL29, LCAT, LGI4, LIFR, LIMS2, LRIG3, LRRC2, LRRC3B, MAMDC2, MATN2, MICU3, MIR99AHG, MME, MMP11, NECAB1, NEK2, NKAPL, NPHP3, NR3C1, NR3C2, NUF2, PAMR1, PAFAH1B3, PAQR4, PARK2, PEAR1, PGM5, PKMYT1, PLEKHM3, PLSCR4, POU6F1, PPAP2B, PPP1R12B, PRCD, PRX, PYCR1, RAPGEF3, RBMS2, SCN4B, SDPR, SLC35A2, SH3BGRL2, SPRY2, STAT5B, SYN2, TK1, TMEM220, TMEM255A, TMOD1, TPM3, TPX2, TSHZ2, TSLP, TSTA3, TTC28, WISP1, USHBP1, USP44, IBSP and ZWINT, and combinations thereof. The one or more genes may encode an mRNA selected from an mRNA in Table 9. The isothermal amplification may comprise a set of nested primers that anneal to the target nucleic acid. The isothermal amplification may comprise priming amplification of the target nucleic acid with an endoribonucleotide primer. The endoribonucleotide primer may comprise a 3' blocking group, wherein the isothermal amplification will not proceed until the 3' blocking group is removed. The isothermal amplification may not proceed unless the target nucleic acid is primed with a primer that is complementary to a corresponding sequence of the target nucleic acid. The isothermal amplification 3' blocking group may be removed by an enzyme selected from a nicking enzyme, an endonuclease and a polymerase. The endonuclease may not be RNase H2. The endonuclease may be BsoBI. The computational unit may comprise a classifier that assigns a score to the target nucleic acid expression level, wherein the score reflects a quantitative difference between the target nucleic acid expression level and a reference expression level. The reference expression level may comprise an expression level of the target nucleic acid in a reference sample. The reference sample may be normal or healthy. The reference sample may be affected by a condition or disease. The reference expression level may be an average of the expression levels of the target nucleic acid in a plurality of reference samples. The quantitative difference between the target nucleic acid expression level and average of the expression levels of the target nucleic acid in a plurality of reference samples may be selected from about 3 standard deviations from the reference mean expression level, about 2 standard deviations from the reference mean expression level, and about 1 standard deviation from the reference mean expression level. The quantitative difference may be determined by a ratio of the target nucleic acid expression level to the reference expression level. The condition may be a presence of a cancer or a risk of a cancer. The risk of the cancer may be a recurrence risk or a malignancy risk. The presence or risk may be determined with a negative predictive value of at least about 85%, about 90%, about 95%, about 98%, and about 99%. The device may require three or fewer interactions by a user in order to obtain an interpretation of the target nucleic acid expression level. The device may further comprise a communications unit, wherein the communications unit is capable of receiving and/or transmitting information about the cellular specimen to and/or from the device. The information about the cellular specimen is selected from information about a subject from which the cellular specimen was derived; the condition; a tissue type from which the cellular specimen was derived; the target nucleic acid; the target nucleic acid expression level; a location on a surgical specimen from which the cellular specimen was derived; a classifier that should be selected to and combinations thereof. The device may comprise a control nucleic acid to monitor the integrity of a process performed by the device and/or the integrity of the cellular specimen. The control nucleic acid may be synthetic RNA. The process may be selected from a reverse transcription, the isothermal amplification, cell lysis, cell homogenization, and nucleic acid detection.

Further disclosed herein are methods comprising: obtaining a cellular specimen containing a target nucleic acid; inserting the cellular specimen into a device disclosed herein; assessing a presence, absence or risk of a condition or disease in the cellular specimen; and directing a user of the device to perform or not perform a procedure based on a result of the assessing. The procedure may be selected from an operation, a surgery, a biopsy, a sampling, a test, a treatment, a therapy, and combinations thereof. The therapy or treatment may be selected from a drug, a diet, a radiation treatment, a biological therapeutic. The procedure may be an expansion of an operation or surgery that is being performed simultaneously with the assessing. The user may be selected from a surgeon, a nurse, a doctor, a medical practitioner, a medical assistant, a technician, an individual with no medical training, and a researcher. The obtaining may comprise obtaining the cellular specimen from a non-user of the device. The obtaining may comprise obtaining a sample from a subject, wherein the sample, a portion thereof, or a surface thereof comprises the cellular specimen. The obtaining the cellular specimen may comprise obtaining the cellular specimen from at least about 1%, about 10%, about 20%, about 30%, about 40%, about 50%, about 60%, about 70%, about 80%, about 90%, about 95%, or about 100% of the surface of the sample. The sample may be a tumor or portion thereof. The sample may comprise blood, spinal fluid, lymph tissue, or bone marrow. The obtaining the cellular specimen may comprise contacting the cellular specimen with a sample collection unit, wherein the cellular specimen is within the subject while contacting. The assessing may consist of analyzing the cellular specimen. The assessing may consist of quantifying an amount of a biomarker associate with a cancer in the cellular specimen, wherein an increase or a decrease of said at least one biomarker indicates the presence or absence of a cancer in the cellular specimen. The assessing may consist of receiving a result from the device, wherein the result verifies the presence, absence or risk of a condition or disease in the cellular specimen. The method may be performed in less than about 60 minutes, less than about 50 minutes, less than about 40 minutes less than about 30 minutes, less than about 20 minutes, less than about 15 minutes, less than about 10 minutes, less than about 5 minutes, or less than about 2 minutes. The disease or condition may be selected from a benign condition, pre-cancerous condition, early-stage cancer, and a non-metastatic cancer. The disease or condition may be selected from breast cancer, prostate cancer, colon cancer, lung cancer, brain cancer, skin cancer, gastrointestinal cancers, biliary tract cancer, testicular cancer, blood-derived cancer, an autoimmune disorder, pancreatic cancer, an oral cancer, a cervical cancer, a uterine cancer, and an ovarian cancer. At least one step of the method may be performed within a surgical suite, operating room, procedure room, or examination room.

Disclosed herein are methods of amplifying a target nucleic acid in a sample comprising: obtaining a cellular specimen that contains the target nucleic acid, wherein the obtaining comprises a touch prep method; contacting the target nucleic acid with an oligonucleotide that hybridizes to the target nucleic acid, a plurality of nucleotides and a polymerase.

Further disclosed herein are methods of amplifying a target nucleic acid in a sample comprising: obtaining a cellular specimen that contains the target nucleic acid, wherein the obtaining comprises a brush biopsy; contacting the target nucleic acid with an oligonucleotide that hybridizes to the target nucleic acid, a plurality of nucleotides and a polymerase.

Disclosed herein are methods of amplifying a target nucleic acid, comprising contacting the target nucleic acid with: an oligonucleotide designed to hybridize to the target nucleic acid, wherein the oligonucleotide: comprises a ribonucleotide; and possesses a 3' terminal modification that prevents polymerase-mediated extension of the oligonucleotide when: in the absence of an enzyme activity that removes the 3' terminal modification, and the oligonucleotide is bound to a non-target nucleic acid; and either: a polymerase that has the enzyme activity that removes the 3' terminal modification, or a polymerase and an additional enzyme, wherein the additional enzyme has the enzyme activity that removes the 3' terminal modification. The polymerase may be a DNA polymerase. The DNA polymerase may be a genetically modified/engineered enzyme that can polymerize nucleic acids and extend the oligonucleotide possessing the 3' terminal modification. The DNA polymerase may be Bst2.0. The additional enzyme may be a restriction enzyme. The restriction enzyme may be BsoBI. The restriction enzyme may be an endonuclease. The endonuclease may cleave a single strand of the target nucleic acid, wherein the target nucleic acid is a double stranded nucleic acid. The restriction enzyme may be Nt. Bst NBI. The strand that is not cleaved may comprise a modified nucleic acid. The modified nucleic acid may be dCTPs. The amplifying may comprise a reaction selected from an isothermal amplification, a loop-mediated amplification, a strand displacement reaction a modification thereof, and a combination thereof. The ribonucleotide may be an internal nucleotide of the oligonucleotide. The method may further comprise reverse transcribing an RNA to produce a complementary DNA (cDNA), wherein the cDNA is the target nucleic acid. The amplifying and the reverse transcribing may occur in a single reaction vessel. The amplifying may occur in a first reaction vessel and the reverse transcribing occurs in a second reaction vessel. The method may further comprise detecting an amplicon produced by the amplifying. The detecting may comprise isolating the amplicon based on a property selected from charge, size, and a combination thereof. The detecting may comprise use of a reporter to identify or quantify the amplicon. The reporter may be selected from a fluorescent reporter, a visual reporter, an electrochemical reporter, a luminescent reporter, a colorometric reporter, turbidity, a fluorescent hybridization-based detector, and an electrochemical hybridization-based detector. The fluorescent reporter may be selected form an intercalating dye, SYTO-9, and SYBR. The electrochemical reporter may be methylene blue. The reporter may comprise a molecule attached to a solid phase where the amplicon can interact with the reporter. The reporter may generate a signal directly, directs a signal to be transmitted or generated, or interferes with the generation, detection, or transmission of a signal. The method may comprise amplifying a plurality of target nucleic acids to produce a plurality of amplicons. The detecting may comprise use of a first reporter to identify a first amplicon and a second reporter to identify a second amplicon, wherein the first reporter and the second reporter are different. The amplifying and detecting may occur in a single reaction vessel.

INCORPORATION BY REFERENCE

All publications, patents, and patent applications mentioned in this specification are herein incorporated by reference to the same extent as if each individual publication, patent, or patent application was specifically and individually indicated to be incorporated by reference in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 20A shows expression of COL10A1, MMP11, and IBSP for 995 RNA Seq samples. Gene expression is presented as cumulative frequency plots.

FIG. 20B shows expression of COL10A1, MMP11, and IBSP for 110 microarray samples. Gene expression is presented as cumulative frequency plots. Comparison of RNA Seq (FIG. 20A) and microarray results show that these results are not platform specific.

FIG. 20C shows the advantage of combining multiple analytes. These density maps show a combination of COL10A1 with either MMP11 or IBSP for 995 110 custom gene expression microarray samples.

FIG. 20D shows density maps for a combination of COL10A1 with either MMP11 or IBSP for 995 RNA Seq samples. Again, comparison to RNA Seq (FIG. 20D) and microarray (FIG. 20C) shows that results are not platform specific.

FIG. 24 depicts a variable importance plot that shows the relative contribution of individual genes when evaluated using a Random Forest model. Each gray dot represents one randomized model. The solid black dot represents the mean for each gene across all randomized models.

DETAILED DESCRIPTION OF THE INVENTION

Figure 1A:
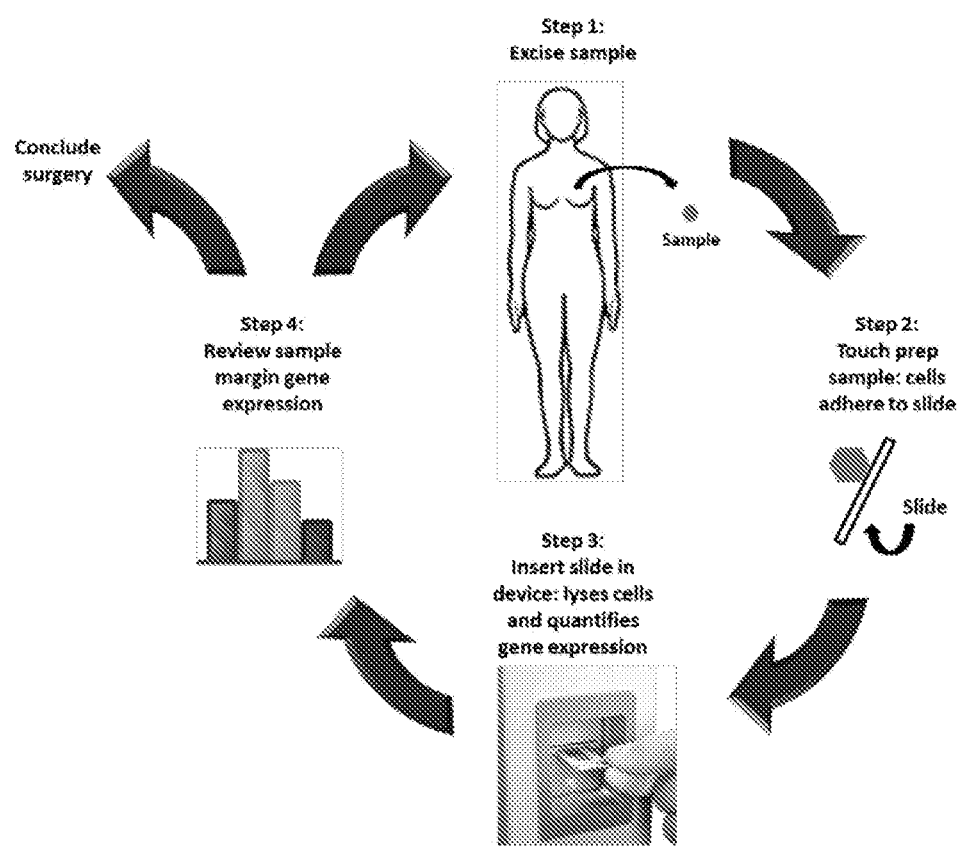
FIG. 1A shows steps of a single surgical procedure using an integrated intraoperative device.

Disclosed herein are kits, methods and devices for obtaining and analyzing gene expression from cells on the surface of surgical specimens for postoperative test and/or intraoperative test. As shown in FIG. 1A, a sample, such as a breast tumor, is removed from a patient in a surgical procedure. A poly-lysine coated slide is pressed to the surfaces of the sample, leaving cells from the surfaces of the sample on the slide. The slide is inserted into a device that lyses the cells and rapidly scores the expression levels of select genes in the sample. The device operates a disease-specific classifier, (e.g. a breast cancer disease classifier (BCDC)), that interprets the expression levels together as the absence, presence or risk of a disease or condition in the cells from the sample surface. For example, high or low expression levels of these genes, relative to expression levels of these genes in normal/healthy cells, indicate cells on the surface of the sample are affected by the disease or condition. If such gene expression is detected, additional tissue from the surgical site can be immediately removed and similarly tested until there are no longer cells on the surface that are determined to be affected by the disease or condition. In contrast, a lack in difference of expression levels between the cellular specimen and healthy/normal cells would generate a score directing the surgeon to conclude the surgical procedure. Thus, all unwanted cells may be removed in a single surgery, while preserving surrounding healthy tissue.

Figure 25:
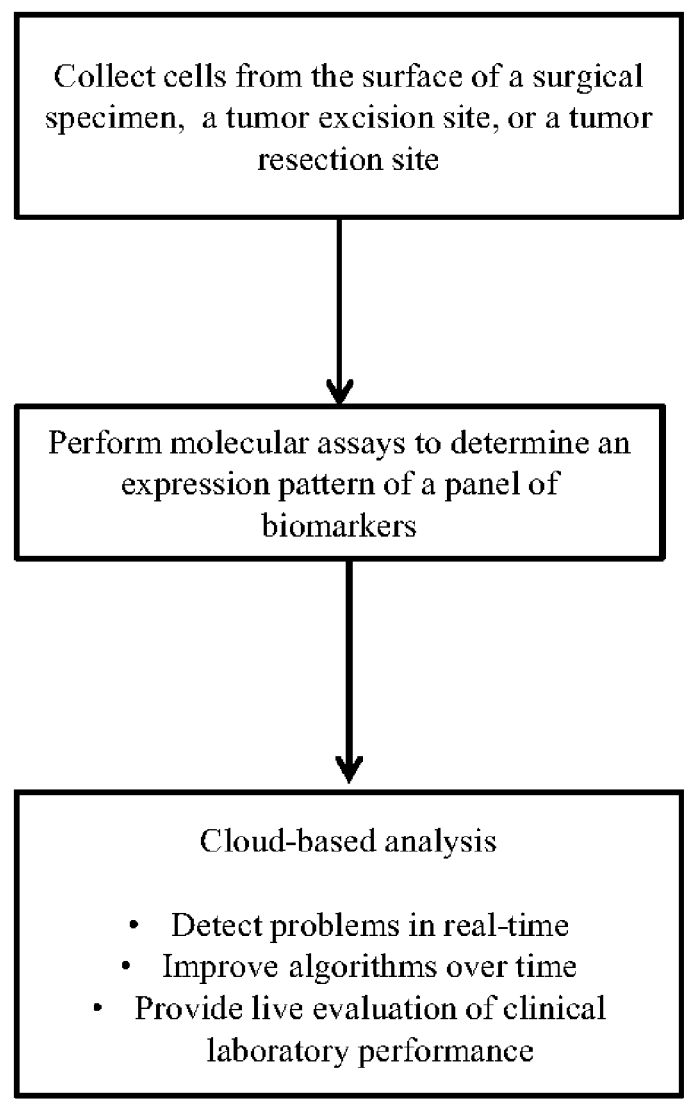
FIG. 25 shows a flow chart for a cloud-based analysis of a biological sample.

There are several advantages of the disclosed kits, methods and devices. First, determining whether a surgical procedure successfully removed the entire tumor is a critical question in the treatment of early-stage solid cancers. Yet some studies have found that the current gold-standard technique only detects half of positive surgical margins (PSM). Such low sensitivity of detection leaves untreated residual tumor and places patients at high risk of recurrence and disease-specific mortality. The disclosed provides kits, methods and devices that detect a panel of genes that distinguishes rare malignant tumor cells, e.g., invasive carcinoma, from adjacent healthy tissue with high sensitivity and accuracy. The disclosed kits, methods and devices may detect at least 20%, 30%, 40%, 50%, 60%, 70%, 80%, 90%, 95%, 99%, 99.9%, or more of the surface of surgical specimen. The disclosed kits, methods and devices may detect at least 20%, 30%, 40%, 50%, 60%, 70%, 80%, 90%, 95%, 99%, 99.9%, or more PSM. The disclosed kits, methods and devices may provide at least 20%, 30%, 40%, 50%, 60%, 70%, 80%, 90%, 95%, 99%, 99.9%, or more sensitivity of detection. The disclosed kits, methods and devices may provide at least 20%, 30%, 40%, 50%, 60%, 70%, 80%, 90%, 95%, 99%, 99.9%, or more accuracy of detection. The disclosed systems, kits, methods and devices may be used to provide cloud-based analysis of a biological sample. The data may be used for detecting problems in real-time, improving algorithms for detecting, diagnosis, predicting, prognosis of a cancer in a subject, and/or for evaluating real-time laboratory performance (FIG. 25). The disclosed systems, kits, methods and devices may detect positive margin and may be used as a research tool. For example, many clinical trials use recurrence as an endpoint. Positive margins are the greatest risk factor for recurrence, but current technologies (e.g. histopathology) do not detect positive margins in many patients. Undetected positive margins are arguably the strongest confounding variable for clinical trials that use recurrence as an endpoint, but current methods are not adequate to account for this confounding variable. Multiple large trials therefore appear to have failed their statistical milestones, when accounting for positive margins as a confounding variable would have identified high-risk patients and resulted in statistically significant decreases in recurrence. When used as a research tool, the disclosed positive margin test would direct a clinical trialist to include or exclude patients based on margin status. The test result may direct a clinical trialist to stratify patients into risk groups (e.g. high-risk, low-risk) based on margin status. The disclosed systems, kits, methods and devices may combine expression-based disease classifier with a method that comprehensively analyzes the entire surface of a surgical excision. Accurate, comprehensive margin analysis may reduce recurrence by detecting tumor cells, residual tumor cells and/or cancer remission at a treatable stage. The disclosed systems, kits, methods and devices may prevent at least 1, 2, 3, 4, 6, 7, 8, 9, 10 or more recurrences by detecting residual disease at a treatable stage. In some embodiments, the disclosed kits, methods and devices prevent at least 1 disease recurrence, e.g., a cancer recurrence or relapse. The disclosed systems, kits, methods and devices may detect the presence of a tumor cell and/or a positive surgical margin, thereby providing information about the likelihood of a cancer remission or relapse in a subject within 5 years of a surgical procedure. Absence of the tumor cell and/or positive surgical margin may indicate a reduction of a risk of a cancer remission or relapse in a subject within 5 years of a surgical procedure by at least 20%, 30%, 40%, 50%, 60%, 70%, 80%, 90%, 95%, 99%, 99.9%, or more. Absence of the tumor cell and/or positive surgical margin may indicate the subject has at least 20%, 30%, 40%, 50%, 60%, 70%, 80%, 90%, 95%, 99%, 99.9%, or more likelihood of being cancer free and/or cancer remission free. In some cases, the subject has been diagnosed with a cancer. In some cases, the subject has undergone a surgical procedure to remove a tumor and/or cancer cells. The disclosed systems, kits, methods and devices may provide information for determining success of a surgical procedure for removing a tumor from a subject. The disclosed systems, kits, methods and devices may involve analyzing a pattern of expression of at least one biomarker associated with a cancer. Absence of the biomarker indicates complete removal of a tumor. The pattern expression of at least one biomarker may comprise a combination of at least 2, 3, 4, 5, 6, 7, 8, 9, 10, 20, 30, 40, 50, 60, 70, 80, 90, 100, 120, 140, 160, 180, 200, or more biomarkers disclosed herein. The pattern expression of a combination of biomarkers may comprise a combination of at most 2, 3, 4, 5, 6, 7, 8, 9, 10, 20, 30, 40, 50, 60, 70, 80, 90, 100, 120, 140, 160, 180, 200 biomarkers disclosed herein. The pattern expression of a combination of biomarkers may comprise a combination of at least 3 biomarkers disclosed herein. The pattern expression of a combination of biomarkers may comprise a combination of at least 4 biomarkers disclosed herein.

The disclosed systems, kits, methods and devices may be used to evaluate successful removal of tumor from a subject. The systems, kits, methods and devices provide for detecting positive surgical margin on the surface of a surgical specimen. For example, a presence of positive surgical margin in the surgical specimen indicates incomplete removal of tumor cells from the subject. In another example, an absence of positive surgical margin in the surgical specimen indicates complete removal of tumor cells from the subject. The systems, kits, methods and devices may test at least 5%, 10%, 20%, 30%, 40%, 50%, 60% 70%, 80%, 90%, 95%, 99%, 100% of the surface of the surgical specimen. The surgical specimen may be fixed. The surgical specimen may be unfixed. The surgical specimen may be shipped to a laboratory for analysis, e.g., detection of positive surgical margin using systems, kits, methods, and devices disclosed herein. The surgical specimen may be preserved and/or stored in a reagent for a period of time before analysis using systems, kits, methods, and devices disclosed herein. The surgical specimen may be preserved and/or stored for at least 1 hour, 2 hours, 3 hours, 4 hours, 5 hours, 6 hours, 7 hours, 8 hours, 9 hours, 10 hours, 11 hours, 12 hours, 24 hours or more before analysis systems, kits, methods, and devices disclosed herein. The surgical specimen may be preserved and/or stored for at least 1 day, 2 days, 3 days, 4 days, 5 days, 6 days, 7 days, 8 days, 9 days, 10 days, 11 days, 12 days, 15 days, 24 days, 30 days, or more before analysis systems, kits, methods, and devices disclosed herein. The surgical specimen may be preserved and/or stored for at least 1 month, 2 months, 3 months, 4 months, 5 months, 6 months, 7 months, 8 months, 9 months, 10 months, 11 months, 12 months or more before analysis systems, kits, methods, and devices disclosed herein. The surgical specimen may be preserved and/or stored for at least 1 year, 2 years, 3 years, 4 years, 5 years, 6 years, 7 years, 8 years, 9 years, 10 years, or more before analysis systems, kits, methods, and devices disclosed herein.

The disclosed systems, kits, methods and devices may be used to evaluate successful removal of tumor from a subject. The systems, kits, methods and devices provide for detecting cancer and/or the presence of invasive carcinoma cells in a biological sample collected from a subject. The biological sample may be an aspirate fluid from a breast of a subject. The subject may be a human. The subject may be a female. The subject may be a male. The subject may be a pet. The subject may be a laboratory and/or clinical study model organism. The subject may be a dog, a cat, a pig, a cow, a rat, a mouse, a hamster, a guinea pig, a monkey, or a chimpanzee. Detection of a tumor cell in the biological sample may indicate the presence of a cancer. For example, the presence of a tumor cell in the biological sample may indicate a cancer remission in the subject. The absence of a tumor cell in the biological sample may indicate an absence cancer remission in the subject. The biological sample may be shipped to a laboratory for analysis, e.g., detection of tumor cells using systems, kits, methods, and devices disclosed herein. The biological sample may be preserved and/or stored in a reagent for a period of time before analysis using systems, kits, methods, and devices disclosed herein. The biological sample may be preserved and/or stored for at least 1 hour, 2 hours, 3 hours, 4 hours, 5 hours, 6 hours, 7 hours, 8 hours, 9 hours, 10 hours, 11 hours, 12 hours, 24 hours or more before analysis systems, kits, methods, and devices disclosed herein. The biological sample may be preserved and/or stored for at least 1 day, 2 days, 3 days, 4 days, 5 days, 6 days, 7 days, 8 days, 9 days, 10 days, 11 days, 12 days, 15 days, 24 days, 30 days, or more before analysis systems, kits, methods, and devices disclosed herein. The biological sample may be preserved and/or stored for at least 1 month, 2 months, 3 months, 4 months, 5 months, 6 months, 7 months, 8 months, 9 months, 10 months, 11 months, 12 months or more before analysis systems, kits, methods, and devices disclosed herein. The biological sample may be preserved and/or stored for at least 1 year, 2 years, 3 years, 4 years, 5 years, 6 years, 7 years, 8 years, 9 years, 10 years, or more before analysis systems, kits, methods, and devices disclosed herein. The biological sample may comprise nipple aspirate fluid. The biological sample may comprise ductal lavage aspirates. The biological sample may comprise a tumor or a partial thereof. The biological sample may be collected by needle aspiration. The biological sample may be collected by core biopsy. The biological sample may be collected by incisional biopsy.

The disclosed systems, kits, methods and devices may be used to evaluate treatment response in a subject. Evaluating treatment response is a major challenge for clinical trials. There is a desert need for surrogate endpoints other than recurrence or death so that patients can be enrolled at early, more treatable stages; and so that large, expensive trials will not need to last for years. Pathologic Complete Resonse (pCR) is one popular, although flawed, surrogate endpoint. The FDA has emphasized the limitations of pCR while also acknowledging the need for surrogate endpoints. pCR suffers from many of the same challenges that plague margin analysis: it is difficult to detect small tumors using microscopy because only a few microscopic sections are used to represent a substantial tissue mass. Results are therefore often inaccurate and highly variable.

The systems, methods, and markers described herein provide a much-needed solution. The tissue specimen, or a portion thereof, is analyzed to detect the patterns of disclosed biomarkers that characterize a solid tumor (e.g. breast cancer). The biomarkers can be detected from a microscopic section of the tissue (e.g. a slide, or an imprint of a section through the interior of the tissue) or from a portion of the tissue specimen, or from the entire specimen. The signals are analyzed using machine learning methods to generate a classification or score. The classification can be tumor or healthy. The score can indicate relative tumor abundance. The analysis can be performed at the time of diagnosis (e.g. on a core biopsy, a needle biopsy, or an incisional biopsy). The analysis can be performed after a course of treatment. The comparison of analyses can be used to determine or quantify response to the treatment, e.g. a cancer treatment, chemotherapy, radiotherapy, antibody treatment, cancer vaccination.

The disclosed systems, kits, methods and devices may provide instructions and/or recommendations to a health care professional, e.g., a physician, a nurse, a surgeon, to perform a surgical procedure on a subject. In some cases, the instructions may direct a physician or a surgeon to perform addition surgical procedure on a subject. The disclosed systems, kits, methods and devices may provide instructions and/or recommendations to a health care professional, e.g., a physician, a nurse, a surgeon, to prescribe one or more therapy to a subject. Exemplary therapies include, but are not limited to, chemotherapy, radiotherapy, antibody therapy, trastuzumab (Herceptin®), endocrine therapy, or combinations thereof. A variety of antibodies may be used to treat a cancer. The antibodies may be naked monoclonal antibodies, conjugated monoclonal antibodies, bispecific monoclonal antibodies, radiolabeled monoclonal antibodies, chemolabeled monoclonal antibodies. Exemplary monoclonal antibodies for use of treating a cancer include, but are not limited to, alemtuzumab (Campath®), trastuzumab (Herceptin®), ibritumomab tiuxetan (Zevalin®), brentuximab vedotin (Adcetris®), ado-trastuzumab emtansine (Kadcyla® or TDM-1), denileukin diftitox (Ontak®), blinatumomab (Blincyto), Bevacizumab (Avastin®), and Cetuximab (Erbitux®).

The disclosed systems, kits, methods and devices may be used to determine a presence or absence of a tumor cell in a surgical specimen, a biopsy, an aspirate fluid, or ductal aspirate lavage. The systems, kits, methods and devices provide high resolution of rare malignant cells in a high background. Unlike contemporary methods for detecting tumor cells in a biological sample, e.g., a surgical specimen, where at least, 50%, 60%, 70%, 80%, 90%, 95%, or 99% of cells are tumor cells (Table 21), the disclosed systems, kits, methods and devices may detect rare malignant cells in a population of healthy cells in a biological sample. The malignant cells may be less than 1%, 2%, 3%, 4%, 5%, 6%, 7%, 8%, 9%, 10%, 15%, 20%, 30%, 40%, 50%, 60%, 70%, 80%, 90%, 95%, or 99% of the population of the biological sample. The malignant cells may be at most 1%, 2%, 3%, 4%, 5%, 6%, 7%, 8%, 9%, 10%, 15%, 20%, 30%, 40%, 50%, 60%, 70%, 80%, 90%, 95%, or 99% of the population of the biological sample. In addition to predicting the likelihood of a cancer or a cancer remission in a subject as are contemporary methods, the disclosed systems, kits, methods and devices determine a presence or an absence of a cancer or a cancer remission in a subject.

TABLE 21

Gene expression signatures used for breast cancer diagnosis and prognosis testing

| Signature | Test Type | Test Patient Cohort | Predictive Value | Target Gene List | Reference Gene List |
| --- | --- | --- | --- | --- | --- |
| oncotypeDX | qRT-PCR | Stage I or II ER + LN negative | Recurrence risk chance of metastasis | K167, STK15, Survivin, CCNB1, MYBL2, GSTM1, CD68, ER, PR, BCL2, SCUBE2, MMP11, CTSL2, ERBB2, GRB7 | ACTB, GAPDH, RPLP0, GUS, TFRC, BAG1, |
| Mammaprint | microarray | Stage I or II ER + LN negative LN positive (size <5 cm) some HER2+ | 10-year metastasis-free survival rate | BBC3, EGLN1, ESM1, GFBP5, FGF18, SCUBE2, TGFB3, WISP1, FLT1, STK32B, RASSF7, DCK, MELK, EXT1, GNAZ, EBF4, QSCN6L1, CCNE2, ECT2, CENPA, LIN9, KNTC2, MCM6, NUSAP1, ORC6L, TSPYL5, RUNDC1, PRC1, RFC4, RECQL5, CDCA7, DTL, COL4A2, GPR180, GPR126, RTN4RL1, DIAPH3, CDC42BPA, PALM2, ALDH4A1, AYTL2, OXCT1, PECI, GMPS, GSTM3, SLC2A3, FLT, FGF18, COL4A2, GPR180, EGLN1, MMP9, LOC100288906, C9arf30, ZNF533, C16arf61, SERF1A, C2Darf46, LOC730018, LOC100131053, AA555029_RC, LGP2, NMU, JHDM1D, AP2B1, MS4A7, RAB6B | MTDH, PITRM1, UCHL5 |

TABLE 21-continued

Gene expression signatures used for breast cancer diagnosis and prognosis testing

| Signature | Test Type | Test Patient Cohort | Predictive Value | Target Gene List | Reference Gene List |
|---|---|---|---|---|---|
| 97-gene genomic grade index (MapQuant DX) | microarray | Grade I, II and III ER+ | Histologic behavior Relapse-free survival Risk of recurrence | LAMB2, FLJ23554, SESN1, FLJ20477, CDCA3, TIMELESS, TPX2, OIP5, CENPA, BBS1, KPNA2, KIF11, HMGB3, CCNB2, CCNE2, KIF20A, DDX39, EXO1, KNTC2, RNASEH2A, SPAG5, POLQ, GTSE1, ON5ON, FLJ0641, CDCA8, RACGAP1, UBE2S, ESPL1, KIF4A, ASPM, DKFZp762E1312, NUSAP1, MCM10, C20arf24, FLJ10156, DC13, KNSL7, HSMPP8, RRM2, BUB1B, ZWINT, TTC10, CYBRD1, PCR1, C10arf3, 13CDNA73, STARD13, FLJ21062, FLJ21827, CX3CR1, CDC25A, BLM, TTK, MYBL2, MELK, CDK2, FOXM1, CCNB1, STK6, BM039, BRRN1, PLK1, CDC2, TRIP13, HMMR, AURKB, MCM4, BUB1, MCM2, MLF1IP, CENPF, SLC7A5, BIRC5, TROAP, CDC20, MAD2L1, NUDT1, GMPS, KIF2C, SHMT2, CENPE, DLG7, MKI67, CDKN3, CCNA2, LMNB1 | SIRT3, H2AFZ, ORMDL2, CCT5, UBE2N, MARS, FEN1 |
| 8-gene recurrence score | qRT-PCR | Stage I or II ERE+/PR+ | Metastasis-free survival Risk of recurrence | DTL, ECT2, PRC1, RFC4, SCUBE2, STK32B, ZNF533 | MTDH |
| 14-gene distant metastasis signature | Microarray verified (qRT-PCR based) | TNBC | Chance of relapse metastasis-free survival | RGS4, CXCL13, HAPLN1, HRBL, MATN1, PRTN3, SSX3, PRS28, ABO, CLIC5, RFXDC2, PRRG3 | EXOC7, ZNF3 |
| 158-gene signature | microarray | HER2+, ER+/−, any stage or grade | Disease-free survival Benefit from anit-HER2 therapies | LTBP1, SPTBN2, GPR172A, ZNF609, LOC116143, ELMO3, PXDN, CASP6, PGM2L1, INHBA, IRF6, GRHL1, KPNA3, LPGAT1, MGC40579, SH3YL1, COL8A1, S100A11, ZNF690, CD55, COMP, SLK, KIAA1549, DCBLD1, PLAU, AFTIPHILIN, GRB7, DDEF2, LAD1, PKP3, CXCR4, PERLD1, TSPAN7, S100B, ANPEP, | ST3GAL2, ST6GALNAC6, KLF9, C11ORF57, PPP5C, CLCN7, RBM5, ARIH2, HSPBP1, GLRX2, C7ORF25, NUDT9, SENP5, PEX11B, MED19, ZNF281, C12ORF29 |

TABLE 21-continued

Gene expression signatures used for breast cancer diagnosis and prognosis testing

| Signature | Test Type | Test Patient Cohort | Predictive Value | Target Gene List | Reference Gene List |
|---|---|---|---|---|---|
| | | | | GPC3, SOX10, EDNRB, SH3KBP1, STON2, RBP4, C6ORF188, PDE2A, STAT5A, RNF166, MFAP, STXBP1, SOCS1, ATP8B2, TIGAL, LORND1, TGFBR3, MAP7D3, CYORF15B, GPX3, ALAS2, PLAC8, CLSTN3, HEMGN, NLGN2, HMHA1, CRMP1, FYN, ZAP70, FLNC, AXIN2, FGF2, LAT, NDN, ARHGAP19, RASIP1, TF, ATOH8, MAP4, C6ORF190, SH3BP5, SNCA, RAC2, SLC38A5, PIM1, KIRREL, TMEFF1, CX3XR1, SDPR, MLXIPL, C17ORF68, SFRS5, MTHFR, AFP, DKFZP686E10196, DRCTNNB1A, IL17RD, PPP1R14A, EPB41, SNF1LK2, ITGA4, 8MAR, PRKCA, KIAA1754L, OSBPL3, PLXNA4B, SLC25A42, BIN3, EDG5, STARD4, HHIP, CD3D, LC16A7, ETS1, LTBP4, C14ORF49, CD69, PELI2, CDON, FAIM3, FRT1, ABCD4, SEMA6A, CLF2, ADD3, FAM46A, DMN, WDHD1, ZNF276, FAM89A, PTPRCAP, LOC133308, UBE2G1, BMP4, TM2A, KIAA1826, PRSS12, SEMA7A, TLE4, GAS7, GYPC, GLTSCR1, LOC90624, TCF7, DPYSL2, COLEC12 | |
| PAM50 (Nanostring/Prosigna) | microarray and qRT-PCR | All breast cancer patients | Intrinsic subtyping Benefit of neoadjuvant therapy Overall survival | FOXC1, MIA, KNTC2, CEP55, ANLN, MELK, GPR160, TMEM45B, ESR1, FOXA1, ERBB2, GRB7, GFR4, BLVRA, CDC20, CCNE1, ACTR3B, SFRP1, KRT14, KRT17, KRT5, MLPH, CCNB1, CDC6, TYMS, UBE2T, RRM2, MMP11, ORC6L, MDM2, KIF2C, PGR, MKI67, BCL2, EGFR, PHGDH, | BAG1, MYC, CXXC5 |

TABLE 21-continued

Gene expression signatures used for breast cancer diagnosis and prognosis testing

| Signature | Test Type | Test Patient Cohort | Predictive Value | Target Gene List | Reference Gene List |
|---|---|---|---|---|---|
| | | | | CDH3, NAT1, SLC39A6, MAPT, UBE2C, PTTG1, EXO1, CENPF, CDCA1, MYBL2, BIRC5 | |

The disclosed systems, kits, methods and devices may be used to generate data for prognosis, diagnosis, treat, and/or prevent cancers. Breast cancer, for example, is one of the most prevalent cancer and most common cause of cancer deaths in women. According to the WHO, breast cancer incidence rose 20% between 2008 and 2012, with 1.7M global diagnoses in 2012. Breast cancer is generally incurable in the metastatic setting. Once metastatic disease is detected, the median survival is typically about 18-24 months. With technologies, women are diagnosed at early, potentially curative stages. Despite decades of advances in adjuvant therapies, local control remains the determinant of clinical outcomes for breast cancer.

In general, local control of solid tumors generally involves surgical excision of the entire tumor. Breast conservation therapy (BCT) is a combination of breast conservation surgery (BCS) plus radiotherapy and appropriate adjuvant or neoadjvant medical therapy (e.g. chemotherapy, endocrine therapy, and targeted molecular therapy). BCT and mastectomy have equivalent survival, and over the past decade BCS has replaced mastectomy as the surgical treatment of choice for women with early-stage breast cancer. Generally, BCS excises the entire tumor, bounded by a thin margin of healthy tissue. Surgical specimens are examined grossly and by histopathology to ensure the procedure achieved local control.

Positive Surgical Margins (PSM) refer to malignant cells along the cut surface of a surgical specimen. PSM indicate minimal residual disease (MRD): topologically, slicing through a tumor mass results in malignant cells on the surface of the excised specimen. MRD is usually unacceptable for any malignancy, solid or liquid. Typically, BCS removes the entire tumor bounded by a thin margin of healthy tissue, in which case no malignant cells would be detected on the surface of the excised specimen.

Figure 22:
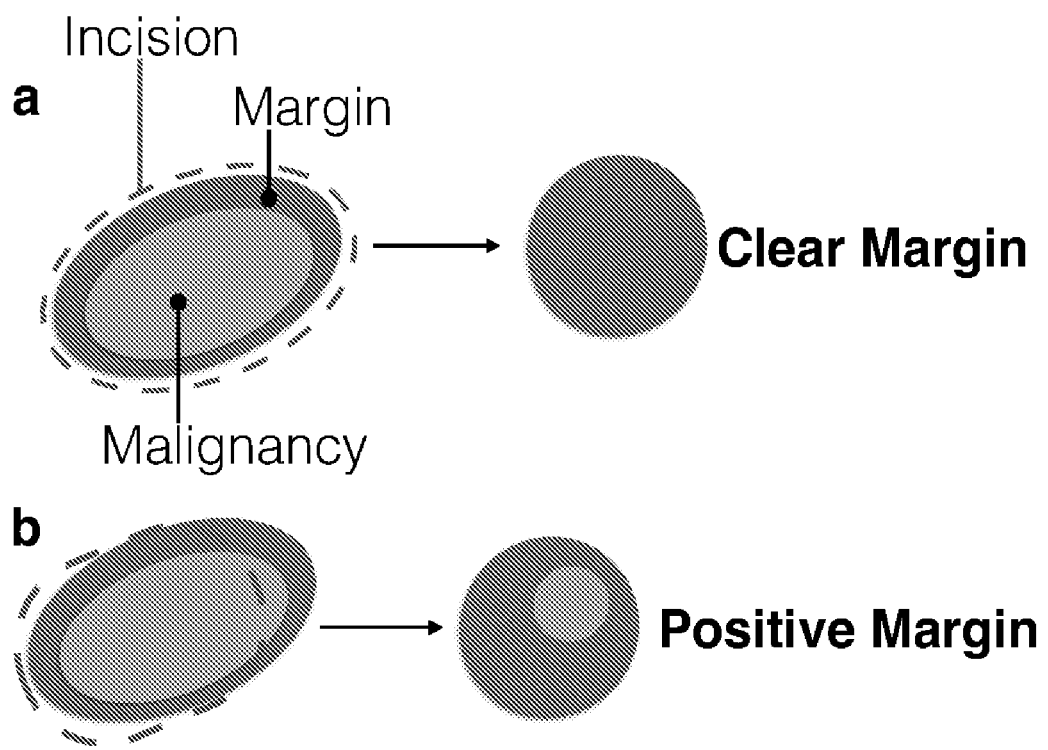
FIGS. 22A-22B depict criteria for determining a surface of the surgical specimen for collecting potential positive margin cells.

Like most surgical oncology, the goal of breast conservation surgery is to remove the entire tumor, bounded by a thin margin of healthy tissue. The surface of the specimen therefore does not contain malignant cells. In many cases, surgeons cannot see or feel the tumor, and slicing through part of the tumor is a common mistake. In these cases, the surface of the excised specimen contains malignant cells (FIGS. 22A-22B). The surface of an excised specimen is topologically equivalent to the wall of the incision. Patients with malignant cells on the surface of the surgical specimen therefore have residual tumor in their body. A high-resolution molecular test that detects malignant cells on the surface of the specimen will improve the ability to detect malignant cells on surgical margins. In addition, since microscopy currently only examines a small fraction of the surface (<<1%), tests that increase the amount of the sampled surface will improve the ability to detect malignant cells on surgical margins. The disclosed inventions provide both high-resolution molecular assays and methods to increase the amount of surface area examined on a surgical specimen For solid tumors like breast cancer, PSM convey a high risk of recurrence and death among patients eligible for breast conservation therapy (BCT). Obtaining clear margins has long been a challenge of surgical oncology. Clear margins remain the standard of care, and have been codified in consensus statements (Society for Surgical Oncology and American Society for Radiation Oncology. See, Moran et al. Society of Surgical Oncology—American Society for Radiation Oncology Consensus Guideline on Margins for Breast-Conserving Surgery With Whole-Breast Irradiation in Stages I and II Invasive Breast Cancer. Journal of Clinical Oncology. (2014) May; 32(14)1507-1515); and clinical guidelines (American Society of Clinical Oncology) and the National Comprehensive Cancer Network. See, National Comprehensive Cancer Network (NCCN). NCCN Clinical Practice Guidelines in Oncology (NCCN Guidelines). Invasive Breast Cancer: Margin Status in infiltrating carcinoma. Version 1.2012. 2012; BINV-F. Available [with login] at: http://www.nccn.org/professionals/physician_gls/pdf/breast.pdf PSM have a higher risk for death than other variable among women eligible for BCT. Despite the research attention devoted to other variables (e.g. positive lymph nodes, intrinsic molecular subtypes), PSM confers the greatest risk of death.

Histopathology is the current gold-standard method to detect positive surgical margins. Histopathology examines a lesion in the context of its surrounding tissue. Histology typically examines a mass in situ (e.g., in the context of surrounding tissue), however detecting malignant cells along the margin of a surgical specimen may introduce inaccuracy of margin analysis.

A recent retrospective analysis at Harvard's Brigham and Women's Hospital reported that histology (when used to evaluate margins) has a 50.9% sensitivity, 69.5% specificity, 35% positive predictive value, and an 81.4% negative predictive value. In other words, microscopy only detects 50.9% of the margins that actually had tumor and among the margins that microscopy detected as malignant, only 35% actually had tumor along the margin. See, Tang et al., Lumpectomy specimen margins are not reliable in predicting residual disease in breast conserving surgery. *The American Journal of Surgery*. (2015), 210:93-98. The overall accuracy was 64.9%, only 50.9% of residual tumors are detected by histopathology but the false negative rate (FNR) is about 49.1%. By contrast, the present disclosure provides systems, kits and methods for detecting positive margin on the surface of an excision from a tumor with high resolution of malignant cells in a high background biological specimen, where majority of the cells are healthy non-tumor cells. The systems, kits and methods provided herein has a may detect positive margin with a sensitivity of at least 50%, 60%, 70%, 80% 90%, 95%, 99%, or higher. The systems, kits and methods may detect positive margin with a specificity of at least 50%, 60%, 70%, 80% 90%, 95%, 99%, or higher. The systems, kits and methods may detect positive margin with a accuracy of at least 50%, 60%, 70%, 80% 90%, 95%, 99%, or higher. In some cases, the systems, kits and methods provided herein has a may detect positive margin with a sensitivity of about 99.8%. In some cases, the systems, kits and methods provided herein has a may detect positive margin with a specificity of about 97.8%. In some cases, the systems, kits and methods provided herein has a may detect positive margin with an accuracy of about 98.9%.

Without being bound to any theory, high incidence of FNR of histology may be associated with technical and statistical limitations. In general practice, a positive margin may be defined as malignant cells touching the cut edge of a specimen. However, this is limited by the technical challenges of sectioning adipose specimens and interpreting margins. Several factors may be considered, for example, the probability that the aberrant cell along the edge is actually malignant, the probability of a fold in the section, difficulty in determining the edge of mounted section, or technical errors during sample preparation. As such, statistical analysis provides more accurate analytical results.

A critical procedure is to detect malignant cells along the margin; however, analyzing a perfect sphere with a 2 cm height may require at least 3,000 serial microscopic sections (e.g., 0.6 micrometers thick) to cover the surface of the entire specimen. Most laboratories analyze 2-6 sections. By estimation, current practice determines whether there are malignant cells on the surface of a specimen after sampling 0.067% of the surface. In this example, pathologists would have to increase their per-case workload by about 1,500% to solve this problem using existing technology. Since additional sections often need to be analyzed for hormonal receptor and Her2/ERBB2 status, existing technology fails to comprehensively sample the entire surface. While some laboratories have attempted to section the edge of the specimen, borders are irregular and often challenging to section without distorting the boundary. Histopathology is a statistical sampling technique that is often underpowered to reliably detect positive margins. Accordingly, there is a need to improve the sensitivity and accuracy of detecting positive margins. Improving detection of PSM may reduce recurrence, improve survival, and reduce overtreatment.

Patients with histologic positive margins after lumpectomy may have increased ipsilateral breast tumor recurrence compared to patients with negative margins. Numerous examples have shown that PSM increases the risk of recurrence. In one study, Meric, et al. examined 1,043 consecutive women with Stage I or II breast carcinoma who underwent breast conservation therapy between 1970 and 1994, and found that positive surgical margins increase the risk of recurrence. See, Meric et al., Positive surgical margins and ipsilateral breast tumor recurrence predict disease-specific survival after breast-conserving therapy. Cancer. (2003) Feb. 15; 97(4):926-33. PMID: 12569592. This study reveals that positive surgical margins decrease the risk of disease-specific survival. In this cohort, the 10-year risk of death from breast cancer was 3.9 times higher for patients with PSM, relative to patients with negative margins (95% CI: 1.4-11.5, p=0.011). Among variables present at diagnosis, PSM has high prediction of disease-specific death. Tumor recurrence in the ipsilateral breast (IBTR) was one variable with a higher relative risk of death than PSM (RR 5.5, 95% CI: 2.8-11.0, p=0.001). Other findings have reported consistent results, for example, Voogd et al. reported a 10-year actuarial risk of systemic recurrence of 60% for patients with positive margins after breast conservation surgery, compared with 29% for those with negative margins. See, Voogd et al., Danish Breast Cancer Cooperative Group. Breast Cancer Cooperative Group of the European Organization for Research and Treatment of Cancer. Differences in risk factors for local and distant recurrence after breast-conserving therapy or mastectomy for stage I and II breast cancer: pooled results of two large European randomized trials. *J Clin Oncol.* (2001) Mar. 15; 19(6):1688-97. PMID: 11250998. More recently, the Early Breast Cancer Trialists' Collaborative Group (EBCTCG) estimated that an early intervention like ours will save one life for every four recurrences that it prevents. Relative recurrence risk from PSM is expected to be higher today because adjuvant therapies improve recurrence and survival rates among patients with negative margins, but the increased recurrence risk of PSM are not addressed by increased radiation or medical therapies.

Attempts to quantify the impact of PSM using histology may underestimate relative risk. Assuming the technology is used to detect negative margins has a 49.1% FNR, a proportion of recurrences in the negative margin cohort may be attributable to undetected positive margins (e.g., false negatives). Positive margins may include malignant cells some distance from the cut edge of a specimen. Typically, subsurface 'positive' margins do not increase the risk of recurrence; and are often inappropriately classified as positive margins (false positives). Both errors underestimate relative risk: the negative margin cohort included false negatives, and the positive margin cohort contained false positives. As such, improved PSM detection will identify patients who would benefit from enhanced surgical excision. Since PSM convey a high risk of recurrence and death for breast conservation therapy patients, improved detection is one of the most promising strategies to improve clinical outcomes.

The disclosed kits, methods and devices, also referred to as ClearMargin™ test, may help standardize the detection and interpretation of PSM, and may reduce overtreatment. While there is a straightforward link between increased accuracy and improvements in recurrence and survival, the clinical benefit of technical standardization may be less obvious. Inconsistencies in the evaluation of PSM by pathologists, and the way surgeons interpret those calls, currently leads to highly variable reexcision rates. For example, some surgeons reoperate on 70% of patients with negative margins. In another example, other surgeons reoperate on 0% of patients with negative margins (p=0.003). Reexcision rates for negative margins also may vary widely between institutions (range: 1.7%-20.9%; p=0.001). See, McCahill et al. Variability in Reexcision Following Breast Conservation Surgery. *JAMAA*. (2012) Feb. 1; 307(5):467-75. PMID: 22298678. The dramatic variations in practice patterns reflect clinical uncertainty.

There are numerous factors contribute to clinical uncertainty. First, stopathology is a flawed technique to detect PSM. Further, histopathology is user-dependent, and subject to interpretation and bias. With the current high recurrence rate and statistically under-sampled histology, surgeons face potential malpractice liability if they fail to reoperate on PSM. Variation in clinical practice is a major problem, and one that can be addressed with technology. A more accurate test will reduce recurrence and improve survival, while standardized technology will improve overtreatment. The disclosed kits, methods and devices may provide help to standardize the interpretation of PSM, in accordance with clinical guidelines and evidence-based medicine. Standardization will spare women from undergoing unnecessary follow-up surgeries, thereby decreasing overtreatment.

For instance, the device lyses the cells and measures the expression levels of select genes in a very small time frame. This enables the surgeon to assess the presence of a disease or condition at surgical margins and remove additional tissue as needed from the surgical site during the same surgery in which the initial sample is removed. The ability to accomplish this is based on the novel means for nucleic acid amplification disclosed herein, wherein RNA is reverse transcribed and isothermally amplified to detectable levels within a few minutes. This provides a means for removing all affected tissue within a single surgery, which is especially beneficial when the risks of additional anesthesia or surgeries are confounded by comorbidities. In addition, overall surgical and medical costs are reduced for the patient and healthcare system.

In addition, the methods, kits and devices provide for greater assurance that all affected cells have been removed during a surgery, relative to assurance provided by traditional pathological assessment of surgical samples. Traditionally, the surfaces of excised samples are analyzed visually by pathologists following a surgical procedure, and only a very small percentage of the entire sample surface is analyzed, often resulting in a false conclusion that surgical margins are clear. Knowing this, some surgeons are more aggressive and routinely excise a large region of healthy tissue surrounding an affected area in order to avoid additional surgeries and in an effort to remove all affected tissue. Conversely, some surgeons, loath to disfigure their patients more than necessary, excise the least amount of tissue possible, but more often are required to perform an additional surgery. One study found that randomly assigning patients to receive an additional tissue excision benefited 15% of patients, at the cost of unnecessarily removing additional tissue from all patients (Chagpar, A et al. (2015). A Randomized, Controlled Trial of Cavity Shave Margins in Breast Cancer. New England Journal of Medicine). In the case of the present invention, comprehensive characterization of the sample surface removes the uncertainties surgeons face with regard to the sufficiency of tissue removal. This characterization can be performed both intra-operatively and postoperatively. The methods and devices disclosed herein allow these surgeons to determine when a sufficient amount of tissue has been excised in order to remove an affected area, while preserving unaffected tissue. Thus these methods and devices will save lives, reduce medical costs, and fulfill the promise of personal medicine: identifying the correct treatment for an individual patient.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The systems and methods of the present invention may employ, unless otherwise indicated, conventional techniques of immunology, biochemistry, chemistry, molecular biology, microbiology, cell biology, bioengineering, genomics, recombinant DNA, statistics, bioinformatics, and machine learning, which are within the skill of the art. See, e.g., Sambrook, Fritsch and Maniatis, Molecular Cloning: A laboratory manual, 4th edition (2012); Current Protocols in Molecular Biology (F. M. Ausubel, et al. eds., (1987)); the series Methods in Enzymology (Academic Press, Inc.): PCR 2: A practical approach (M. J. MacPherson, B. D. Hames and G. R. Taylor eds. (1995)), Culture of animal cells: A manual of basic technique and specialized applications, 6th Edition (R. I. Freshney, ed. (2010)); Hastie, Tibshirani, and Friedman (2009), Elements of statistical learning, 2nd edition; Crawley (2005), Statistics: An introduction using R, (John Wiley and Sons, Ltd); Witten, Frank and Hall (2011), Data mining: Practical machine learning tools and techniques 3rd edition (Elsevier), and Kuhn and Johnson (2013), Applied Predictive Modeling (Springer), which are hereby incorporated by reference.

As used in the specification and claims, the singular forms "a", "an" and "the" include plural references unless the context clearly dictates otherwise. For example, the term "a cell" includes a plurality of cells, including mixtures thereof.

The terms "determining", "measuring", "evaluating", "assessing," "assaying," and "analyzing" can be used interchangeably herein to refer to any form of measurement, and include determining if an element is present or not. These terms can include both quantitative and/or qualitative determinations. Assessing may be relative or absolute. "Assessing the presence of" can include determining the amount of something present, as well as determining whether it is present or absent.

As used herein, a "nucleic acid sample" can refer to any substance containing or presumed to contain nucleic acid. The sample can be a biological sample obtained from a subject. The nucleic acids can be RNA, DNA, e.g., genomic DNA, mitochondrial DNA, viral DNA, synthetic DNA, or cDNA reverse transcribed from RNA. The nucleic acid may be extracted from a biological sample, e.g., tissue, cell, biopsy.

As used herein, "amplification" of a nucleic acid sequence generally refers to in vitro techniques for enzymatically increasing the number of copies of a target sequence. Amplification methods include both asymmetric methods (in which the predominant product is single-stranded) and conventional methods (in which the predominant product is double-stranded). A "round" or "cycle" of amplification can refer to a polymerase chain reaction (PCR) cycle in which a double stranded template DNA molecule is denatured into single-stranded templates, forward and reverse primers are hybridized to the single stranded templates to form primer/template duplexes, primers are extended by a DNA polymerase from the primer/template duplexes to form extension products. In subsequent rounds of amplification the extension products are denatured into single stranded templates and the cycle is repeated.

The terms "template", "template strand", "template DNA" and "template nucleic acid" can be used interchangeably herein to refer to a strand of DNA or cDNA that is copied by an amplification cycle.

The term "sequencing", as used herein, can refer to a method by which the identity of at least 10 consecutive nucleotides (e.g., the identity of at least 20, at least 50, at least 100, at least 200, or at least 500 or more consecutive nucleotides) of a polynucleotide are obtained.

The term "mutation", as used herein, generally refers to a change of the nucleotide sequence of a genome as compared to a reference. Mutations can involve large sections of DNA (e.g., copy number variation). Mutations can involve whole chromosomes (e.g., aneuploidy). Mutations can involve small sections of DNA. Examples of mutations involving small sections of DNA include, e.g., point mutations or single nucleotide polymorphisms, multiple nucleotide polymorphisms, insertions (e.g., insertion of one or more nucleotides at a locus), multiple nucleotide changes, deletions (e.g., deletion of one or more nucleotides at a locus), and inversions (e.g., reversal of a sequence of one or more nucleotides).

The term "locus", as used herein, can refer to a location of a gene, nucleotide, or sequence on a chromosome. An "allele" of a locus, as used herein, can refer to an alternative form of a nucleotide or sequence at the locus. A "wild-type allele" generally refers to an allele that has the highest frequency in a population of subjects. A "wild-type" allele generally is not associated with a disease. A "mutant allele" generally refers to an allele that has a lower frequency that a "wild-type allele" and may be associated with a disease. A "mutant allele" may not have to be associated with a disease. The term "interrogated allele" generally refers to the allele that an assay is designed to detect.

The term "single nucleotide polymorphism", or "SNP", as used herein, generally refers to a type of genomic sequence variation resulting from a single nucleotide substitution within a sequence. "SNP alleles" or "alleles of a SNP" generally refer to alternative forms of the SNP at particular locus. The term "interrogated SNP allele" generally refers to the SNP allele that an assay is designed to detect.

The term "copy number variation" or "CNV" refers to differences in the copy number of genetic information. In many aspects it refers to differences in the per genome copy number of a genomic region. For example, in a diploid organism the expected copy number for autosomal genomic regions is 2 copies per genome. Such genomic regions should be present at 2 copies per cell. For a recent review see Zhang et al. Annu. Rev. Genomics Hum. Genet. 2009. 10:451-81. CNV is a source of genetic diversity in humans and can be associated with complex disorders and disease, for example, by altering gene dosage, gene disruption, or gene fusion. They can also represent benign polymorphic variants. CNVs can be large, for example, larger than 1 Mb, but many are smaller, for example between 100 bases and 1 Mb. More than 38,000 CNVs greater than 100 bases (and less than 3 Mb) have been reported in humans. Along with SNPs these CNVs account for a significant amount of phenotypic variation between individuals. In addition to having deleterious impacts, e.g. causing disease, they may also result in advantageous variation.

As used herein the term "imprint cytology" refers to a technique for preparing a surgical specimen for pathological assessment. The excised surgical specimen may be sent fresh to the pathologist who processes it immediately. The cut surfaces are pressed or dabbed onto a solid surface, e.g., a glass slide, which may be then fixed and stained. In some settings, it is used as an adjunct or alternative to fine needle aspiration biopsy, frozen sectioning, and other pathological techniques. An example of imprint cytology is touch imprint cytology or touch-prep method.

As used herein the term "tumor margin" refers to the tissue surrounding a discernible tumor. In the case of surgical removal of a solid tumor, the tumor margin is the tissue cut away with the discernible tumor that usually appears to be normal to the naked eye. More particularly, as used herein, "margin" refers to the edge, border or boundary of a tumor. The margin generally extends from about 1 mm to about 4 mm from the primary tumor but can be greater depending upon the size of the primary solid tumor.

As used herein, the terms "surgical margin", "tumor free margin", "free margin", "normal skin margin", or "normal tissue margin" are used interchangeably. They refer to the visible normal tissue or skin margin that is removed with the surgical excision of a tumor, growth, or malignancy. Surgical margin as read in a pathology report define the histological measurement of normal or unaffected tissue surrounding the visible tumor under a microscope on a glass mounted histology section.

As used herein, the terms "surgical specimen", "cellular specimen", or "surgical resection" are used interchangeably. They refer to specimens obtained by the therapeutic surgical removal of an entire diseased area or organ (and occasionally multiple organs). These procedures are often intended as definitive surgical treatment of a disease in which the diagnosis is already known or strongly suspected.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

I. Kits

Disclosed herein are kits comprising devices and reagents to analyze cellular specimens using the devices and methods disclosed herein. The kits may comprise a standard. The kits may comprise a control. The control may be utilized to detect and/or confirm the presence of a control cellular material, a control nucleic acid or a control analyte. The control nucleic acid may be an amplified nucleic acid. The control nucleic acid may be a synthetic nucleic acid. The control nucleic acid may be an exogenous nucleic acid (e.g. added to the cellular specimen or sample from which it is derived). The control nucleic acid may comprise a nucleic acid selected from genomic DNA, mitochondrial DNA, chloroplast DNA, microbial DNA, cDNA, messenger RNA, ribosomal RNA, micro RNA, an amplicon thereof, and a combination thereof. The control nucleic acid may encode pre-determined internal reference genes against which the target nucleic acid(s) are compared to obtain a normalization ratio. A plurality of control nucleic acids may comprise a control nucleic acid signature. The control nucleic acid signature may indicate a cell type. The cell type may be cells of epithelial origin. The cell type may be cells of breast tissue origin. The cell type may be an adipocyte or pre-adipocyte. Presence of only an adipocyte signature in the cellular specimen may exclude malignancy. The cell type may be a vascular cell type. The control may be a control for obtaining the cellular specimen. The method may be a control for homogenizing and/or lysing the cellular specimen. The control may be for amplifying the nucleic acids of the cellular specimen. The control may be for cDNA synthesis.

Intraoperative Kit

An intraoperative test can be provided as a kit that contains (a) primers and probes to detect a panel of nucleic acids, (b) oligonucleotides to prime cDNA synthesis, (c) primers and probes to detect endogenous references, (d) primers and probes to detect endogenous controls, (e) primers and probes to detect exogenous controls. The kit may include synthetic exogenous controls to test key steps of the workflow. Controls may include synthetic DNA to verify and calibrate the amplification of DNA. Controls may include synthetic RNA to verify and calibrate cDNA synthesis and subsequent amplification. The kit may include negative controls to ensure that amplification is not the result of cross-over contamination. The kit for the intraoperative test may include a sample acquisition device, which could consist of a slide with a functionalized surface coating that is used to obtain biologic material from the surface of a surgical specimen. The kit may contain blotting paper to remove occult blood or fluids from the specimen before using the sample collection device to obtain the biologic sample. The kit can contain instructions directing the user to blot the biologic sample prior to sample acquisition. The kit may contain a disposable testing cartridge. The obtained sample can be transferred from the sample collection device to the testing cartridge manually or automated by the instrument. The testing cartridge can contain the buffers and reagents required to perform the test. Alternatively, reagents may be supplied separately from the testing cartridge. Reagents may be supplied in in liquid form, as concentrates, or as dried components, which are either reconstituted manually or by an instrument. The testing cartridge can contain a label that indicates which test the instrument should perform. The testing cartridge may have microfluidic components. The testing cartridge can be in the form of microfluidic circuit embedded on a CD. The testing cartridge can contain dried reagents. The testing cartridge can perform cell lysis, nucleic acid purification, cDNA synthesis, amplification, and detection. The testing cartridge may contain or accommodate magnetic beads to aid nucleic acid isolation. The testing cartridge may contain chambers or fluidic circuits with a functionalized coating. The functionalized coating can be used to purify nucleic acids. For example, the functionalized coating can be a ChargeSwitch coating, to which nucleic acids adsorb under specific buffer conditions (e.g. pH). The testing cartridge can perform sequential reactions. For example, the cartridge can perform cDNA synthesis followed by amplification. As another example, the test cartridge can perform one round of amplification, followed by a second, or nested, amplification. The cartridge can perform the first amplification in a large, pooled chamber, followed by parallel distribution to multiple smaller chambers where subsequent amplification is performed. Detection may be performed in the second amplification chambers. The testing cartridge can have ultra-microelectrodes embedded in one or more microfluidic chambers. The testing cartridge can be transparent, which allows optical detect, including detection by turbidity or fluorescence. The test cartridge can be controlled or operated by a reusable instrument, which is provided separately.

Postoperative Kit

An postoperative test can be provided as a kit that comprises (a) a sample acquisition device for collecting a biological sample; (b) a set of reagents for analyzing nucleic acid molecules of the biological sample; (c) a set of instructions for analyzing the nucleic acid molecules of (b), and (d) a set of reagents for storing the biological sample prior to the analyzing in (b) and (c). The kit may comprise (e) primers and probes to detect a panel of nucleic acids, (f) oligonucleotides to prime cDNA synthesis, (g) primers and probes to detect endogenous references, (h) primers and probes to detect endogenous controls, (i) primers and probes to detect exogenous controls, (j) a set of instruction for performing test on the surgical specimen, (k) a platform for analyzing the test result, and (l) a set of instructions for analyzing the test result. The kit may include reagents for lysing and/or homogenizing the collected surgical specimen. The kit may include reagents for extracting nucleic acids from the specimen. The kit may include synthetic exogenous controls to test key steps of the workflow. Controls may include synthetic DNA to verify and calibrate the amplification of DNA. Controls may include synthetic RNA to verify and calibrate cDNA synthesis and subsequent amplification. The kit may include negative controls to ensure that amplification is not the result of cross-over contamination. Reagents may be supplied in liquid form, as concentrates, or as dried components, which are either reconstituted manually or by an instrument. The kit may be used to collect surgical specimens and to perform postoperative test and data analysis in the same geographical location. The kit may be used to collect surgical specimen at a first geographical location and to perform postoperative test and/or data analysis at a second geographical location. As a non-limiting example, the collected surgical specimen may be preserved and/or stored using reagents provided in the kit and shipped for postoperative test and data analysis afar. The stored surgical specimen may be stable to endure shipping and harsh handling during transition, without causing substantial damage to the nucleic acid molecules of the surgical specimen. The stored surgical specimen may be shipped at room temperature, at low temperature, e.g. 4° C., −20° C., or in dry ice.

The kit may comprise a plurality of primers for PCR amplifying and/or for sequencing nucleic acids isolated from the collected specimen. The kit may provide at least 1, 2, 3, 4, 5, 6, 7, 8, 9, 10, 20, 50, 100, 200, 500, 1000, or more primers. The kit may provide between about 1-3, 1-10, 5-20, 1-1000, 10-500, 20-200, or 50-100 primers. The primers may have 5, 10, 15, 20, 25, 30, 40, 50, 100, 150, 200 or more nucleotides. The primers may have between about 1-8, 5-10, 6-20, 15-30, 20-50, 30-60, 40-80, 50-100, or 10-200 nucleotides.

The kit may be provided to users, for example clinical pathology laboratories, a healthcare personnel, a physician, a nurse, a medical care assistance, or a home healthcare assistance. The kit may be intended as a stand-alone solution. Alternatively, the kit may be combined with other kits and instruments. For example, the kit may be used to detect positive surgical margins postoperatively does not necessarily require the speed and automation required for unspecialized users to rapidly perform a test in an operating room. A kit for postoperative indications can therefore leverage existing equipment and more routine reagents. A postoperative kit may therefore contain a sample acquisition device and analyte-specific reagents. The sample collection device may be a glass slide coated with a functionalized surface. Analyte-specific reagents may be nucleic acid primers and/or probes to detect the panel of target and control nucleic acids. The kit may contain instructions to perform a test using reagents from other vendors. For example, the kit may instruct users to use a Qiagen purification kit to isolate mRNA from the cellular samples collected using the provided sample collection device. The kit may comprise spin column technology (e.g. RNeasy Plus Micro Kit) or magnetic bead-based technology (e.g. ARCTURUS® PicoPure® RNA Isolation Kit, Dynabeads® mRNA DIRECT™ Micro Kit) that may isolate mRNA, total RNA, or total nucleic acids. The disclosed kit may contain a squeegee or cell scraper to enhance sample removal from the provided sample collection device when using a kit or reagents from another vendor. The kit may comprise a storage device for the collected surgical specimen. The storage device may be a sample collection tube, an Eppendorf, a container, or any device that is suitable for storing substances. The kit may contain instructions to use a cDNA synthesis kit from another vendor. As an example, the cDNA synthesis kit may contain the SuperScript® III reverse transcriptase, AffinityScript RT, M-MuLV RNase H+ reverse transcriptase, RE3 Reverse Transcriptase, or Quantiscript Reverse Transcriptase with dNTPs in a compatible buffer. The disclosed kit may contain primers to perform cDNA synthesis. The primers may contain a reporter label comprising a tag, fluorescence label, a magnetic bead, or a barcode. The reporter label may be targeted to specific nucleic acids. The reporter label may be used to identify nucleic acids. The primers may be used for sequencing of targeted nucleic acids with or without amplification of the nucleic acids. The sequencing may be any sequencing technologies known in the art. The disclosed kit may provide instructions for performing sequencing using reagents enclosed therein. The disclosed kit may contain instructions to perform cDNA synthesis using random oligonucleotide primers, poly-A primers, or analyte-specific primers. The disclosed kit may contain instructions for the user to amplify cDNA using enclosed reagents, or reagents provided by another vendor. For example, the instructions may direct users to use enclosed primers to perform analyte-specific amplification using reagents provided by another vendor. The amplification could be performed using PCR, quantitative PCR (QPCR), real-time PCR, digital PCR (dPCR), digital droplet PCR (ddPCR), or isothermal amplification. The real-time PCR reagents from another vendor could consist of Thermo Scientific TaqPath™ qPCR Master Mixes, which can be provided as general purpose reagents. Synthesis of mRNA to cDNA and subsequent amplification can be performed using the same kit, for example the TaqPath™ 1-Step RT-qPCR Master Mix. The disclosed kit may contain analyte-specific probes and fluorescent reporters. Alternatively, the disclosed kit may contain primers without analyte-specific probes, which would be compatible for an intercalating fluorescent reporter, for example a SYBR dye. The postoperative kit can be performed on instruments described herein. Alternatively, the disclosed kit can include instructions that direct a user to perform a PCR, e.g. real-time PCR and/or quantification PCR, using an instrument from another vendor. As an example, the analysis could be performed on a LightCycler®, LightCycler® 2.0, COBAS® TaqMan® Analyzer, COBAS® TaqMan® 48 Analyzer, 7500 FastDx®, JBAIDS, or FilmArray®. Detection of the target analytes could be performed without amplification, for example, on a Nanostring instrument. The disclosed kit may contain primers, and/or instructions for the user to perform next-generation sequencing, e.g., RNAseq, of the collected biological sample. The next-generation sequencing platform can be a commercially available platform. Commercially available platforms include, e.g., platforms for sequencing-by synthesis, ion semiconductor sequencing, pyrosequencing, reversible dye terminator sequencing, sequencing by ligation, single-molecule sequencing, sequencing by hybridization, and nanopore sequencing. Platforms for sequencing by synthesis are available from, e.g., Illumina, 454 Life Sciences, Helicos Biosciences, and Qiagen. Illumina platforms can include, e.g., Illumina's Solexa platform, Illumina's Genome analyzer, which are described in Gudmundsson et al., Genome-wide association and replication studies identity four variants associated with prostate cancer susceptibility. Nat. Genet. 2009 41:1122-1126, Out et al. Deep sequencing to reveal new variants in pooled DNA samples. Hum. Mutat. 2009 30:1703-12, Turner, Massively parallel exon capture and library-free resequencing across 16 genomes. Nat. Methods 2009 6:315-6, U.S. Patent Application Publication nos. 20080160580 and 20080286795, and U.S. Pat. Nos. 6,306, 597, 7,115,400, and 7,232,656, which are hereby incorporated in their entireties. 454 Life Science platforms include, e.g., the GS Flex and GS Junior, and are described in U.S. Pat. No. 7,323,305, which patent is hereby incorporated in its entirety. Platforms from Helicos Biosciences include the True Single Molecule Sequencing platform. Platforms for ion semiconductor sequencing include, e.g., the Ion Torrent Personal Genome Machine (PGM) and are described in U.S. Pat. No. 7,948,015, which patent is hereby incorporated in its entirety. Platforms for pyrosequencing include the GS Flex 454 system and are described in U.S. Pat. Nos. 7,211,390; 7,244,559; 7,264,929, which patents are hereby incorporated in their entireties. Platforms and methods for sequencing by ligation include, e.g., the SOLiD sequencing platform and are described in U.S. Pat. No. 5,750,341. Platforms for single-molecule sequencing include the SMRT system from Pacific Bioscience and the Helicos True Single Molecule Sequencing platform.

II. Devices

Disclosed herein are integrated devices comprising: a sample input unit that receives a cellular specimen comprising a target nucleic acid; a nucleic acid analysis unit that measures a target nucleic acid expression level of the target nucleic acid, wherein measuring the target nucleic acid expression level comprises an isothermal amplification of the target nucleic acid; and a computational unit that interprets the target nucleic acid expression level as an indication of the presence or absence of a condition affecting the cellular specimen. The device may perform a test, wherein a result of the test indicates the presence, absence or risk of a condition affecting the cellular specimen. The devices may receive and analyze a plurality of target nucleic acids. The devices may further comprise additional units. Additional units include, but are not limited to a sample preparation unit and a nucleic acid detection unit. Any one of the units described herein may be combined or integrated in a single unit. For example, a single unit of the device may perform the functions of the sample input unit, the nucleic acid analysis unit, and the computational unit. In addition, a user of the device may perform any one of the functions of the units instead of the unit itself. Thus, any one unit or part of the device may be optionally utilized or not utilized. An alternative or additional device may be employed for the purpose or function of one or more units of the devices disclosed herein. The units of the device may be enclosed in a single housing. The units of the device may be enclosed in more than one housing.

The device may sonicate and/or homogenize cells of the cellular specimen to produce a cellular homogenate or a cellular lysate. The device may isolate or purify a nucleic acid from the lysate or homogenate. Alternatively, the device does not purify nucleic acids of the cellular specimen. For instance, the device may employ optimized buffers and enzymes for manipulation and/or analysis of the nucleic acids, wherein the optimized buffers and enzymes have been engineered or molecularly evolved to tolerate impurities that inhibit older generation enzymes that would have been used for the manipulation and/or analysis. Buffers and heat (extending the 95° C. denaturation phase of a PCR program to 10 min) may be used to lyse the cells, and the enzymes used to amplify the target nucleic acids in the remaining crude lysate without purification. The device may perform a nucleic acid amplification. Commercially available nucleic acid amplification kits or components thereof that amplify nucleic acids directly from blood or tissue may be employed by the device.

The devices may be operable for users without laboratory training. Molecular analysis of solid tissues by untrained users may enable applications from food safety to intraoperative tumor analysis. The devices may require less than about 20, less than about 18, less than about 15, less than about 12, less than about 10, less than about 9, less than about 8, less than about 7, less than about 6, less than about 5, less than about 4, less than about 3, or less than about 2 user interactions to perform the test. The device may perform the test with 2 or fewer user inputs. The device may perform the test in an operating room. The device may perform the test while a patient is undergoing a surgical procedure. The device may perform the test while the patient is anesthetized. The device may perform the test at a workstation, in a food processing plant, in a reference lab, or at a field site.

The devices described herein may be configured to occupy a small volume. The devices, or units thereof, together or in combination, may occupy a total volume that is about 5 cubic feet or less, about 4 cubic feet or less, about 3 cubic feet or less, about 2 cubic feet or less, about 1.9 cubic feet or less, about 1.8 cubic feet or less, about 1.7 cubic feet or less, about 1.6 cubic feet or less, about 1.5 cubic feet or less, about 1.4 cubic feet or less, about 1.3 cubic feet or less, about 1.2 cubic feet or less, about 1.1 cubic feet or less, about 1 cubic foot or less, about 0.9 cubic feet or less, about 0.8 cubic feet or less, about 0.7 cubic feet or less, about 0.6 cubic feet or less, about 0.5 cubic feet or less, about 0.4 cubic feet or less, about 0.3 cubic feet or less, about 0.2 cubic feet or less, or about 0.1 cubic feet or less. The devices or portions thereof as disclosed herein may be portable and/or encompassed in a hand-held device.

The devices disclosed herein may have a small mass. For example, a combined total weight of the sample input unit, sample preparation unit, nucleic acid analysis unit, and housing may be about 10 kg or less, about 9 kg or less, about 8 kg or less, about 7 kg or less, about 6 kg or less, about 5 kg or less, about 4 kg or less, about 3 kg or less, about 2 kg or less, about 1.5 kg or less, about 1 kg or less, about 0.9 kg (900 g) or less, about 800 g or less, about 700 g or less, about 600 g or less, about 500 g or less, about 400 g or less, about 300 g or less, about 200 g or less, or about 100 g or less. A combined total weight of the device may be about 100 g to about 500 g, about 300 g to about 1000 mg (1 kg), about 0.5 kg to about 3 kg, about 1 kg to about 6 kg, about 4 kg to about 10 kg, or more than about 10 kg.

Devices described herein may be self-contained, including a power source and ability to display or transmit results of the test. Devices described herein may be connected to external entities (e.g. computers, servers, power sources) via wires. Alternatively or additionally, devices described herein may be connected to external entities without wires. For example, devices described herein may be connected to external entities by transmitters and receivers that link the device to units or subunits that are necessary for operation or transmitting information (e.g., test instructions and/or results). The devices may be connected via wire or by wireless means to peripheral devices that add or augment existing functions of the devices, or to communication devices, such as, by way of non-limiting example, a local network, a server, or a service that provides connections to telephone, fax, or internet communications networks.

A. Sample Collection Unit

The devices disclosed herein may further comprise a sample collection unit. The sample collection unit may be an integrated unit of the device. The sample collection unit may be a separate unit from the device. Disclosed herein are systems comprising a device described herein and an additional unit or component. The additional unit or component may comprise the sample collection unit.

The devices disclosed herein may comprise a sample collection unit. The sample collection unit may be used to hold or carry the cellular specimen and present or deliver the cellular specimen to the device. The sample collection unit may be used to transfer the cellular specimen to a receptacle that contains reagents for preserving, storing, or analyzing the cellular specimen. For example, the sample collection unit may be immersed in the reagents inside a receptacle to release the cellular specimen into the reagents. The released cellular specimen can be analyzed by, for example, nucleic acid sequencing, and/or nucleic acid amplification. The sample collection unit may be inserted into the sample input unit. The sample collection unit may be selected from a slide, a plate, a tube, a chip, a nitrocellulose membrane, and a paper. The sample collection unit may comprise a surface. The surface may comprise glass, plastic (e.g., polystyrene, polypropylene, or other plastic), a film, a nanofiber matrix, a cellulose matrix (e.g., filter paper), or other solid substance. The surface may comprise a coating. Exemplary coatings include, but are not limited to, poly-lysine (e.g., poly-l-lysine, poly-d-lysine, poly-ornithine, collagen, laminin, fibronectin, and mucopolysacharrides such as, e.g., heparin sulfate, hyaluronidate and chondroitin sulfate), and hydrogel, among others. The coating may have a binding property. The coating may be used to selectively or non-selectively bind cells. The coating may selectively bind one or more specific cell types, e.g., ductal, epithelial, or glandular cells. The coating may bind to a specific cell type. For instance, the coating may be selected to bind to certain cell types but not to, e.g., adipocytes. The surface may comprise a coating that binds ductal and/or glandular cells, but does not bind adipocytes. A surface with these properties is advantageous for evaluating malignant or premalignant lesions of the breast because the majority of the breast parenchyma is adipose and connective tissue, which are not captured by the surface, while most types of breast malignancies or pre-malignancies are derived from cells of epithelial origin, for example mammary ducts and glands. A surface with said properties would reduce lipid inhibitors that would otherwise complicate subsequent molecular analysis. The surface may comprise a coating which selectively binds cells that express a specific marker or set of markers on a cell surface. By way of example only, the surface may comprise a coating which selectively binds cells that express one or more hormone receptors on the cell surface, e.g., one or more hormone receptors associated with breast cancer. Exemplary hormone receptors associated with breast cancer include, e.g., estrogen receptor and progesterone receptor.

The sample collection unit may comprise a filter paper (e.g. Whatman FTA® paper). The filter paper may be used for both sample collection and nucleic acid extraction. Accordingly, in some embodiments of an exemplary device, the device comprises a sample collection unit, sample input unit and sample preparation unit, wherein all three units are integrated. The cellular specimen may be added directly to sample collection unit. The filter paper may comprise a cellulose matrix impregnated with reagents suitable for cell lysis, extraction and retention of nucleic acids from a biological sample. The reagents may comprise one or more of a weak base, a chelating agent, an anionic detergent, and a uric salt or uric acid. The cellulose matrix may comprise a solid support for retention of the nucleic acids in the sample. The weak base may comprise a pH of about 6 to 10, or about pH 8 to 9.5. The weak base may act as a buffer to maintain a composition pH of about 6 to 10 or about pH 8.0 to 9.5, for example, pH 8.6. Suitable weak bases include organic and inorganic bases. Suitable inorganic weak bases include, e.g., an alkali metal carbonate, bicarbonate, phosphate or borate (e.g., sodium, lithium, or potassium carbonate). Suitable organic weak bases include, e.g., tris-hydroxymethyl amino methane (Tris), ethanolamine, triethanolamine and glycine and alkaline salts of organic acids (e.g., trisodium citrate). The chelating agent may be, e.g., EDTA. The chelating agent may be used to bind cations which act as nuclease cofactors, thereby inactivating nucleases present in the sample or in the paper. The anionic detergent may be used to lyse the sample and to denature proteins in the sample. Exemplary anionic detergents include, but are not limited to sodium dodecyl sulfate (SDS) and sodium lauryl sarcosinate (SLS). The uric salt or uric acid may act as a free radical trap, thereby enhancing the stability of extracted and stored nucleic acids. The target nucleic acid(s) may be analyzed on the filter paper, or may be eluted for further analysis. The sample may be treated prior to sample collection with filter paper. For example, the specimen can be blotted with filter paper to remove occult blood or fluids prior to collecting the surface layer of cells with the sample collection unit. The filter paper can be applied to the specimen, or the specimen can be pressed against the filter paper. In some implementations, the filter paper can be provided in a kit attached to a firm surface such as a slide.

The sample collection unit may comprise subject information about the subject. For example, the sample collection unit may comprise a code, a barcode, a marker, a symbol or some other recognizable imprint/label that conveys to the device the subject identity. As a result, subsequent results of a test performed by the device may be transmitted to an electronic medical record (EMR) or other database in connection with the device. Alternatively or additionally, the subsequent results of a test performed by the device may be transmitted to another person or device. The sample collection unit may comprise source information about the cellular specimen. The source may be selected from an environmental source, a food source, a plant source, and a water source.

The sample collection unit may comprise test information about the test to be performed (e.g., which classifier (i.e. disease classifier) is to be performed on the cellular specimen). The test information may be presented as a code, a barcode, a marker, a symbol or some other recognizable imprint/label that conveys to the device which classifier should be performed. Recognition of this test information by the device may activate the test.

The sample collection unit may comprise location information about the location, source and/or orientation of the cellular specimen. For example, the sample collection unit may consist of multiple slides. Each slide may be labeled prior to or while obtaining the cellular specimen with a label to indicate a source of the cellular specimen. As an illustration, the labels could indicate the cellular specimen is derived from the superior surface, inferior surface, medial surface, lateral surface, proximal surface, or distal surface of a surgical specimen (e.g., excised tissue/tumor). By way of non-limiting example, malignant cells detected on the lateral surface could direct the surgeon to excise more tissue laterally. Alternatively, a single slide could comprise multiple labels indicating superior surface, inferior surface, medial surface, lateral surface, proximal surface, or distal surface, etc., with an area next to each label for the respective cellular specimen. The sample input unit may comprise one or more receivers for one or more sample collection units. The device may then only require that the one or more sample collection units be inserted into the sample input unit in order for the computational unit to interpret the target nucleic acid expression level as an indication of the presence or absence of a condition (e.g. malignancy) affecting the cellular specimen on respective surfaces of the sample. The device's interpretation may direct the surgeon to excise additional tissue from an area of a surgical excision site corresponding to a sample surface found to contain cells affected the condition.

Sample collection units may be prepared with subject, source, test and/or location information in advance of a surgical procedure, so that the device only requires that the cellular specimen be collected on the sample collection unit and the sample collection unit inserted into the device. Little or no other information would have to be entered into the device. The act of inserting the sample collection unit into the device may be the only act required to initiate and/or run the test. This would be a major advantage for performing molecular testing outside of a clinical lab because risk and complexity increase with every manual step or user interaction. An entirely automated device or almost entirely automated device (i.e. only insertion of cellular specimen is required) also has the advantage of minimizing the time of an operation.

B. Sample Input Unit

The sample input unit may be a component of a device described herein which is configured to receive the cellular specimen. The sample input unit may be configured to receive the sample collection unit that contains or presents the cellular specimen. The sample input unit may maintain contact with the sample collection unit while the cellular specimen is processed and/or transferred to the sample preparation unit, or transferred directly to the nucleic acid analysis unit. The sample collection unit may be selected from a slide, a swab, a tube, a vial, a container, a chip, a paper, and a plate. The sample input unit may be configured to receive the cellular specimen directly (e.g. without a sample collection unit). The sample unit may comprise the slide, swab, tube, vial, container, chip, paper, or plate, to any of which the cellular specimen may be directly added.

C. Sample Preparation Unit

The device may further comprise a sample preparation unit for processing one or more cells of the cellular specimen. Processing may comprise disrupting. The sample preparation unit may disrupt one or more cells of the cellular specimen. Disrupting the one or more cells may release cellular contents from the cell(s) and/or disrupt its cell wall/membrane. Disrupting the one or more cells may release nucleic acids, including the target nucleic acid, from the cell(s). The sample preparation unit may be a single unit that homogenizes and/or lyses cells of the cellular specimen and/or extracts/isolates/purifies nucleic acids of the cellular specimen. The sample preparation unit may comprise a microfluidics unit, microfluidics device, microfluidics channel or microfluidics circuit for processing one or more cells of the cellular specimen. The sample preparation unit or microfluidics unit may comprise a homogenization unit for homogenizing the cells, a lysis unit for lysing the cells, and/or a nucleic acid extraction unit for extraction, isolation and/or purification of nucleic acids from the cellular specimen, and combinations thereof. The homogenization unit, cell lysis unit and/or nucleic acid extraction unit may be combined in one or more reaction chambers. The reaction chamber, also referred to as a tube, reaction vessel, or reaction container, may be a defined volume with rigid or semi-rigid walls covered or uncovered, in series or parallel to other containers, independent or nested within another chamber.

The sample preparation unit may be an integrated unit of the device. The sample preparation unit may be a separate unit from the device. The sample preparation unit may be inserted into the device before the cellular specimen is inserted into the sample input unit. The sample preparation unit may be contained/housed in a cartridge. The sample preparation unit may be used for a single test. The sample preparation unit may be discarded after a single test. The sample preparation unit may be a disposable cartridge. By using a disposable cartridge, cross-contamination between a first cellular specimen and a second cellular specimen may be eliminated or reduced. The sample preparation unit and sample collection unit may be integrated into a single unit that is inserted into the sample input unit. The sample collection unit may be joined or combined with the sample collection unit to produce the single unit that is inserted into the sample input unit. Inserting the single unit into the sample input unit may initiate the test.

The sample preparation unit may rapidly obtain/access nucleic acids from the cellular specimen. The sample preparation unit may rapidly obtain nucleic acids from a solid sample. The sample preparation unit may rapidly obtain nucleic acids from a cellular specimen derived from a surface of a solid sample, section thereof, or portion thereof. The sample preparation unit may obtain nucleic acids in less than about 15 minutes, less than about 10 minutes, less than about 5 minutes, less than about 3 minutes, less than about 2 minutes, or less than about 1 minute from inserting the cellular specimen into the sample input unit. The sample preparation unit may obtain nucleic acids in less than about 30 seconds, less than about 20 seconds, less than about 15 seconds, less than about 10 seconds, less than about 5 seconds, or less than about 3 seconds from inserting the cellular specimen into the sample input unit.

The sample preparation unit and/or nucleic acid extraction unit may be combined in one reaction chamber. The device may comprise a unit that performs any combination of cell homogenization, cell lysis, and nucleic acid extraction. These units may be combined in one reaction chamber and/or volume with the nucleic acid analysis unit, sample input unit and/or computational unit.

The sample preparation unit may perform a nucleic acid extraction according to any means known in the art or otherwise described herein. The nucleic acid extraction may be performed by the device in an automated fashion. The nucleic acid extraction may be initiated after the cellular specimen is applied to the sample input unit (see, e.g., FIGS. 1A-D and 3, identifiers 110, 111 and 322) or sample collection unit (see, e.g., FIG. 3, identifier 311). The nucleic acid extraction may be initiated by the user, or may be initiated automatically upon application of the cellular specimen to the device described herein. The user may initiate the nucleic acid extraction by a single command, action or touch (e.g., by pressing a button). The nucleic acid extraction may be initiated automatically upon application of the cellular specimen to the sample input unit (see, e.g., FIG. 1C-D).

Nucleic acid extraction may comprise lysing, disrupting, sonicating, shaking or homogenizing the cellular specimen. Nucleic acid extraction may comprise releasing the nucleic acids from the cellular specimen. Nucleic acid extraction may not require purifying the nucleic acids.

Nucleic acid extraction may occur in less than about 60 minutes, less than about 50 minutes, less than about 40 minutes, less than about 30 minutes, less than about 20 minutes, less than about 19 minutes, less than about 18 minutes, less than about 17 minutes, less than about 16 minutes, less than about 15 minutes, less than about 14 minutes, less than about 13 minutes, less than about 12 minutes, less than about 11 minutes, less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, less than about 1.5 minutes, less than about 1 minute (60 seconds), less than about 50 seconds, less than about 40 seconds, less than about 30 seconds, less than about 25 seconds, less than about 20 seconds, less than about 10 seconds, or less than about 5 seconds. The nucleic acid extraction may be carried out in between about 30-60 seconds. Nucleic acid extraction may occur between about 2 to about 5 minutes.

Nucleic acid extraction of the sample may be performed under low temperature. Nucleic acid extraction of the sample may be performed under room temperature. Nucleic acid extraction may be performed and expedited under heated conditions.

Lysing the cellular specimen may comprise contacting the cellular specimen with a lysing agent. The lysing agent may be in a solution. The lysing agent may be a solution. The lysing agent may be a liquid. The lysing agent may be a lysis buffer. Lysing agents may include one or more detergents. Exemplary detergents include, but are not limited to, CHAPS, CHAPSO, sodium dodecyl sulfate (SDS), ethyl trimethyl ammonium bromide, Triton-X 100, Triton X-114, NP-40, Brij-35, Brij-58, Tween-20, Tween 80, octyl glucoside, and octyl thioglucoside. Detergents may be used to disrupt cell membranes and may also denature proteins. The lysing agents may disrupt cells and extract the nucleic acids from the cells. Lysing agents may include chaotropic agents. The chaotropic agents may denature contaminating and potentially interfering proteins. Chaotropic agents include, but are not limited to, guanidinium isothiocyanate, urea, butanol, ethanol, guanidinium chloride, lithium perchlorate, lithium acetate, magnesium chloride, phenol, propanol, sodium dodecyl sulfate, and thiourea.

The cellular specimen may be contacted, coated and/or immersed in a liquid, such as, e.g., a buffer before or after inserting the cellular specimen into the sample input unit. The buffer may comprise one or more of: a pH buffering agent, a salt, a nuclease inhibitor, a calcium chelator (e.g., EDTA), and a lysing agent. The pH buffering agent may comprise a weak base described herein. Nuclease inhibitors may include, e.g., anti-nuclease antibodies, aurintricarboxylic acid, and calcium chelators such as EDTA. Anti-nuclease antibodies are described in U.S. Pat. No. 6,664,379, which is hereby incorporated by reference. Exemplary lysing agents are described herein.

Disrupting the cells of the cellular specimen may comprise disrupting the cells in the liquid by shear and/or mechanical forces. The cellular specimen may be subjected to grinding or crushing in the liquid. Shear forces may be propagated to the sample by the liquid. Shear forces may be propagated to the sample by displacing the liquid and the sample through a flow channel. The flow channel may be a microfluidic channel, e.g., a microfluidic circuit. The flow channel may be a macrofluidic channel. The flow channel may comprise one or more curves, bends, edges, or corners. In some cases, the flow channel comprises one or more protrusions or sharp edged particles (see, e.g., U.S. Pat. No. 5,304,487, hereby incorporated by reference). The channel may comprise a sinusoidal curvature. The sinusoidal curvature may have a period (e.g., an interval distance between two peaks of a sinusoidal wave form). The period may be about 0.01 to about 0.1 mm, about 0.05 to about 0.5 mm, about 0.1 to about 1 mm, about 0.5 to about 5 mm, about 1 mm to about 10 mm (1 cm), or greater than 1 cm. The flow channel may have a uniform or variable diameter. The flow channel may have a diameter between about 0.01 to about 0.1 mm, about 0.05 to about 0.5 mm, about 0.1 to about 1 mm, about 0.5 to about 5 mm, about 1 mm to about 10 mm (1 cm), or greater than 1 cm. The device may be compatible with use of microfluidic channels for tissue lysis, for example, homogenization of samples may be performed in the microfluidic circuit. Homogenization of samples may be performed in a larger-volume sample tube (e.g., 200 microliters), and the sample is transferred to a microfluidic chip using automated liquid handling.

The device or sample preparation unit may comprise a scraping device or mechanism that removes the cellular specimen from the sample collection unit. The cellular specimen may be suspended in a liquid and flowed from the sample input unit into the flow channel or a reservoir connected to the flow channel. The flow channel may be a restricted flow channel comprising a narrower diameter than the reservoir. The liquid containing the sample may be displaced from the reservoir to the restricted flow channel and back to the reservoir multiple times. The displacement of the liquid containing the cellular specimen from the reservoir to the restricted flow channel and back may be performed in an automated fashion. The cellular specimen may be prepared with a homogenizer (e.g. disposable Dounce) and followed by a syringe-based method. Shear forces may be generated in an enclosed sample preparation unit, for example, a microfluidic or microfluidic circuit using the principle of convexity from a Dounce homogenizer to form a stationary unit that generates shear forces as the fluid is flowed past the constriction created by the convexity. The fluid may be flowed back and forth multiple times to generate additional shear forces.

Nucleic acid extraction may comprise contacting the cellular specimen with shear forces, including but not limited to grinding, crushing, liquid flow, turbulence, agitation, mixing, and sonication. Shear forces may be provided by a device selected from, but not limited to, a Dounce homogenizer, a syringe, a pump, an agitating device, a probe, and a plunger. The shear forces may be provided in an automated fashion. For example, the device may be controlled by an actuator.

Shear forces may be generated by sonication. The device may comprise a vibrating probe that generates the sonication. The vibrating probe may be at least partially submerged in the liquid. The vibrating probe may propagate sound waves through the liquid. The vibrating probe may comprise piezoelectric crystals which are used to expand and contract the base of the probe at a defined frequency and power. The vibrating probe's vibration may generate pressure waves that result in cavitation. Cavitation may occur when a liquid is subjected to rapid changes of pressure that cause the formation of cavities where the pressure is relatively low. When subjected to higher pressure, the cavities may implode and generate intense shockwaves.

Shear forces may be generated by ultrasonic waves. The device may employ Adaptive Focused Acoustics™ (AFA) Technology (Covaris, Inc.) or similar technology to generate the ultrasonic waves. AFA technology may subject the cellular specimen to a propagation of focused pressure waves. The focused pressure waves may have a high frequency (e.g., 100 kHz-100 MHz; greater than 500 kHz; greater than or approximately equal to 1 MHz; etc.) and a short wavelength (e.g., approximately 1.5 mm at a frequency of 1 MHz). AFA technology may not necessarily require use of a physical probe submerged in a liquid medium, and thus may obviate contact of a solid probe with the sample. Accordingly, AFA technology may be used to minimize contamination of the sample and obviate a need to clean a probe between samples. AFA technology is described in U.S. Pat. Nos. 8,353,619 and 7,757,561, which are hereby incorporated by reference.

The device may employ a Bulk Lateral Ultrasound (BLU™) device, or a similar device that generates BLU energy or similar energy, to generate ultrasonic waves. BLU energy may transmit bulk acoustic waves through the liquid, which may contain the cellular specimen or sample comprising the cellular specimen. The device may comprise a piezoelectric chip in the shape of a segmented Fresnel lens. The piezoelectric chip may generate the BLU energy. The BLU device may comprise a piezoelectric chip and a segmented Fresnel lens that generates highly controllable ultrasonic waves. Segmented rings from a cutout of a full Fresnel lens may create an interference pattern that result in sound waves which deliver a lateral thrust. Like AFA, BLU energy may be used to perform a variety of functions, including solubilization, mixing, heating/cooling, lysing and shearing. The piezoelectric chip may be manufactured using micro-electro-mechanical systems (MEMS) processes similar to microchip fabrication processes. BLU may produce bulk fluid movement in a microplate well or vial, and may be able to act on a smaller volume than alternative techniques likes Surface Acoustic Waves, Focused Acoustic Waves, or conventional mechanical shaking. The BLU device/energy may be used to lyse cells and shear nucleic acids of the cellular specimen by using the differential between pressure gradients. At high power, pressure differentials may reach 4,000 psi, equivalent to the pressure density on the surface of an exploding hand grenade.

The device may comprise an ST-30 instrument that generates shear forces for next-generation sequencing purposes. The ST-30 instrument may accommodate barcoded matrix tubes, which are partially submerged in a water bath. The ST-30 instrument may hold up to about 8 samples in a wheel, which raises the samples above the water level and acts as a cantilevered centrifuge. Sample tubes are lowered to 5.69 mm above the FASA transducer. BLU may be used to evenly distribute sonication energy throughout the sample. The evenly distributed shearing forces may result in reproducible extraction of biomarkers from biological samples, including solid tissue samples. The amount of energy introduced into a sample through BLU may be precisely controlled, which makes it straightforward to process clinical samples in different phases. BLU may also obviate the need for a solid probe to contact the liquid and thus may be used to minimize contamination of the sample. BLU has been used to process liquid samples. It was surprisingly discovered that BLU technology may be used to rapidly process solid biological samples as well. The ability to process both solid and liquid samples with the same underlying technology is a major breakthrough for point-of-care (POC) applications. Accordingly, the nucleic acid extraction unit of the device may comprise a BLU device. The BLU device may be configured to homogenize and/or lyse the sample and/or extract nucleic acids from the sample in an automated fashion. BLU technology and devices are described in U.S. Pat. No. 8,319,398, which is hereby incorporated by reference.

Disrupting the cellular specimen may be achieved by heating the sample. For example, the cellular specimen may comprise adipose tissue. Heat, alone or in combination with application of mechanical or shear forces, may be sufficient to disrupt the adipose tissue.

The nucleic acid extraction may not comprise contacting the cellular specimen with a liquid. The cellular specimen may be applied to a support surface such as a piece of paper, a slide, a cotton ball, a piece of glass, a metal, an alloy, a gel, or a piece wood. For example, in some cases wherein a biological sample is applied to Whatman FTA® paper (e.g., by touching the sample to the paper, by rolling the sample comprising the cellular specimen across the paper, or by crushing the sample onto the paper), the reagents impregnated into the Whatman FTA® paper serve to lyse the cellular specimen and extract the nucleic acids from the cellular specimen. In such cases, no extra steps are required for nucleic acid extraction subsequent to application of the cellular specimen to the sample input unit.

After disrupting, the cellular specimen may be used for nucleic acid analysis without purification of the nucleic acids (e.g., as a crude sample). Alternatively, the cellular specimen may undergo purification to separate nucleic acids from non-nucleic acid components. For example, nucleic acids may be purified by organic extraction. Exemplary organic extraction methods include, but are not limited to, use of phenol, phenol/chloroform/isoamyl alcohol, or similar formulations, TRIzol and the like. Organic extraction may be followed by precipitation of the nucleic acids, for example, with ethanol precipitation or salt-induced nucleic acid preparation. Purification of nucleic acids from non-nucleic acid components may comprise incubation with one or more proteases to eliminate unwanted protein from the sample, e.g., digestion with proteinase K, or other like proteases. See, e.g., U.S. Pat. No. 7,001,724, which is hereby incorporated by reference. Purification methods may be directed to isolate DNA, RNA, or both. When both DNA and RNA are isolated together during or subsequent to an extraction procedure, further steps may be employed to purify one separately from the other. Extracted nucleic acids may also be isolated, for example, by size, sequence, or other physical or chemical characteristics.

The cellular specimen may be contacted with a solid or semi-solid support for a time sufficient to bind nucleic acids of the cellular specimen. The support may be in the form of beads, gels, particles, wells, spin columns, tubes, probes, dipsticks, pipette tips, slides, filter, fibers, membranes, papers, matrices, and combinations thereof. The support may comprise one or more materials, including but not limited to ferrite core, glass, silica, celluloses, agaroses, polyesters of hydroxy carboxylic acids, polyanhydrides of dicarboxylic acids, copolymers of hydroxy carboxylic acids and dicarboxylic acids, polymers of polylactic acid (PLA), polymers of polyglycolic acid (PGA), Poly Lactic-co-Glycolic Acid (PLGA) polymers, polymers of acrylates, ethylcne-vinyl acetates, acyl substituted cellulose acetates, non-degradable urethanes, styrenes, vinyl chlorides, vinyl fluorides, vinyl imidazoles, chlorosulphonated olefins, ethylene oxide, vinyl alcohols, TEFLON (DuPont, Wilmington, Del.), nylons, and combinations thereof. A surface of the support may be functionalized to enhance the binding properties for the class of desired molecules. The support may be functionalized by coating with a binding agent capable of binding to one or more desired molecules. The desired molecules may comprise nucleic acids, or may comprise non-nucleic acid molecules. The solid support may be magnetized (for example, may be in the form of magnetized beads or particles). Following contact of the cellular specimen with the solid or semi-solid support, the support may be washed to remove undesired contaminants. Nucleic acids bound to the support may then be eluted from the solid support, thereby resulting in a purified nucleic acid sample, or may remain bound to the solid support. Nucleic acid analysis reactions may be carried out on the solid support.

The solid support may be coated with a charge switch material capable of changing its charge based upon pH of its surrounding environment. For example, the charge switch material may be positively charged at a certain pH range and may switch to a negative charge at another pH range. Commercially available supports coated with a charge switch material include, but are not necessarily limited to, ChargeSwitch™ beads (Invitrogen), which may be magnetized. Exemplary charge switch materials and solid supports coated with charge switch materials are described in U.S. Patent Application Publication No. 20080305528, which is hereby incorporated by reference. The nucleic acid extraction method may comprise disruption of the cellular specimen by any means described herein, followed by an incubation of the disrupted cellular specimen with ChargeSwitch™ beads in a pH environment in which the beads are positively charged. The incubation may be for a time sufficient to allow binding of nucleic acids (which may be negatively charged) in the disrupted biological sample to the positively charged beads. The positively charged beads may then optionally be washed to remove unbound material. The beads may then be switched to a pH environment in which the beads are less positively charged, are uncharged, or are negatively charged. The switch in the charge of the beads may release the bound nucleic acids into solution, thereby producing purified nucleic acids. The charge switch material described here may also be used as a coating to a tube, reaction chamber, fluidic connection or transfer, device, pipette tip, etc.

In particular embodiments, the cellular specimen is subjected to BLU homogenization in a solution comprising positively charged beads. During homogenization by BLU, nucleic acids may bind to the positively charged beads. Following homogenization, the positively charged beads may be collected by any means known to those of skill in the art or otherwise described herein, such as, e.g., by centrifugation or magnetic forces. The resulting collected beads may then be switched to a pH environment in which the beads are less positively charged, are uncharged, or are negatively charged. The switch in the charge of the beads releases purified nucleic acids into solution.

The devices and methods disclosed herein may comprise obtaining nucleic acids from one or more samples. For example, the devices and methods disclosed herein may use sonication to rapidly obtain nucleic acids from solid tissues. The device may comprise a transducer that generates sonication energy. The transducer may not have to directly contact the sample (contact-free sample processing reduces contamination and crossover between patient samples). Devices and methods disclosed herein may obtain nucleic acids from a sample, such as a complex solid tissue, in as little as about 30 seconds. Obtaining the one or more nucleic acids may occur in less than about 600 seconds, less than about 500 seconds, less than about 400 seconds, less than about 300 seconds, less than about 200 seconds, less than about 100 seconds, less than about 60 seconds, or less than about 30 seconds. Obtaining the one or more nucleic acids may occur in less about 12-18 hours. Obtaining the one or more nucleic acids may occur in less than about 6 days, less than about 5 hours, less than about 4 hours, less than about 3 hours, less than about 2 hours, or less than about 1 hour. Obtaining the one or more nucleic acids may occur in less about 12-18 days. Obtaining the one or more nucleic acids may occur in less than about 6 days, less than about 5 days, less than about 4 days, less than about 3 days, less than about 2 days, or less than about 1 day.

D. Nucleic Acid Analysis Unit

The devices disclosed herein may comprise a nucleic acid analysis unit. The nucleic acid analysis unit may analyze one or more nucleic acids from the cellular specimen. The nucleic acid analysis may analyze the sequence, the expression level, the chemical modifications, or the associated proteins of the one or more nucleic acids. The nucleic acid analysis unit may analyze the target nucleic acid from the cellular specimen. The nucleic acid analysis unit may analyze a plurality of target nucleic acids from the cellular specimen. The plurality of target nucleic acids may correspond to a plurality of genetic loci. Two or more genetic loci of the plurality of genetic loci may be located in the same gene. Two or more genetic loci of the plurality of genetic loci may be located in different genes. The plurality of genetic loci may comprise less than about 100 genetic loci, less than about 95 genetic loci, less than about 90 genetic loci, less than about 85 genetic loci, less than about 80 genetic loci, less than about 75 genetic loci, less than about 70 genetic loci, less than about 65 genetic loci, less than about 60 genetic loci, less than about 55 genetic loci, less than about 50 genetic loci, less than about 45 genetic loci, less than about 40 genetic loci, less than about 35 genetic loci, less than about 30 genetic loci, less than about 25 genetic loci, less than about 20 genetic loci, less than about 15 genetic loci, less than about 10 genetic loci, less than about 5 genetic loci, less than about 4 genetic loci, less than about 3 genetic loci, or less than about 2 genetic loci. The nucleic acid analysis unit may analyze only a single target nucleic acid from the cellular specimen.

Multivariate Analysis

Provided herein is a device capable of performing a multivariate analysis, or analysis of multiple single analytes. The multivariate analysis may comprise detecting multiple analytes (e.g. target nucleic acids and reference nucleic acids), where one or more analytes are a reference analyte, and comparing the target analyte to the reference analyte. A single analyte (e.g. a single marker to detect a single pathogen) may generate a single output. For a single-analyte test, A=1, independent analytes are analyzed and returns R=1 results, where A=R. The device may perform a multivariate analysis of the signal corresponding to target analytes; comprising: selecting a subset (SS) of replicate measurements based on measurement performance, which is determined by kinetic or end-point parameters; determining the Usable Value (UV) of each analyte by combining or averaging the SS of replicate measurements; determining a Reference Value Set (RVS) by combining or averaging the UV for multiple Reference Analytes (RA); and normalizing the signal corresponding to a Target Analyte (TA) by obtaining the ratio of UV for the TA to the RVS for the RA. The multivariate analysis may be used to detect or diagnose a complex disease, which is only characterized by multiple analytes in the composition and is specifically not characterized by any one of the component analytes; assign a subtype or subcategory to the cellular specimen (e.g. breast cancer subtype); and stratify risk (e.g. probability of malignancy, probability of a future event).

The multivariate analysis may include a test that detects, excludes or provides a risk for the presence, behavior or outcome of the condition or disease. The multivariate analysis may comprise a series of controls to evaluate or verify the performance of one or more steps in the preparing of the sample, performing of the molecular analysis, transforming of the biologic information into an electronic signal, or detecting of the electronic signal. The controls may be biological substances obtained from the subject. The controls may be biological substances obtained from the cellular specimen. The controls may be obtained from a sample from which the cellular specimen was derived. The control may be exogenous to the sample from which the cellular specimen was derived.

Described herein is also a device capable of analyzing multiple single-analytes (e.g. multiple pathogens, where a pathogen is an analyte that generates a single output, although that output may be a continuous variable and does not necessarily need to be a discrete variable). The device may also perform a multi-analyte test (e.g. multiple genes to detect a complex disease, including one that is molecularly heterogeneous). For multiple, single-analyte tests, A independent analytes are analyzed and returns R results, where A=R. Currently, it has been a challenge to investigate, diagnose and monitor diseases and conditions that are not defined by a single variable. These include diseases that are complex or multifactorial in their etiology, and diseases that are heterogeneous on a molecular, cellular, or tissue level. This also includes conditions with heterogeneity within an individual patient. Breast cancer is a well-known example of a complex disease, which is not characterized by a single biomarker or molecular event. There are distinct subtypes of breast cancer that are molecularly heterogeneous. Moreover, a single breast cancer tumor may be molecularly heterogeneous, such that there may be variation between cells, clonal derivatives, or metastatic lesions. The primary tumor may be heterogeneous. Heterogeneity is a major challenge that has confounded biologic and medical advances for millennia. It remains a challenge to generate a result (R) based on the analysis of multiple analytes (A), where A>R, and frequently R=1. For example, existing platforms may accommodate multiple samples in theory, in practice these platforms may not process enough for most multi-analyte nucleic acid tests. The number of genes may become another distinguishing factor.

The devices described herein may analyze multiple genes or expression levels thereof. The number of genes the device may analyze is between 1-1000 genes, between 200 to 400 genes, between 150-800 genes, between 100 to 500 genes, between 50 to 300 genes, between 20 to 80 genes, between 10 to 25 genes, between 5 to 15 genes, between 4 to 12 genes, between 3 to 9 genes, or between 2 to 6 genes. The number of genes the device may analyze is about 1000 genes, 900 genes, 800 genes, 500 genes, 400 genes, 300 genes, 200 genes, 150 genes, 100 genes, 50 genes, 25 genes, 20 genes, 10 genes, 9 genes, 8 genes, 7 genes, 6 genes, 5 genes, 4 genes, 3 genes, 2 genes, or 1 gene. The number of genes the device may analyze is more than 1000 genes, more than 900 genes, more than 800 genes, more than 500 genes, more than 400 genes, more than 300 genes, more than 200 genes, more than 150 genes, more than 100 genes, more than 50 genes, more than 25 genes, more than 20 genes, more than 10 genes, more than 9 genes, more than 8 genes, more than 7 genes, more than 6 genes, more than 5 genes, more than 4 genes, more than 3 genes, more than 2 genes, or more than 1 gene.

The devices described herein may be incorporated with microfluidic chips for accommodating up to tens of thousands of reactions. Multiple replicates may be performed to overcome noise of gene expression signals due to the large number of genes being analyzed. Five technical replicates may be performed and 1-2 outliers are discarded to obtain reliable results. The device may also perform point-of-care analysis of RNA.

The device may analyze varied or multiple forms of nucleic acids from the cellular specimen. The device may analyze RNA (e.g. messenger RNA). The device may analyze DNA. The platform may analyze both RNA and DNA. As an example, DNA (e.g. genomic DNA) derived from the cellular specimen may be used as a positive control to calculate or to normalize the total number of cells in the specimen. The expression level of the RNA is normalized against the corresponding amount of DNA in the cellular specimen. The primers across splice junctions typically target mRNA or cDNA sequences greater than 50-150 nucleotides and are designed in such a way that DNA does not interfere with the analysis or quantification of RNA.

The nucleic acid analysis unit may analyze nucleic acids from the cellular specimen and corresponding nucleic acids from control cells or tissues (e.g. normal or abnormal cells). The analysis may be quantitative. The analysis may be qualitative. The nucleic acid analysis unit may quantify the expression levels of the nucleic acids. The nucleic acids may be selected from RNA, mRNA, spliced RNA, non-spliced RNA, DNA, cDNA, genomic DNA, and combinations thereof. The nucleic acid analysis unit may alternatively or additionally quantify a protein or a peptide. Non-limiting examples of nucleic acids are those encoding ACTR3B, ALK, ANLN, AURKA, BAG1, BcI2, BCL2, BCR-Abl, BIRC5, BLVRA, BRAF, c-KIT Cathepsin L2, CCNB1, CCNE1, CD20 antigen, CD30, CD68, CDC20, CDC6, CDH3, CENPF, CEP55, CXXC5, Cyclin B1, EGFR, ER, ERBB2, ESR1, EXO1, FGFR4, FIP1L-PDGFRalpha, FOXA1, FOXC1, GPR160, GRB7, GSTM1, HOXB13, IL17BR, Ki-67, KIF2C, KRAS, KRT14, KRT17, KRT5, MAPT, MDM2, MELK, MIA, MKI67, MLPH, MMP11, MYBL2, MYC, NAT1, NDC80, NUF2, ORC6L, PDGFR, PGR, PHGDH, PML/RAR alpha, PR, PTTG1, RRM2, SCUBE2, SFRP1, SLC39A6, STK15, Stromelysin 3 (MMP11), Survivin, TMEM45B, TPMT, TYMS, UBE2C, UBE2T, and UGT1A1. Alternatively, or additionally, the nucleic acid may encode a gene selected from ABCA10, ABCA9, ADAM33, ADAMTS5, ANGPT1, ANKRD29, ARHGAP20, ARMCX5GPRASP2, ASB1, CA4, CACHD1, CAPN11, CAV1, CAV2, CAV3, CBX7, CCNE2, CD300LG, CDC14B, CDC42SE1, CENPF, CEP68, CFL2, CHL1, CLIP4, CNTNAP3, COL10A1, COL11A1, CRIM1, CXCL3, DAB2IP, DMD, DPYSL2, DST, EEPD1, ENTPD7, ERCC6L, EZH1, F10, FAM126A, FBXO31, FGF1, FIGF, FMO2, FXYD1, GIPC2, GLYAT, GPR17, GPRASP1, GPRASP2, HAGL, HAND2-AS1, HLF, HMMR, HOXA2, HOXA4, HOXA5, IGSF10, INHBA, IL11RA, ITM2A, JADE', JUN, KIAA0101, KIF4A, KLHL29, LCAT, LGI4, LIFR, LIMS2, LRIG3, LRRC2, LRRC3B, MAMDC2, MATN2, MICU3, MIR99AHG, MME, MMP11, NECAB1, NEK2, NKAPL, NPHP3, NR3C1, NR3C2, NUF2, PAMR1, PAFAH1B3, PAQR4, PARK2, PEAR1, PGM5, PKMYT1, PLEKHM3, PLSCR4, POU6F1, PPAP2B, PPP1R12B, PRCD, PRX, PYCR1, RAPGEF3, RBMS2, SCN4B, SDPR, SLC35A2, SH3BGRL2, SPRY2, STAT5B, SYN2, TK1, TMEM220, TMEM255A, TMOD1, TPM3, TPX2, TSHZ2, TSLP, TSTA3, TTC28, WISP1, USHBP1, USP44, IBSP and ZWINT.

The nucleic acid analysis unit may be capable of performing any number of reactions, including but not limited to in vitro transcription, cDNA synthesis, labeling, fragmentation, amplification, sequencing, and other reactions.

The devices disclosed herein may be capable of performing multiplex detection and/or measurement of a plurality of target nucleic acids. The devices may perform a nucleic acid analysis comprising detection and/or measurement of about 1, about 2, about 3, about 4, about 5, about 6, about 7, about 8, about 9, about 10, about 20, about 30, about 40, about 50, about 100, about 200, about 500, about 1000, or more than about 1000 target nucleic acids. The device may detect and/or measure about 1 to about 10 target nucleic acids, about 5 to about 50 target nucleic acids, about 10 to about 100 target nucleic acids, about 50 to about 500 target nucleic acids, about 100 to about 1000 target nucleic acids, or more than about 1000 target nucleic acids. Accordingly, any of the devices disclosed herein may be configured for multiplex detection and/or measurement of about 1, about 2, about 3, about 4, about 5, about 6, about 7, about 8, about 9, about 10, about 20, about 30, about 40, about 50, about 100, about 200, about 500, about 1000, or more than about 1000 target nucleic acids. The devices disclosed herein may be configured to/for multiplex detection and/or measurement of about 1 to about 10 target nucleic acids, about 5 to about 50 target nucleic acids, about 10 to about 100 target nucleic acids, about 50 to about 500 target nucleic acids, about 100 to about 1000 target nucleic acids, or more than about 1000 target nucleic acids.

The nucleic acid analysis unit may be capable of performing a gene expression analysis. In gene expression analysis studies, transcribed mRNA may be reverse-transcribed into cDNA. cDNA may be amplified and/or detected by any means known to those of skill in the art. A cDNA synthesis reaction may be carried out using a reverse-transcriptase or other enzyme with reverse transcriptase activity. The cDNA synthesis step may be performed with target-specific primers, degenerate primers, or primers that recognize the poly-A tail of mRNA. The RNA may be amplified without a conversion step to cDNA.

The nucleic acid analysis unit may be capable of detecting polymorphisms or mutations in DNA or RNA. The polymorphism may be a single nucleotide polymorphism. The mutation may be a copy number variation. The mutation may be a deletion, an insertion, or an inversion of at least one nucleic acid molecule. The nucleic acid analysis may be capable of detecting structural variations, including copy number variations, translocations, deletions, inversions and other rearrangements that differ from a reference sequence. The nucleic acid analysis may be capable of detecting epigenetic modifications to DNA, including covalent modifications such as methylation and functional alterations resulting from genetic and epigenetic changes, including loss of heterozygosity, monoallelic expression, biallelic expression, and parent-of-origin expression.

Nucleic Acid Amplification

In general, the nucleic acid analysis units of the devices disclosed herein perform an amplification of the target nucleic acid. The target nucleic acid may be selectively amplified. For example, target-specific primers may selectively amplify the target nucleic acid, e.g., reverse-transcribed cDNA, RNA, genomic DNA, and the like. The target nucleic acid may be non-selectively amplified.

Isothermal amplification may be a class of amplification methods that is distinguished from PCR because each step does not require a different temperature, although multiple temperatures may be used during the course of an isothermal method, for example some isothermal methods perform optimally when initiated or preceded by a heat denaturation step. The use of multiple temperatures should therefore not be used to exclude a method that has been described as isothermal in the scientific literature. The term "isothermal method" as used herein may be defined as a class of amplification methods that does not comprise PCR. The target nucleic acid may be amplified, selectively or non-selectively, via isothermal amplification.

The isothermal amplification may occur in less than about 60 minutes, less than about 50 minutes, less than about 40 minutes, less than about 30 minutes, less than about 20 minutes, less than about 19 minutes, less than about 18 minutes, less than about 17 minutes, less than about 16 minutes, less than about 15 minutes, less than about 14 minutes, less than about 13 minutes, less than about 12 minutes, less than about 11 minutes, less than about 10 minutes, less than about 9 minutes, less than about 8 minutes, less than about 7 minutes, less than about 6 minutes, less than about 5 minutes, less than about 4 minutes, less than about 3 minutes, less than about 2 minutes, less than about 1.5 minutes, less than about 1 minute (60 seconds), less than about 50 seconds, less than about 40 seconds, or less than about 30 seconds. The amplification reaction may occur in about 1 minute to about 5 minutes. The amplification reaction may occur in about 2 minutes to about 5 minutes. The polymerization reaction may occur in less than about 3 minutes. The polymerization reaction may occur in less than about 2.5 minutes. The amplification reaction may occur in less than about 2 minutes. The amplification reaction may occur in less than about 1.5 minutes.

The isothermal amplification may produce an amplicon of less than about 50 base pairs, less than about 60 base pairs, less than about 70 base pairs, less than about 80 base pairs, less than about 100 base pairs, less than about 110 base pairs, less than about 120 base pairs, less than about 130 base pairs, less than about 140 base pairs, less than about 150 base pairs, less than about 160 base pairs, less than about 170 base pairs, less than about 180 base pairs, less than about 190 base pairs, or less than about 200 base pairs. The amplification may produce an amplicon of less than about 100 base pairs, less than about 200 base pairs, less than about 300 base pairs, less than about 400 base pairs, less than about 500 base pairs, less than about 600 base pairs, less than about 800 base pairs, less than about 900 base pairs, or less than about 1000 base pairs. The amplification may produce an amplicon of less than about 1000 base pairs, less than about 2000 base pairs, less than about 3000 base pairs, less than about 4000 base pairs, less than about 5000 base pairs, less than about 6000 base pairs, less than about 8000 base pairs, less than about 9000 base pairs, or less than about 10,000 base pairs.

The isothermal amplification may further comprise reverse transcribing an RNA to produce a complementary DNA (cDNA), wherein the cDNA is amplified. Reverse transcribing RNA is well known and understood by a person of skill in the art. Briefly, the reverse transcribing comprises contacting the RNA with a reverse transcriptase enzyme, primer that anneals to the RNA (e.g. a poly-T primer or random hexamer) and deoxyribonucleotides. The reverse transcriptase extends the primer with deoxyribonucleotides to produce the cDNA. The single cDNA is strand may be subsequently amplified with a method such as PCR. Reverse transcribing RNA may be performed in the same reaction volume as the subsequent amplification. The isothermal amplification may involve using a Hot Start Taq DNA polymerase including, but is not limited to, HotStarTaq Plus DNA Polymerase (QIAGEN, cat no. 203601), SpeedSTAR HS DNA Polymerase (CLONTECH, cat no. RR070A), Cheetah HotStart Taq DNA Polymerase (Chemometec, cat no. 29050), Hot Start Taq DNA Polymerase (NEB, cat no. M0495S), OneTaq® Hot Start DNA Polymerase (NEB, cat no. M0481S), EpiMark Hot Start Taq DNA Polymerase (NEB, cat no. M0490S), and Maxima Hot Start Taq DNA Polymerase (Thermo Fisher Scientific, cat no. EP0601).

The isothermal amplification is carried out at a constant temperature. The isothermal amplification does not require a thermal cycler. Isothermal amplification methods include, but are not necessarily limited to, variations, modifications and adaptions of Loop-mediated Isothermal Amplification (LAMP), Helicase-Dependent Amplification (HDA), Recombinase Polymerase Assay (RPA), Transcription-Mediated Amplification (TMA), Nucleic Acid Sequence-Based Amplification (NASBA), Signal mediated amplification of RNA Technology (SMART), Strand Displacement Amplification (SDA), Rolling Circle Amplification (RCA), Isothermal Multiple Displacement Amplification (IMDA), Single Primer Isothermal Amplification (SPIA), Recombinase Polymerase Assay (RPA), and Self-sustained Sequence Replication (3SR). Any of such amplification methods may be coupled with reverse transcription to yield amplification of cDNA reverse-transcribed from RNA. Some methods may directly amplify RNA, including microRNAs without a reverse transcription step. Some methods use a target sequence to trigger an amplification reaction, where the amplicons may or may not include the target sequence, but instead may indicate the presence of the target sequence. Each of these examples should be taken as a representative of a family of similar and derivative methods.

HDA may employ a helicase, rather than heat, to separate two strands of a DNA duplex into single-stranded templates. Sequence-specific primers may hybridize to the templates and be extended by DNA polymerases to amplify the target nucleic acid. This process may repeat itself, resulting in exponential amplification. Because HDA uses a helicase instead of heat to denature the DNA duplex, multiple cycles of replication may be performed at a single incubation temperature, thereby obviating the need for thermocycling equipment.

RPA may employ use of three enzymes: (i) a recombinase, (ii) a single-stranded DNA-binding protein (SSB) and (iii) a strand-displacing polymerase. The recombinase may be used to hybridize oligonucleotide primers to the target nucleic acid(s) at low temperatures (e.g., 37° C.). The denaturation of a DNA template may not be required. If the target nucleic acid is present, a strand exchange and a "D-loop" formation may be initiated by the SSB. The 3' ends of the oligonucleotides may be extended by the strand displacing polymerase, thereby copying the displaced strand. The resulting copy and the original may then be used as targets for subsequent cycles, resulting in exponential amplification.

TMA may employ the use of two enzymes, a reverse transcriptase that creates a double-stranded DNA copy from an RNA or double-stranded DNA template, and an RNA polymerase to generate RNA amplicons from the double-stranded DNA template. Each RNA amplicon may serve as a new target for the reverse transcriptase. TMA may result in an exponential amplification of the original target nucleic acid that may produce over a billion amplicons in less than 30 minutes.

NASBA amplification may comprise a promoter-directed, enzymatic process that induces in vitro continuous, homogeneous and isothermal amplification of the target nucleic acid. NASBA amplification may result in generation of RNA copies of the target nucleic acid. NASBA amplification may comprise use of reagents including, but not limited to, a first DNA primer with a 5'-tail comprising a promoter, a second DNA primer, reverse transcriptase, RNase-H, T7 RNA polymerase, NTPs and dNTPs.

SMART amplification may employ use of two single-stranded oligonucleotide probes, wherein each probe includes one region that may hybridize to the target nucleic acid and another region that hybridizes to the other probe. The two probes may be designed such that they may only anneal to each other in the presence of the specific target, thereby forming a three-way junction (3WJ). SMART amplification may employ use of Bst DNA polymerase. Following 3WJ formation, Bst DNA polymerase may extend the short (extension) probe by copying the opposing template probe to produce a double-stranded T7 RNA polymerase promoter sequence. The double-stranded T7 promoter sequence may enable generation of multiple copies of RNA amplicons which may be detected by any means known in the art.

RCA may comprise hybridization of a single primer to a circular nucleic acid. Extension of the primer by a DNA polymerase with strand displacement activity may result in the production of multiple copies of the circular nucleic acid concatenated into a single DNA strand.

IMDA may comprise strand displacement replication of the nucleic acid sequences by multiple primers. Two sets of primers are used to flank the target nucleic acid. A first set of primers may be complementary to one strand of the nucleic acid molecule to be amplified. A second set of primers may be complementary to the opposite strand. The 5' ends of the primers in both sets may flank the target nucleic acid sequence of interest when hybridized to the target nucleic acid. Amplification may proceed by replication initiated at each primer and continue through the nucleic acid sequence of interest. IMDA may result in displacement of intervening primers during replication by the polymerase.

SPIA may employ use of a single chimeric primer for isothermal amplification. The chimeric primer may comprise ribonucleotides at its 5' end and deoxyribonucleotides at its 3' end. Amplification may be initiated by hybridizing the chimeric primer to a complementary sequence in the target nucleic acid. DNA polymerase having strong displacement activity may be used to initiate extension of the hybridized primer. Following initiation of the primer extension step, the 5' RNA portion of the extended primer (RNA-DNA hybrid) may be cleaved by RNase H, including RNA H2, thereby freeing part of the primer-binding site on the target DNA strand for binding by the RNA portion of a new chimeric primer. SPIA may use a DNA polymerase with reverse transcriptase activity to create and amplify cDNA from RNA in a single tube.

3SR may comprise continuous cycles of reverse transcription and RNA transcription to replicate a nucleic acid target via a double-stranded cDNA template.

Loop-Mediated AMPlification (LAMP).

The kinetics of isothermal amplification reactions can be divided into two phases: generation of an intermediate product (IP), and amplification of the intermediate product (IP). The IP for LAMP is a dumbbell structure with two loops on either end named Forward Loop (F-loop) and Backwards Loop (B-Loop). The amplification phase of LAMP alternates between two IP: one with a F-loop on the 3' end and the other with a B-loop on the 3' end. Amplification of both IP generate products with alternately inverted repeats of the target sequence on the same strand. Unlike PCR, which generates a single-sized product, LAMP generates a series of concatamers that appear like a ladder that merges into a smear at higher molecular weights when analyzed by electrophoresis.

There are two major versions of LAMP: one uses 4 primers and a modified version that uses 6 primers. The version with 6 primers can be twice as fast. The 4 primers in the first version may be called: FIP (Forward Inner Primer); F3; BIP (Backward Inner Primer); and B3. The modified version contains an additional 2 primers: Loop F primer and Loop B primer. FIP (BIP) consists of the sequence of the F1c (B1c) and F2 (B2) regions. F1, F2, F3 are about 20 bp long sequences selected from the target gene. B1, B2, B3 are about 20 bp long sequences selected from the complementary strand. F1c and F1, B1 and B1c are complementary regions.

The LAMP reaction is initiated by a tailed forward primer (FIP) that anneals to the target sequence (F2c). DNA polymerase displaces the complementary strand through 3' primer extension. *Thermus aquaticus* DNA polymerases used for PCR are not suitable for LAMP because they have 5' to 3' exonuclease activity, which would degrade rather than displace the complementary strand. Instead, LAMP usually uses a modified version of the DNA polymerase large fragment from thermophilic *Bacillus stearothermophilus*.

The 5' tail (F1c) of the forward primer FIP is complementary to a portion of the amplicon sequence (F1). The newly synthesized strand is displaced by extension of a second forward primer (F3) that binds distally to the first primer. A tailed reverse primer binds to sequence E in both newly synthesized strands (Step 3). The 5' tail of the reverse primer (D') is complementary to target sequence D. Extension of the reverse primer generates the complement of the first strand. The second reverse primer binds distal to the first reverse primer and displaces the newly synthesized reverse strand.

The displaced strand is one of two intermediate products, and where the magic begins: the 3' end of the reverse strand now ends with sequence A, which is complementary to the internal sequence A'. The 3' end forms a hairpin. The 3' end primes the DNA polymerase, which uses the internal sequence serves as a template for DNA synthesis. The LAMP reaction cycles between two intermediate dumbbell products (Tanner and Evans, *Current Protocols in Molecular Biology* 15.14.1-15.14.14, January 2014).

LAMP amplification may proceed at a temperature that facilitates a strand displacement reaction. The temperature may range from about 40° C. to about 85° C. The temperature may range from about 60° C. to about 65° C. LAMP amplified products may have a structure comprising alternately inverted repeats of the target nucleic acid sequence on a single strand. Such amplification methods may be highly specific for amplification of a target nucleic acid, and may result in rapid amplification of the target nucleic acid, generating, for example $10^9$ copies in less than 1 day. LAMP amplification may be directed to mRNA gene expression studies, for example, by addition of a reverse transcriptase to a LAMP amplification reaction mixture or using a polymerase with reverse transcriptase activity.

The device may comprise a microfluidics device configured for performing an isothermal amplification reaction. The microfluidics device may be configured for performing a LAMP amplification assay. The LAMP amplification assay can be carried out via a microfluidic compact disc device. The microfluidic compact disc device can further be configured to detect amplified products by electrochemical detection. FIG. 1D depicts an exemplary device that comprises a microfluidics device.

Amplifying the target nucleic acid(s) of the cellular specimen may comprise contacting the target nucleic acid(s) with one or more endoribonucleotide primers. The endoribonucleotide primer may comprise a blocking group (e.g. 3' blocking group), such that the polymerization reaction will not proceed until the blocking group is removed. The blocking group may be removed by an enzyme. The enzyme may be a polymerase with proofreading capability. The enzyme may be a protease. The enzyme may be a restriction enzyme. The enzyme may be a nuclease. The nuclease may be an endonuclease or an exonuclease. The nuclease may be an endoribonuclease. The nuclease may be an RNAse. The RNAse may be an RNAseH. The RNAseH may be RNAseH2.

SDA amplification may refer to an isothermal amplification technique based upon the ability of a restriction endonuclease to nick the unmodified strand of a hemiphosphorothioate form of its recognition site. Exemplary restriction endonucleases suitable for SDA amplification include HincII, BsoBI, and an engineered nicking endonuclease. The engineered nicking endonuclease may be Nt.Bst.NB1. SDA may also employ an exonuclease deficient DNA polymerase such as Klenow exo minus polymerase, or Bst polymerase, to extend the 3'-end at the nick and displace the downstream DNA strand. SDA amplification may comprise coupling sense and antisense reactions in which strands displaced from a sense reaction serve as targets for an antisense reaction and vice versa, resulting in exponential amplification. SDA amplification is described in Westin et al. 2000, *Nature Biotechnology*, 18, 199-202.

Figure 8:
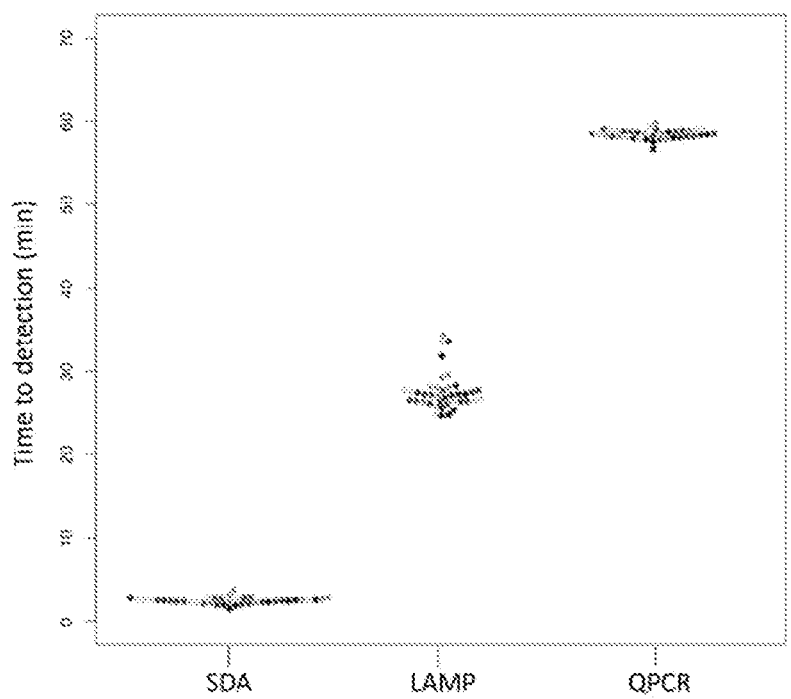
FIG. 8 shows a BeeSwarm plot comparing targeted DNA amplification methods.

FIG. 8 demonstrates that SDA is faster than either LAMP or qPCR, and has the least amount of variation between experimental and technical replicates.

Endoribonucleotide Strand Displacement Assay (ERIN SDA)

Primer-based nucleic acid amplification reactions depend on the specificity of the primer hybridization to the template. Isothermal methods typically proceed at lower temperatures, which permit off-target primer hybridization and amplification of undesired templates. Non-specific amplification has two opposing disadvantages. In some cases, it can be detected as a false-positive result. In other cases, non-specific amplification competes with the amplification of the intended template, and can lead to false negative results. Specificity is therefore an important characteristic of isothermal methods used for clinical applications.

One strategy to increase specificity is the modification of primers to prevent 3' strand extension. Primers are only activated once they hybridize to the template nucleic acid and are cleaved by an enzyme such as RNase H. For example, primers may consist of (1) a modification that prevents 3' strand extension by DNA polymerase, and (2) a single ribonucleotide near the 3' end that serves as a cleavage site for RNase H. The described primers would be inactive in solution, and only cleavable when hybridized to the template nucleotide. Cleavage by RNase H removes the bases 3' to the ribonucleotide cleavage site, leaving an accessible 3'-OH group available as a substrate for 3' strand extension by the DNA polymerase. In other words, the primer is only activated when hybridized to its specific template.

Walder, et al. (U.S. Pat. No. 8,911,948) note that this strategy has been employed using RNase as the cleaving enzyme in cycling probe assays, in PCR assays (Han et al., U.S. Pat. No. 5,763,181; Sagawa et al., U.S. Pat. No. 7,135,291; and Behlke and Walder, U.S. Pat. App. No. 20080068643) and in polynomial amplification reactions (Behlke et al., U.S. Pat. No. 7,112,406). These methods are limited by several limitations, including the requirement for an expensive hot-start DNA polymerase. The assays have also been limited by undesirable cleavage of the oligonucleotide primer used in the reaction. Undesirable cleavage can include water and divalent metal ion catalyzed hydrolysis 3' to RNA residues, hydrolysis by single-stranded ribonucleases and atypical cleavage reactions catalyzed by Type II RNase H enzymes at positions other than the 5'-phosphate of an RNA residue.

Others have attempted to overcome these limitations with an optimized RNase H enzyme. Some optimized assays consist of thermophilic or mesophilic RNase H. The disadvantage of RNase H PCR is the requirement for high-concentration enzyme. High-concentration RNase H is extremely expensive. In addition, many of these methods have been developed for PCR, which is slow and requires a thermocycler.

Isothermal amplification offers several advantages over PCR. Isothermal methods do not require a thermocycler, and enzyme-based methods have the potential to be much faster than heat-based thermocycling reactions. The combination of speed and fewer hardware requirements makes isothermal methods attractive for point-of-care applications and environments with limited resources. In addition, reductions in the analysis time provide major advantage for routine applications in existing labs. However, the potential of isothermal has been limited by non-specific amplification and the need for complex primer design (e.g. in loop-mediated amplification). These reasons contribute to the focus of isothermal methods primarily on simple genomes like bacteria, which do not exhibit the background seen in complex genomes like humans.

As an example, strand-displacement amplification can be performed with genetically engineered polymerases (e.g. Bst2.0). Under optimized conditions, SDA can amplify target sequences in less than 2 minutes. However, the utility of the assay is limited by background amplification. For example, SDA amplifies no-template controls (NTCs) in less in 5-6 minutes.

The ubiquity of molecular diagnostic techniques has made analysis time an important challenge. The disclosed assay has advantages over other strategies to increase the speed of nucleic acid analysis. For example, Neuzil, et al. developed a rapid PCR that can be performed in six minutes (Pavel Neuzil, Chunyan Zhang, Juergen Pipper, Sharon Oh, and Lang Zhuo. Ultra fast miniaturized real-time PCR: 40 cycles in less than six minutes. *Nucleic Acids Research*, 2006, Vol. 34, No. 11 e77). However, such rapid PCR is limited by hardware, sample number, may require confocal optical detection.

Until now, SDA has been limited to simple targets like bacterial genomes, which have minimal complexity. The initial draft of the human genome revealed why applications of SDA have been limited to simple genomes: in contrast to bacterial genomes, which have minimal repetitive sequences, 50% of the human genome is composed of repetitive sequences (PMID 11237011). Complex genomes often require primer sequences in less than optimal locations. Complex genomes create challenges for assays like SDA where repetitive elements constrain primer design and frequently require primers with partial 3' complementarity.

This invention discloses methods that combine the advantages of rapid isothermal methods and specific amplification.

These methods are generally referred to herein as endoribonucleotide strand displacement assay (ERiN SDA).

ERiN SDA comprises isothermal amplification that balances specificity, sensitivity and unprecedented speed relative to traditional SDA or PCR. ERiN SDA may amplify targets from a complex genome (e.g. human genome) in less than 2 min, while reducing background amplification that occurs in existing isothermal amplification methods.

ERiN SDA does not require the use of RNaseH, which substantially decreases the cost of each reaction. It provides simple primer design. Since the initiation kinetics are limited to the binding and dissociation of multiple enzymes, the method can be used to amplify templates rapidly. Thus, the advantages of ERiN SDA include speed, specificity, reduced cost, and elimination of background. In contrast to rhPCR, the reaction does not contain RNase and can therefore be directly used to analyze RNA in a single-tube reaction with an enzyme that contains reverse transcriptase activity. ERiN SDA may improve analysis of routine and difficult targets.

ERiN SDA offers advantages for routine clinical labs. As an example, the outbreak of Zaire ebolavirus exposed limited domestic testing capabilities in the U.S. and Europe. Since only a limited number of labs are authorized by the Department of Defense to perform testing for dangerous pathogens like Zaire ebolavirus, the throughput of each lab limits the number of samples that can be processed during an emergency. Testing delays impact quarantine and clinical treatment decisions. The disclosed methods provide rapid methods that can be implemented on existing diagnostic systems, which can be used without additional training or capital investments. For example, during the outbreak, the FDA granted emergency use authorization for a real-time PCR test developed by the Naval Medical Research Unit. This test takes an hour to analyze 14 samples in triplicate. In contrast, the methods described herein would require (as a conservative maximum) 15 minutes on the instrument. The disclosed methods could therefore immediately quadruple the nation's diagnostic throughput by increasing the number of samples that existing labs can process using existing equipment and protocols. This example illustrates advantages of the disclosed methods for existing laboratories. In addition, these methods enable decentralized testing. The disclosed methods do not require thermocyclers, and can be performed by personnel with limited training in settings with limited resources. Exemplary ERiN primer sequences and exemplary ERiN SDA method is demonstrated in Example 17.

ERiN SDA may comprise residues that are resistant to enzymatic cleavage (e.g. nuclease cleavage). Residues that are resistant to enzymatic cleavage are generally incorporated in the primer, 3' to the RNA residue. Residues and groups that confer resistance to enzymatic cleavage include one or more abasic residues (e.g. C3 Spacer), phosphorodithioates, phosphorothioates, and methyl phosphonates. In some cases these residues can be used to control the kinetics of the enzymatic cleavage reaction that activates the primer.

ERiN SDA may employ internal primers with 5' tails that contain a recognition sequence for an endonuclease. The endonuclease may be BsoBI. BsoBI is compatible with optimal buffer and temperature conditions for the DNA polymerase Bst2.0 (New England Biolabs). The DNA polymerase may incorporate a modified deoxyribonucleotide. In one implementation of SDA, the DNA polymerase may incorporate thiolated dCTP into the nascent strand (e.g., 2'-deoxycytidine-5'-O-(1-thiotriphosphate) [dCTP$_{\alpha S}$]). Under normal conditions, the endonuclease cleaves both strands of the recognition site; however, the newly formed strand is resistant to endonuclease cleavage because SDA is performed with the modified deoxyribonucleotide. For example, the top strand of the BsoBI site (C/TCGGG) is cleaved, but the newly synthesized complementary strand contains dCTP$_{\alpha S}$ (GAGC$_{\alpha S}$C$_{\alpha S}$/C$_{\alpha S}$), which is incorporated into dsDNA through phosphorothioate linkages which are resistant to BsoBI. Under this strategy, the endonuclease nicks the top strand. The nicked top strand has a 3'-OH and serves as a primer for 3' strand extension.

ERiN SDA may employ external primers ("bump primers") to increase reaction kinetics by initiating synthesis distal to the internal primers and displacing the newly synthesized strand formed by the internal primer. ERiN SDA may use nested primers (forward and reverse tailed, inner primers; and forward and reverse untailed, outer primers).

Figure 9:
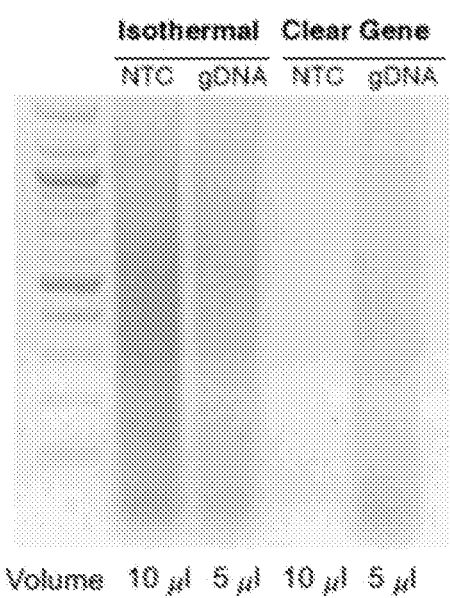
FIG. 9 shows an agarose electrophoresis gel of ERiN SDA amplification product.
Figure 10:
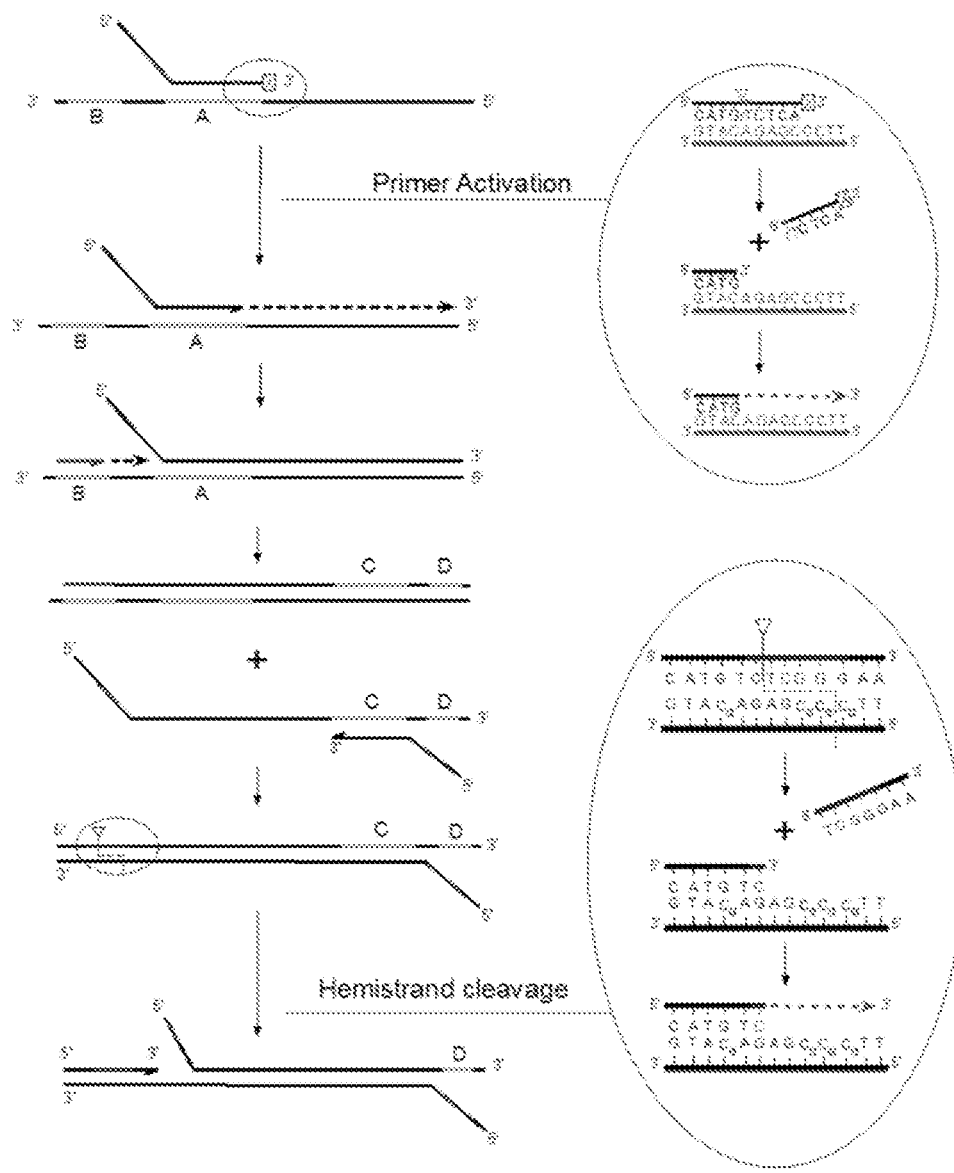
FIG. 10 shows key steps of the ERiN SDA mechanism.
Figure 11:
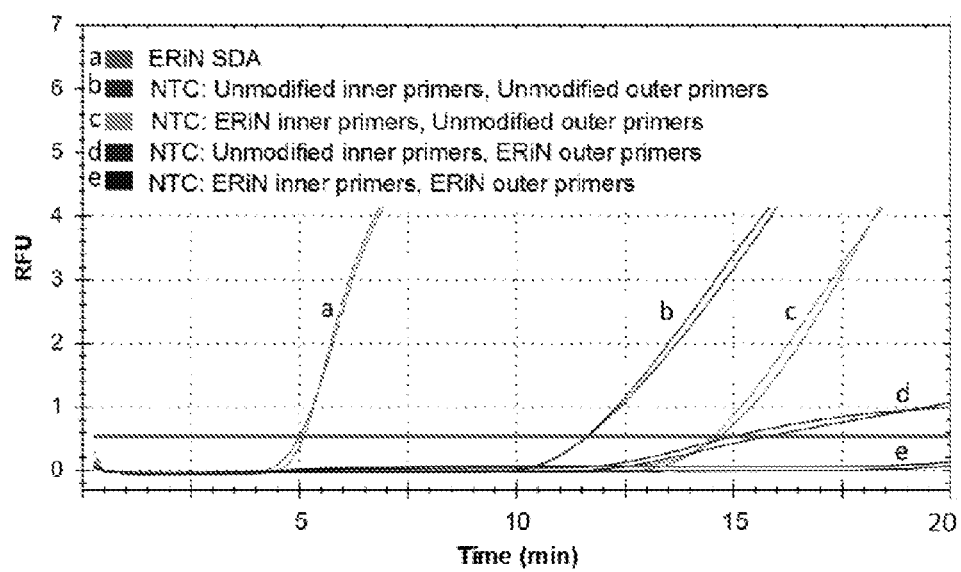
FIG. 11 shows ERiN Primers eliminate background from SDA in the absence of RNase H2.

ERiN SDA primers may be modified primers. Modified primers may be used to overcome non-specific amplification. ERiN SDA primer modifications may decrease background. Modified ERiN SDA primers may delay NTC amplification. Modified ERiN SDA primers may eliminate NTC amplification. ERiN SDA primer modifications may eliminate background amplification when used on both inner and outer primers. FIG. 9 shows ERiN SDA eliminates background, as demonstrated by agarose electrophoresis in tris-acetate EDTA buffer (Lane A: 100 bp DNA ladder; Lane B: SDA no template control (NTC); Lane C: SDA human genomic DNA template (purified from HeLa cells); Lane D: ERiN SDA (NTC); Lane E: ERiN SDA human genomic DNA template (purified from HeLa cells); volume is doubled in NTC lanes to further demonstrate that ERiN modification reduce background in SDA). The simplified mechanism of endoribonucleotide (ERiN) primers is illustrated in FIG. 10. There are two components to the ERiN primer strategy. First, the 3' terminus of ERiN primers are blocked and cannot be amplified until the blocking group is removed (FIG. 10). Second, ERiN primers are specifically activated when they in complex with their target sequence (see Primer Activation, FIG. 10). ERiN SDA prevents the amplification of no template controls (NTC) beyond the widely used 20 min cutoff time of traditional SDA (FIG. 11, see data for experimental "e"). ERiN primers therefore overcome the primary limitation of SDA.

The tail of the first primer contains a recognition site for the endonuclease. SDA replaces dCTP with a modified cytidine, such as, by way of non-limiting example, 2'-Deoxycytidine-5'-O-(1-Thiotriphosphate) (C$_{\alpha S}$). C$_{\alpha S}$ blocks endonuclease cleavage of the newly synthesized strand, resulting in hemistrand cleavage. The endonuclease cleavage generates a 3'-hydroxyl group that can be extended by DNA polymerases. The combination of isothermal stand extension and hemicleavage of the resulting amplicon continuously generates template.

Figure 12A:
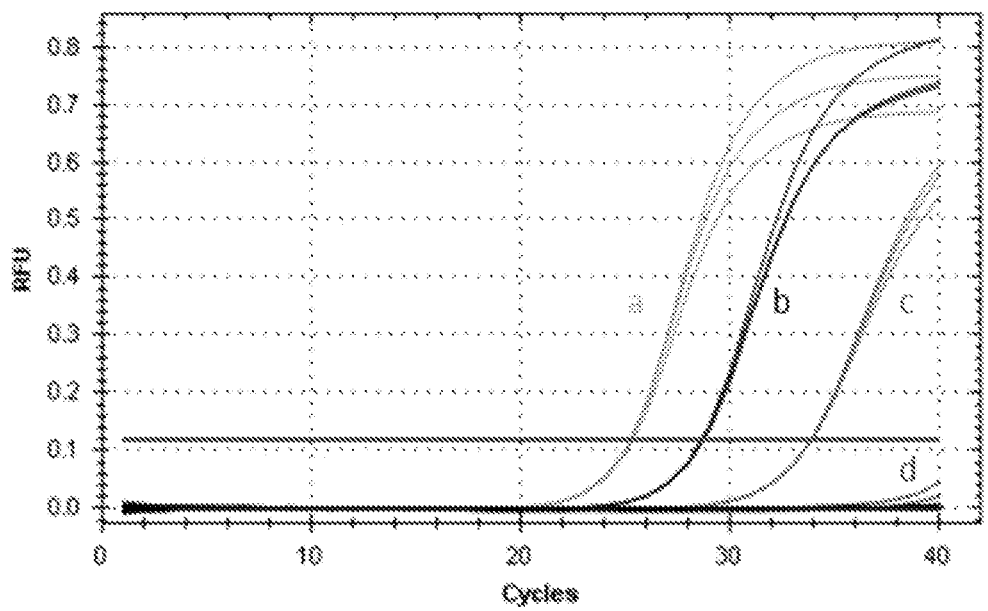
FIG. 12A shows RNase H2 is required to activate ERiN primers in PCR.

ERiN primers do not require RNase H2 in stark contrast to the requirement for RNase H2 for PCR (see, e.g., FIG. 12A). This can be used to solve two primary challenges. First, RNase H2-dependent assays (e.g. RNase H2-dependent PCR, rhPCR, (Dobosy et al., 2011)) require high concentrations of RNase H2 with high activity. High concentrations of RNase H2 with high activity are expensive, and cost prohibitive for many applications, including resource-limited settings for which isothermal amplifications are ideally suited. Second, RNase H2 has specific buffer and temperature requirements, which limit the range of reaction conditions under which RNase-dependent methods can be performed, and may inhibit the RFU$_{max}$ in SDA (see, e.g., FIG. 12B). A major disadvantage of assays that require RNase (e.g. RNase H-dependent PCR (rhPCR) and RNase H-dependent LAMP (rhLAMP)) is that primers for cDNA synthesis form targets for RNase when they hybridize to the template RNA. RNase-dependent assays are therefore not suitable for analysis of RNA because they degrade the template RNA. This is particularly problematic for applications that require cDNA synthesis and amplification in the same tube. For example, performing cDNA synthesis and clean-up as separate steps before cDNA amplification introduces errors that complicate the accurate quantification of RNA. Applications for rhPCR are therefore primarily limited to discriminating single nucleotide variations (e.g. SNPs) and other sequences with high similarity. Thus these results indicate RNA can be directly amplified if the DNA polymerase contains reverse-transcriptase activity, allowing for cDNA synthesis and cDNA amplification to be performed in the same tube. The fact that RNase is not necessary to activate ERiN primers can therefore be used to reduce the cost of performing a rapid, specific assay, and increases the range of conditions where ERiN primers can be utilized (e.g. single-tube cDNA synthesis and amplification), while increasing sensitivity/accuracy by decreasing background. ERiN SDA primers may also be used for loop-mediated isothermal amplification (LAMP) without the requirement for the RNase H2 enzyme.

ERiN SDA may employ a DNA polymerase. The DNA polymerase may be an engineered version of a Bst DNA polymerase or large fragment thereof.

The key steps of the ERiN SDA mechanism are illustrated in FIG. 10. Primers with EndoRiboNucleotides (ERiN) are cleaved, for example by RNase, generating a 3'-OH that can be extended by DNA polymerases. ERiN primers contain a blocking group on the 3' terminus that prevents their extension until they are cleaved by RNase H2. RNase H2 specifically recognizes RNA-DNA heteroduplexes and has a low tolerance for mismatches. ERiN primers are therefore only activated when they bind their target DNA sequence.

ERiN SDA may be performed in a volume of about 5 µl, about 10 µl, about 15 µl, about 20 µl, about 25 µl, about 30 µl, about 35 µl, about 40 µl or about 50 ERiN SDA may be performed in a 25 µl volume.

ERiN SDA primers may amplify low concentrations of a target nucleic acid from human genomic DNA in a short period of time. ERiN SDA primers may amplify low concentrations of a target nucleic acid in less than about 20 minutes, less than about 18 minutes, less than about 16 minutes, less than about 14 minutes, less than about 12 min, less than about 10 minutes, less than about 8 minutes, less than about 6 minutes, less than about 4 minutes, less than about 2 minutes, or less than about 1 minute.

Low concentrations of a target nucleic acid may be selected from about 1 copy per µl, about 5 copies per µl, about 10 copies per µl, about 5 copies per µl, about 10 copies per µl, about 15 copies per µl, about 20 copies per µl, about 25 copies per µl, about 30 copies per µl, about 35 copies per µl, about 40 copies per µl, about 45 copies per µl, about 50 copies per µl, about 55 copies per µl, about 60 copies per µl, about 65 copies per µl, about 70 copies per µl, about 75 copies per µl, and about 100 copies per µl.

ERiN SDA provides a method to detect specific nucleic acid sequences in less than 2 minutes, with undetectable background. The BCDC provides a panel of biomarkers that can distinguish all invasive breast cancers from healthy tissue. Combining these two advances generates a test that can rapidly detect all invasive breast cancers.

Clinical screening tests require a detection time that is 2 standard deviations greater than the mean detection in order to confidently detect 95% of the analytes at the limit of detection ($LoD_{95\%}$). Many clinical tests require greater confidence (e.g. the test must detect 99.7% of analytes). On average, no template controls (NTC) in SDA amplify within 12 min (see, e.g., FIG. 12B), which constrains the LoD. FIG. 13 illustrates the importance of reducing background amplification. The maximum reaction time of an assay is defined by the earliest time that a NTC replicate ever amplifies, which in this case is just greater than 18 min. The time required to detect 25 targets at a concentration of 25 copies/µl with a standard deviation of 2 is 16 min. The time required to detect 25 targets at a concentration of 25 copies/µl with a standard deviation of 3 is 18 min. ERiN primers reduced background and therefore raised the $LoD_{99\%}$ to 25 copies per microliter. This is the statistical mechanism through which ERiN primers increase assay sensitivity. FIG. 13 shows that the $LoD_{99\%}$ for SDA is greater than any of the tested concentrations. Since the LoD of SDA without ERiN primers is greater than 125 copies/µl, ERiN SDA primers increase the sensitivity of SDA by at least 5-fold.

Isothermal amplification does not require a thermocycler. However, isothermal amplification may require a temperature regulator. The temperature regulator may keep the temperature of the nucleic acid analysis unit constant. The temperature regulator may keep the temperature of the nucleic acid analysis unit within a mean of about 0.1 degree, about 0.2 degree, about 0.3 degree, about 0.4 degree, about 0.5 degree, about 0.6 degree, about 0.7 degree, about 0.8 degree, about 0.9 degree, about 1 degree, about 2 degrees, about 3 degrees, about 5 degrees, about 8 degrees or about 10 degrees of a single temperature. The temperature regulator may deviate less than 5%, less than 3%, less than 1%, less than 0.1%, less than 0.01%, less than 0.001%, or less than 0.0001% from the target temperature.

Thermocycling PCR

The nucleic acid analysis unit may, alternatively or additionally, be capable of performing an amplification reaction of the target nucleic acid, wherein the amplification reaction requires two or more temperatures. The amplification reaction may require a thermocycler. The amplification reaction may be selected from a traditional polymerase chain reaction (PCR) amplification, a ligase chain reaction (LCR), a ligase detection reaction (LDR), a multiplex PCR reaction, a nested PCR reaction, a real-time PCR amplification, a loop-mediated amplification (LAMP), a rolling circle amplification, a reverse transcription, an isothermal amplification, a strand displacement amplification (SDA), and a combination thereof.

The method of performing a polymerase chain reaction is well known and well understood in the art. Many modification and variations have been developed. Briefly, a polymerase chain reaction involves cycles of annealing a pair of primers to complementary regions of the target nucleic acid, and extending the primers with free nucleotides using a nucleic acid polymerase. This generally involves heating the target nucleic acid, adjusting the temperature of the reaction to an optimal primer annealing temperature, and further adjusting the temperature of the reaction to an optimal polymerizing temperature. The process is repeated for a number of cycles until the target nucleic acid has been amplified sufficiently for subsequent use/analysis. The number of cycles may be about 5 to about 50. The annealing temperature may be about 40 degrees Celsius to about 80 degrees Celsius. The PCR may be performed on a complementary DNA (cDNA) reverse transcribed from RNA. The PCR may be performed in the same reaction container as the reverse transcribing. The method may further comprise adding a ribonuclease to the reaction container after the PCR, in order to remove/destroy the RNA before subsequent use/analysis of the amplicons produced by PCR.

The PCR may be an RNase H dependent PCR. RNase H dependent PCR (rhPCR) may comprise the use of an RNase H and one or more blocked rhPCR primers. The RNase H may be RNase H2. The RNase H2 may be from *Pyrococcus abyssi*. A blocked rhPCR primer may include an RNA base, and optionally a C3 spacer, at or near the 3' end of the rhPCR primer, which blocks DNA polymerase-mediated extension of the rhPCR primer. When the rhPCR primer anneals to a DNA template, it creates an RNA:DNA base pair that is recognized by RNase H. RNase H cleaves the primer at this cite, removing the blocking modification, thereby allowing the DNA polymerase-mediated extension to progress. rhPCR is typically more specific than traditional PCR because the RNase H only cleaves the rhPCR primer when the primer has annealed and when there are no mismatches between the rhPCR primer and complementary target sequence.

Nucleic Acid Detection

The devices disclosed herein may comprise a means for detecting the target nucleic acids. The device may comprise a nucleic acid detection unit that detects the target nucleic acid(s) and/or other nucleic acids in the cellular specimen. Detecting target nucleic acids may be based on a predetermined threshold for a target nucleic acid. Detecting the target nucleic acid may be based on a dynamic threshold. Detecting the target nucleic acid may be quantitative. Detecting the target nucleic acid may be qualitative. Detecting the target nucleic acid may be based on a previously calibrated titration curve. The devices disclosed herein may comprise a nucleic acid detection unit that detects the target nucleic acid. The nucleic acid detection unit may share a reaction chamber/volume/solution with the nucleic acid analysis unit, the computation unit and/or the sample input unit. The nucleic acid detection unit may be combined in a reaction chamber/volume/solution with the nucleic acid analysis unit, the computation unit and/or the sample input unit. The nucleic acid detection unit may be a distinct reaction chamber/volume/solution from the nucleic acid analysis unit, the computation unit or the sample input unit. Target nucleic acids, whether amplified or non-amplified, may be detected by various means known to those of skill in the art or otherwise described herein. The target nucleic acids may be selectively amplified, and the amplification process may comprise production of a detectable signal. For instance, in some cases, amplification may comprise a rapid nucleic acid synthesis reaction that produces detectable ions (e.g., pyrophosphate ions) as synthesis byproducts. In some cases wherein target nucleic acids are selectively amplified, amplification may introduce a detectable moiety to the amplified products. The detectable moiety may be any molecule that enables detection of the target. Exemplary detectable moieties include, but are not limited to, chelators, fluorescent agents, luminescent agents, photoactive agents, radioactive moieties (e.g., alpha, beta and gamma emitters), paramagnetic ions, and enzymes that produce a detectable signal in the presence of certain reagents (e.g., horseradish peroxidase, alkaline phosphatase, glucose oxidase). The cDNA synthesis and amplification steps may be enhanced by coating elements of the nucleic acid testing unit with a non-stick coating. Elements of the nucleic acid testing unit may include the reaction chambers. The non-stick coating layer may be formed by a polymeric silicon dioxide layer (SiO2-SiO2)n that binds to polytetrafluoroethylene (PTFE) (CF2-CF2)n (Huang, et al. fM to aM nucleic acid amplification for molecular diagnostics in a non-stick-coated metal microfluidic bioreactor. *Scientific Reports* 4, Article number: 7344. December, 2014.)

The amplification may comprise incorporation of labeled nucleotides comprising a detectable moiety into the resulting amplicon. The amplification may result in generation of double-stranded polynucleotides, which may selectively bind to various intercalating dyes, minor groove binding dyes, and major groove binding dyes. The intercalating dye may be selected from SYTO-9, SYTO-11, SYTO-12, SYTO-13, SYTO-14, SYTO-15, SYTO-16, SYTO-17, SYTO-18, SYTO-19, SYTO-20, SYTO-21, SYTO-22, SYTO-23, SYTO-24, SYTO-25, LCGreen Plus, LCGreenI, EVAGreen, Chromofy, fluorescent nanotags attached to intercalating dyes, thiazole orange. Exemplary intercalating dyes suitable for use in detection of double-stranded polynucleotides include, e.g., methylene blue, ethidium bromide, propidium iodide, and the like. Exemplary minor groove binding dyes include, e.g., 4',6-diamidino-2-phenylindole (DAPI), Hoescht dyes, SYBR GREEN, 4-[(3-methyl-6-(benzothiazol-2-yl)-2,3-dihydro-(benzo-1,3-thiazole)-2-methylidene)]-1-methyl-pyridinium iodide (BEBO), and the like. Double-stranded polynucleotides may also be stained. Exemplary major groove binding dyes include, but are not limited to, methyl green. Intercalating dyes, minor groove binding dyes, and major groove binding dyes may emit a detectable signal upon binding to double-stranded polynucleotides. The amplicons may selectively bind a detectable probe comprising a detectable moiety. For instance, oligonucleotide probes may be designed to selectively bind to the target nucleic acid or amplicon thereof. The oligonucleotide probes may comprise a detectable moiety and optionally a quencher moiety. The probe may be a non-oligo probe such as PNA with a peptide backbone. The quencher moiety quenches the detectable moiety when the probe is in an unhybridized state, but does not quench the detectable moiety when the probe is hybridized to its target sequence. The quencher moiety may quench the detectable moiety when the probe is intact. The probe may selectively hybridize to the amplified target nucleic acid (amplicon). Extension of a primer across the hybridized probe may cleave the quencher moiety from the detector moiety, thus enabling detection of the detector moiety.

Detecting target nucleic acid(s) may comprise a method selected from an electrochemical detection method, an optical detection method, an electrophoretic detection method, and method for assessment of turbidity, and combinations thereof. Optical detection methods include, but are not limited to, fluorescence detection, luminescence, turbidity, and colorimetric assay, among others.

The detection unit may comprise an optical or fluorescent detection system. The detection unit may transform detection of the target nucleic acid or detection of an expression level of the target nucleic acid into an electronic signal. The detection can be in the form of transmitted, reflected, or absorbed light from and internal or external light source. The light can be focused on the sample, or provided in an array of light sources (e.g. an array of light emitting diodes). The light may pass through a filter before, after, or before and after reaching the sample. The excitation and emission filters can have different properties. Sample measurements (e.g. turbidity) can be based on illumination from one direction and detected using light from another angle. The angle between illumination and detection can be 90 degrees. Sample measurements can (e.g. fluorescence, colorimetry) can be made by illuminating the sample from one direction (e.g. above the sample) and detecting light from the same direction (e.g. also above the sample). Sample measurements can be illuminated from one direction (e.g. above the sample) and detected from the opposite direction (e.g. below the sample), where the light source passes through the sample.

The detection unit may comprise an electrical detection system. The electrical detection system may comprise electrochemical detection. Electrochemical detection may comprise use of a probe that interacts with the target nucleic acid or amplicon thereof. The probe may comprise a redox indicator. The probe may comprise a nanoparticle. The probe may comprise a nucleic acid intercalator. The detection unit may transform detection of the probe into an electronic signal. Electrochemical (EC) detection of biologic species or electrochemical sensor is based on electrochemical reactions that occur during biorecognition reactions. These reactions may be exhibited as changes of EC properties (e.g. current/potential, redox kinetics, impedance) or changes of non-EC properties (e.g. conformation changes, mass transportation, van der Waals interactions), resulting in fluctuations of an EC signal. The resultant signal readouts may take the form of an electrical current, electrical potential, or electrical impedance in steady state or in changes thereof during the recognition process, which correspond to the kinetics of recognition. An EC sensor may be ex situ, in which sample pre-treatment and fluidic processing are performed "off-chip." An EC sensor may also be in situ, which incorporates all the sample processing steps "on-chip," and may be more desirable for clinical applications, such as point-of-care diagnosis. Typically, these sensors require higher sensitivity and specificity for non-pretreated samples. Additionally, in situ EC sensors may monitor changes of EC properties, which is more desirable for studying biologic processes during nucleic acid (e.g. DNA, RNA) recognition. For example, LED-based fluorescent detection of real-time PCR can require up to 20 seconds to illuminate the sample and acquire a signal. This timescale was appropriate for PCR methods that proceed over 60-90 minutes. However, rapid amplification methods like ERiN SDA can amplify target sequences from genomic DNA in less than 2 minutes, which creates challenges extracting an amplification curve from 6 data points. In contrast, square-wave voltammetric (SWV) measurement with in situ electrodes can make thousands of measurements per second, providing a higher resolution of the kinetics of rapid amplification reactions (over 115,000 more data points during a 2 minute reaction). In situ electrodes can be used to detect electrically active reporters in solution (e.g. with voltammetry), or to detect interactions with a substrate physically attached to the electrode surface (e.g. with electrochemical impedance spectroscopy).

The EC nucleic acid sensor may comprise an electrode, capture probe and reporter probe. The capture probe may be an element used to recognize and bind to the target nucleic acid(s). The capture probe may comprise a nucleic acid sequence that hybridizes to the target nucleic acid. The capture probe is usually immobilized onto a solid substrate, such as an electrode surface. The target nucleic acid(s) may also be immobilized on nanomaterials or other biomolecules. The reporter probe may be a molecule that generates the EC signal in response to EC reactions. The capture probe and/or reporter probe may be created with high specificity to the target DNA. Additional components, such as electrode coatings and intermediate molecular linkers, may also be commonly integrated for improved sensor performance. The EC nucleic acid sensor may comprise a plurality of capture probes and/or a plurality of reporter probes. The capture/reporter probe(s) may be appropriately varied in accordance with the test, cellular specimen and/or target nucleic acid. Common molecules used as probes (capture and reporter) include, but are not limited to, single-stranded oligonucleotides, aptamers, peptides, and DNA-related proteins. The capture probe and/or reporter probe may be combined together as a single unit for improved integration. The EC nucleic acid sensor may comprise components and/or molecules that are modified or linked with properly integrated nanomaterials. Without being bound by any theory, because of their high surface-to-volume ratios and biologic compatibilities, nanomaterials not only increase the signal intensity but also help to accumulate/separate specific DNA molecules during EC reactions, which greatly improves a single nucleotide read, especially for sequence-specific recognition. A wide variety of nanomaterials may be applied, wherein the most common include metal nanoparticles, cadmium sulfide nanoparticles, CNTs, and SiNWs.

Electrochemical detection of target nucleic acids may employ use of an electroactive indicator which may be a double-stranded DNA (dsDNA) intercalator ("electroactive intercalator"). Electroactive intercalators may include intercalating dyes, major groove binders, and minor groove binders. The electroactive intercalator may be charged and therefore electrically active independent of its association with DNA, or its electrochemical properties may be altered by its interaction with DNA. The electroactive intercalator may remain charged after its association with DNA but the intercalator is sequestered by the DNA and unable to participate in the electrical current. The presence or quantity of double-stranded DNA may be inferred from a reduction in current that corresponds to the sequestration of the electrochemical intercalator in the double-stranded DNA. Exemplary electroactive intercalators include, but are not limited to methylene blue (MB), Malachite Green, Crystal Violet, SYBR Green, and hydroxy napthol blue. In particular embodiments, amplified target nucleic acids are detected using MB electrochemical detection. Intercalation of MB into the amplified target nucleic acid(s) may result in reduction of am oxidation peak current (iPA) and reduction peak current (iPC), which may be monitored by voltammetry. Such monitoring may provide a quantitative indication of amplicon concentration: e.g., a decrease in the reduction peak current may indicate an increase in MB intercalation due to generation of double-stranded amplicons (see, e.g., Kivlehan, et al., 2011; Defever, et al., 2011). Similarly, intercalation of Malachite Green, Crystal Violet, SYBR Green, and hydroxy napthol blue may result in reduction of the oxidation peak current (iPA) and reduction peak current (iPC), which may also be monitored by voltammetry. Such methods may be used to assess relative concentrations of target sequences, and infer absolute concentrations with spiked standards. Voltammetry methods suitable for a method described herein may include, e.g., linear sweep voltammetry, staircase voltammetry, squarewave voltammetry, cyclic voltammetry, and the like.

Electrochemical detection of target nucleic acids may employ use of a nanoparticle. The nanoparticle may be conjugated to the capture probe, reporter probe or electrode. The nanoparticle may increase detection sensitivity. The nanoparticle may comprise a metal sulfide. The nanoparticle may comprise platinum. The metal sulfide may be cadmium sulfide, zinc sulfide or lead sulfide. The nanoparticle may be captured with a gold substrate.

The electronic detection system may provide for a reduced cost and complexity of the system relative to an optical detection system, which would otherwise require optical components to generate, transmit, focus, align and detect light. For example, ultra-micro electrical probes can be manufactured using nano-imprinted lithography (NIL) (see, e.g., Ferrario, et al. Prospective of Using Nano-Structured High Performances Sensors Based on Polymer Nano-Imprinting Technology for Chemical and Biomedical Applications. *Sensors and Biosensors* 54; 2010, pp 197-200). NIL can be combined with imprint-based microfluidic (MI) manufacturing to produce microfluidic circuits with integrated microelectrodes. Combining NIL and MI manufacturing can cost-effectively scale production of disposable microfluidic test cartridges with electrochemical detectors for ~80.50 USD. The electronic detection system may comprise a local control device (see, e.g., FIG. 3 component 321). The electronic detection system may comprise an electronic reader board (see, e.g., FIG. 1 component 134) which interfaces with a testing subsystem through a clamp. The electronic signal may be processed by a microprocessor in the local control device. An integrated touch screen (see, e.g., FIG. 3 component 345) may display instrument status, identities of the selected test, subject information, and/or user information; testing parameters; testing progress; and final results. The EC sensor may be based on controlling the biorecognition process with transducers and/or controllers. Exemplary EC sensors are described in Wei et al., "DNA diagnostics: Nanotechnology-enhanced electrochemical detection of nucleic acids", Pediatric Research (2010) 67, 458-468; doi:10.1203/PDR.0b013e3181d361c3.

The nucleic acid detection unit may be capable of performing a fluorescence detection method. The nucleic acid detection unit may comprise one or more fluorescence detection device. Fluorescence detection may be achieved using a variety of fluorescence detection devices. The fluorescent detector device may comprise one or more of (i) a light source configured to generate excitation light, which excitation light may excite a fluorophore to generate emission light and (ii) a light detector configured to detect emission light. The light source may be a laser light source, or may be a small light source such as, e.g., an LED or chip-mounted laser. The light detector may be, without limitation, a CCD camera, a confocal detection system, a complementary metal-oxide-semiconductor (CMOS) light sensor, or N-type metal-oxide-semiconductor (NMOS) light sensor.

The nucleic acid detection unit may be capable of performing a luminescence detection method. The nucleic acid detection unit may comprise one or more luminescence detection device. An exemplary approach for luminescence detection of target nucleic acids employs the use of switchable lanthanide chelate complementation probes. The switchable lanthanide chelate complementation probes may be designed to hybridize to adjacent or nearly adjacent sequences on a target nucleic acid. One probe may comprise a non-fluorescent lanthanide ion carrier chelate, and another probe may be labeled with a light absorbing antenna ligand. Hybridization of both probes to the target nucleic acid may bring them in sufficiently close proximity to induce formation of a detectable lanthanide chelate complex. Switchable lanthanide chelate complementation reporter technology may minimize background signal and induce highly specific target-specific signal generation.

The nucleic acid detection unit may be capable of performing a colorimetric detection method. The nucleic acid detection unit may comprise one or more colorimetric detection device. Colorimetric detection of target nucleic acids may employ use of labeled nucleotides in a target-specific amplification reaction mixture. The nucleotides may be labeled with a detectable label such as, e.g., biotin. Incorporation of the labeled nucleotides into target amplicons may then be detected by any means known to those of skill in the art. For example, in cases wherein biotinylated nucleotides are incorporated into the target amplicons, detection may comprise removal of unincorporated labeled nucleotides, followed by addition of labeled avidin or streptavidin. The avidin or streptavidin may be labeled with any detectable moiety. Exemplary detectable moieties are described herein. The detectable moiety is horseradish peroxidase. The horseradish peroxidase may be reacted with a substrate to produce a colorimetric signal, which may be detected by any means known to a skilled artisan.

The nucleic acid detection unit may be combined or integrated with another unit of the device. The nucleic acid detection unit may be combined or integrated with another unit of the device in the same reaction chamber/volume. The nucleic acid detection unit may be combined or integrated with the nucleic acid analysis unit where reactions such as, e.g., cDNA synthesis and/or amplification occur. The reaction chamber may contain a multi-electrode cell and other components for performing voltammetry measurements. In other embodiments, the nucleic acid analysis unit comprises a first reaction chamber where reactions such as, e.g., cDNA synthesis and/or amplification occur, and a downstream second reaction chamber comprises the nucleic acid detection unit containing a three-electrode cell and other components for performing voltammetry measurements. The multi-electrode cell may comprise about 2 electrodes to about 10 electrodes. The multi-electrode cell may comprise about 2 electrodes to about 20 electrodes. The multi-electrode cell may comprise about 2 electrodes to about 100 electrodes. The cell may contain 4 electrodes. Alternatively, the cell may contain a series of electrodes that take multiple readings of the sample fluid volume. The device may be configured for multiplex detection. The nucleic acid analysis unit of such a device may comprise a plurality of addressable reaction chambers. Amplification and detection of each target nucleic acids may occur in separate addressable reaction chambers.

The three-electrode cell may comprise a working electrode, a reference electrode, and a counter electrode. The three-electrode cell may be operably linked to a potentiostat. The potentiostat may comprise hardware configured to control and maintain a voltage difference between the working electrode and the reference electrode. The potentiostat may control and maintain a voltage difference between the working and reference electrodes by adjusting the current at an auxiliary electrode. The potentiostat may be operably linked to a computer system. Exemplary computer systems are described herein. The computer system may comprise a computer-executable code for controlling the operations of the potentiostat. The computer system may comprise one or more of: a user interface which enables a user to control the operations of the potentiostat, and a computer readable medium for storing voltammetry data. The electrodes may be microelectrodes or ultra-micro electrodes. Electrodes may be comprised of a metal, e.g., gold, silver, or some combination of these metals. Electrodes may be coated or functionalized with a chemical substrate or a biologic substrate. The electrode system and potentiostat may be configured to perform square wave voltammetry.

The nucleic acid detection unit may detect the target nucleic acid(s) in real-time, e.g., during the course of the amplification reaction, and/or may comprise endpoint detection, e.g., following termination of an amplification reaction.

Any of the foregoing processes, e.g., sample lysis, nucleic acid extraction, and nucleic acid analysis, including detection, may be carried out by a microfluidics device. The microfluidics device may comprise components such as valves, mixers, channels, plates, centrifugal force elements, pumps, electrowetting apparatuses, droplet generators, droplet actuators, reaction chambers, and other components configured to enable movement and/or partitioning of fluids within the device. Droplet actuators may be configured to effect droplet movement and operations such as, e.g., dispensing, splitting, transporting, merging, mixing, agitating, and the like. The microfluidics device may comprise components for temperature control, storage and/or dispensation of reagents, and detection. The systems disclosed herein may comprise modular elements that may be integrated into multiple applications. Exemplary microfluidics devices suitable for any of the devices and methods described herein may comprise, but are not necessarily limited to, chips, circuits, compact discs, and the like.

The device may further comprise a non-nucleic acid analysis unit and/or a non-nucleic acid detection unit. The non-nucleic acid analysis and/or detection unit may analyze and/or detect a protein, a peptide, metabolite or gas. The protein, peptide, metabolite or gas may be located on/in a cell, a cellular membrane, an intracellular membrane, an extracellular matrix, a space between cells of the cellular specimen, or a biologic fluid.

The nucleic acid analysis unit may obtain target nucleic acid sequence information from the target nucleic acid. The nucleic acid analysis unit may comprise an oligonucleotide. The nucleic acid analysis unit may obtain target nucleic acid sequence information from the target nucleic acid by hybridization of the oligonucleotide to the target nucleic acid. The oligonucleotide may be a probe or a primer. The probe or primer may only bind the target nucleic acid if the sequence of the probe or primer is at least 80%, at least 85%, at least 90%, at least 95%, at least 96%, at least 97%, at least 98%, at least 99%, or at least 100% complementary to a corresponding sequence in the target nucleic acid. The nucleic acid analysis unit may obtain target nucleic acid sequence information from the target nucleic acid by a method selected from sequencing, primer amplification, probe hybridization or lack of any thereof, and combinations thereof. The target nucleic acid sequence information may comprise information selected from a sequence of the target nucleic acid or portion thereof and an expression level of the target nucleic acid.

The nucleic acid analysis unit may further detect information about a sequence of the target nucleic acid. The sequence may comprise a mutation that is associated with the presence or risk of a condition or disease. The sequence may be associated with a response to a treatment for the condition or disease. The response may be positive or negative. The sequence may be associated with the absence of a condition or disease. The sequence may be associated with a healthy or normal condition. The sequence may be a wild-type sequence. The sequence may not possess a mutation.

E. Computational Unit

The devices disclosed herein may comprise a computational unit for interpreting the target nucleic acid expression level as a level that is indicative of the absence, presence or risk of a condition or disease. The devices disclosed herein may comprise a computational unit for comparing the target nucleic acid expression level to a reference expression level. The target nucleic acid expression level and/or the reference expression level may be a relative expression level or an absolute expression level. The reference level may be provided by the classifier. The reference level may be a range of expression. The range of expression may have thresholds or limits, beyond which expression is no longer considered the reference expression level. The computational unit may calculate a score based on the target nucleic acid expression level. Calculating the score may comprise comparing the target nucleic acid expression level and the reference expression level. Calculating the score may comprise a multivariate analysis. The multivariate analysis may account for the expression levels of a plurality of target nucleic acids. The multivariate analysis may calculate a score for each target nucleic acid of the plurality of target nucleic acids, by comparing the target nucleic acid expression level for each target nucleic acid to the reference expression level for each target nucleic acid. The score(s) may be calculated as a categorical variable based on the number of target nucleic acids that possess an expression level outside of or different from the reference expression level. The score may be calculated as a continuous variable based on the value of multiple target nucleic acid expression levels of multiple target nucleic acids. The score or multivariate analysis may direct a treatment or therapy.

The target nucleic acid expression level may be an expression level associated with a presence of a condition or disease. The target nucleic acid expression level may be an expression level associated with an absence of a condition or disease. The target nucleic acid expression level may be an expression level associated with a risk of the condition or disease. The target nucleic acid expression level may be an expression level associated with an onset of the condition or disease. The target nucleic acid expression level may be an expression level associated with an early stage of the condition or disease. The target nucleic acid expression level may be an expression level associated with a response to a treatment for the condition or disease. The response may be positive or negative. The target nucleic acid expression level may be an expression level associated with a healthy or normal condition.

The reference expression level may the expression level of the target nucleic acid in a reference sample. The reference sample may comprise a healthy cell. The reference sample may comprise a cell known to be affected by a disease or condition of interest. The reference sample may comprise a cell known to have a risk for developing a disease or condition of interest. The reference sample may comprise a cell known to have a high risk for developing a disease or condition of interest (e.g. the cell comprises a genetic mutation predisposing the cell or the subject from which the cell was derived to develop the disease or condition). The reference expression level may be an expression level associated with an absence of a condition or disease. The reference expression level may be an expression level associated with a presence of a condition or disease. The reference expression level may be an expression level associated with a risk of the condition or disease. The reference expression level may be an expression level associated with an onset of the condition or disease. The reference expression level may be an expression level associated with an early stage of the condition or disease. The reference expression level may be an expression level associated with a response to a treatment for the condition or disease. The response may be positive or negative. The reference expression level may be an expression level associated with a healthy or normal condition. The reference expression level may be an expression level that is not influenced by a condition, state, or disease. The reference expression level may an expression level of the target nucleic acid in a tissue type or cell type that is the same tissue type or cell type as that of the cellular specimen. The reference expression level may be the same in multiple conditions, states or diseases, whereas the target nucleic acid expression level may differ in the two conditions, states, or diseases. For example, the reference expression level may be the same in tumor and adjacent healthy tissue, whereas the target nucleic acid expression level is different in tumor and adjacent healthy tissue.

The target nucleic acid expression level and/or reference expression level may be normalized to account for a difference in cell number between the cellular specimen and the reference sample. The test and/or reference expression level may be normalized by the expression level of a normalization gene. The normalization gene may also be referred to as a housekeeping gene. Non-limiting example of housekeeping genes include beta-actin, U36B4, 18S, GAPDH, RPLPO, GUS and TFRC.

The expression level of the normalization gene is the same in the cellular specimen and the reference sample. The expression level of the normalization gene may be used to calculate a relative standard curve of the target nucleic acid expression level.

The computational unit may determine a score that reflects a quantitative difference between the target nucleic acid expression level and the reference expression level. The quantitative difference may be indicative of the absence of the disease or condition in the subject, the presence of the disease or condition in the subject, the risk of the condition or disease in the subject, onset of the condition or disease in the subject, early stage of the condition or disease in the subject, response to a treatment for the condition or disease in the subject, or a healthy or normal condition in the subject.

The quantitative difference may be due to the target nucleic acid expression level being less or more than the reference expression level. The quantitative difference may be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. The quantitative difference may be about 100%, about 200%, about 300%, about 400%, about 500%, or greater. The quantitative difference may be a fold difference. The fold difference may be about 2-fold to about 10-fold. The fold difference may be about 2-fold to about 100-fold. The fold difference may be about 2-fold to about 1000-fold.

The quantitative difference may be a ratio of the target nucleic acid expression level to the reference expression level. The ratio of the subject expression level to the reference expression level may be about 1:2, about 1:3, about 1:4, about 1:5, about 1:6, about 1:7, about 1:8, about 1:9, about 1:10, about 1:20, about 1:50, about 1:100, or about 1:1000. The ratio of the subject expression level to the reference expression level may be about 1:1000, about 1:100, about 1:50, about 1:20, about 1:10, about 1:9, about 1:8, about 1:7, about 1:6, about 1:5, about 1:4, about 1:3, or about 1:2.

The reference level may be a mean or average expression level with a standard deviation. The quantitative difference may be a number of standard deviations that the target nucleic acid expression level differs from the reference expression level. The number of standard deviations may be about 1, about 2, or about 3. The computational unit may quantify the number of cells in the cellular specimen. The computational unit may normalize the quantitative difference by comparing the number of cells in the cellular specimen to a cell number of the reference sample.

The quantitative difference may be indicative of a condition or disease status. The condition or disease status may be selected from the risk of the disease or condition, the presence of the disease or condition, the absence of the disease or condition, the response of the disease or condition to a therapy, the aggressiveness of the disease or condition, and the stage of the disease or condition.

Cartridges

The devices disclosed herein may comprise a cartridge, also referred to herein as a test cartridge. The computational unit may receive or house the cartridge. The cartridge may be a permanent part of the device. The cartridge may be inserted into and removed from the device as required. The test cartridge may contain information about a test or program that needs to be performed. The physical presence of the cartridge may provide information about which test or program to perform. The physical presence of the cartridge may constitute a command to initiate the test. The cartridge may contain the control information. The cartridge may contain information about the subject and/or may be capable of receiving information about the subject. The cartridge may contain information that directs the hardware and/or software of the device. The cartridge, hardware and/or software of the device may contain information or settings that direct the processing or analysis time, an intensity/duration of the homogenization step, number of target nucleic acids to analyze, method of normalization, method of evaluating controls, method of calculating a score, and a method of determining which information to display, print, or transmit. The cartridge may be selected from a compact disc (CD) and a stick drive.

The test cartridge contains a test for an indication, condition and/or disease. The test cartridge contains multiple tests for an indication (e.g. sepsis, antibiotic resistance, cancer). The cartridge may also direct the instrument to perform multiple independent tests (e.g. different bacteria, different strains of bacteria, different properties of the strains), or choose between different multi-analyte tests (a disease classifier for breast cancer, brain tumors, colon cancer, etc.). The device may receive information from the cartridge by a barcode or by reading information stored on the cartridge, using a mechanism similar to a CD or DVD reader. The physical cartridge itself contains the information that directs the device (e.g. a dedicated instrument for breast cancer surgery). The cartridge may contain a software program or portions thereof.

Classifiers

Figure 7:
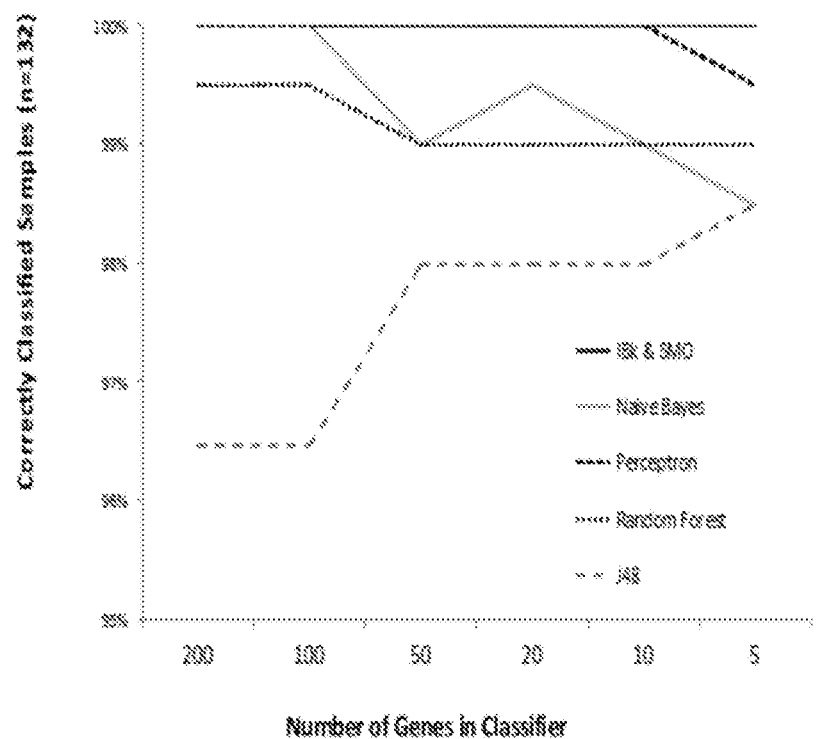
FIG. 7 shows the relationship between the number of attributes (genes, selected using the GainRatioAttributeEval function) and performance of breast cancer disease classifiers implemented using six machine learning methods.

The devices disclosed herein may comprise a classifier. The computational unit may comprise the classifier. The cartridge may comprise the classifier. The classifier may comprise a panel of genes corresponding to a plurality of target nucleic acids, each with unique thresholds and weights, and the rules that define the method of combining multiple inputs in a way that distinguishes two classes. Classes may be two conditions, sates, or diseases. By way of non-limiting example, the first condition may be a diseased condition and the second condition may be a healthy condition. The classifier may determine a presence or risk of a disease or condition based on the reference information and the target nucleic acid sequence information. The classifier may contain the reference information. The reference information may be a reference expression level of the target nucleic acid expressed in a reference sample. The reference information may be reference expression levels of a plurality of target nucleic acids expressed in one or more reference samples. FIG. 7 shows the relationship between the number of attributes (genes, selected using the GainRatioAttribute- Eval function) and performance of breast cancer disease classifiers implemented using six machine learning methods. The six machine learning methods were the support vector algorithm SMO, the k-Nearest Neighbor algorithm Lazy-IBk, the neural network Multilayer Perceptron, Naïve Bayes, J48 Decision Tree, and the Random Forest algorithm that generates a forest of trees.

The classifier may be developed with a machine learning algorithm. The panel of genes may be selected or optimized by statistics and/or the machine learning algorithm. An expression threshold that indicates the presence or the risk of the disease or condition may be determined with statistics and/or the machine learning algorithm. Rules and weights for combining a plurality of target nucleic acids may be developed or optimized with statistics and/or the machine learning algorithm. The machine learning algorithm may be developed or optimized by machine learning. The machine learning algorithm may be developed by constructing and/or studying (learning from) algorithms and making predictions on resulting data. The machine learning algorithm may be developed by building a model from example inputs in order to make data-driven predictions or decisions rather than following strictly static program instructions. The classifier may be developed by a comparison, validation, cross-validation, combination and/or selection of existing machine learning algorithms. The existing machine learning algorithms may be selected from k-nearest neighbor (IBk), the Bayesian Naive classifier (Naive Bayes), the support vector machine (SVM), Random Forest, Decision Tree, ZeroR, and the neural network (multilayer perceptron, MLP), and combinations thereof. The existing machine learning algorithm may be implemented using any number of custom or commercial packages, including WEKA, a public collection of machine learning algorithms for data mining tasks.

The classifier may be a breast cancer disease classifier (BCDC). BCDCs are panels of genes, each with unique thresholds and weights, which together distinguish invasive breast adenocarcinoma from adjacent health tissue. Genetic data from The Cancer Genome Atlas (TCGA), (see *Nature* 2012 vol. 490, pages 61-70) provided the source information to develop disease classifiers for breast cancer. TCGA established a Biospecimen Core Resource (BCR) that adheres to rigorous protocols and increases the confidence that pre-analytical variables were reasonably controlled.

The breast cancer disease classifier may be selected from Prosigna™, OncoTypeDX, BreastOncPx, MapQuant Dx™, MammaPrint® 70-gene signature, Mammostrat® Breast Cancer Test, Breast Cancer Index$^{SM}$, NexCourse® Breast IHC4, SCMGENE predictor, Rotterdam Signature, Celera Gene Expression Assay, and CompanDX®, and modifications thereof. The breast cancer classifier may be PAM50 (Parker, et al., J Clin Oncol. 2009 Mar. 10; 27(8):1160-7) or a modification thereof.

Output/Readout (Including Time to Readout)

The device may be connected or in communication with a display or printer, so that the information produced by the device may be displayed or printed, respectively.

Alternatively or additionally, the device communicates information via wire or wireless communication with a computer or web-based program. The device may receive and/or transmit information related to the test or result(s) thereof. For example, the device may receive information about the subject and the test/program to be performed, and transmits information such as the result of assessing the target nucleic acid expression level. The system may receive and/or transmit the information via the internet. Receiving and/or transmitting the information may comprise the use of a bluetooth device. By way of non-limiting example, the information may comprise instructions for a breast cancer test, a prostate cancer test, or a colon cancer test, such as analyzing a sample from a colonoscopy biopsy.

The device may comprise a unit that scans a patient identifier (e.g. barcode or QR code on a wristband). Typically, hospitals print a set of adhesive barcodes that encode a unique identifier for the patient, linking them to their record in an electronic database. Alternatively or additionally, the device may comprise a near-field reader to scan a barcode, decode a unique identifier, access patient information, and/or annotate the report with the patient information. In this case, the manual steps may comprise (1) scanning the patient information, (2) inserting the test cartridge, and (3) inserting the sample. Alternatively, the manual steps may comprise (1) scanning the patient information, (2) inserting the sample onto the test cartridge, and (3) inserting the test cartridge into the instrument. In situations where operators are confident that the results are definitively linked to a specific patient (e.g. when a surgical sample is removed and analyzed in an operating room during an operation) the manual steps may comprise (1) inserting the sample onto the test cartridge, and (2) inserting the test cartridge into the instrument.

The device may upload/send the result of interpreting the target nucleic acid expression level to an electric medical record (EMR) and/or one or more surgeons, pathologists, oncologists, or healthcare coordinators. The device may upload/send duplicate or unique data to a manufacturer of the device. As a non-limiting example, the device may upload/send quality reference information to the manufacturer alone or in addition to data transmitted to clinical personnel. The device may upload/send details about the specific analytes to a device used to store and assimilate biometric profiles. As a non-limiting example, the device may transmit the estrogen receptor status from a breast cancer sample to a database designed to collect molecular information about breast cancer tumors as part of a clinical trial. When implemented globally, the described device has the capacity to obtain more detailed molecular information about a disease in a single year than has ever been previously obtained. The described device may be implemented as an instrument to perform clinical research without diagnosing, informing, or directing clinical care.

The devices described herein may be designed to provide results. The results may be results of comparing the target nucleic acid information to reference nucleic acid information. The results may be molecular results or results of a molecular analysis. The device may also provide additional information in addition to the molecular results. For example, the device may implicitly or explicitly incorporate information from external sources including incidence; prevalence; relevance to the patient (which may be inferred from age, body mass, a questionnaire about the importance of cosmetic outcome, functional outcome (e.g. a young woman who wants to breastfeed in the future would be adversely affected by surgical damage to the mammary glands and ducts), weighed against questions about the personal preference to be reassured that the tumor is entirely removed and is unlikely to require further treatment. The device may also incorporate or be incorporated into a network that includes the molecular output in combination with the importance, or impact of the result on the patient or society. In contrast to a diagnostic test that would result in medical interventions with dangerous or irreversible impact on the patient or society (e.g. an amputation, or blocking the import of citrus products from an economically fragile region), the method described herein may be predicated on test results including but not limited to a previous biopsy of the same lesion, subsequent pathology analysis of the same specimen, or patient history (e.g. previous breast cancer in another location).

The devices disclosed herein may generate output from a single- or multi-analyte test that comprises a discrete variable; a continuous variable, whether or not the continuous variable is proportional to an outcome, diagnosis, or probability of a future event; or a continuous variable reported for the user to make a determination about a discrete variable, possibly by incorporating other information. An output of the device described herein may be designed to be incorporated into information other than the reported output variable. For example, the results of a test performed during an operation may only be valid if performed on a lesion that was previously diagnosed (e.g. as breast cancer). As another example, the negative predictive value relies on the incidence and prevalence of a disease, which a device described herein may incorporate into the analysis. The device may be designed to report a discrete variable or continuous variable, which will provide a decision support tool.

The devices and methods described herein enable rapid analysis of samples and provide results rapidly. For instance, the systems and methods described herein may produce the result(s) in less than about 12, less than about 11, less than about 10, less than about 9, less than about 8, less than about 7, less than about 6, less than about 5, less than about 4, less than about 3, less than about 2, or less than about 1 hour from sample collection. Devices and methods described herein may produce the result(s) in less than about 59, less than about 58, less than about 57, less than about 56, less than about 55, less than about 54, less than about 53, less than about 52, less than about 51, less than about 50, less than about 49, less than about 48, less than about 47, less than about 46, less than about 45, less than about 44, less than about 43, less than about 42, less than about 41, less than about 40, less than about 39, less than about 38, less than about 37, less than about 36, less than about 35, less than about 34, less than about 33, less than about 32, less than about 31, less than about 30, less than about 29, less than about 28, less than about 27, less than about 26, less than about 25, less than about 24, less than about 23, less than about 22, less than about 21, less than about 20, less than about 19, less than about 18, less than about 17, less than about 16, less than about 15, less than about 14, less than about 13, less than about 12, less than about 11, less than about 10, less than about 9, less than about 8, less than about 7, less than about 6, less than about 5, less than about 4, less than about 3, less than about 2 minutes from sample collection. Devices and methods described herein may produce the result(s) in less than about 1 minute from sample collection. Devices and methods described herein may produce the result(s) in about 5 to about 12 hours, about 1 to about 6 hours, about 0.5 to about 2 hours, about 20 to about 60 minutes, about 10 to about 30 minutes, about 5 to about 15 minutes, or about 1 to about 10 minutes from sample collection. Devices and methods described herein may produce the result(s) in less than 10 minutes from sample collection. Devices and methods described herein may produce the result(s) in less than 5 minutes from sample collection. Surgical environments demonstrate the importance of rapid analysis. A surgeon may require test results before concluding an operation. Prolonging an operation may expose an open incision to infectious agents, increases the difficulty of maintaining aseptic personnel and instruments, and exposes the patient to additional anesthetic agents and conditions. Prolonged anesthesia increases the risk of complications during the procedure, and in the future. For example, the duration of anesthesia in children has been linked to neurological impairment later in life.

Computer/Processor Unit

The devices disclosed herein may comprise a computer system or processor. The devices disclosed herein may communicate with a computer or processor. The devices disclosed herein provide computer devices for rapid and automated analysis of nucleic acids. The computer system may provide a report communicating results from the analysis of the target nucleic acid and/or the comparison of the target nucleic acid information to reference nucleic acid information. The computer system may execute instructions contained in a computer-readable medium. The computer may be associated with one or more controllers, calculation units, and/or other units of a computer system, or implanted in firmware. One or more units/functions of the system may be implemented in hardware and/or software. Software may be stored in any computer readable memory unit such as flash memory, RAM, ROM, magnetic disk, laser disk, or other storage medium as described herein or known in the art. Software may be communicated to the computer by any known communication method including, for example, over a communication channel such as a telephone line, the internet, a wireless connection, or by a transportable medium, such as a computer readable disk, flash drive, etc. The one or more steps of the methods described herein may be implemented as various operations, tools, blocks, modules and techniques which, in turn, may be implemented in firmware, hardware, software, or any combination of firmware, hardware, and software. When implemented in hardware, some or all of the blocks, operations, techniques, etc. may be implemented in, for example, an application specific integrated circuit (ASIC), custom integrated circuit (IC), field programmable logic array (FPGA), or programmable logic array (PLA).

Figure 4:
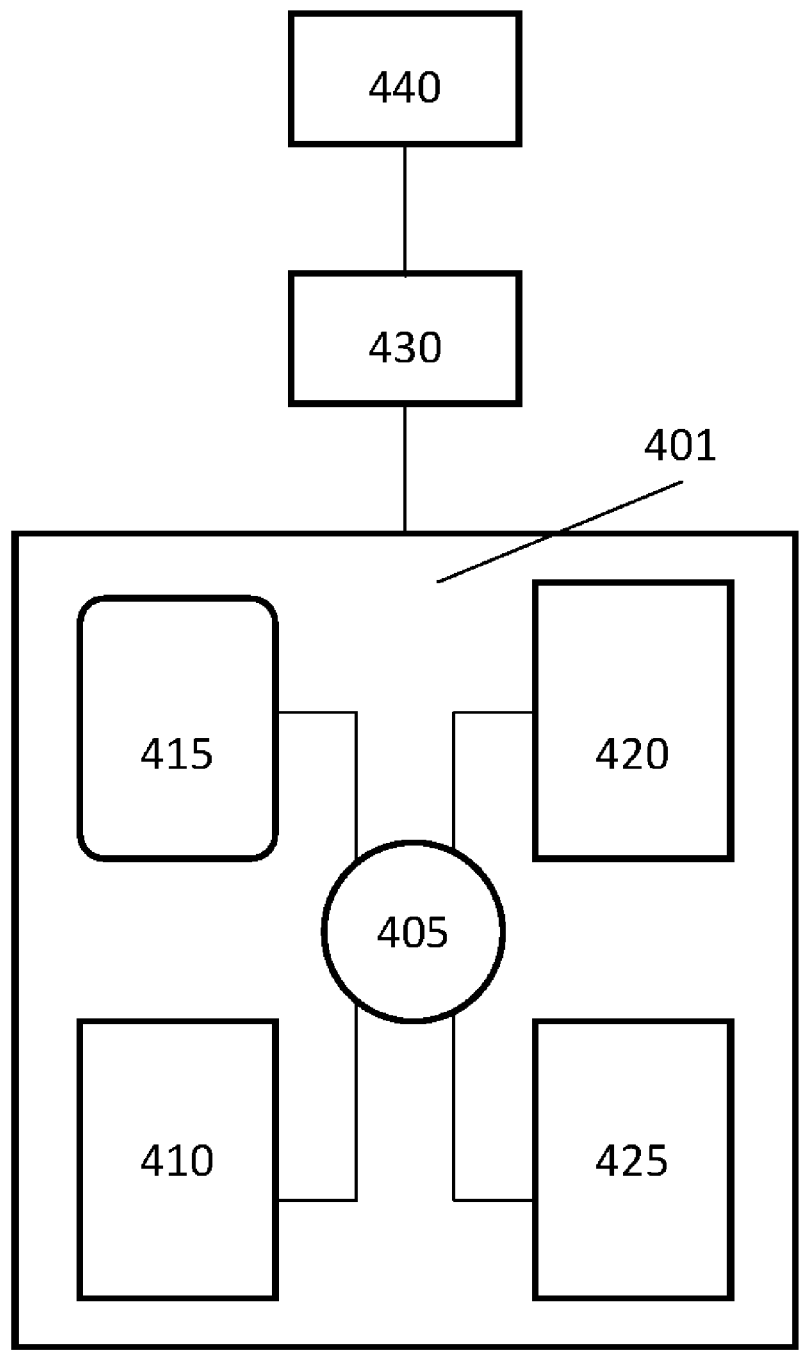
FIG. 4 depicts an exemplary computer system for implementing one or more methods described herein.

FIG. 4 depicts a computer system 400 adapted to enable a user to detect, analyze, and process patient data. The system 400 includes a central computer server 401 that is programmed to implement exemplary methods described herein. The server 401 includes a central processing unit (CPU, also "processor") 405 which may be a single core processor, a multi core processor, or plurality of processors for parallel processing. The server 401 also includes memory 410 (e.g. random access memory, read-only memory, flash memory); electronic storage unit 415 (e.g. hard disk); communications interface 420 (e.g. network adaptor) for communicating with one or more other systems; and peripheral devices 425 which may include cache, other memory, data storage, and/or electronic display adaptors. The memory 410, storage unit 415, interface 420, and peripheral devices 425 are in communication with the processor 405 through a communications bus (solid lines), such as a motherboard. The storage unit 415 may be a data storage unit for storing data. The server 401 is operatively coupled to a computer network ("network") 430 with the aid of the communications interface 420. The network 430 may be the Internet, an intranet and/or an extranet, an intranet and/or extranet that is in communication with the Internet, a telecommunication or data network. The network 430 in some cases, with the aid of the server 401, may implement a peer-to-peer network, which may enable devices coupled to the server 401 to behave as a client or a server.

The storage unit 415 may store files, such as subject reports, and/or communications with the caregiver, sequencing data, data about individuals, or any aspect of data associated with the invention.

The server may communicate with one or more remote computer systems through the network 430. The one or more remote computer systems may be, for example, personal computers, laptops, tablets, telephones, smart phones, handheld devices, or personal digital assistants.

In some situations the system 400 includes a single server 401. In other situations, the system includes multiple servers in communication with one another through an intranet, extranet and/or the Internet.

The system may be adapted to store subject-specific or sample-specific information. For example, the system may be adapted with computer-executable instructions for analysis of specific biomarkers or genes to be tested. The system may comprise computer-executable instructions for reporting a positive result or negative result for presence of a biomarker by comparing to a defined threshold. The defined threshold may be set by a user or may be pre-loaded onto the system. In some cases, the system comprises computer-executable instructions for defining a threshold. For example, the system may comprise an interface wherein a user may provide information on a subject (e.g., a patient) or a sample to be tested. The subject-specific information or sample-specific information may be used by the system to calculate a subject-specific or sample-specific threshold. The system may be adapted with subject-specific or sample-specific information such as, for example, polymorphisms, mutations, patient history, demographic data, barcoded information, and/or other information of potential relevance. Such information may be stored on the storage unit 415 or the server 401 and such data may be transmitted through a network.

Devices and methods as described herein may be implemented by way of machine (or computer processor) executable code (or software) stored on an electronic storage location of the server 401, such as, for example, on the memory 410, or electronic storage unit 415. During use, the code may be executed by the processor 405. In some cases, the code may be retrieved from the storage unit 415 and stored on the memory 410 for ready access by the processor 405. In some situations, the electronic storage unit 415 may be precluded, and machine-executable instructions are stored on memory 410. Alternatively, the code may be executed on a second computer system 440.

Aspects of the systems and methods provided herein, such as the server 401, may be embodied in programming. Various aspects of the technology may be thought of as "products" or "articles of manufacture" typically in the form of machine (or processor) executable code and/or associated data that is carried on or embodied in a type of machine readable medium. Machine-executable code may be stored on an electronic storage unit, such memory (e.g., read-only memory, random-access memory, flash memory) or a hard disk. "Storage" type media may include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" may refer to any medium that participates in providing instructions to a processor for execution.

Hence, a machine readable medium, such as computer-executable code, may take many forms, including but not limited to, tangible storage medium, a carrier wave medium, or physical transmission medium. Non-volatile storage media may include, for example, optical or magnetic disks, such as any of the storage devices in any computer(s) or the like, such may be used to implement the system. Tangible transmission media may include: coaxial cables, copper wires, and fiber optics (including the wires that comprise a bus within a computer system). Carrier-wave transmission media may take the form of electric or electromagnetic signals, or acoustic or light waves such as those generated during radio frequency (RF) and infrared (IR) data communications. Common forms of computer-readable media therefore include, for example: a floppy disk, a flexible disk, hard disk, magnetic tape, any other magnetic medium, a CD-ROM, DVD, DVD-ROM, any other optical medium, punch cards, paper tame, any other physical storage medium with patterns of holes, a RAM, a ROM, a PROM and EPROM, a FLASH-EPROM, any other memory chip or cartridge, a carrier wave transporting data or instructions, cables, or links transporting such carrier wave, or any other medium from which a computer may read programming code and/or data. Many of these forms of computer readable media may be involved in carrying one or more sequences of one or more instructions to a processor for execution.

Display/Output

The results of the nucleic acid analysis, generating a subject report, and/or communicating the report to a caregiver may be presented to a user with the aid of a user interface, such as a graphical user interface.

The computer system may be used for one or more methods or method steps, including, e.g., sample collection, sample processing, nucleic acid analysis, receiving subject-specific information such as patient history or medical records, receiving and storing measurement data regarding a detected level of one or more biomarkers in a subject or a biological sample, analyzing said measurement data determine a diagnosis, prognosis, therapeutic efficacy (e.g., efficacy of breast tumor removal), sample-specific pathogen profile, generating a report, and reporting results to a receiver.

A client-server and/or relational database architecture may be used in any of the methods described herein. In general, the client-server architecture is a network architecture in which each computer or process on the network is either a client or a server. Server computers may be powerful computers dedicated to managing disk drives (file servers), printers (print servers), or network traffic (network servers). Client computers may include PCs (personal computers) or workstations on which users run applications, as well as example output devices as disclosed herein. Client computers may rely on server computers for resources, such as files, devices, and even processing power. The server computer handles all of the database functionality. The client computer may have software that handles front-end data management and receive data input from users.

After performing a calculation, a processor may provide the output, such as from a calculation, back to, for example, the input device or storage unit, to another storage unit of the same or different computer system, or to an output device. Output from the processor may be displayed by a data display, e.g., a display screen (for example, a monitor or a screen on a digital device), a print-out, a data signal (for example, a packet), a graphical user interface (for example, a webpage), an alarm (for example, a flashing light or a sound), a light or one of multiple colored lights, or a combination of any of the above. In an embodiment, an output is transmitted over a network (for example, a wireless network) to an output device. The output device may be used by a user to receive the output from the data-processing computer system. After an output has been received by a user, the user may determine a course of action, or may carry out a course of action, such as a medical treatment when the user is medical personnel. For example, an output communicating a positive or negative breast cancer margin may be used by a physician to determine whether or not to perform an additional tumor resection while the subject is still in surgery. An output device may be the same device as the input device. Example output devices include, but are not limited to, a telephone, a wireless telephone, a mobile phone, a PDA, a flash memory drive, a light source, a sound generator, a fax machine, a computer, a tablet computer, a computer monitor, a printer, an iPod, and a webpage. The output device is integrated into a system described herein. The user station may be in communication with a printer or a display monitor to output the information processed by the server. Such displays, output devices, and user stations may be used to provide an alert to the subject or to a caregiver thereof.

Data relating to the present disclosure may be transmitted over a network or connections for reception and/or review by a receiver. The receiver may be but is not limited to the subject to whom the report pertains; or to a caregiver thereof, e.g., a health care provider, manager, other healthcare personnel, or other caretaker; a person or entity that performed and/or ordered the molecular analysis; a genetic counselor. The receiver may also be a local or remote system for storing such reports (e.g. servers or other systems of a "cloud computing" architecture). In one embodiment, a computer-readable medium includes a medium suitable for transmission of a result of an analysis of a biological sample.

Data related to the present disclosure may be encrypted. Data may be encrypted on the instrument itself. Data may be encrypted when transmitted to a local server or network (e.g. an EMR), or an external server or network (e.g. a remove server, a cloud server, or to a recipient via the internet).

F. Exemplary Devices

The devices disclosed herein may comprise an integrated system. The integrated system may comprise the sample input unit, the nucleic acid analysis unit and the computational unit. The following described systems are exemplary and by no means limit the invention.

Figure 1B:
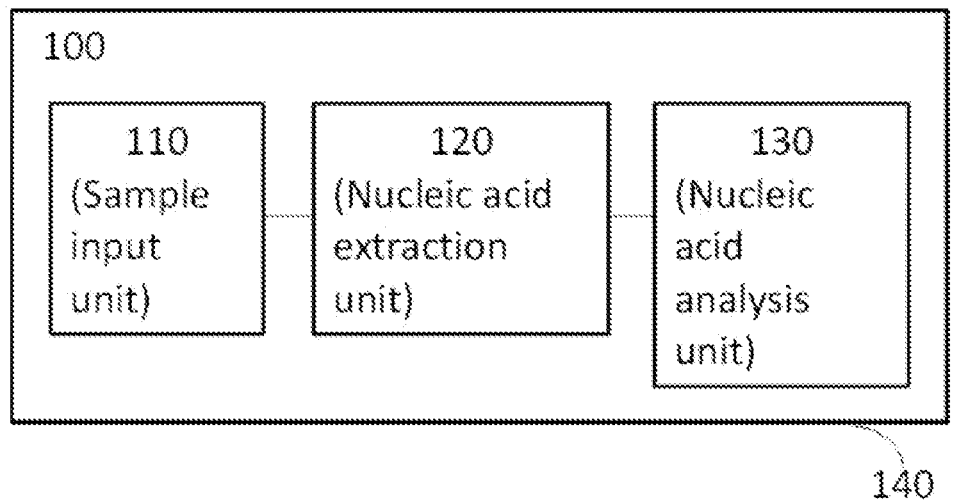
FIG. 1B depicts an exemplary device system for rapid analysis of biological samples.

FIG. 1B depicts an exemplary system 100 for nucleic acid analysis. Components of the exemplary system include, but are not limited to sample input unit 110, sample preparation unit 120, and nucleic acid analysis unit 130. The sample input unit 110 may be operably linked to the sample preparation unit 120. For example, the device may be configured to move a sample collected by the sample input unit to the sample preparation unit 120 without user intervention. The sample preparation unit 120 may be operably linked to the nucleic acid analysis unit 130. The device may be configured to move nucleic acids extracted by the sample preparation unit 120 to the nucleic acid analysis unit 130 without user intervention. At least one of the sample input unit 110, sample preparation unit 120, and nucleic acid analysis unit 130 are enclosed by a housing 140. For example, at least two of the sample input unit, 110, sample preparation unit 120, and nucleic acid analysis unit 130 are enclosed in the housing 140. In particular instances, the sample preparation unit 120 and nucleic acid analysis unit 130 are enclosed in the housing. In particular instances, the sample input unit 110, nucleic acid extraction unit sample preparation unit 120, and nucleic acid analysis unit 130 are enclosed in the housing 140. In some cases, all three of the sample input unit 110, sample preparation unit 120, and nucleic acid analysis unit 130 are enclosed in the housing 140. In some cases, the housing enclosure 140 may represent a single physical entity within which are embedded one or more units 110, 120, and/or 130. For example, housing enclosure 140 may be a polymer shaped or molded into the shape of a chamber within which targeted nucleic acid amplification is performed. In some cases unit 110 may be a physical object that the user contacts to the device to initiate a series of operations. In some cases physically interacting unit 110 is the only action necessary to initiate the performance of a complex molecular analysis that would otherwise involve manual procedures typically performed by those with specialized training in clinical laboratory techniques.

Figure 1C:
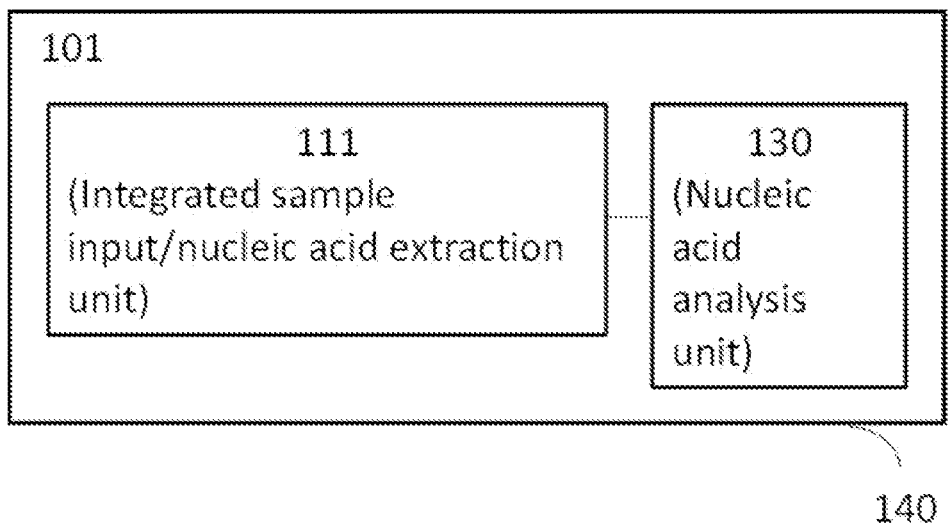
FIG. 1C depicts an exemplary device system for rapid analysis of biological samples.
Figure 1D:
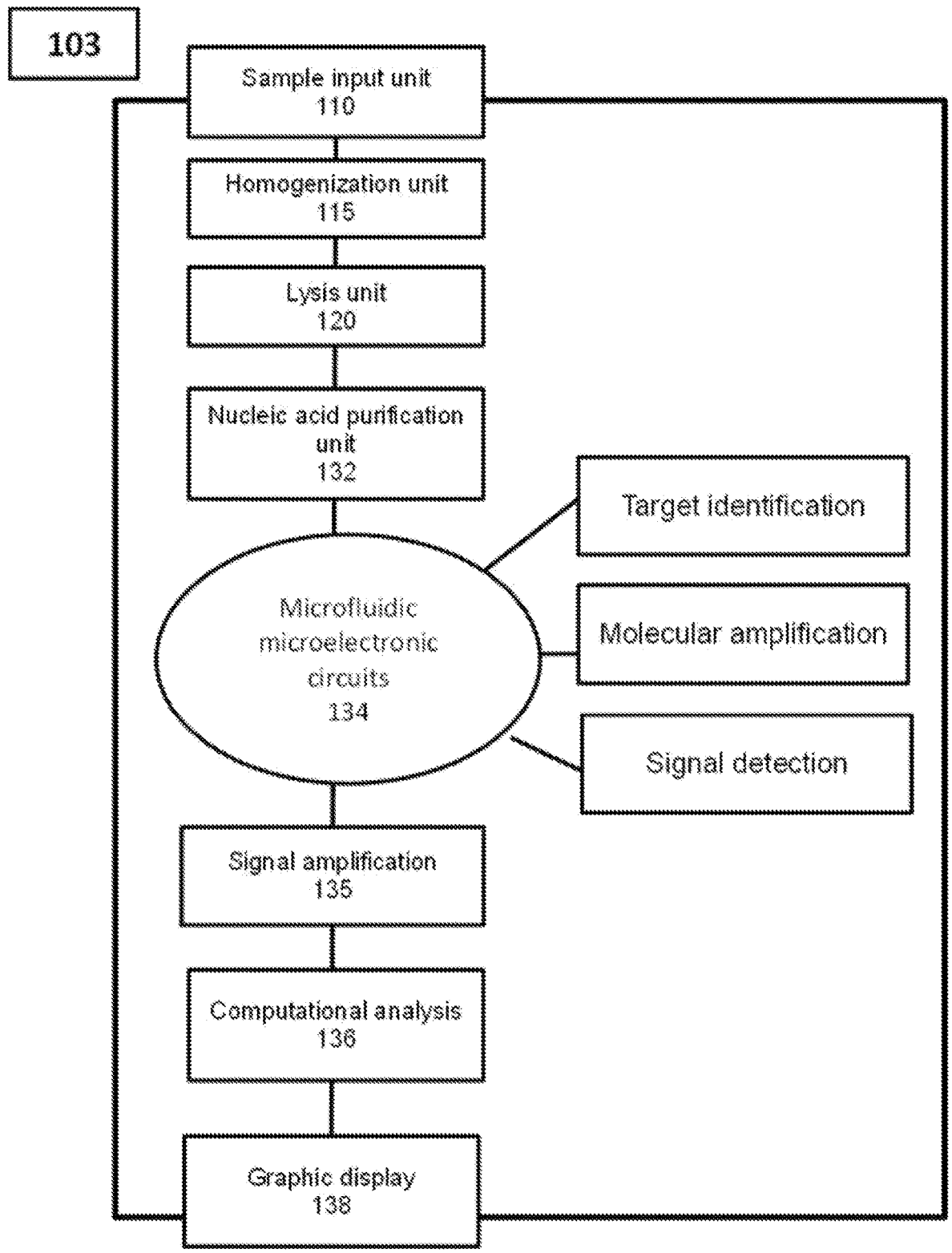
FIG. 1D depicts an exemplary device system for rapid analysis of biological samples.

FIG. 1C depicts another exemplary system 101 for nucleic acid analysis, comprising an integrated sample input/sample preparation unit 111 and a nucleic acid analysis unit 130. The integrated sample input/sample preparation unit 111 and nucleic acid analysis unit 130 may be enclosed in a housing 140. The integrated sample input/sample preparation unit 111 may be operably linked to the nucleic acid analysis unit 130. In some cases, system 101 is configured to move nucleic acids extracted by the integrated sample input/nucleic acid extraction unit 111 to the nucleic acid analysis unit 130. Unit 110 may be a discrete unit and sample preparation unit 120 may be integrated with nucleic acid analysis unit 130.

FIG. 1D depicts another exemplary system 103 for nucleic acid analysis. Components of the exemplary system include, but are not limited to, sample input unit 110, cell/tissue disruption unit (115), sample preparation unit 120 (e.g., a cell lysis unit which may include nucleic acid extraction), and nucleic acid analysis unit 130. The sample preparation unit 120 may perform a cell/tissue homogenization. Alternatively, a separate unit (not depicted) may perform a cell/tissue homogenization preceding cell lysis by the sample preparation unit 120. Components of nucleic acid analysis unit 130 may include, but are not necessarily limited to, a nucleic acid purification unit 132, operably linked to a microfluidics/microelectronics circuit 134, operably linked to a signal amplification unit 135, operably linked to a computational analysis unit 136, operably linked to a graphical display unit 138. In some cases components of the signal detection unit depicted as an element of unit 134 physically contacts the solution contacting the amplified or amplifying molecules. In other cases the detection unit is entirely external to the molecular amplification unit. The microfluidics/microelectronics circuit 134 transforms biologic information; e.g. presence or quantity of biologic molecule or the presence or quantity of a specific mutation or variant including covalent modifications of a specific nucleotide at a specific position in a specific sequence; into an electronic signal. The computational analysis unit 136 may perform and record predetermined signal processing and analyses, which may be specific for the test requested by the user. Unit 136 may generate custom or predetermined records and reports for a plurality of users, including updates of system status, test progress, and condensed results for the user. 136 may record, print or transmit multiple outputs in the form of reports or records. 136 may be operably linked to display unit 138. Display unit 138 may be textual, graphic, or a combination of textual and graphical displays. In some cases 138 is a touch screen that may display information and receive commands from the user. In some cases, the sample input unit 110, sample preparation unit (e.g., lysis unit) 120, and nucleic acid analysis unit 130 are enclosed in a housing 140. Fluidic connections may operably link unit 110 to 120 or 120 to 130 or 110 to 120 to 130. When one or more of units 110, 120, or 130 are embedded in the physical entity of 140, the fluidic connections between said units may also be embedded in the physical entity of 140. In some cases the units and connections are in the form of an integrated fluidic circuit.

Figure 3:
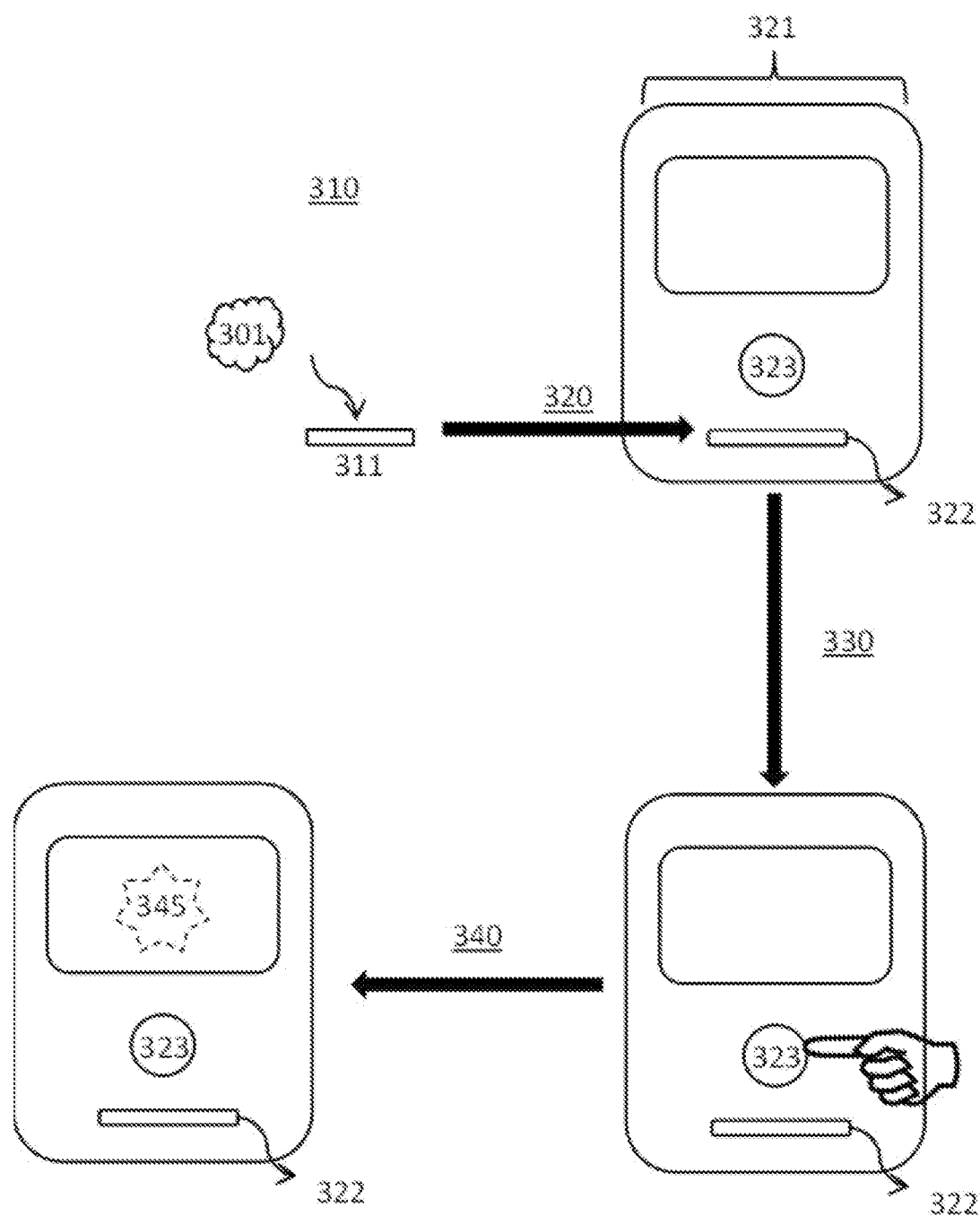
FIG. 3 depicts an exemplary method for rapid analysis of biological samples.

FIG. 3 depicts an exemplary embodiment of a system 300 for analysis of a biological sample 301. Step 310 may comprise applying all or a portion of a sample 301 to a sample collection unit 311. Step 320 may comprise physically contacting the sample collection unit 311, which comprises at least a portion of sample 301, with sample input unit 322 of a system 321 described herein. The sample collection unit 311 may be, e.g., a slide, a tube, a well, a plate, a vial, a chip or cartridge, (e.g., a microfluidic chip or cartridge), a card, a compact disc, a paper, nitrocellulose membrane, or any other sample collection device known to those of skill in the art, such as, e.g., any of the sample collection devices described herein. The sample input unit 322 may be an inlet port configured for the insertion and optional removal of the sample collection unit. For example, the sample input unit may be a slide holder, a tube holder, a plate holder, a vial holder, a chip or cartridge holder, a card slot, a compact disc holder, a well, and the like. In some cases input unit 311 is an instrument used to collect the specimen, e.g. a hollow cylinder used to perform a core biopsy or aspiration, or swab used to perform a buccal scraping, from which the user or system derives the testing sample. In some cases input unit 311 is supplied as a companion to the testing system. In some cases the input unit is provided as a sterile device. In some cases input unit 311 is a receptacle that physically contacts the system before the user applies the sample. In some cases the input unit is designed to receive the sample before the user contacts the input unit to the system, in which case the act of physically contacting the unit to the device may constitute a request or command. In some cases the act or command of physically contacting unit 311 to unit 322 is the only user interaction that the system requires to select and perform the test.

The sample input unit 322 may comprise an inlet port configured for the insertion and optional removal of the sample collection unit. For example, the sample input unit may comprise a slide holder, a tube holder, a plate holder, a vial holder, a chip or cartridge holder, a card slot, a compact disc holder, a well, and the like. In some cases, unit 322 is a clamp that provides an operational connection to unit 311. In some cases the operation connection provided by unit 322 is fluidic. In some cases the operation connection provided by unit 322 is fluidic and electronic. In some embodiments, the system 321 contains a mechanical sample transfer unit 324, which physically transfers all or part of sample 301 from collection unit 311, after unit 311 has physically contacted sample input unit 322. The mechanical sample transfer unit 324 may deposit sample 301 into a disruption unit 115, sample preparation unit 120, analysis unit 134, or a unit operationally connected to one of these or another unit that stores, prepares, processes, or analyzes the sample.

The sample input unit 322 may be sealable upon insertion of the sample collection unit, in order to minimize contamination or cross-contamination in the environment or within the system. In some cases, the system 321 further comprises a user interface 323. In some instances, the user may touch the user interface 323 to begin an automated sample processing and/or detection protocol. The user interface 323 may comprise, e.g., a touch pad, a keyboard, a mouse, a button, or a touch screen. Step 330 may comprise interacting with the user interface 323 to start the automated sample processing and/or detection protocol. Step 340 may comprise the system 321 displaying a test result 345 to the user. In some cases, step 330 comprises the act of physically contacting a unit with system 321. For example, the act of contacting unit 311 to unit 322 may comprise a command to initiate the analysis. In some cases, the identity of unit 311 may encode the identity of the requested test. In some cases, the presence of a specific type of unit 311 constitutes a request to perform a specific multivariate molecular analysis, and the act of contacting unit 311 to unit 323 comprises a command to initiate and perform the specific test corresponding to the identity of unit 311. In some cases, the identity of unit 311 is indicated by the shape or size of the unit. In some cases, the identity of unit 311 is indicated by markings, codes, labels, or information on unit 311. In some cases, the identity of unit 311 is indicated by information stored on or in the unit, for example digital code stored on a medium as an element of the unit 311. In some cases, the identifier on unit 311 instructs system 321 to reference predetermined instructions, stored within or retrieved by system 321. In some cases, unit 311 contains complete or partial instructions necessary to perform analysis.

A clamp on the local control system 321 provides microfluidic and electronic interfaces to the testing subsystem 134. Testing subsystem may be included on a testing cartridge. The testing cartridge contains lyophilized enzymes and synthetic polynucleotides, which are reconstituted by buffers and reagents delivered by the fluidic system. The fluidic system transfers liquids from reagent bottles that are connected to the local control system. The testing subsystem 134 may contain an array of reaction chambers with integrated microelectronics. Microfluidic circuits deliver, combine, and mix reagents. The fluidics system controls liquid delivery and progression through the fluidic circuit. Reactions are monitored and detected by voltammetry through currents delivered by the electronic interface.

G. System Controls

The devices and systems disclosed herein may comprise a control, wherein the control confirms a process performed by the system has been performed properly, sufficiently and/or accurately. These controls ensure the system can be used at point-of-care to provide reliable results upon which further surgical procedure or treatment is based and immediately performed.

The control may be an exogenous control. The control may be synthetic. The control may be used to test the function of a step in a workflow of the system. The control may be used to confirm a reaction performed by the system has been performed as designed. The control may be synthetic DNA. The synthetic DNA may be used to determine whether the isothermal amplification is amplifying the intended target nucleic acid. The synthetic DNA may be used to determine if an enzyme required for the reaction is active or if it has been damaged, degraded or destroyed by improper shipping and/or storing. The exogenous control may reveal whether an unwanted or unknown inhibitor or contaminant is interfering with or inhibiting the reaction. The efficiency of a control reaction may be influenced by inhibitors present in the sample (e.g. heme is a notorious amplification inhibitor, which could be present in varying amounts in cellular specimens prepared by touch-prep methods). The exogenous control may also be used to calibrate the system or a portion thereof. Exogenous controls (DNA or RNA) may be used to adjust a reaction efficiency. For example, if a slope of an exogenous control amplification curve deviates from the slope of the cellular specimen's respective amplification curve, the efficiency can be compensated, and subsequently applied to the other reactions (e.g. either by adjusting the evaluates used to calculate efficiency, or by using the control in normalization).

The exogenous control may be synthetic RNA. Synthetic RNA may test the reverse transcription reaction primers and enzymes. The methods disclosed herein comprise use of synthetic RNA to monitor RNA integrity in a point of care system that analyzes multiple nucleic acids. The synthetic RNA may be used to detect degraded RNA in the samples. For example, the lysis buffer can contain synthetic RNA, which would be degraded if there were nucleases in the cellular specimen. However, RNA degradation may not be an issue for the systems and methods disclosed herein as reverse transcription is typically performed on RNA of the cellular specimen immediately upon disrupting (e.g. lysing) the cells of the cellular specimen or immediately upon inserting the cellular specimen into the system.

The control may be an endogenous control. The endogenous control may be an analyte in the sample. The endogenous control may be total RNA, genomic DNA, or expression level of an off-target nucleic acid.

H. Users/Locations

A user of the device does not necessarily require a specialized education or training to carry out any of the methods described herein. The user may or may not have a college education. The user may or may not have a specialized education. The user may be a surgeon, a surgical technician, or a nurse. The user may be a healthcare worker. The healthcare worker may perform the methods disclosed herein at a site selected from an emergency department, urgent care facility, cardiac care facility, radiology facility (e.g. a radiologist), a rural care environment, a medical, and an evaluation facility in a developing economy where an infrastructure for current screening tests (e.g. mammograms) are not available. The user may be someone who does not contact the device or physically use the device, but supplies information or materials (i.e. cellular specimen) to an operator of the device and/or receives information produced by the device.

The devices and methods described herein may be used in various settings. These setting may include, but are not limited to, a hospital, a clinical laboratory improvement amendments (CLIA) lab, an operating room, or a central facility that serves an operating room, a non-CLIA lab, an emergency room, a specialized care unit, a hospital ward, a mobile care site, an outpatient clinical suite such as, e.g., an outpatient surgical suite, a veterinary care center, outpatient facility, permanent or temporary structure, including a field unit, in a vehicle, for example, an automobile, airplane, helicopter, train, ship, boat, submarine, or ambulance, in a home or office, a food or beverage processing facility, a slaughterhouse, a farm, a harvesting facility, and the outdoors. The setting may be in a developing country where current tests or screens are unavailable. Use of the systems and methods disclosed herein may provide a test result without the subject having to travel large distances between their home and a healthcare facility.

The devices, methods and tests disclosed herein may be performed in hospital labs. Typically, the test is performed during an operation ("intraoperative testing"). The test or portion thereof may be performed after an operation. The test or portion thereof may be performed in a pathology lab while the patient waits. The test may differ from a similar test known in the art by the fact that the test or portion thereof is performed during the operation and not after the operation.

The devices provided herein may be used outside or inside of a hospital. The devices may be used outside or inside of a hospital lab. The devices may be used outside or inside of a pathology lab. The devices may be used outside or inside of a research lab. The devices may be used outside or inside of an ambulatory surgical center. By way of non-limiting example, many breast conservation surgeries are performed in ambulatory surgical centers where there are no pathologists or laboratory medicine facilities. Accordingly, methods and devices described herein can be used in operating rooms, e.g., during a surgery, of a site selected from a hospital, clinic, pathology lab, research lab, and an ambulatory surgical center.

III. Methods

Disclosed herein are methods comprising: obtaining a cellular specimen containing a target nucleic acid; inserting the cellular specimen into a device disclosed herein; assessing a presence, absence or risk of a condition or disease in the cellular specimen; and directing a user of the device to perform or not perform a procedure based on a result of the assessing. The methods may further comprise performing a reaction/process described herein as being performed by the disclosed devices. That is, a reaction or process that is described to be performed by the device may be performed manually instead.

The risk of the condition or disease may be a risk of developing a condition or disease, a risk of residual condition or disease after a procedure, or a risk that the condition or disease will be aggressive. The methods may comprise determining the likelihood that a disease or condition will respond to a therapy. The risk of the condition or disease may be a risk of developing a cancer, a risk of residual cancer after a procedure or a risk that the cancer will be aggressive. The methods may comprise determining the likelihood that the cancer will respond to a therapy.

The methods disclosed herein may further comprise assessing whether administering a therapy or treatment to the subject is advisable. The methods may further comprise directing a device user (e.g., physician, surgeon) to administer a therapy or treatment to the subject. The therapy or treatment, by way of non-limiting example, may be selected from a drug, a diet, a radiation treatment, a chemotherapeutic agent, a biological therapeutic, an injection, a physical therapy, and an exercise. The biological therapeutic may be naturally-occurring. The biological therapeutic may be synthetic. The biological therapeutic, by way of non-limiting example, may be an antibody, antibody drug conjugate, or bispecific antibody. The methods may further comprise directing a person (e.g., physician, surgeon) to perform or expand a surgical procedure on the subject. The surgical procedure, by way of non-limiting example, may be selected from a surgery, an injection, an excision, a laser treatment, and a biopsy. The device user may be a person who uses information provided by the device, but does not actually interact with the device. For example, the device user may be a surgeon who provides a surgical specimen to an assistant. The assistant obtains the cellular specimen from the sample, inserts the cellular specimen into the device and conveys a result of the device's analysis of the cellular specimen to the surgeon, thereby directing the surgeon to administer a therapy, treatment, procedure, etc.

The methods disclosed herein may further comprise expanding a surgery or procedure on the subject after determining the presence or risk of the condition or disease. The methods may further comprise expanding the surgical procedure immediately after receiving direction from the device. Expanding the surgery or procedure may occur in less than about 1 minute, less than about 2 minutes, less than about 3 minutes, less than about 5 minutes, less than about 10 minutes, less than about 15 minutes, less than about 20 minutes, less than about 25 minutes, less than about 30 minutes, less than about 35 minutes, less than about 40 minutes, less than about 45 minutes, less than about 50 minutes, less than about 55 minutes, less than about 60 minutes, less than about 75 minutes, less than about 90 minutes, less than about 120 minutes, or less than about 180 minutes from obtaining the cellular specimen. Expanding the surgery or procedure may involve excising/testing second margins or making additional shavings during a Mohs procedure. Expanding the surgery or procedure may involve converting an initial procedure into a more invasive procedure (e.g. obtaining shavings from the walls of a lumpectomy cavity, or converting a lumpectomy to a mastectomy).

The methods disclosed herein may be performed in less than about 180 minutes, less than about 120 minutes, less than about 100 minutes, less than about 80 minutes, less than about 60 minutes, less than about 50 minutes, less than about 45 minutes, less than about 40 minutes, less than about 35 minutes, less than about 30 minutes, less than about 25 minutes, less than about 20 minutes, less than about 15 minutes, less than about 10 minutes, less than about 5 minutes, less than about 4 minutes, less than about 3 minutes, or less than about 2 minutes. The methods disclosed herein may be performed in less than about 1 minute.

Obtaining the Cellular Specimen

Disclosed herein are methods comprising obtaining a cellular specimen. The methods may comprise obtaining the cellular specimen from a subject. The cellular specimen may be present in, obtained from, or derived from an environment. The cellular specimen may be present in, obtained from, or derived from a biological sample. The biological sample may be an animal sample. The biological sample may be a human sample. The biological sample may be a water sample. The biological sample may be a plant sample. The biological sample may be a food product.

Obtaining the cellular specimen may occur in various settings. For example, obtaining the cellular specimen from the subject may occur at a site selected from a hospital, a CLIA lab, an operating room, an outpatient surgical suite, an outpatient facility, a medical clinic, including physician offices, examination rooms and procedure room, in a vehicle, for example, an automobile, fixed-wing aircraft, rotary wing airplane, train, ship, boat, submarine, or ambulance, in a home or office, in a permanent or temporary structure including a field clinic, and an outdoor site.

Obtaining the cellular specimen may be performed by a user (e.g., a user of a device described herein). The user may be selected from a physician, surgeon, dermatologist, pathologist, nurse, nurse practitioner, a medical assistant, a dentist, an emergency medical technician, a paramedic, a veterinarian, and a health care professional. The cellular specimen may be obtained by a third party (e.g. non-user of the device/machine). The cellular specimen may be obtained by a customs or border agent, TSA agent, employee or contractor for the Department of Defense, affiliated with a public health agency, or acting on the orders of public health officials. In some instances, the cellular specimen is not obtained by a user. The cellular specimen may be obtained by the device itself or from another system/device, for example, a simple biopsy device or complex stereotactic biopsy system. The devices described herein may be configured to obtain a cellular specimen from the subject or the environment in an automated fashion. The devices described herein may be configured to obtain the cellular specimen from pathogens or biologic hazards in an automated fashion. Obtaining the cellular specimen may be performed by the subject. Obtaining the cellular specimen may be performed by a caretaker of the subject. Obtaining the cellular specimen may be performed by an employee of a food processing plant or farm, a government inspector, or a third-party contractor.

The methods disclosed herein may comprise obtaining a cellular specimen from the subject. Obtaining the cellular specimen from the subject may be non-destructive. Obtaining the cellular specimen may avoid obfuscating the surface of the cellular specimen or the sample from which it was derived. Obtaining the cellular specimen from the subject may be non-invasive. Obtaining the cellular specimen from the subject may comprise taking off one or few top layers of cells of the sample without destroying the sample for subsequent pathology review. An example of destructive sampling may be emerging technology (iKnife) that uses mass spectrometry to analyze smoke from electrocautery. Electrocautery may destroy the tissue, or render it useless for further pathological inspection/analysis, because remaining tissue is charred creating artifacts when the specimen is sectioned for histopathology. Details and importance of obtaining cellular specimens pertaining to the methods and devices disclosed herein are further described throughout the present application.

Obtaining the cellular specimen may comprise excising a tissue or portion thereof from the subject. Obtaining the cellular specimen may comprise a brush biopsy. Obtaining the cellular specimen may comprise an imprint cytology method. The imprint cytology may be a touch-preparation (touch prep) method where the biological specimen is pressed firmly against solid surface to collect surface material from the specimen. The touch prep may be used to non-destructively obtain the top layer of cells from the tissue or portion thereof, while preserving the sample for subsequent routine analysis (e.g. histopathology). Multiple clinical studies have demonstrated that touch-prep can have a negative predictive value greater than 90%: 97% (D'Halluin F, Tas P, Rouquette S, et al. Intra-operative touch preparation cytology following lumpectomy for breast cancer: a series of 400 procedures. *Breast*. 2009. August; 18(4):248-53), 98% (Valdes E K, Boolbol S K, Cohen J M, et al. Intra-operative touch preparation cytology; does it have a role in re-excision lumpectomy? Ann Surg Oncol. March 2007; 14(3):1045-50), 99% (Bakhshandeh M, Tutuncuoglu SO, Fischer G, et al. Use of imprint cytology for assessment of surgical margins in lumpectomy specimens of breast cancer patients. Diagn Cytopathol. October 2007; 35(10):656-9), 97% (Andrew J. Creager, Jo Ann Shaw, Peter R. Young, and Kim R. Geisinger. Intraoperative evaluation of lumpectomy margins by imprint cytology with histologic correlation: a community hospital experience. *Archives of Pathology & Laboratory Medicine*. 2002. Vol. 126, No. 7, pp. 846-848), 99% (Klimberg V S, Westbrook K C, Korourian S. Use of touch preps for diagnosis and evaluation of surgical margins in breast cancer. *Ann Surg Oncol.* 1998; 5: 220-226), and 100% (Charles E. Cox; Ni Ni Ku; Douglas S. Reintgen; Harvey M. Greenberg; Santo V. Nicosia; Stephen Wangensteen. Touch Preparation Cytology of Breast Lumpectomy Margins with Histologic Correlation. Arch Surg. 1991. Vol 126, pp. 490-493). Imprint cytology has been criticized for requiring subspecialists for appropriate interpretation. While visual interpretation is a limitation of touch-prep, these studies present compelling clinical evidence that the method is a powerful technique to collect malignant cells for nucleic acid analysis.

The tissue or portion thereof may be a complex solid tissue composed of multiple morphologically or molecularly identifiable cell types. The imprint cytology method or 'touch prep' method may comprise pressing a sample collection unit to the surfaces of the tissue or portion thereof, thereby a sampling the surfaces of the tissue or portion thereof. The sampling may be comprehensive. By comprehensive, it is meant that the sampling collects cells or portions thereof, or components thereof (e.g. nucleic acids) on the sample collection unit from at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99% or at least about 100% of the surface of the tissue or portion thereof. The sampling may collect cells from at least about 80% of the surface of the tissue or portion thereof.

The cellular specimen may be obtained using imprint cytology acquisition strategies, one form of which is a 'touch prep' or similar method. A 'touch prep' is referred to as a type of imprint cytology. Generally, the term 'touch prep' refers to both the process of preparing the slide, rapid staining the slide, and analyzing the slide under a microscope. The 'touch prep' method may involve smearing or spreading the obtained cellular specimen onto a slide or a plurality of slides. The 'touch prep' method may involve pressing the slide to the biological sample. The 'touch prep' method may involve pressing the slide to the excised tissue. The 'touch prep' method may involve pressing the slide to a tissue on or within the subject. The 'touch prep' method may involve pressing the slide to an area, wall or margin surrounding a tissue or biological sample on or within the subject. The 'touch prep' method may involve pressing the slide to an area, wall or margin surrounding a site where a tissue was excised. Touch prep may be performed in less than 10 hours, less than 9 hours, less than 8 hours, less than 7 hours, less than 6 hours, less than 5 hours, less than 4 hours, less than 3 hours, less than 2 hours, or less than 1 hour. Touch prep may be performed in less than about 60 minutes, less than about 55 minutes, less than about 50 minutes, less than about 45 minutes, about less than 40 minutes, about less than 35 minutes, about less than 30 minutes, about less than 25 minutes, less than about 20 minutes, less than about 15 minutes, less than about 10 minutes, less than about 5 minutes, less than about 3 minutes, less than about 2 minutes, or less than about 1 minute. Touch prep may be performed in less than about 60 seconds, less than 50 seconds, less than 40 seconds, less than 60 seconds, less than 20 seconds, less than about 10 seconds, less than about 5 seconds, less than about 2 seconds, or less than about 1 second. The 'touch prep' method may be performed in a few seconds per slide. The 'touch prep' method may be performed in 10 seconds per slide. The 'touch prep' method may be performed in 5 seconds per slide. The 'touch prep' method may be performed in 2 seconds per slide. The 'touch prep' method may be performed by a surgeon, a nurse, an assistant, a cytopathologist, a person with no medical training or the subject. The 'touch prep' method may be operated manually. The 'touch prep' method may be operated automatically by a machine. The 'touch prep' method may be performed intraoperatively to detect or rule out malignant cells along the surgical margin (e.g. during a breast lumpectomy). During the 'touch prep' method, the excised tissue may be pressed against a sample collection unit 311 which is a glass slide coated with poly-Lysine, or other surface described herein. The cellular specimen obtained by a touch prep method may be used to determine the presence or absence of malignant cells along the margin of excised tissue. In some cases, the surface comprises sample collection unit 311 described in FIG. 3. In some cases, the sample is then applied to a sample input unit of a device described herein (see, e.g., FIGS. 1B-D), units 110 and 112, (FIG. 2) unit 210, and (FIG. 3) unit 322).

The cellular specimen may be obtained by oral swab, buccal swab or other means of screening passengers or a large number of individuals. The cellular specimen may be obtained by capillary blood draw (e.g., finger prick), venous or arterial blood draw, lumbar puncture, or bone marrow biopsy.

The cellular specimen may be obtained by a biopsy. The biopsy may be selected from, but is not limited to, a punch biopsy, a shaving biopsy, a needle biopsy, a core biopsy, an incisional biopsy, a liquid flush biopsy, an aspiration biopsy, a scraping biopsy, and a brush biopsy. The biopsy may be an excisional biopsy. The excisional biopsy may preserve functionality or cosmetic appearance by limiting the excision of adjacent healthy tissue. The excisional biopsy may comprise s a lumpectomy or breast conservation surgery, where the goal is to excise the entire tumor bounded by a thin margin of healthy tissue.

The methods comprise obtaining an outer layer or portion of a cellular specimen, e.g., a resected tumor. The outer layer or portion may have a depth into the sample. The depth may be about 1 µm, about 1.5 µm, about 2 µm, about 3 µm, about 4 µm, about 5 µm, about 6 µm, about 7 µm, about 8 µm, about 9 µm, or about 10 µm. The depth may be, e.g., about 10 µm, about 15 µm, about 20 µm, about 30 µm, about 40 µm, about 50 µm, about 60 µm, about 70 µm, about 80 µm, about 90 µm, about 100 µm, or more. The depth may be about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 1.5 mm, about 2 mm, about 3 mm, about 4 mm, about 5 mm, about 6 mm, about 7 mm, about 8 mm, about 9 mm, about 10 mm, or more. The depth may be greater than 10 mm. The depth may be greater than 5 mm. The depth may be greater than 2 mm. The depth may be about 10 mm. The depth may be about 5 mm. The depth may be about 2 mm. The depth may be any ideal depth of tissue determined by the user, such as, e.g., a surgeon. The method may comprise calculating the ideal depth of tissue such that the outer layer portion is predicted to contain non-tumor cells. The outer layer portion may be predicted to contain a clean margin (e.g., a continuous layer of non-tumor cells). Variations in sampling and reporting techniques among surgeons and pathologists account for variation in the rate of re-excisions (e.g. defining a clear margin by the distance between the edge of the excision and edge of the tumor: 1 mm v. 5 mm). The disclosed methods improve clinical care by providing an approach to standardize analysis and reporting of surgical margins. The methods may comprise assessing the outer layer or portion for the presence or absence of one or more abnormal cells, dividing cells, infected cells, tumor cells, pre-cancerous cells, pre-malignant cells, foreign cells, or infections agents.

Methods for obtaining the cellular specimen may be selected from any means known to those of skill in the art. Obtaining the cellular specimen may comprise excising a tissue from the subject (including, but not limited to a biopsy procedure) or drawing a biological fluid from the subject. The sample may be obtained surgically. For example, the biological sample may be obtained in a direct approach. The methods may comprise using a surgical instrument to manually collect tissue from a surgical site, e.g., from the surgical wall. Excising the tissue from the subject may comprise using a surgical instrument. Exemplary surgical instruments include, but are not limited to, electrocautery devices, scalpels, razors, including fixed-depth razors and variable-depth razors, fine needle aspirators, blades, curved blades, and grating devices, among others. The electrocautery device may be a Bovie. The electrocautery device may be used to obtain a biologic sample through a direct approach where the uncharred tissue is sufficient to perform a reliable analysis. The scalpel may be used to preserve tissue morphology. Obtaining the sample or portion thereof with the fixed-depth razor may rely on a space preceding the edged blade that establishes a fixed depth of tissue (e.g. disposable razors that have a fixed depth). Obtaining the sample or portion thereof with the fixed-depth razor may alternatively or additionally rely on a distance that an edged blade of the fixed-depth razor extends below a plane defined by a surface of the razor. The combination of (a) space preceding the edged blade, and/or (b) the distance that the edged blade extends below the plane of the razor may be manufactured to specify an ideal depth of tissue. In such cases, a fixed-depth razor approach may provide a method to standardize sample acquisition and reporting (nationally and internationally). Variable-depth razors may obtain samples of different depths. Different users (i.e. surgeons) may prefer different depths, which may be accomplished with the variable-depth razor, where the depth of the shaving is either determined by the space preceding the razor or the distance that the edged blade extends below the plane of the razor. Either variable may be manipulated to achieve the desired depth. The razor may have a curved blade. The curved blade may be used to create both sharp corners and straight walls of the sample. The depth of the sample may be determined with a fixed- or variable-depth razor by defining or manipulating (a) the space preceding the edged-blade, (b) the distance that the sharp edge extends below the plane of the razor, or both. The grating device may comprise multiple edges. In contrast to a single sharp edge, a device with multiple edges may be used to sample tissue from a wall of an incision. The grating device may be linear or curved. The grating device may have a tip selected from a blunt tip, a single edged tip, and a rounded tip. The tip may have multiple edges. The grating device may be used for stochastic sample collection. The grating device may not require the careful attention and visualization required to operate a single blade. The grating device may be used to avoid inadvertent penetration of adjacent blood vessels or nerves.

Obtaining the cellular specimen directly from the wall of the incision may preserve the sample for gross- and histopathologic analysis. Alternatively or in addition to directly sampling the wall of the surgical lesion, diseased, infected, or malignant cells may also be obtained along the surface of the sample, which may be referred to herein as indirectly sampling. An advantage of indirect sampling is prevention of a surgical complication (e.g. bleeding, nerve damage, damaging the wall of the excision), and is analogous to the current standard of analyzing surgical specimens by gross visualization and histopathology.

The methods may comprise obtaining a resected tissue. The methods may comprise obtaining serial sections of the resected tissue. The methods may comprise analyzing serial sections of the resected tissue. The serial sections may comprise alternating serial sections. The serial sections may comprise consecutive serial sections. The methods may comprise analyzing the serial sections. The methods may comprise preserving the serial sections for routine pathologic analysis.

The methods of obtaining the cellular specimen may comprise a biopsy, such as a core biopsy or fine needle aspiration, sometimes guided by stereotactic equipment. If the results are suspicious or definitive for cancer, the surgeon may perform an excisional biopsy, for example, a breast conservation surgery (BCS or lumpectomy), a partial mastectomy, a quadrantectomy, a mastectomy, a radical mastectomy, or a super-radical mastectomy. The developmental embryology of the mammary system may be used to map and dissect only the glandular subsystem containing malignant tissue.

The methods of obtaining the cellular specimen may be directed by a device that analyzes a surgical specimen (e.g. excised tissue) or surface thereof. The device may be a probe. The probe may analyze the surgical specimen or surface thereof with electromagnetic waves. The probe may detect a dye in the surgical specimen. The dye may be radioactive. A first signal may be projected by the device if the surface of the excised tissue is affected by a disease or condition (e.g. malignancy) and a second signal may be projected if the surface of the excised tissue is healthy, wherein the first signal and the second signal are different. For example, low frequency radio waves may be projected by the device if the surface of the excised tissue is malignant, relative to higher frequency radio waves that are projected if the surface of the excised tissue is healthy. The device may possess an algorithm that is responsible for classifying the surface as malignant or healthy. The device may differentiate between malignant and healthy tissue by a difference in dielectric properties between these tissues. The healthy and/or malignant tissues may be breast tissue. The healthy and/or malignant tissues may be ductal aspirate lavage. The healthy and/or malignant tissues may be aspirate fluid from a breast. The device may be a MarginProbe™ System. The device may be used in combination with the devices disclosed herein in an effort to ensure surgical margins are clear or if additional tissue should be excised. The device may be used in combination with the devices disclosed herein during a surgical procedure to determine if surgical margins are clear or if additional tissue should be excised. The device may be used in combination with the devices disclosed herein after a surgical procedure to determine if surgical margins are clear or if additional tissue should be excised. The determination of surgical margins can be performed in the surgical room or outside of the surgical room. The determination of surgical margins can be performed in a different geographical location of the surgical procedure.

The methods disclosed herein may comprise characterizing the biological sample. Characterizing the biological sample may be comprehensive. Characterizing the sample may comprise characterizing the entire biological sample. Characterizing the sample may comprise characterizing at least about 10%, at least about 20%, at least about 30%, at least about 40%, at least about 50%, at least about 60%, at least about 65%, at least about 70%, at least about 75%, at least about 80%, at least about 85%, at least about 90%, at least about 92%, at least about 94%, at least about 96%, at least about 98%, or at least about 99% of the biological sample. Characterizing the sample may comprise characterizing an entire surface of the sample. Comprehensive analysis of the surgical specimen is important both during and after a surgical procedure. One of the primary limitations of existing intraoperative technologies is that they do not analyze the entire surface of a surgical specimen. The MarginProbe™ system, for example analyzes punctate samples that only comprise a limited portion of the specimen surface. The methods and devices disclosed herein provide a major advance for the field by enabling a comprehensive analysis of the surface of the surgical specimen during an operation. One of the major limitations of margin analysis is that the analysis does not comprehensively evaluate the entire surface of a surgical specimen. The sample acquisition method described herein may be used to sample the entire surface of the specimen. The disclosed sample acquisition method may be used to sample a portion of the specimen surface, where the portion is greater than 99%, greater than 95%, greater than 90%, greater than 85%, greater than 80%, greater than 75%, greater than 70%, greater than 65%, greater than 60%, greater than 50%, greater than 40%, greater than 30%, greater than 20%, greater than 10, greater than 5%, greater than 1% of the surface of the specimen. The surface of the specimen may be the entire surface of the specimen. Existing methods to evaluate the surface of a surgical specimen involve statistical sampling methods that only represent a small fraction of the specimen's entire surface (often less than 0.5%). For example, histopathology has been the gold-standard method to detect positive margins on a surgical specimen. Histopathology involves taking serial microscopic sections of the specimen. Pathologists have estimated that histopathology could require thousands of microscopic sections to comprehensively evaluate the entire surface of a typical breast lumpectomy specimen. Most labs examine 4-15 microscopic sections to determine whether there are malignant cells along the surface of the specimen, a sampling strategy that only represents <0.05% of the surface of the specimen. Routine histopathology is statistically underpowered to evaluate margin status. Multiple studies have found that margins status (positive or negative) is the single greatest clinical factor in breast cancer prognosis. The disclosed methods of obtaining a comprehensive sample from the entire specimen surface could therefore have profound clinical benefits. For this indication, even a sampling method that obtains 1% of the specimen surface would represent almost a 2,000% increase over existing practice. The false negative rate (FNR) of detecting positive breast cancer margins using histopathology is greater than 15%. In some cases, it may be greater than 20% or greater than 30%. The FNR of existing tests may account for up to 20% of deaths from breast cancer. The methods described herein to reduce the FNR of positive surgical margins are a clinical imperative, and a major advance to the field.

The sampling strategy can encode spatial information. By way of non-limiting example, about 6 to about 10 slides may be used to capture a specimen, or spatial information from a specimen. The spatial information may include, but is not limited to, features or aspect that are superior, inferior, medial, lateral, proximal, distal, superficial, or within the sample/specimen. For example, one slide can contain cells from the lateral edge of the surgical specimen. If the sample from that slide tests positive for malignant cells, the device directs the surgeon to excise additional tissue from the lateral wall of the incision.

Obtaining the cellular specimen may take less than about 180 minutes, less than about 120 minutes, less than about 100 minutes, less than about 80 minutes, less than about 60 minutes, less than about 50 minutes, less than about 45 minutes, less than about 40 minutes, less than about 35 minutes, less than about 30 minutes, less than about 25 minutes, less than about 20 minutes, less than about 15 minutes, less than about 10 minutes, less than about 5 minutes, less than about 4 minutes, less than about 3 minutes, less than about 2 minutes, or less than about 1 minute.

The touch prep method may take less than about 15 minutes, less than about 10 minutes, less than about 5 minutes, less than about 4 minutes, less than about 3 minutes, less than about 2 minutes, or less than about 1 minute. The touch prep method may take less than about 10 minutes. The touch prep method may take less than about 5 minutes. The touch prep method may take less than about 2 minutes. The touch prep method may take less than about 1 minute.

Manual Steps/Interaction with Devices

The methods may be used to perform a test with a device disclosed herein with minimal user input or interaction. The number of user steps required to process biologic samples is one of the major obstacles preventing molecular analysis from being performed outside of a clinical lab, and limiting the time required to process clinical samples. Thus, the devices and methods disclosed herein overcome these obstacles with novel means for obtaining and applying molecular information.

The methods disclosed herein may comprise one or more manual interactions with the device. The manual interaction may comprise inserting the cellular specimen into any one of the devices disclosed herein. The manual interaction may comprise pressing/touching a button/icon of the device. Alternatively, the device may operate automatically without the user pressing/touching a button/icon of the device. The manual interactions may comprise pressing a surgical specimen against a glass slide, inserting the glass slide into the device, and optionally pressing one or more buttons.

For example, the devices and methods described herein may enable a user to perform the test in less than 5 user steps from sample collection, including, by way of non-limiting example, inputting patient information, linking test results to a medical record, and obtaining a test result. The devices and methods described herein may enable a user to perform the test in less than 4, 3, or 2 user steps from sample collection to obtaining a test result. The devices and methods may enable the user to perform the test in a single user step from sample collection to obtaining a test result. The devices and methods described herein may not require user interaction with more than 5 instruments. The devices and methods described herein may not require user interaction with more than 4, 3, 2, or 1 instrument. The devices and methods described herein may require user interaction with a single instrument. For example, a device described herein can comprise a single instrument. The devices described herein may not comprise more than 5, 4, 3, 2, or 1 instrument.

The methods described herein may comprise one or more computer-based user interactions. The computer-based human interactions may occur during a surgical procedure. The device may not require the user to perform more than about 1, more than about 2, more than about 3, more than about 4, more than about 5, more than about 6, more than about 7, more than about 8, more than about 9, or more than about 10 computer-based user interactions the surgical procedure. The computer-based user interaction may be performed, for example, with input devices such as a keyboard, a button, a mouse, a pointer, and motion or voice detection. The computer-based user interaction(s) may be input via a touch screen. The devices may be preprogrammed prior to a surgical procedure to anticipate an expected type of cellular specimen (e.g. a cellular specimen with a suspected disease or condition). During the surgical procedure, only a small number of computer inputs are required for sample analysis. A single computer-based user interaction may be required to analyze a cellular specimen during a surgical procedure. The cellular specimen may be inserted on an instrument or cartridge that contains all commands or information necessary to complete the analysis; in these cases, no computer interaction is required. The act or process of physically contacting one or more units with the device itself constitute the necessary information to retrieve or initiate a preprogrammed set of parameters or instructions required to perform the test. The act or process of physically touching a unit to the device may constitute a request to perform the test. The unit that contacts the device may be selected from the sample collection unit, the sample preparation unit, the cartridge, and any combination thereof. The act of physically contacting the sample collection unit to the device may constitute a request to perform a specific test. As a non-limiting example, the sample collection unit, sample preparation unit, and the test cartridge may be contained in a single device, and the act of contacting the device to the instrument can constitute the command to perform the test. Moreover, the device can contain information that directs the device to perform the indicated test, whereby contacting the device with the sample collection unit is the only manual step required to command the instrument and perform the test. These cases exemplify situations where the device requires no other interactions with the device. Surgical environments demonstrate the importance of reducing user interactions with a device or device. Interacting with a sterile device/unit would not compromise the aseptic technique of a surgeon, while performing a single physical interaction, e.g. pushing one button or touching a screen, would place the patient at risk of infection. Chaotic and noisy surgical environments also demonstrate the limitations of commanding the device by voice or gesticulations. Decentralized environments also demonstrate the importance of reducing user interactions with a device or device. For example, molecular testing of food supply requires a dedicated molecular analysis lab with trained personnel. Establishing an adequate environment may be challenging in a dusty processing facility, and trained personnel cannot be deployed in every point that food products enter the food chain. It is therefore important to limit the number of user interactions with the device so that the device can be deployed in complex decentralized environments, and operated by users without specialized training.

The one or more manual interactions with the device may altogether take less than about 10 minutes, less than about 5 minutes, less than about 4 minutes, less than about 3 minutes, less than about 2 minutes, or less than about 1 minute. The one or more manual interactions with the device may take less than one minute altogether.

Exemplary Methods

Figure 2:
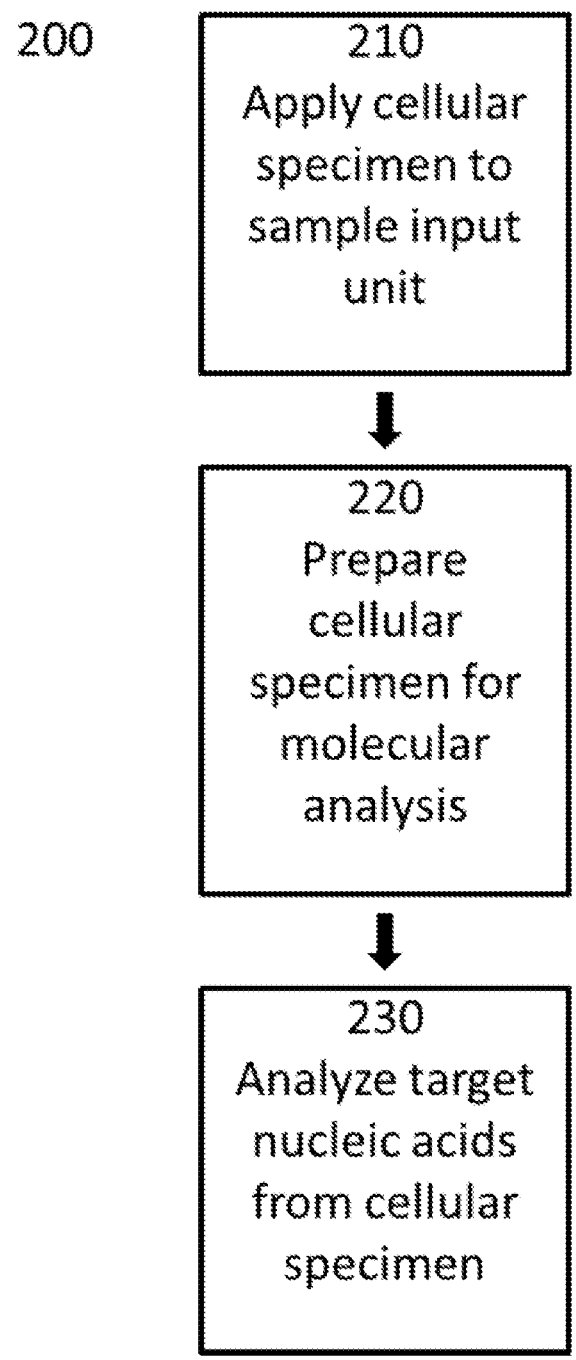
FIG. 2 depicts an exemplary workflow of a method for rapid analysis of biological samples.

Devices described herein may implement a method for rapid molecular analysis of the sample. FIG. 2 depicts a workflow for an exemplary method 200, comprising step 210 of applying the cellular specimen to the sample input unit described herein, step 220 of preparing the cellular specimen for molecular analysis, and step 230 of analyzing the target nucleic acid(s) in the cellular specimen. Preparation step 220 may comprise disrupting the cells and or tissues, making the target nucleic acid accessible for analysis, and removing inhibitors or contaminants that could interfere with subsequent molecular amplification or analysis. In some cases, preparation step 220 comprises biochemical extraction of a class of molecules. In some cases, preparation step 220 consists essentially of disrupting or homogenizing the cellular specimen to produce a crude lysate. In some cases, the molecular analysis does not require purifying or isolating the target nucleic acid(s).

An exemplary method described herein may comprise (i) tissue disruption and cell lysis, (ii) cDNA synthesis, (iii) isothermal amplification, and (iv) electrochemical detection. Reaction components may be optimized to minimize the time patients will be under anesthesia by eliminating unnecessary purification steps. For example, in some instances the methods use a single buffer that is compatible with all four steps in the above exemplary method. Any or all of the four steps may be performed by the device under the operation of the user. Any or all of the four steps may be carried out in a single reaction chamber of the device or an operably connected series of reaction chambers, without requiring intervening purification.

The methods may further comprise performing a postoperative test. In contrast to intraoperative tests, which may be performed on patients who have been diagnosed (e.g. by biopsy), or with a suspicion of a diagnosis (e.g. a lesion of the breast with characteristic radiologic findings consistent with carcinoma), postoperative testing provides an adjunct tool to complement subsequent or concurrent diagnostic methods. For example, the methods described here may be used to detect positive surgical margins (malignant cells on the surface of the surgical specimen, indicating residual tumor in the patient). Histopathology is currently the gold-standard method to detect positive surgical margins, although the false negative rate may be 20-30%. The methods described here can be used as a postoperative test to complement diagnosis by histopathology. The postoperative test may be an expression panel performed on cells that are collected, for example, by touch prep or brush biopsy, and analyzed in a pathology laboratory either on an automatic device described herein or through a series of manual steps to isolate RNA and subsequently quantify the panel on available systems like a real-time thermocycler or nCounter®. The cDNA synthesis and amplification steps may be performed concurrently or subsequently. The processes may be performed in the same facility as the surgical procedure, or in a different facility. As an example, for a real-time thermocycler analysis, cDNA synthesis and amplification may occur concurrently. Alternatively, cDNA synthesis may be performed using kits and reagents from one vendor, followed by real-time analysis performed on a thermocycler or heat block using reagents provided by another vendor. The isothermal assay described herein can be used for a postoperative test. A more routine assay like PCR may be used for the postoperative test. The postoperative test directs surgeons to perform more extensive surgical procedure. The postoperative test may additionally direct physicians to administer chemotherapy and/or radiotherapy.

Both the intra-operative or postoperative test may include controls to detect cancers that are not breast cancer. A gene expression panel that only tests thyroid cancer versus no thyroid cancer will likely miss cancers of the thyroid that originated elsewhere. As another example, a postoperative test may include genes to detect other cancers that may not be breast cancer. There are factors that mitigate the importance of detecting non-breast cancers in the breast. Without being bound by any theory, the breast is not a common metastatic site for cancers from other organs. Typically, another test is performed to examine the lesion itself, which may serve as subsequent or concurrent diagnosis by another means. For instance, the postoperative test described herein specifically examines the margins, while another test will be used to determine whether the lesion is benign or pathologic, malignant, the type of tumor or infiltration, and prognostic criteria like tumor grade. The secondary test may be a molecular analysis (e.g. a classifier like OncotypeDX or PAM50, which includes a classifier to detect lesions with normal expression patterns) performed on a section through the lesion (either the primary lesion, a secondary or tertiary lesion in the ipsilateral breast, micro-metastases to lymph nodes, or occult metastases).

IV. Cellular Specimens/Samples

Provided herein are devices and methods that analyze a cellular specimen. The devices and methods may detect diseased or infected cells in the cellular specimen. The cellular specimen may comprise a biological material removed from a subject. The cellular specimen may be a random or non-random cellular specimen from the subject. Random cellular specimens include cellular specimens utilized for environmental monitoring and testing, food pathogen screening or detection, and screening for infectious agents in a facility or population. The cellular specimen may be obtained or removed from the subject for any reason. The cellular specimen may be specifically collected for evaluation purposes by a method selected from, by way of non-limiting example, fine needle aspiration, blood draw, and incisional biopsy; as part of a therapeutic strategy (e.g. excisional biopsy, which may include a breast cancer lumpectomy); or for cosmetic purposes (e.g. non-malignant dermatologic procedures or cosmetic surgery). The cellular specimen may contain biological information that is used to understand, evaluate, diagnose, or direct the treatment of, a disease or condition. The cellular specimen may contain biological information that is used to evaluate a screen or direct subsequent action (e.g. remove a batch of food products from distribution for a specific purpose).

The cellular specimen generally contains a cell. The cellular specimen may comprise a portion, a component, or a lysate of the cell. However, the methods and devices disclosed herein also provide for analyzing a target nucleic acid in a cellular specimen that does not contain a cell. The cellular specimen may be associated with a cell. For example, the cellular specimen may be an extracellular fluid, an extracellular matrix, a bodily fluid, a bodily excretion/secretion, or a combination thereof. The extracellular/bodily fluid may comprise the target nucleic acid. The target nucleic acid may be a viral nucleic acid. Thus the methods and devices are capable of assessing a viral load. The target nucleic acid may be a bacterial nucleic acid.

The cellular specimen may contain no biological markers for a disease or condition, and the absence of specific markers may be used to understand, evaluate, exclude, diagnose or direct the treatment of the subject.

The cellular specimen may be selected from a single cell, a plurality of cells, a tissue or portion thereof, and an organism or portion thereof. The cellular specimen may comprise a layer of cells and/or portions thereof. The cellular specimen may comprise a single layer of cells and/or portions thereof. The cellular specimen may comprise a plurality of layers of cells or portions thereof. The layer(s) of cells or portions thereof may be less than about 1 micron thick, less than about 2 microns thick, less than about 3 microns thick, less than about 4 microns thick, less than about 5 microns thick, less than about 6 microns thick, less than about 7 microns thick, less than about 8 microns thick, less than about 9 microns thick, or less than about 10 microns thick. The layer(s) of cells or portions thereof may be less than about 20 microns thick, less than about 30 microns thick, less than about 40 microns thick, less than about 50 microns thick, less than about 60 microns thick, less than about 70 microns thick, less than about 80 microns thick, less than about 90 microns thick, or less than about 100 microns thick. The layer(s) of cells or portions thereof may be about 1 micron thick, about 2 microns thick, about 3 microns thick, about 4 microns thick, about 5 microns thick, about 6 microns thick about 7 microns thick, about 8 microns thick, about 9 microns thick, or about 10 microns thick. The layer(s) of cells or portions thereof may be about 20 microns thick, about 30 microns thick, about 40 microns thick, about 50 microns thick about 60 microns thick, about 70 microns thick, about 80 microns thick, about 90 microns thick, or about 100 microns thick. The cellular specimen may comprise a cell wall or a cell membrane. The layer(s) of cells or portions thereof may be less than 20 microns thick. The layer(s) of cells or portions thereof may be less than 10 microns thick. The layer(s) of cells or portions thereof may be less than 5 microns thick. The layer(s) of cells or portions thereof may be less than 2 microns thick. The layer(s) of cells or portions thereof may be about 10 microns thick. The layer(s) of cells or portions thereof may be about 5 microns thick. The layer(s) of cells or portions thereof may be about 2 microns thick. The layer(s) of cells or portions thereof may be about 1-100 microns thick, about 5-90 microns thick, about 2-20 microns thick, about 5-40 microns thick, about 1-5 microns thick, about 1-3 microns thick. The cell wall or cell membrane may be intact (e.g. not disrupted/lysed) before the cellular specimen contacts the sample input unit.

The cellular specimen may be derived from a lumpectomy, a cancer, a solid tumor, a malignant tumor, a primary tumor, a lymph node, an early stage tumor, a localized tumor, a benign tumor that is at risk of becoming malignant, benign tumor, where the tumor does not have a risk of becoming malignant, and a non-metastatic tumor.

The cellular specimen may be obtained/derived/prepared from the surface, layer or section of a sample. The cellular specimen may be obtained/derived/prepared from the surface of a surgical specimen. The cellular specimen may be obtained from an excised tissue or portion thereof. The excised tissue or portion thereof may be a complex solid tissue. The complex solid tissue may be composed of multiple morphologically distinct cell types. The complex solid tissue may be composed of multiple molecularly identifiable/distinct cell types. The cellular specimen may be derived from the surface of the surgical specimen via a touch prep method.

The cellular specimen may be a biological entity. The cellular specimen may be extracted, derived, purified or isolated from the biological entity. The biologic entity may be any living or previously living cellular organism.

The cellular specimen may be at least partially obtained by removal of a specimen or sample from a subject. The removal may be a mechanical removal (e.g. by scalpel, razor or needle). The removal may be a chemical removal. The removal may be an ultrasonic, electric or laser removal. The removal may be a biopsy. The biopsy may comprise a removal of a biologic specimen. The biopsy may not be restricted by a method of acquisition, the instruments used to collect the specimen, or the individual or machine performing the biopsy procedure. The biopsy may include, but is not limited to a punch biopsy, a shaving biopsy, a needle biopsy, a core biopsy, an incisional biopsy, a liquid flush biopsy, an aspiration biopsy, a scraping biopsy, and a brush biopsy. The biopsy may be an excisional biopsy. The excisional biopsy may preserve functionality or cosmetic appearance by limiting the excision of adjacent healthy tissue. The excisional biopsy may comprise a lumpectomy or breast conservation surgery.

The sample may be a biological sample. The terms "sample" and "biological sample" are used interchangeably herein, unless otherwise specified. In some cases, the cellular specimen is the sample. In some cases, the cellular specimen is a portion of the sample. In one example, the sample may be a volume of blood analyzed from a larger specimen of blood. In another example, the cellular specimen may be a specific portion of the sample, for example the supernatant of centrifuged blood specimen or the surface of a solid mass excised by a surgeon.

The sample(s) may comprise a substance, specimen or material comprising entities selected from cells; extracellular elements, whose existence is or was dependent on cells; a combination of cells and extracellular material that was previously contained within, associated with the surface of secreted or excreted from a biological entity. The sample may be derived, purified, isolated, extracted, excised or otherwise removed from a tissue. As used herein, "tissue" may refer to a collection of cells, extracellular elements and liquid that function or exist together in a biologic entity. The tissue may have rigid, flexible, or dynamic structures. The tissue may be a solid tissue or liquid tissue. The "solid tissue" may refer to a tissue, as defined herein, with a rigid or semi-rigid structure that may be soft or hard, flexible or rigid, may have reproducible or recognizable macroscopic or microscopic structure or substructures, and may be amorphous. Solid tissues may be broadly defined as any tissue that does not meet the classification criteria of a liquid tissue, where a liquid tissue is a tissue whose constituent components, as found in the biologic source, are freely physically interchangeable and may be separated from one another without mechanical or enzymatic disruption.

The tissue may be selected from, by way of non-limiting example, a muscle, adipose, skin, mammary tissue, a gland tissue, a follicle, blood, cerebral spinal fluid and bone marrow.

The sample may comprise bacteria, viral particles, proteins, prions, remnants thereof, portions thereof, derivatives thereof, and combinations thereof. The sample may be obtained from a subject for which molecular testing would be useful or informative, and should not be limited to the specific examples described herein.

The sample may be obtained from a subject. The subject may be previously diagnosed with the disease or condition. The sample may be a biological sample. The biological sample may be a substance presumed to comprise a nucleic acid. The sample may be a solid sample or a liquid sample. Exemplary solid samples include, by way of example only, feces, tissue biopsy (such as tumor biopsy, resected tumor, or other tissue biopsy that includes endoderm, mesoderm, ectoderm, or some combination thereof), food sample, hair, nails, skin, clothing, etc. Exemplary liquid samples may include whole blood, plasma, serum, cerebrospinal fluid, ascites, sweat, tears, saliva, urine, buccal sample, semen, vaginal fluid, cavity rinse, food sample, or organ rinse. The liquid sample may be a cell-free or essentially cell-free liquid sample (e.g., plasma, serum, saliva, sweat, urine, tears, sputum). The anatomic location may be an organ, for example a solid lesion removed from the breast, brain, prostate, lymph node; alternatively an organ may be a liquid physiologic system, for example, blood, cerebral spinal fluid, urine, secretions, or excretions.

The subject sample may be a surgical sample. The molecular test may detect disease or infected cells along a margin of a surgical sample. The surgical sample may be a biopsy. The surgical sample may be an extracted tissue. The subject sample may be a fluid sample (e.g., lymph, blood, urine, plasma, serum, saliva). The subject sample may be swab sample, swabbed from skin, or in or around an external or internal orifice, such as the mouth, ear, nose, urethra, cervix, vagina or anus. The diseased cells may be tumor cells. The diseased cells may be cancerous cells. The diseased cells may be pre-cancerous cells. The diseased cells may be abnormal cells. The tests may be used, for example, for tissue conservation surgeries. The tissue may be breast tissue. The tests may detect malignant tissue and guide surgeons to perform more extensive excisions. The diseased cells may be cells that possess a nucleic acid with a genetic mutation. Also provided herein are molecular tests that detect a pathogen on/in a subject sample.

The devices, kits and methods described herein may provide for rapid screening of food products. As an example, food producers need a rapid screening test that may be implemented in production facilities. Food safety is a rapidly changing field. Three major forces are shaping the future of food safety: increased regulation, global trade, and testing technologies. Both regulators and industry are pushing for decentralized testing. Advances in molecular technologies may amplify and detect pathogens in the field. Devices, kits and methods disclosed herein provide a mechanism to perform molecular testing in an automated manner. Solving these obstacles may allow tests to be performed by end-users without formal training in laboratory or diagnostic medicine, and extends modern molecular testing from reference or hospital-based labs and into broader society.

Although the molecular targets will differ, tests for both food safety and malignant surgical margins require a high negative predictive value. While negative predictive value is important to screen for diseases or pathogens, definitive diagnostic tests require high sensitivity and specificity. Provided herein are sample analysis systems for biomarkers that may be configured to direct subsequent therapy.

The cellular specimen may comprise one or more cells. The cells may be obtained from a subject. The term "subject", as used herein, generally refers to a biological entity containing expressed genetic materials. The biological entity may be a plant, animal, or microorganism, including, e.g., bacteria, viruses, fungi, and protozoa. The subject may be tissues, cells and their progeny of a biological entity obtained in vivo or cultured in vitro. The subject may be a mammal. The mammal may be a human. The mammal may be a dog, a cat, a hamster, a mice, a rat, a sheep, a cow, a monkey, or a chimpanzee. The human may be diagnosed or suspected of being at high risk for a disease. The disease may be cancer. The cancer may be, e.g., breast cancer. The subject may be diagnosed with the cancer. The subject may have been diagnosed with the cancer by a fine needle aspiration biopsy or a core biopsy. The subject may be suspected of having the cancer. The subject may have a strong likelihood of having the cancer. The subject may have a high risk of developing the cancer. The subject that has a high risk of developing the cancer may be known to have an inherited mutation predisposing the subject to the cancer. The human may not be diagnosed or suspected of being at high risk for a disease.

The cells and/or tissues may be obtained from the surface of a tumor in the subject. The tumor may be of solid or liquid tumor origin, and may be tested from solid or liquid tissue: for example circulating lymph cells (liquid tissue that presents as a solid mass in lymph node). The tumor may be a cancer. The cancer may be malignant or has malignant potential. The patient may be suspected of having cancer. The patient may have been diagnosed as having cancer. The cancer risk may be recurrence risk. Exemplary cancers include but are not limited to breast cancer, prostate cancer, skin cancer, lung cancer, colon cancer, brain cancer, bone cancer, cervical cancer, oral cancer, pancreatic cancer, rectal cancer, and lymphoma. The oral cancer may be selected from throat cancer, mouth cancer, and esophageal cancer.

V. Target Nucleic Acids

Disclosed herein are devices, kits and methods for analyzing one or more target nucleic acids. The target nucleic acid is a nucleic acid that corresponds to a gene of interest or a gene of which abnormal expression is associated with a condition other than normal/healthy. In contrast, an off-target nucleic acid is a nucleic acid of which expression changes or differences between samples or cellular specimens would not provide any indication of a presence or absence of a disease or condition. Gene expression of an off-target nucleic acid may remain constant or may not differ in the presence versus absence of the disease or condition.

The terms "nucleic acid", "polynucleotide", and "oligonucleotide" may be used interchangeably to refer to a polymeric form of nucleotides of any length. The polynucleotide may comprise any combination of deoxyribonucleotides, ribonucleotides, and analogs thereof (such as, e.g., methylated nucleotides). The polynucleotide may have three-dimensional structure, and may perform any function which is known or unknown. The following are non-limiting examples of polynucleotides: coding or non-coding regions of a gene or gene fragment, genomic loci, exons, introns, messenger RNA (mRNA), transfer RNA, ribosomal RNA, small RNA, microRNA, ribozymes, cDNA, recombinant polynucleotides, branched polynucleotides, plasmids, vectors, isolated DNA of any sequence, genomic DNA, mitochondrial DNA, isolated RNA of any sequence, nucleic acid probes, and primers. If present, modifications to the nucleotide structure may be imparted before or after assembly of the polymer. The sequence of nucleotides may be interrupted by non-nucleotide components. The polynucleotide may be further modified after polymerization, such as by conjugation with a labeling component. The sequence of the nucleic acid may be modified during or preceding the molecular amplification, for example by removing a 3' blocking group when a primer specifically binds to its target.

The terms "target nucleic acid" and "target" refer to a polynucleotide of interest under study and are used interchangeably herein, unless specified otherwise. For example, the target nucleic acid may contain one or more sequences that are of interest and under study. The target nucleic acid may comprise, for example, a genomic sequence. The "genomic sequence" may refer to a sequence that occurs in a genome, e.g., a nuclear genome or mitochondrial genome. Because RNAs are transcribed from a genome, a "genomic sequence" may encompass sequences transcribed from a genome, e.g., may encompass sequences present in mRNA, a cDNA copy of an mRNA sequence. RNAs may encompass sequences of exons and introns. RNAs may also encompass sequences of spliced RNA. The target nucleic acid may be a cancer-associated gene. The cancer-associated gene may be a nucleic acid encoding a protein that is over-expressed or under-expressed in a cancer patient. The cancer-associated gene may comprise a mutation that causes the cancer. The cancer-associated gene may be a tumor suppressor gene. The cancer-associated gene may be an oncogene. The cancer-associated gene may be selected from, by non-limiting example, PC cell-derived growth factor (PCDGF), epidermal growth factor receptor (EGFR), receptor tyrosine-protein kinase erbB-2 isoform b (HER2/neu), MUC4, Insulin-like growth factor I receptor (IGF-IR), cyclin-dependent kinase inhibitor 1B (p27 (kip1)), Protein kinase B (Akt), HER3 protein precursor (HER3), receptor tyrosine-protein kinase erbB-4 (HER4), PTEN, PIK3CA, SHIP, Grb2, Gab2, 3-phosphoinositide dependent protein kinase-1 (PDK-1), TSC1, TSC2, mTOR, mitogen inducible gene 6 (MIG-6)/ERBB receptor feedback inhibitor 1, proto-oncogen tryopsin protein kinase (src), KRAS, BRAF, MEK mitogen-activated protein kinase kinase kinase 1, MYC, TOPO II topoisomerase (DNA) II, FRAP1, NRG1, estrogen receptor 1 (ESR1), progesterone receptor (PGR), CDKN1B, MAP2K1, NEDD4-1, FOXO3A, PPP1R1B, PXN, ELA2, CTNNB1, AR, EPHB2, KLF6, ANXA7, NKX3-1, PITX2, MKI67, PH domain and leucine rich repeat protein phosphatase 1 (PHLPP1), Engrailed 2 (EN2), ITIH4 fragment 1 (BC-1), ITIH4 fragment 1b (BC-1b), C3a-desArg, casein kinase II alpha 1 subunit isoform a, keratin 2a, D-amino-acid oxidase, glycosyltransferase-like 1B, transgelin 2, complement component 4A preproprotein, complement component 3 precursor, inter-alpha (globulin), fibrinogen beta chain preproprotein, transthyretin, delta-like 1, dendritic cell-specific transmembrane protein, beta tubulin 1 class VI, fumarylacetoacetate hydrolase domain containing 1 isoform 2, MAX dimerization protein 3, nuclear prelamin A recognition factor isoform b, tubulin beta 6, caldesmon 1 isoform 4, keratin 14, granzyme H, keratin 6 irs, ankyrin repeat domain 30A, zinc finger protein 291, dermcidin precursor, talin 1, keratin 1, vacuolar protein sorting 16 isoform 3, tubulin, alpha 3, splicing coactivator subunit SRm300, ribosomal protein S6 kinase, 52 kDa, polypeptide 1, myeloid-associated differentiation marker, oxysterol-binding protein-like protein 9 isoform e, p47 protein isoform a, H2B histone family, member R, proteasome 26S ATPase subunit 3, drebrin-like isoform a, ELL associated factor 2, yippee-like 4, D-amino-acid oxidase, ATP-binding cassette sub-family C member 12 isoform b (ABCC12b), apolipoprotein L1 isoform b precursor, myosin XV, splicing factor, arginine/serine-rich 8, isoform 1, p21-activated kinase 7, germ cell associated 1 isoform 2, piggyBac transposable element derived 4, keratin 6 isoform K6e, discoidin, CUB and LCCL domain containing 1, zonadhesin isoform 1, nuclear receptor subfamily 4 group A member 1 isoform a (NR4A1a), peroxisome proliferator-activated receptor binding protein, dual oxidase 1 precursor, casein kinase II alpha 1 subunit isoform a, tubby isoform b, ring finger protein 180, WD repeat and FYVE domain containing 3 isoform 1, inter-alpha (globulin) inhibitor H4 (plasma Kallikrein-sensitive glyco), Nedd4 binding protein 2, glycosyltransferase-like 1B, transmembrane emp24 protein transport domain containing 4, thymosin-like 3, Ca2+-dependent secretion activator isoform 2, diacylglycerol O-acyltransferase 2 like 6, immunoglobulin superfamily member 10, keratin 10, ribulose-5-phosphate-3-epimerase isoform 1, regulating synaptic membrane exocytosis 1 isoform 1, protein phosphatase 1, regulatory subunit 15B, connector enhancer of kinase suppressor of Ras 2, FYN binding protein (FYB-120/130) isoform 1, alpha-2-HS-glycoprotein, baculoviral IAP repeat-containing protein 2, brain-specific angiogenesis inhibitor 3, calpain 2 large subunit, desmoglein 1 preproprotein, eukaryotic translation initiation factor 3 subunit 8 110 kDa, erythrocyte membrane protein band 4.9 (dematin), coagulation factor XII precursor, coagulation factor II precursor, histatin 1, kininogen 1, polymerase (DNA directed), delta 1, catalytic subunit 125 kDa, pro-platelet basic protein precursor, protein S (alpha), phosphoribosyl pyrophosphate synthetase-associated protein 1, transgelin 2, transforming growth factor beta induced 68 kDa, transthyretin, vasodilator-stimulated phosphoprotein isoform 1, weel tyrosine kinase, zyxin, poly(A) binding protein cytoplasmic 3, zinc finger protein 526, apolipoprotein C-III precursor, complement component 3 precursor, developmentally regulated GTP binding protein 2, interleukin 2 receptor alpha chain precursor, pad-1-like, proteoglycan 1 secretory granule precursor, v-rel reticuloendotheliosis viral oncogene homolog A nuclear factor o, differentially expressed in FDCP 8, delangin isoform A, CREB binding protein, glypican 5, serum deprivation response protein, H1 histone family member 1, bridging integrator 2, olfactory receptor family 6 subfamily C member 3, alpha-1-antitrypsin precursor, ADP-ribosylation factor-like 9, RUN and TBC1 domain containing 1, acetyl-Coenzyme A acetyltransferase 2, ubiquinol-cytochrome c reductase Rieske iron-sulfur polypeptide 1, olfactory receptor family 8 subfamily S member 1, calcium channel voltage-dependent alpha 1E subunit, neurogranin, notch4 preproprotein, tubby like protein 4 isoform 1, keratin 9, pleckstrin and Sec7 domain containing, sodium channel voltage-gated type X alpha, solute carrier family 12 (potassium/chloride transporters) member 7, hornerin, heterogeneous nuclear ribonucleoprotein A0, Lysosomal associated multispanning membrane protein 5, PDZ and LIM domain 5 isoform a, proline-rich protein BstNI subfamily 2, leucyl/cystinyl aminopeptidase isoform 1, DnaJ (Hsp40) homolog subfamily B member 4, alpha-2-macroglobulin precursor, complement component 4A, corneodesmosin precursor, alpha-synuclein isoform NACP112, peroxisome proliferative activated receptor gamma coactivator 1, fibrinogen beta chain preproprotein, F-box and leucine-rich repeat protein 15, SET binding protein 1, epithelial protein lost in neoplasm beta, headcase, tubulin alpha 8, phosducin-like, proline-rich protein HaeIII subfamily 1, EGF, CD2, CD3, CDS, CD7, CD13, CD19, CD20, CD21, CD23, CD30, CD33, CD34, CD38, CD46, CD55, CD59, CD69, CD70, CD71, CD97, CD117, CD127, CD134, CD137, CD138, CD146, CD147, CD152, CD154, CD195, CD200, CD212, CD223, CD253, CD272, CD274, CD276, CD278, CD279, CD309 (VEGFR2), DR6, PD-L1, Kv1.3, thy-1 membrane glycoprotein preproprotein, MUC1, uPA, SLAMF7 (CD319), MAGE 3, MUC 16 (CA-125), KLK3, Mesothelin, p53, Survivin, G250 (Renal Cell Carcinoma Antigen), PSMA, apolipoprotein C1, haptoglobin alpha 1, apolipoprotein A1, Transferrin, Haptoglobin alpha 1, HOXC4, 5 alpha reductase, α-fetoprotein, beta-catenin, Bcl2, Ovarian cancer related tumor marker (CA125), apoptotic cysteine protease, COX-2, netrin receptor DCC, tumor nacrosis factor receptor superfamily member 6B (DcR3), bone marrow proteoglycan (EMBP), pithelial-derived neutrophil-activating protein 78 (Ena78), FGF8a, FGF8b, FLK-1, Gastrin 17, gonadotropin releasing hormone (GnRH), heparanase, heat shock 70 kDa protein 70, interleukin 13 receptor (IL-13R), nitric oxide synthase, inducible (iNOS), KIAA0205, v-ras, melanoma-associated antigen 1 (MAGE1), Mammaglobin, MAP17, melan-A, MMP2, Mox1, MUM-1, NY-ESO-1, Osteonectin, p15, p170, p9'7, PAI-1, PDGF, Plasminogen, PRAME, PSM, RAGE-1, Rb, RCAS1, SART-1, STAT3, Eukaryotic translation elongation factor 1 alpha 2 (STn), TGF-α, TGF-β, Thymosin β 15, IFN-α, TPA, TRP-2, Tyrosinase, VEGF a, VEGF b, ZAG, and p16INK4.

Nucleotides may be organic chemicals in the form of deoxyribonucleotides or ribonucleotides. Deoxyribonucleotides may be selected from guanine, adenine, thymine, and cytosine, and covalent modifications thereof, derivatives thereof, and metabolites thereof. Covalent modification may include but are not limited to methylation, e.g. 5-methylcytosine, and hydroxymethylation, e.g., 5-hydroxymethylcytosine. Ribonucleotides may be selected from guanine, adenine, uracil, and cytosine, and covalent modifications, derivatives thereof, and metabolites thereof.

The target nucleic acid may include a region of gene associated with a disease. There is no limitation to the type of diseases which a method disclosed herein may be applied to. The target nucleic acid may include a region associated with an oncogene. The oncogene may be associated with a disease. The disease may be breast cancer. Exemplary genes encoding proteins associated with breast cancer may include, but are not limited to, ACTR3B, ALK, ANLN, AURKA, BAG1, BcI2, BCL2, BCR-Abl, BIRC5, BLVRA, BRAF, c-KIT Cathepsin L2, CCNB1, CCNE1, CD20 antigen, CD30, CD68, CDC20, CDC6, CDH3, CENPF, CEP55, CXXC5, Cyclin B1, EGFR, ER, ERBB2, ESR1, EXO1, FGFR4, FIP1L-PDGFRalpha, FOXA1, FOXC1, GPR160, GRB7, GSTM1, HOXB13, IL17BR, Ki-67, KIF2C, KRAS, KRT14, KRT17, KRT5, MAPT, MDM2, MELK, MIA, MKI67, MLPH, MMP11, MYBL2, MYC, NAT1, NDC80, NUF2, ORC6L, PDGFR, PGR, PHGDH, PML/RAR alpha, PR, PTTG1, RRM2, SCUBE2, SFRP1, SLC39A6, STK15, Stromelysin 3 (MMP11), Survivin, TMEM45B, TPMT, TYMS, UBE2C, UBE2T, and UGT1A1, among others. Additionally, or alternatively, exemplary genes encoding proteins associated with breast cancer may include, but are not limited to, ABCA10, ABCA9, ADAM33, ADAMTS5, ANGPT1, ANKRD29, ARHGAP20, ARMCX5GPRASP2, ASB1, CA4, CACHD1, CAPN11, CAV1, CAV2, CAV3, CBX7, CCNE2, CD300LG, CDC14B, CDC42SE1, CENPF, CEP68, CFL2, CHL1, CLIP4, CNTNAP3, COL10A1, COL11A1, CRIM1, CXCL3, DAB2IP, DMD, DPYSL2, DST, EEPD1, ENTPD7, ERCC6L, EZH1, F10, FAM126A, FBXO31, FGF1, FIGF, FMO2, FXYD1, GIPC2, GLYAT, GPR17, GPRASP1, GPRASP2, HAGL, HAND2-AS1, HLF, HMMR, HOXA2, HOXA4, HOXA5, IGSF10, INHBA, IL11RA, ITM2A, JADE', JUN, KIAA0101, KIF4A, KLHL29, LCAT, LGI4, LIFR, LIMS2, LRIG3, LRRC2, LRRC3B, MAMDC2, MATN2, MICU3, MIR99AHG, MME, MMP11, NECAB1, NEK2, NKAPL, NPHP3, NR3C1, NR3C2, NUF2, PAMR1, PAFAH1B3, PAQR4, PARK2, PEAR1, PGM5, PKMYT1, PLEKHM3, PLSCR4, POU6F1, PPAP2B, PPP1R12B, PRCD, PRX, PYCR1, RAPGEF3, RBMS2, SCN4B, SDPR, SLC35A2, SH3BGRL2, SPRY2, STAT5B, SYN2, TK1, TMEM220, TMEM255A, TMOD1, TPM3, TPX2, TSHZ2, TSLP, TSTA3, TTC28, WISP1, USHBP1, USP44, IBSP and ZWINT.

In particular cases, the panel of target nucleic acids comprises one or more of ESR, PGR, and ERBB2. ESR, PGR, and ERBB2 are over-expressed in at least 20%, 30%, 40%, 50%, 60%, 70%, 80%, 90%, 95%, 99%, or more of invasive breast cancers. For example, the panel of target nucleic acids is over-expressed in at least 87% of invasive breast cancers, which corresponds well with the incidence of clinical triple negative subtypes.

In other cases, the panel of target nucleic acids comprises one or more of COL10A1, MMP11, IBSP, and CST1 are over-expressed in 20%, 30%, 40%, 50%, 60%, 70%, 80%, 90%, 95%, 99%, or more of invasive breast cancers. For example, the panel of target nucleic acids is over-expressed in at least 87% of invasive breast cancers, which corresponds well with the incidence of clinical triple negative subtypes. The panel of target nucleic acids may be amplified using a pair of primers selected from SEQ ID NO: 33-SEQ ID NO: 52. The panel of target nucleic acids may be amplified using a pair of primers that has at least 20%, 30%, 40%, 50%, 60%, 70%, 80%, 90%, 95%, 99%, or more homology over 9 nucleotides from SEQ ID NO: 33-SEQ ID NO: 52. The panel of target nucleic acids may be amplified using a pair of primers that has at least 20%, 30%, 40%, 50%, 60%, 70%, 80%, 90%, 95%, 99%, or more homology over 12 nucleotides from SEQ ID NO: 33-SEQ ID NO: 52. The panel of target nucleic acids may be amplified using a pair of primers that has at least 20%, 30%, 40%, 50%, 60%, 70%, 80%, 90%, 95%, 99%, or more homology over 15 nucleotides from SEQ ID NO: 33-SEQ ID NO: 52. The panel of target nucleic acids may be amplified using a pair of primers that has at least 20%, 30%, 40%, 50%, 60%, 70%, 80%, 90%, 95%, 99%, or more homology with a sequence from SEQ ID NO: 33-SEQ ID NO: 52.

The devices, kits and methods disclosed herein may further analyze proteins or metabolites corresponding to the one or more nucleic acids.

VI. Uses

The methods, devices and kits disclosed herein may be used for diagnosing, prognosing, assessing, monitoring and/or treating a disease or condition in a subject. The methods, devices and kits disclosed herein may be used for determining an indication. The term "indication" may refer to the purpose of a test executed by the devices, methods or kits disclosed herein. Determining the indication may comprise determining whether the cellular specimen or portion thereof is malignant or benign. Determining the indication may comprise determining an anatomic origin of the cellular specimen or portion thereof. The devices and methods disclosed herein may be useful for determining a risk of a condition or disease. The risk of the condition or disease may be a risk of developing a condition or disease, a risk of residual condition or disease after a procedure (e.g. risk of recurrence), or a risk that the condition or disease will be aggressive. The methods may comprise determining the likelihood that the condition or disease will respond to a therapy. The risk of the condition or disease may be a risk of developing a cancer, a risk of residual cancer after a procedure (e.g. risk of recurrence), or a risk that the cancer will be aggressive. The methods may comprise determining the likelihood that the cancer will respond to a therapy.

The disease may be a cancer. The cancer may be selected from a pre-cancerous condition, early stage cancer, cancer, and non-metastatic cancer. The cancer may be selected from a stage 0 cancer, a stage II cancer, a stage III cancer, and a stage IV cancer. Early stage cancer may be a stage 0 cancer, a stage I cancer or a stage II cancer. In some cases, the early stage cancer may be a stage III cancer. The cancer may be a localized or isolated cancer. The cancer may be selected from breast cancer, prostate cancer, colon cancer, lung cancer, brain cancer, skin cancer, testicular cancer, oral cancer, pancreatic cancer, stomach cancer, cervical cancer, uterine cancer, endometrial cancer, and ovarian cancer.

The disease or condition may be breast cancer. The breast cancer may be selected from ductal carcinoma in situ, invasive ductal carcinoma (including, but not limited to, adenoid cystic carcinoma, low-grade adenosquamous carcinoma, medulllary carcinoma, mucinous carcinoma, papillary carcinoma, micropapillary carcinoma, and tubular carcinoma), triple negative breast cancer, inflammatory breast cancer, metastatic breast cancer, Paget disease of the nipple, phyllodes tumor, and angiosarcoma. The breast cancer may be Her2-positive, ER-positive, PR-positive, or any combination thereof. The breast cancer may be Her2-negative, ER-negative, PR-negative, or any combination thereof. The breast cancer may be a non-invasive tumor that progresses, is progressing, is at risk of progressing, or is likely to progress to an invasive breast cancer. The breast cancer may be a ductal carcinoma in situ (DCIS). Breast cancers may be cured if and when the malignant tissue is surgically removed. The breast cancer may comprise a breast tumor. The breast tumor may be resected. One or more margins of the resected breast tumor may be evaluated for the presence or absence of cancerous cells. The presence of malignant cells along the surgical margin may be an indication for an additional surgical procedure. The breast tumor may be resected with breast conservation surgery (BCS). The goal of the BCS may be to remove the tumor, bounded by a thin margin of healthy tissue. The BCS may balance the need to remove the entire tumor with the poor outcomes that result from removing excessive healthy tissue. The rate of positive margins after BCS is typically between 22-44%. The link between positive surgical margins (e.g., margins containing detectable cancer cells) and recurrence has been demonstrated in multiple large, multi-center trials. On average, approximately 33% of patients require additional surgeries to remove more tissue after an initial BCS. Additional surgeries are expensive: direct surgical costs are estimated to be over $500 million a year. More importantly, the rate of recurrence (tumor returning) increases dramatically with the number of surgeries required to obtain negative margins. Some studies estimate that the risk of recurrence is 68% higher for women who require 3 surgeries, compared to women who require 1 surgery. Recurrence requires additional intensive treatment, and many women die. There have been multiple attempts to address positive breast cancer margins. Most require surgeons to disrupt clinical practice, or are based on antiquated commercialization strategies that require hospitals to make large capital investments in emerging technology. The methods and devices disclosed herein may help surgeons identify positive margins during the initial operation and conservatively excise additional tissue, thereby preventing additional surgeries and recurrence.

The kits, devices and methods disclosed herein may be used for molecular analysis of solid samples (e.g. tissues, tumors, etc.). The kits, devices and methods may be used for liquid samples processing (e.g. blood, urine, and cerebrospinal fluid).

The kits, methods and devices disclosed herein have various practical applications. For example, the kits, methods and devices disclosed herein may be used for a postoperative test of biological samples obtained by an invasive or non-invasive procedure on-site or elsewhere. As another example, the kits, methods and devices disclosed herein may be used for a rapid point-of-care analysis of biological samples obtained by an invasive or non-invasive procedure. Such a rapid point-of-care analysis may help a physician/surgeon determine whether the procedure is completed (e.g., whether the entirety of a diseased tissue is successfully removed) or incomplete. The kit, methods and devices described herein provide for a nucleic acid analysis. The nucleic acid analysis may yield a result that indicates to the physician/surgeon that the procedure is complete. The nucleic acid analysis may yield a result (e.g., a positive detection of a biomarker associated with the disease) that indicates to the physician/surgeon that the procedure is incomplete and should be continued or furthered. Exemplary invasive procedures which may be improved using a method and/or device disclosed herein include, but are not limited to, surgical and dermatologic biopsies and aspirations (e.g. fine needle aspirations, core needle biopsies, sentinel node biopsies), solid tissue biopsies, surgical excisions (e.g., breast lumpectomy, biliary tract surgery), surgical dissections (e.g. axillary node dissection), laparoscopic procedures (e.g. leiomyotoma removal) and endoscopic biopsies (e.g. colon, intra-abdominal). Exemplary non-invasive procedures which may be improved using a method and/or device disclosed herein include, but are not limited to, dermatologic biopsies (e.g. rapid and/or point of care analysis for Mohs procedure), rectal biopsies, cervical scrapings (Pap smear), and cervical biopsies.

While preferred embodiments of the present invention are shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1: Efficient and Rapid Lysis of Complex Solid Tissue Samples

Sonication of complex solid tissues was optimized using commercially available ground bovine samples. 20 mg of tissue were treated with mild sonication on an ST-30 instrument with radio frequency power set at 36 volts, a duty cycle of 33% (⅓ on, ⅔ off), and a frequency of 120 Hz (which was optimized to water as the medium). Additional experiments used higher-power sonication performed with 100 volts on a ST-100 instrument (data not shown). The ST-30 and ST-100 instruments use bulk lateral ultrasound (BLU™) to generate shear forces directed towards the samples. Sonicated samples were compared to samples that were incubated in a 55° C. waterbath for 1.5 hours according to the protocol provided with the commercial ChargeSwitch™ DNA purification kit. All samples were incubated in Invitrogen ChargeSwitch™ Lysis Buffer (L13) buffer according to the manufacturer's protocol.

The standard protocol calls for incubation of tissues in 250 microliters of Invitrogen ChargeSwitch™ Lysis Buffer (L13) for 1.5 h incubation in a 55° C. water bath, followed by immediately purifying DNA with ChargeSwitch™ magnetic beads (Invitrogen). DNA yield was quantified with a NanoDrop UV/Vis spectrometer and normalized to the mass of input tissue (to account for variations of <1 mg between samples). Control data were performed in triplicate and normalized to input tissue mass to account for variations of <1 mg between samples. DNA yield was further verified with a Qubit fluorometer.

Example 2: End-Point and Real-Time PCR Analysis of Nucleic Acids Obtained by Sonication Nucleic acid samples were prepared via the BLU sonication methods described in Example 1. BLU-sonicated samples were compared to nucleic acid samples extracted by the standard Invitrogen protocol described in Example 2. Primers designed to distinguish bovine vs. gallus cytochrome B were used in a PCR assay and an isothermal loop-mediated amplification assay. For the end-point PCR assay, Kapa 2G Robust master mix assay was used according to the manufacturer's instructions. PCR amplicons were visualized on agarose gels, post-stained with GelRed. There was no detectable difference in amplification of DNA that was extracted using sonication and DNA extracted using the commercial chemical and enzymatic purification protocol (no difference, data not shown). These data establish that DNA extracted using sonication provide intact substrates for nucleic acid amplification.

Example 3: Enhancing Sample Lysis and Nucleic Acid Yield from Solid Tissue Samples Incubation time required for sample lysis and nucleic acid purification is decreased from 60 min to 5 min) and yields are increased by incubating ChargeSwitch™ beads at the recommended temperature during vigorous shaking. Samples were incubated at 55 C on an Eppendorf thermal shaker at max rpm. All samples were incubated in Invitrogen ChargeSwitch™ Lysis Buffer (L13) buffer and purified using ChargeSwitch™ magnetic beads according to the manufacturer's protocol. These experiments discovered a method to increase the lysis step for complex solid tissues prepared using the ChargeSwitch™ method. The standard protocol yielded 10.2 ng/ul of DNA from 20 mg of tissue after a 1.5 hour incubation at 55° C. In contrast, thermomixing yielded a mean of 10.0 ng of DNA/ul from 20 mg of tissue after only 10 minutes. Additional thermomixing (e.g. 20 min) also yielded 10.8 ng DNA/ul, indicating that the system (e.g. number of beads) reached the maximum binding capacity. These experiments indicate that the maximum yield had been reached by 10 min and that the time could be further reduced.

Example 4: Analysis of Breast Cancer Margins from Surgically Resected Breast Tumors Fresh clinical samples are obtained from a commercial biorepository. ER+, PR+ and Her2+ samples are included as positive controls. Benign breast samples are used as negative controls. Benign breast samples are obtained from a reduction mammoplasty.

The top layers of cells from fresh surgical tissues are collected using glass slides coated in poly-lysine.

Methods described herein are used for assessment of RNA gene expression. RNA is purified from the samples using bead-based RNA purification protocols. The Qubit RNA HS Assay from Invitrogen is used to determine RNA yield.

RNA integrity is assayed in optimized lysis buffers to determine whether the optimized buffers will be suitable for cell lysis. RNA integrity is measured using Q-ratios after 10, 20 and 30 minutes at 65° C. to stimulate stability under amplification conditions. Sample lysis, cDNA synthesis, isothermal amplification, and electrochemical detection are performed using a single optimized assay buffer. Alternatively, purification steps are added between sample lysis and any other steps involved in nucleic acid analysis.

Purified RNA is reverse-transcribed and subjected to real-time PCR and real-time SDA using methods described herein. Amplification of target amplicons are detected using methylene blue dyes and voltammetry as described herein. Positive reference samples exhibit detectable ESR, PSR, and ERBB2 gene expression. Negative reference samples do not exhibit detectable ER, PR, or Her2 gene expression. Test samples exhibit a range of ESR, PSR, and ERBB2 gene expression levels. Test samples from subjects with breast cancer exhibit, on average, higher ESR, PSR, and ERBB2 gene expression than negative reference samples.

Analytical sensitivity is determined through mixing studies, where RNA isolated from breast tumors are pooled and titrated into RNA isolated from healthy tissue. The limit of detection is determined based on the ratio of malignant: healthy RNA that produces a signal above the designated threshold of the gene classifier.

Example 5: Electrochemical Detection of Isothermal Nucleic Acid Amplification

The electrochemical test fixture on a microfluidics device comprises a 2 microliter reaction chamber with gold working, reference, and counter microelectrodes. Electrochemical measurement is performed with a potentiostat. Using a square-wave voltammetric (SWV) measurement technique enables discrimination of bulk faradaic currents from capacitive interface charging, sensitivity to low concentrations of electroactive species, and rapid data acquisition. Measurement data are acquired and processed using on-board custom software.

Figure 6:
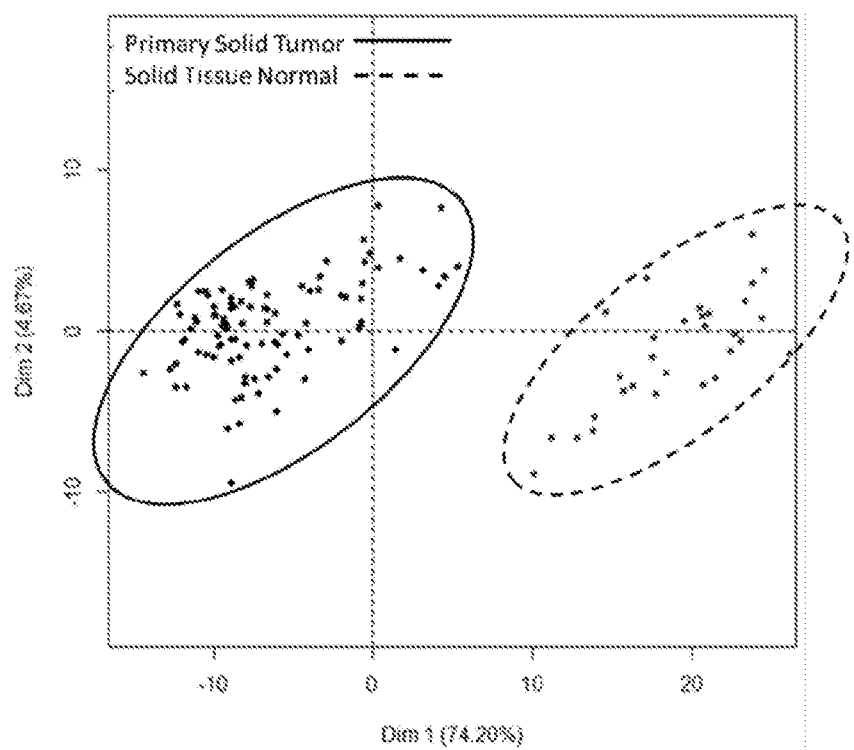
FIG. 6 shows results of the Principal Component Analysis for differentiating healthy and malignant tissue.

Example 6: Principal Components Analysis (PCA) Demonstrates that Gene Expression can be Used to Distinguish Healthy Tissue Samples from Invasive Breast Cancers Principal Component Analysis (PCA) was performed using over 90,000 microarrray probes, which correspond to approximately 19,000 genes across all TCGA samples. The genome-wide analysis provided a somewhat unbiased method to investigate the similarity between these two classes (healthy and malignant breast tissue). Tumor tissue and healthy tissue form distinct clusters with well demarcated space between them (FIG. 6). These results demonstrate that genomic expression contains enough information to distinguish these two classes.

Example 7. Unsupervised Hierarchical Cluster Analysis Confirms that Cancer and Healthy Tissue Cluster According to Expression Profiles Microarray data were obtained from The Cancer Genome Atlas (TCGA) and were processed using R and the BioConductor suite. Hierarchical clustering and heatmap visualizations were also performed using the BioConductor package in the R environment. About 90,000 attributes from 132 samples were analyzed on a custom 244 k Agilent microarray. Each attribute is a microarray probe, which in most cases corresponds to a known mRNA, although in most cases multiple probes correspond to a single gene. Unsupervised hierarchical cluster analysis (HCA) of 90,000 microarray expression probes identified the distinction between classes (healthy tissue and tumor) as the highest-level cluster separation, as indicated by the dendrogram on the left. The dendrogram shows that HCA identifies healthy tissues (H) and tumor tissues (T) as discrete clusters. This confirms the PCA findings that genomic information can be used to distinguish these two classes.

Example 8. Selection of the Most Differentially Expressed Probes

Distribution of gene expression was determined by analyzing the expression of ~90,000 probes across 132 invasive breast cancer samples and healthy breast tissue. From the TCGA data, it was determined that 169 genes were overexpressed (>3 standard deviations (std. dev.) from the mean) and 205 genes were under-expressed (>3 std. dev.) in invasive breast adenocarcinoma, compared to healthy mammary tissue. These results indicated that 200 most differentially expressed genes could be selected and those genes would be greater than 3 std. dev. from the mean. These top 200 differentially expressed genes were also (somewhat) normally distributed, supporting the feasibility of building a disease classifier with only a few genes. These genes included ASPN, IGFBP3, and PPY. ASPN is an example of a gene with increased expression in every tumor. IGFBP3 is an example of a gene with decreased expression in every tumor. PPY exemplifies a normally distributed candidate for a reference gene.

Two hundred probes with the most differential expression between healthy tissues and tumors were then selected. There are two primary reasons to focus on the most differentially expressed genes. First, the sensitivity of the assay (the number of malignant cells that can be detected in a population of healthy cells) is determined by the ratio of expression in the healthy and malignant tissues. Detecting an RNA signature can be considered a problem of dilution: if a malignant cell expresses 100 copies of mRNA, while healthy adjacent cells express 10 copies, an assay that can detect a 1.2-fold difference could detect one malignant cell in background of 8 healthy cells. In other words, the analytic sensitivity would be 1 malignant cell in a population of 9 total cells. (This example is somewhat more complex in practice because most quantification strategies use relative abundance instead of absolute quantification; while there are strategies to normalize expression to validated reference genes or genomic DNA, there is still a concern about diluting the disease-specific signal in a background of stably expressed normalization markers.)

The feasibility of using RNA to detect rare breast cancer cells in a population of healthy parenchymal cells was demonstrated in 1996. Metastases and micrometasteses to lymph nodes are used to stage breast cancer, but surgical resection of the lymphatic system can result in painful lymphedema that persists the rest of a patient's life. Some surgeons therefore work with pathologists to evaluate lymph nodes for breast cancer metastases during a surgical procedure, and only perform more extensive axillary dissections when indicated by positive lymph nodes. Multiple biomarkers have been evaluated for the detection of metastases and micrometastases in lymph nodes. For example, reverse transcriptase PCR of Keratin 19 mRNA has a sensitivity of $10^{-5}$ for metastatic breast cancer cells in lymph nodes (Noguchi, et al. Detection of Breast Cancer Micrometastases in Axillary Lymph Nodes by Means of Reverse Transcriptase-Polymerase Chain Reaction. American Journal of Pathology, Vol. 148, No. 2, February 1996). These results demonstrate the feasibility of using expression to detect rare malignant breast cancer cells in a population of healthy cells, with a sensitivity of one malignant cell in a population of 100,000 healthy cells. However, the authors noted that Keratin 19 was not an ideal biomarker because it could also be detected at low levels in healthy lymph nodes (even by less sensitive techniques like agarose electrophoresis). These biomarkers were developed without the benefit of genome-wide expression profiles, and underscore the importance of selecting microarray probes with the greatest absolute and statistical difference between two classes. The first step in our workflow was therefore to select the probes with the greatest differential expression between cancer and healthy tissues.

The second reason to focus on the most differentially expressed genes is that machine learning algorithms can suffer when the dimensionality of the input space is too high to reliably estimate the classifier's internal parameters with a limited number of instances. In this case, the number of attributes, p (corresponding to probes), vastly exceeded the number of instances (n, patient samples), p>>n. Selecting a subset of attributes based on expression differences provides a rational filtering method to reduce the number of attributes from 90,000 to the 200 probes with the greatest expression difference between healthy and malignant samples.

Microarray data were obtained from the TCGA project and processed with R and the BioConductor package. Individual probe signals were summarized to get probeset values, normalized using the Robust Multi-array Average (RMA) method, and log 2-transformed to create approximately normal signal distributions.

The limma linear model in the R environment was used to rank the most differentially expressed probes (by p-value) for 132 patient samples. The 200 most differentially expressed probes were selected. The selection captured attributes that were both overexpressed and underexpressed. Our previous analysis indicated that the 200 selected probes were 3 std. dev. from the mean. The 200 selected microarray probes were used as input for the subsequent analyses (HCA, feature selection, and machine learning).

Example 9. HCA Shows that the 200 Most Differentially Expressed Probes Provide Greater Separation Between Cancer and Healthy Tissue than 90,000 Microarray Expression Probes Example 7 describes multiple advantages of selecting the most differentially expressed probes from a larger population; however, one concern is that eliminating 99% of the probes will reduce the signal. HCA demonstrates that this is not the case.

Figure 5:
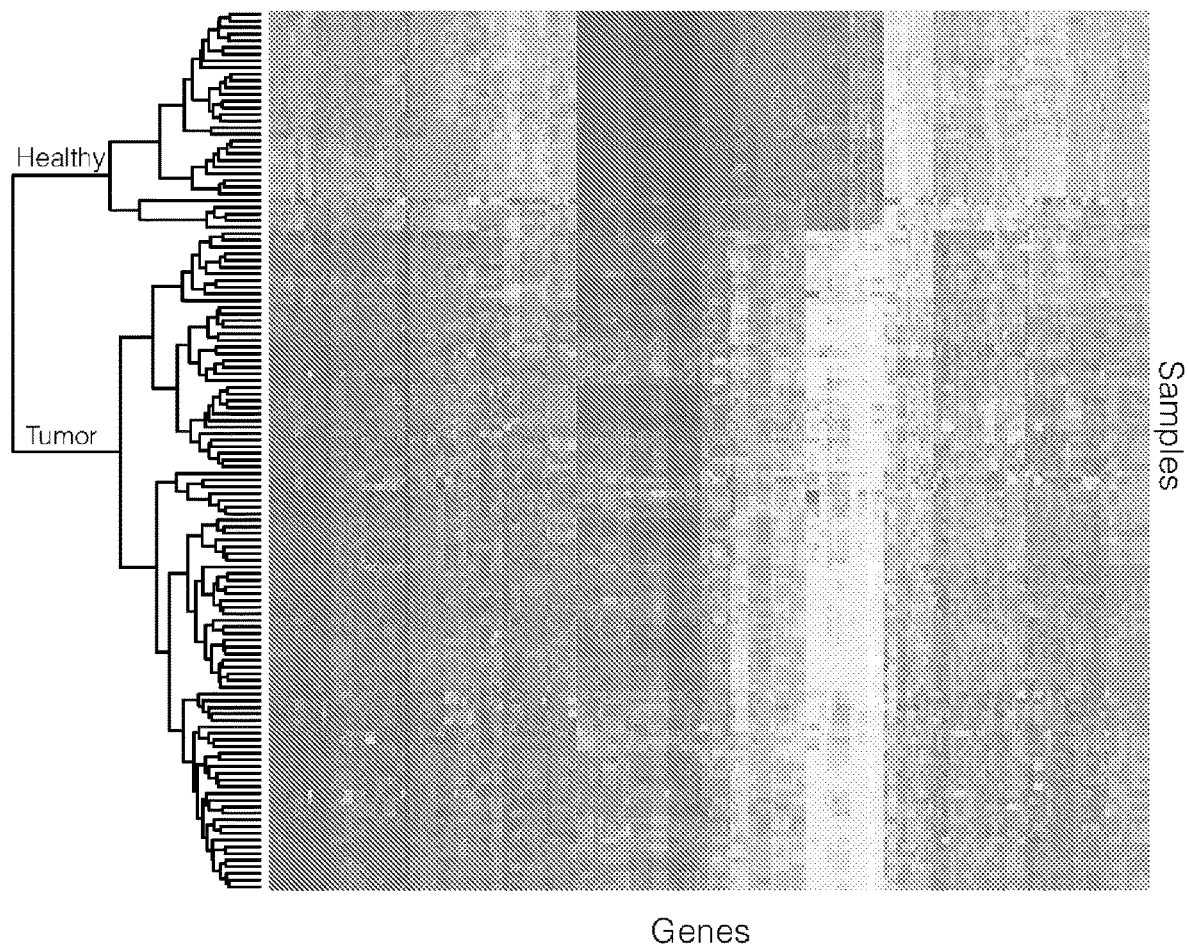
FIG. 5 shows unsupervised hierarchical clustering of 132 breast cancer samples based on expression of 200 genes.

FIG. 5 is a heatmap of the 200 most differentially expressed probes, as determined in Example 7. The HCA for the top 200 probes in FIG. 5 (heatmap 2) was performed identically to the HCA of the 90,000 probes Example 7. The dendrogram on the left represents the distance between the cluster of healthy tissues (H) and the cluster of tumor tissues (T). This experiment shows that selecting a subset of genes maintained the distinction between healthy and tumor tissues. Moreover, the distance between clusters is greater in FIG. 5 (heatmap 2) (based on 200 probes) than as determined in Example 7 (based on over 90,000 probes), indicating that there is a stronger class distinction when less informative probes are removed. These two HCA experiments validate the rational selection method of focusing on the most differentially expressed genes.

Example 10: Using Cross Validation to Estimate Performance of the Classifier Methods Cross-validation is a method of internal validation where the input dataset is split into two parts: a training set and a validation set. The training set is used as input for the learning algorithm. The validation set is used to evaluate the hypothesis. Cross-validation is only accurate when the samples in the validation set are excluded from the entire workflow. The workflow used in these experiments included three steps.

According to Kale, et al., "Obtaining a good estimate of the error rate by internal validation can be easily accomplished by splitting the set of input examples into two parts: a training set, which is used as input to the learning algorithm, and a holdout test set, which is used to evaluate the hypothesis. Since the learning algorithm does not 'see' the examples in the test set before the evaluation, it is easy to prove that this results in an unbiased estimator of the error rate." (Satyen Kale, Ravi Kumar, and Sergei Vassilvitskii. Cross-Validation and Mean-Square Stability. *Symposium on Innovations in Computer Science*. Jan. 7, 2011.)

k-Fold cross-validation is a leave-one-out method of internal validation. Leave-one-out methods partition the data and calculate the average score of the partitions. The dataset is randomly divided into k subsets. These experiments use a 10-fold cross validation, which divides the dataset into 10 subsets.

Conventional wisdom is that the averaging in cross-validation leads to a tighter concentration of the estimate of the error around its mean. Kale, et al. (2011) demonstrated that conventional wisdom is essentially correct by analyzing the gap between the cross-validation estimate and the true error rate. Cross-validation achieves a near optimal variance reduction factor of $(1+o(1))/k$ in a broad family of stable algorithms. In these cases, the k different estimates are essentially independent of each other.

Figure 15A:
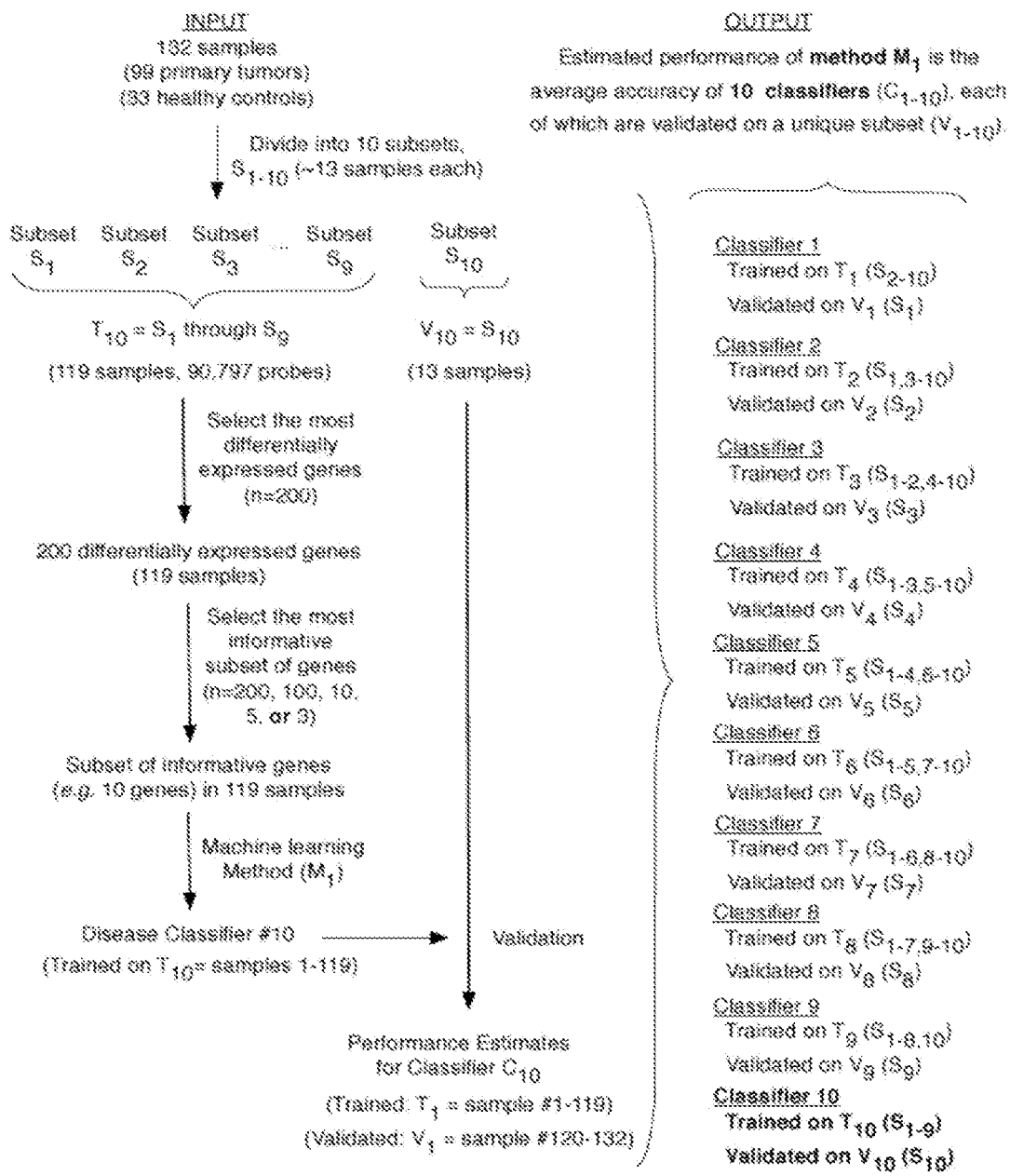
FIG. 15A shows k-Folds Cross-Validation Strategy. This figure illustrates that the cross validation was constructed to accurately test the combination of all 3 steps: (i) attribute filtering (by differential expression and p-value), (ii) attribute selection (using 3 feature attribute methods), and (iii) training (using 9 machine learning methods).

Richard Simon (Chief of Biometrics, NIH) showed that it is critical to set aside the validation set before performing gene selection and training (Simon, R., Radmacher, M. D., Dobbin, K., and McShane, L. M. (2003). Pitfalls in the Use of DNA Microarray Data for Diagnostic and Prognostic Classification. *Journal of the National Cancer Institute*, 95(1), 14-18). This is a common mistake in classifier development, and our strategy is particularly vulnerable because it includes two attribute selection steps: statistics to select the most differentially expressed microarray probes were used, followed by feature selection to identify the most informative subset of the differentially expressed genes. FIG. 15A (cross-validation workflow) illustrates that our cross validation was constructed to include all 3 steps: (i) attribute filtering (by differential expression), (ii) attribute selection (using 3 feature attribute methods), and (iii) training (using 9 machine learning methods).

It should also be noted that cross-validation only validates the method used to generate a classifier. Since a 10-fold cross-validation generates and validates 10 classifiers on 10 subsets, the output from cross-validation is an average of 10 classifiers. The output is an estimate of how a classifier developed and trained according to the proscribed method would perform on an entirely new dataset. To develop the actual classifier, the method used in the cross-validation workflow is performed using all the samples in the dataset (as opposed to only the samples that were randomly assigned to a subset).

In our case, a random number generator based on atmospheric noise was used to randomly assign 132 genome-wide microarray expression samples to 10 subsets. One of the ten subsets (S10) was excluded from the training set and set aside as a validation set (V01=S01), while the classifier was trained on the remaining subsets (Training Subset T01=subsets S01-S09). By repeating the process ten times, every sample is included in one of the naïve validation sets. In other words, the advantage of cross-validation is that it ensures every sample is included in the validation.

To perform cross-validation, differentially expressed genes in each training set were ranked. In contrast to Example 8, where the differentially expressed genes from all samples were selected, in cross validation the limma linear model is used to identify the 200 most differentially expressed probes (by p-value) in each training set (performed individually on T01-T10).

After selecting the most differentially expressed probes in each training set, WEKA was used to implement three feature selection methods. These feature selection methods rank probes by their contribution to a model that separates the two classes (healthy breast tissue or invasive breast cancer). The three feature selection methods were InfoGain (IG), GainRatio (GR), and Correlation-based Feature Selection (CFS). Each feature selection method has its strengths and limitations. IG is a straightforward method with less assumptions and presumably less biases. It ranks attributes by the amount of information they independently contribute to the model, but can be biased if the data are highly branched. GainRatio attempts to overcome the limitations of highly branched datasets, but is agnostic to attributes that are correlated with each other. In genome-wide expression studies, many of the most differentially expressed genes are biologically related, and in some cases directly related to other differentially expressed genes. CFS attempts to overcome the problem of correlated attributes by preferentially selecting high-performing attributes that are independently correlated. In the case of GR and CFS, strategies to overcome specific problems lead to more complex models, which can introduce unexpected biases. These experiments therefore use all 3 feature selection methods.

Figure 15B:
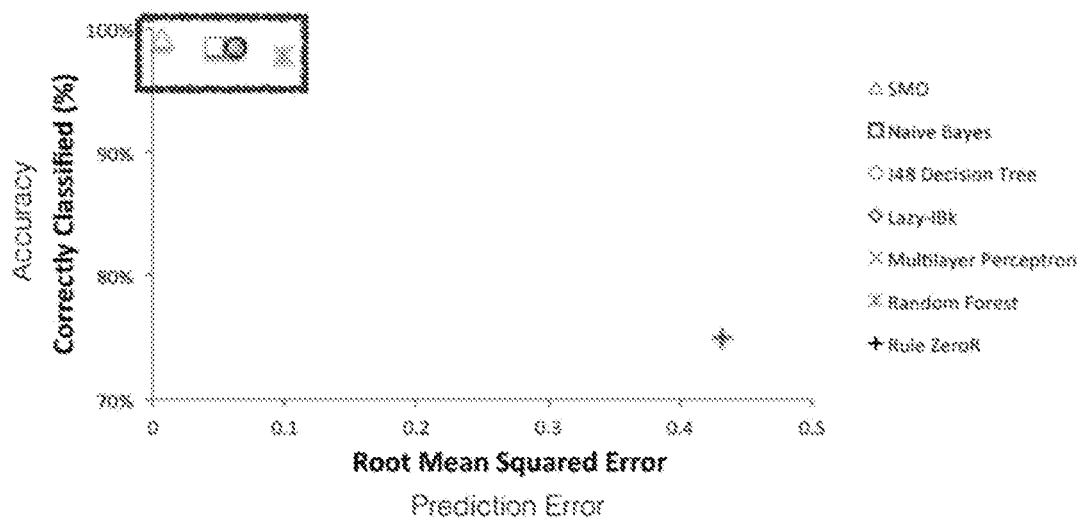
FIG. 15B shows performance of 5 genes when used as input into 7 machine learning methods. 10-fold cross-validation was used to evaluate performance of classifiers developed through a three-part strategy: Step 1 attribute filtering (by differential expression and p-value), Step 2 attribute selection (using feature selection methods), and Step 3 training (using 7 machine learning methods). The 7 machine learning methods were the support vector algorithm SMO, Naïve Bayes, J48 Decision Tree, Lazy-IBk, the Multilayer Perceptron neural network, Random Forest, and the negative control Rule ZeroR. Accuracy was calculated as the percent of correctly classified samples. Predicted error was calculates as root mean square error (RMSE).

Seven machine learning methods were trained on each of the ten training datasets. This step was performed independently for 4 input samples: the 200 most differentially expressed probes, and the top 5 probes selected by each feature selection method. Each trained classifier was then tested on the naïve validation set corresponding to each training set. Root mean squared error (RMSE) was averaged across 10 pairs of training-validation subsets. RMSE estimates the error of a classifier developed according to this workflow, which included (i) selection of 200 differentially expressed probes, (ii) feature selection, and (iii) machine learning. Although some learning methods include their own feature selection, using defined algorithms to preselect the features gave us greater control over probe selection and allowed us to perform more direct comparisons of learning methods. FIG. 15B (Accuracy v RMSE) shows the results of a 10-fold cross validation to estimate the error that a classifier developed according to these methods will have when performed on a naïve dataset.

Example 11: Cross-Validation of Microarray Probes on 132 Samples

Machine learning algorithms were used to develop the BCDC. Datasets were grouped into two classes (healthy and malignant). The 200 most differentially expressed probes were ranked using 3 feature selection methods implemented in WEKA. The feature selection methods were INFOGAIN (IG), GAINRATIO (GR), and CORRELATION-BASED FEATURE SELECTION (CFS). Feature selection methods rank probes by evaluating their contribution to a model that separates the two classes. After ranking genes, WEKA was used to independently perform 9 machine learning methods. WEKA is a collection of machine learning algorithms for data mining tasks, the machine learning equivalent the statistical package R (see Amancio et al. *PLoS One* 2014 volume 9: e94137). A 10-fold cross-validation was used to estimate performance of each of the 9 learning algorithms. Four of the 9 learning algorithms were able to correctly classify all 132 samples, as evaluated by a 10-fold cross validation (Table 1). The 4 algorithms that generated the strongest performing classifiers using 200 genes are k-nearest neighbor (IBk), the Bayesian Naïve classifier (Naïve Bayes), (see Aha et al. Machine Learning 1991 volume 6: pages 37-66), the support vector machine (SMO), and the neural network (multilayer perceptron, MLP).

TABLE 1

Evaluation of learning algorithms by 10-fold cross validation.

| Number | Classifier-Name | Gene Classifier | Correctly Classified (%) | ROC-AUC |
|---|---|---|---|---|
| 1 | Lazy-IBK = 200 | 200-Gene Classifier | 100% | 1 |
| 2 | Lazy-IBK = 100 | | 100% | 1 |
| 3 | Lazy-IBK = 50 | | 100% | 1 |
| 4 | Lazy-IBK = 20 | | 100% | 1 |
| 5 | Lazy-IBK = 10 | | 100% | 1 |
| 6 | Lazy-IBK = 5 | 5-Gene Classifier | 100% | 1 |
| 7 | Naive-Bayes = 200 | | 100% | 1 |
| 8 | Naive-Bayes = 100 | | 100% | 1 |
| 9 | Naive-Bayes = 50 | | 98.99% | 0.99 |
| 10 | Naive-Bayes = 20 | | 99.49% | 1 |
| 11 | Naive-Bayes = 10 | | 98.99% | 1 |
| 12 | Naive-Baves = 5 | | 98.48% | 1 |
| 13 | SMO-200 | | 100% | 1 |
| 14 | SMO-100 | | 100% | 1 |
| 15 | SMO-50 | | 100% | 1 |
| 16 | SMO-20 | | 100% | 1 |
| 17 | SMO-10 | | 100% | 1 |
| 18 | SMO-5 | 5-Gene Classifier | 100% | 1 |
| 19 | Multilayer- | | 100% | 1 |
| 20 | Multilayer- | | 100% | 1 |
| 21 | Multilaver- | | 100% | 1 |
| 22 | Multilayer- | | 100% | 1 |
| 23 | Multilaver- | | 100% | 1 |
| 24 | Multilayer-Perception = 5 | | 99.49% | 1 |
| 25 | Random-Forest = 200 | | 99.49% | 1 |
| 26 | Random-Forest = 100 | | 99.49% | 1 |
| 27 | Random-Forest = 50 | | 98.99% | 1 |
| 28 | Random-Forest = 20 | | 98.99% | 1 |
| 29 | Random-Forest = 10 | | 98.99% | 1 |
| 30 | Random-Forest = 5 | | 98.99% | 1 |
| 31 | J48-Decision-Tree = 200 | | 96.46% | 0.953 |
| 32 | J48-Decision-Tree = 100 | | 96.46% | 0.953 |
| 33 | J48-Decision-Tree = 50 | | 97.98% | 0.969 |
| 34 | J48-Decision-Tree = 20 | | 97.98% | 0.969 |
| 35 | J48-Decision-Tree = 10 | | 97.98% | 0.969 |
| 36 | J48-Decision-Tree = 5 | | 98.49% | 0.982 |

Example 12: Using Cross-Validation to Optimize the Number of Microarray Probes on 132 Samples Results from the 200 attributes (microarray probes) demonstrated the feasibility of using a panel of nucleic acids to distinguish breast cancer from healthy tissue. A series of experiments were then performed to determine the optimal number of attributes in a BCDC. Three feature selection methods were used to rank the probes. The top-ranked probes were used as input for 9 machine learning methods. Ten-fold cross-validation was used to evaluate performance of machine learning methods developed using the top 100, 50, 20, 10, 5, 4, 3, 2, and 1 probes. Table 1 includes the results of 6 machine learning methods using attributes ranked by one of the three feature selection methods. All 6 methods generated classifiers that correctly classified more than 98% of samples as healthy or malignant. Two entirely different methods (IBk and SMO) continued to classify 100% of the samples correctly, even using only 3 probes. The IBk algorithm used in WEKA is a k-nearest neighbor (kNN) classifier. The kNN method is one of the simplest instance-based learning algorithms for supervised classification. It does not rely on assumptions about distribution, and instead determines the class of an unknown object based on the class of the nearest k neighbors. Support Vector Machines (SVM) like SMO are considered one of the most robust pattern recognition methods. SVMs use geometric hyperplanes to separate classes that are projected into multi-dimensional space. Given a set of training examples, an SVM training algorithm builds a model that assigns new examples into one of the categories.

Receiver operator characteristic (ROC) curves were generated for the classifiers with the best performance (IBk and SMO have identical performance and are both represented by SMO in the ROC plot). ROC curves visualize test performance. The BCDC developed using SMO correctly classified 100% of samples, as determined by a 10-fold cross validation on 132 samples. The 3-gene BCDC generated with the k-Nearest Neighbor algorithm IBk also correctly classified 100% of samples (not shown).

Estimating the performance of individual probes was the next focus. The Decision Stump learning algorithm uses a single attribute, which allowed us to perform a series of experiments to estimate the performance of individual probes. CFS was used to select probes in each training set that were the most, second most, third most, fourth most, and fifth most informative (Table 2). The top probe was estimated to correctly classify 98.5% of samples, with a RMSE of 0.0628 (Table 3). Probes with the highest rank were determined by CFS across all 132 samples (Table 4).

TABLE 3

| Probe | Correctly Classified (%) | ROC AUC | RMSE |
| --- | --- | --- | --- |
| 1st Probe | 98.5% | 0.9817 | 0.0628 |
| 2nd Probe | 94.7% | 0.9363 | 0.1599 |
| 3rd Probe | 90.9% | 0.9258 | 0.2600 |
| 4th Probe | 94.0% | 0.9435 | 0.2111 |
| 5th Probe | 90.8% | 0.9036 | 0.2252 |

Table 4. Identification of the top-ranked probes across the entire microarray dataset. Table 2 and Table 3 show performance of the top-ranked probes for each training subset, which is used in cross-validation to estimate the performance expected when the described workflow is repeated across all samples in the entire dataset. In contrast, Table 4 shows the probes selected from the entire dataset and the predicted performance based on cross-validation results in Table 3.

TABLE 4

| Agilent Custom Probe ID | Predicted Accuracy | Predicted ROC AUC |
| --- | --- | --- |
| A_23_P40414 | 98.5% | 0.982 |
| A_23_P57417 | 94.7% | 0.936 |
| A_23_P68608 | 90.9% | 0.925 |
| A_32_P130641 | 94.0% | 0.944 |
| NM_080629_1_6174 | 90.8% | 0.901 |

TABLE 2

Single probes selected for cross-validation. The Feature selection method CFS was used to rank microarray probes in each training set.

| Training Set | Probe 1_CFS | Probe 2_CFS | Probe 3_CFS | Probe 4_CFS | Probe 5_CFS |
| --- | --- | --- | --- | --- | --- |
| T01 | A_23_P57417 | A_23_P57420 | A_23_P4092 | A_32_P38093 | A_32_P130641 |
| T02 | A_23_P57417 | A_23_P57420 | A_23_P4092 | A_24_P251600 | A_32_P38093 |
| T03 | A_23_P57417 | A_23_P4092 | A_32_P157202 | A_23_P11806 | NM_080629_1_6174 |
| T04 | A_23_P57417 | A_23_P57420 | A_23_P11806 | NM_080629_1_6174 | A_32_P38093 |
| T05 | A_23_P57417 | A_23_P57420 | A_23_P4092 | A_23_P75749 | A_24_P484801 |
| T06 | A_23_P57417 | A_23_P4092 | A_32_P38093 | A_23_P11806 | NM_080629_1_6174 |
| T07 | A_23_P214144 | A_23_P40415 | A_23_P40414 | A_23_P16074 | A_23_P16078 |
| T08 | A_23_P57420 | A_23_P4092 | A_32_P38093 | NM_080629_16174 | A_23_P11803 |
| T09 | A_23_P57417 | NM_080629_1_6174 | A_23_P40415 | A_24_P251600 | A_32_P38093 |
| T10 | A_23_P214144 | A_23_P57417 | A_23_P57420 | A_24_P251600 | A_23_P75749 |

Table 3. Cross-validation was used to estimate performance of single probes. The dataset was divided into 10 training sets with a corresponding naïve dataset. Individual probes from each training set (Table 3) were trained using the machine learning method DecisionStump and the resulting classifier was tested on a corresponding naïve validation set. Performances were averaged across the 10 validation sets. For example, the top-ranked probe was selected for each of 10 training sets using CFS. On average, the probe ranked 1st in each training set correctly classified 98.5% of samples as healthy or tumor. The analysis was repeated for the probes ranked 2nd, 3rd, 4th, and 5th in each training set, and validated on the corresponding naïve validation set.

Example 13: Three Negative Controls for the Computational Experiments

Figure 16:
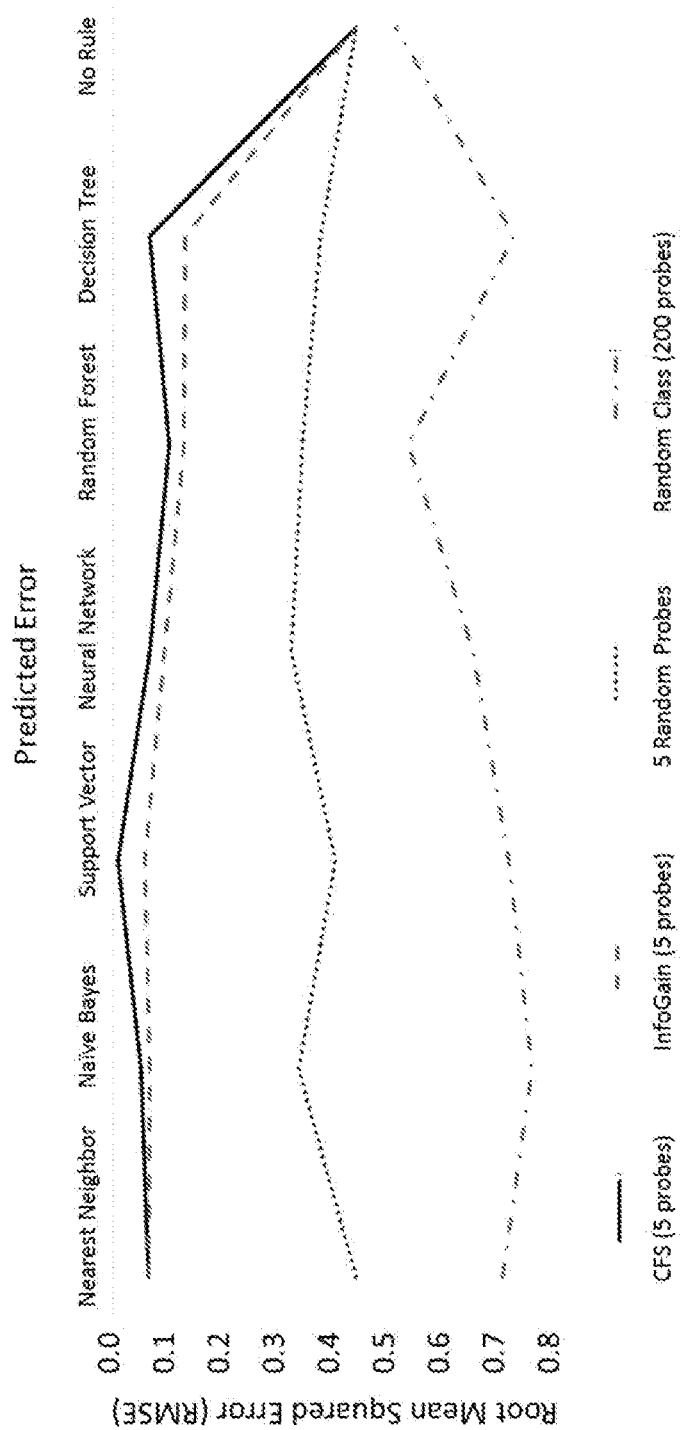
FIG. 16 shows predicted error for 6 machine learning algorithms, one reference and two native controls. The two negative controls were randomly selected microarray probes and randomized samples.

This example illustrates predicted error of machine learning methods. FIG. 16 shows predicted error for 6 machine learning algorithms, one reference, and 2 negative controls. The six machine learning methods were the k-Nearest Neighbor algorithm Lazy-IBk, Naïve Bayes, the Support Vector algorithm SMO, the Neural Network Multilayer Perceptron, Random Forest, and the J48 Decision Tree. The reference method No Rule (also known as ZeroR in FIG. 17) simply guesses that every sample is a member of the most prevalent class. The two negative controls were randomly selected microarray probes and randomized samples. FIG.

16 includes three negative controls. First, one of the machine learning methods (No Rule, corresponding to Rule ZeroR in Weka) is a negative control based on randomly guessing the most prevalent class. For example, if 60% of the samples are malignant, the No Rule method will consistently guess that each sample is malignant, and will be right 60% of the time. No Rule therefore provides a baseline related to prevalence. Ten-fold cross-validation was used to estimate the error of the classifier developed with the machine learning method No Rule. Although the No Rule method claims to use prevalence, and would therefore not be influenced by probe selection, the same workflow was followed that was used for the other machine learning methods: limma was used to select the most differentially expressed probes in each training set; 3 feature selection methods were used to rank and select the most informative probes in each training set; and a No Rule classifier was trained on each of the 10 training sets. The corresponding validation set was used to estimate performance of each of the 10 classifiers when implemented on naïve samples. FIG. 16 shows that the No Rule method has the highest error (0.43) of any machine learning method.

The second negative control consists of 5 randomly selected probes. Since breast cancer is characterized by extensive changes in gene expression, the classifier was expected to perform better than expected by chance. FIG. 16 shows the predicted error of machine learning methods developed using randomly selected probes. The RMSE of each machine learning method approximated the error of the No Rule method, establishing the error of using randomly selected probes as equivalent to a method based on disease prevalence.

For the final negative control, samples were randomly assigned to one of two classes (Class A and Class B). The entire workflow was then performed (limma to select the most differentially expressed genes, feature selection, and machine learning) on each pair of training-validation sets. Since the random classes are arbitrary, the machine learning methods were expect to have poor classification performance. As expected, classifiers based on 5 randomly selected probes had less error than a classifier based on 200 probes in samples that were randomly assigned to classes. In addition, error was most similar between controls and other workflows for the prevalence-based No Rule method.

Example 14: BCDC Development from Genome-Wide Microarray Expression Data of 132 Patient Samples The top 200 differentially expressed probes from Example 8 were used as input into feature selection. Three feature selection methods were performed in parallel: CFS, IG, and GR. The output of feature selection was then used to determine which features should be used to train the machine learning algorithms. The top 5 and top 10 probes were selected from each feature selection method. The input probes were used to train the disease classifier on all 132 microarray samples in the dataset.

Example 15: BCDC Development from Genome-Wide RNA Sequencing Data of 987 Patient Samples After using 132 genome-wide microarray expression samples to discover and validate a panel of genes that identified genes that could distinguish breast cancer from healthy tissue, the analysis was extended to 1,182 RNA Seq samples from TCGA. The same inclusion and exclusion criteria was used as used in the microarray analysis (Table 3) to focus on early-stage tumors that are eligible for breast conservation surgery. These criteria resulted in the exclusion of 12 men, 7 metastatic samples, 133 stage T3 and T3a tumors, and 43 stage T4, T4b, and T4d tumors. The selection process resulted in 987 samples, including 894 early-stage primary tumors and 93 healthy solid tissues.

Biobase (version 2.26.0), Limma (version 3.22.7), BiocGenerics (version 0.12.1) and edgeR (version 3.8.6) packages were implemented in the R environment. The following workflow was used to identify the genes that have the greatest difference (as determined by p-value) between breast cancer and healthy tissue. The voom function performed log transformation. The lmFit function fitted the transformed data to a linear model with regard to the factor. Finally, the eBayes function applied an F-stat model to infer the p-values. Like the limma function for the microarray example, this selection captured attributes that were both overexpressed and underexpressed. Seven machine learning methods were used to develop tests based on the 50 genes identified by this workflow. Cross-validation demonstrates that a test consisting of these genes can distinguish invasive breast tumors from healthy tissue. The genes in the test are disclosed in Table 9.

Feature selection methods were then used to develop 3 tests. Methods above rank genes by differential expression were used according to their inferred p-value. Using this strategy, the 200 most differentially expressed genes between the 894 breast cancer samples and 93 healthy tissue samples were identified. Three tests using genes identified by 3 feature selection methods were developed. Correlation-based feature selection (CFS), GainRatio (GR), and InfoGain (IG) in WEKA were implemented. The 18 genes identified by CFS were used to develop and train a breast cancer disease classifier. GR and IG were used to identify 50 genes each that were used to train a breast cancer disease classifier. The genes in these 3 classifiers are disclosed in Table 9.

Example 16: Development of ERiN SDA, a Novel Isothermal Method

Isothermal amplification mechanisms were used to develop a method that balances sensitivity and unprecedented speed relative to traditional PCR, amplifying targets from complex human genomes in less than 2 min, while reducing background amplification of present isothermal amplification methods.

FIG. 8 demonstrates the advantages of Strand Displacement Amplification (SDA) over alternative approaches. The Beeswarm plot shows 40 replicates of SDA, LAMP, and qPCR. Each method was performed in 20 ml volumes using 3,000 copies/ml of human genomic DNA as template. A Beeswarm plot is a method to graphically represent speed and variation. Traditional plots obscure results by showing overlapping datapoints along the same position on the x-axis. In a Beeswarm plot, identical values are graphed adjacently along the x-axis. Greater spread along the x-axis indicates less variation between datapoints, whereas greater spread along the y-axis indicates greater variation. For each method (qPCR, LAMP, and SDA), 5 experiments were performed, each with 8 technical replicates, with a total of 40 reactions for each method. SDA is faster than either LAMP or qPCR, and has the least amount of variation between experimental and technical replicates.

Reproducibility is represented by the horizontal and vertical distributions on the BeeSwarm Plot, where identical data points are plotted adjacently on the horizontal axis. This figure specifically compares the performance of SDA, real-time PCR and Loop-Mediated Amplification (LAMP). Strand Displacement Amplification (SDA) provided remarkable advantages for speed and reproducibility. It detected 3,000 copies/μl of NBR1 from human genomic DNA in less than 2 min, while it took qPCR 57 min to amplify 3,000 copies/μl of NBR1 from human genomic DNA. Each experiment performed 40 replicates of each method. LAMP has the greatest variation between replicates and technical replicates within an experiment. PCR had an intermediate amount of variation, and SDA had the least variation. These results demonstrated the potential advantages of isothermal methods, in particular SDA, which can amplify human genomic DNA in less than 2 min and has less variation than PCR.

These methods were evaluated using identical targets in human genomic DNA (NBR1, adjacent to the human BRCA1 gene). Table 5 shows that the method comparisons were unbiased: they were based on identical target sequences. Although each method requires a different number of primers (PCR requires 2, SDA requires 4, and LAMP requires 6), whenever possible, identical primer binding sites were used. The difference in primer sequences between PCR, LAMP, and SDA was the non-complementary 5' tails in LAMP and SDA.

TABLE 5

Primers of NBR1, adjacent to BRCA1 on human chromosome 17q21.31

| Oligo # | Name | Description | Primer Sequences |
|---|---|---|---|
| 1 | CG011 | qPCR (forward) | TCCTTGAACTTTGGTCTCC (SEQ ID NO. 1) |
| 2 | CG012 | qPCR (reverse) | CAGTTCATAAAGGAATTGATAGC (SEQ ID NO. 2) |
| 3 | CG011 | LAMP (fwd, outer) | TCCTTGAACTTTGGTCTCC (SEQ ID NO. 3) |
| 4 | CG012 | LAMP (rev, outer) | CAGTTCATAAAGGAATTGATAGC (SEQ ID NO. 4) |
| 5 | CG013 | LAMP (fwd, inner) | ATCCCCAGTCTGTGAAATTGGGCAAAATG CTGGGATTATAGATGT (SEQ ID NO. 5) |
| 6 | CG014 | LAMP (rev, inner) | GCAGCAGAAAGATTATTAACTTGGGCAGT TGGTAAGTAAATGGAAGA (SEQ ID NO. 6) |
| 7 | CG015 | LAMP (loop F) | AGAACCAGAGGCCAGGCGAG (SEQ ID NO. 7) |
| 8 | CG016 | LAMP (loop B) | AGGCAGATAGGCTTAGACTCAA (SEQ ID NO. 1) |
| 9 | CG011 | SDA (fwd, outer) | TCCTTGAACTTTGGTCTCC (SEQ ID NO. 8) |
| 10 | CG012 | SDA (rev, outer) | CAGTTCATAAAGGAATTGATAGC (SEQ ID NO. 9) |
| 11 | CG019 | SDA (fwd, inner) | ACCGCATCGAATGCATGTCTCGGGAAATG CTGGGATTATAGATGT (SEQ ID NO. 10) |
| 12 | CG021 | SDA (rev, inner) | GGATTCCGCTCCAGACTTCTCGGGGTTGGT AAGTAAATGGAAGA (SEQ ID NO. 11) |
| 13 | CG044 | ERiN SDA (fwd, outer) | TCCTTGAACTTTGGTCTCCrCAAAAC/C3Sp (SEQ ID NO. 12) |
| 14 | CG045 | ERiN SDA (rev, outer) | CAGTTCATAAAGGAATTGATAGCrACAGTC/C3Sp (SEQ ID NO. 13) |
| 15 | CG028 | ERiN SDA (fwd, inner) | ACCGCATCGAATGCATGTCTCGGGAAATG CTGGGATTATAGATGTrCAGCCG/C3Sp (SEQ ID NO. 14) |
| 16 | CG029 | ERiN SDA (rev, inner) | GGATTCCGCTCCAGACTTCTCGGGGTTGGT AAGTAAATGGAAGArATAGGA/C3Sp (SEQ ID NO. 15) |

Internal primers ($S_1$ and $S_2$) have 5' tails that contained a recognition sequence for thermophilic restriction endonuclease BsoBI (underlined in Table 5 for SDA primers F Inner [CG019] and $R_{Inner}$ [CG021]). BsoBI was compatible with optimal buffer and temperature conditions for the DNA polymerase Bst2.0. In one implementation of SDA, the DNA polymerase incorporated thiolated dCTP into the nascent strand (see Hemistrand Cleavage, FIG. 10). Under normal conditions, BsoBI would cleave both stands of the recognition site; however, the newly formed strand was resistant to endonuclease cleavage because SDA was performed with a modified deoxyribonucleotide. The version of SDA presented in this example used 2'-deoxycytidine-5'-O-(1-thiotriphosphate) [$dCTP_{\alpha S}$]. The top strand of the BsoBI site (C/TCGGG) was cleaved, but the newly synthesized complementary strand contains dCTP$_{\alpha S}$ (GAGC$_{\alpha S}$C$_{\alpha S}$/C$_{\alpha S}$), which was incorporated into dsDNA through phosphorothioate linkages was resistant to BsoBI. Under this strategy, BsoBI nicked the top strand. The nicked top strand had a 3'-OH and served as a primer for 3' strand extension (see identifier D of FIG. 10). In contrast to DNA polymerases used in SDA that have strand displacement activity because they lack exonuclease activity (exo-) found in more commonly used DNA polymerases (e.g. Taq in PCR), Bst2.0 (New England Biolabs), an engineered version of the Bst DNA polymerase large fragment, was used. External primers (Bump primers: B$_1$ [CG011] and B$_2$ [CG012]) increased the reaction kinetics by initiating synthesis distal to the internal primers and displacing the newly synthesized strand formed by the internal primers.

Isothermal amplifications were performed in 25 μl volumes. 5 μl of each reaction were loaded onto a 1.5% agarose gel (1×TAE) and resolved in 1×TAE running buffer at 75V for 1.5 h. Gels were prestained with SYBR Safe and visualized with a blue light transilluminator and amber filters. FIG. 9 shows agarose electrophoresis of LAMP and SDA amplified targets. The primary product of SDA and ERiN SDA is the ~211 product predicted from Table 6. ERiN SDA resolves the primer-dimer present in SDA NTC.

Although SDA was rapid and reproducible, no template control reactions (NTC) amplify in ~12 min (FIG. 11). In contrast, FIG. 13 shows that 25 copies/μl also amplify in ~12 min. Excessive background precludes discrimination between targets and samples without templates. Until now, SDA has been limited to simple targets like bacterial genomes, which have minimal complexity. The initial draft of the human genome revealed why applications of SDA have been limited to simple genomes: in contrast to bacterial genomes, which have minimal repetitive sequences, 50% of the human genome is composed of repetitive sequences (PMID 11237011). Complex genomes often require primer sequences in less than optimal locations. Table 6 illustrates two primers with 3' complementarity, which can dimerize and create a substrate for continued amplification. Complex genomes create challenges for assays like SDA where repetitive elements constrain primer design and frequently require primers with partial 3' complementarity.

TABLE 6

Example of Primers which can dimerize and create a substrate for continued amplification

| | |
|---|---|
| Consensus (60 bp) | TCCTTGAACTTTGG<u>TCTY</u>CCATTTACTTACCAACC CCGAGAAGTCTCTGGAGCGGAATCC (SEQ ID NO. 16) |
| CG020 (5'-3') | TCCTTGAACTTTGG<u>TCTCC</u> (SEQ ID NO. 17) |
| CG021 (3'-5') | <u>TCTTCC</u>ATTTACTTACCAACCCCGAGAAGTCTG GAGCGGAATCC (SEQ ID NO. 18) |

Modified primers were used to overcome non-specific amplification. The simplified mechanism of endoribonucleotide (ERiN) primers are illustrated in the SDA method in FIG. 10. There are two components to the ERiN primer strategy. First, the 3' terminus of ERiN primers are blocked and cannot be amplified until the blocking group is removed (FIG. 10). Second, ERiN primers are specifically activated when they in complex with their target sequence (see Primer Activation, FIG. 10). ERiN SDA prevents the amplification of no template controls (NTC) beyond the widely used 20 min cutoff time (FIG. 11, see data for experimental "e"). ERiN primers therefore overcome the primary limitation of SDA.

The key steps of the ERiN SDA mechanism are illustrated in FIG. 10. Primers with EndoRiboNucleotides (ERiN) are cleaved, for example by RNase, generating a 3'-OH that can be extended by DNA polymerases. ERiN primers contain a blocking group on the 3' terminus that prevents their extension until they are cleaved by RNase H2. RNase H2 specifically recognizes RNA-DNA heteroduplexes and has a low tolerance for mismatches. ERiN primers are therefore only activated when they bind their target DNA sequence.

The tail of the first primer contains a recognition site (red) for the BsoBI endonuclease. SDA replaces dCTP with 2'-Deoxycytidine-5'-O-(1-Thiotriphosphate) (C$_{\alpha S}$). C$_{\alpha S}$ blocks BsoBI cleavage of the newly synthesized strand, resulting in hemistrand cleavage. BsoBI cleavage generates a 3'-hydroxyl group that can be extended by DNA polymerases. The combination of isothermal stand extension and hemicleavage of the resulting amplicon continuously generates template.

FIG. 11 shows ERiN primers eliminate background from SDA in the absence of RNase H2. Real-time SDA kinetics were measured on a Bio-Rad Mini-Opticon at 70° C. using SYTO-9 as a fluorescent reporter. ERiN modifications decrease background when used on inner primers, or outer primers. ERiN modifications eliminate background amplification when used on both inner and outer primers. ERiN primers amplified low concentrations of the NBR1 template from human genomic DNA in 5 min (a). No template controls (NTC, b) show background amplification with unmodified SDA primers in ~12 min. SDA uses nested primers (forward and reverse tailed, inner primers; and forward and reverse untailed, outer primers). ERiN modifications delayed NTC amplification by ~5 min when ERiN modifications were used for either the inner primers (c) or outer primers (d) under these conditions. ERiN primers eliminated background NTC amplification when ERiN primers replaced both inner and outer primers (e). Reaction kinetics are reported as normalized relative fluorescent units (RFU). The horizontal bar indicates the threshold for fluorescence detection. All reactions were performed in the absence of RNase H2.

FIG. 12A shows results of real-time PCR performed on a Bio-Rad Mini-Opticon thermocycler using Bio-Rad qPCR master mix (containing Taq polymerase, SYBR, dNTPs, and buffer), ERiN primers: oliogos SDA F(inner) and R (inner). Reactions contained RNase H2: 32 mU/ul (a), 10 mU/ul (b), 3.2 mU/ul (c), and 1 mU/ul (d). Reaction kinetics are reported as normalized relative fluorescent units (RFU) and 145 second cycles. As expected, these results demonstrate a dose-dependent requirement for RNase H2 during PCR. Primers did not amplify in the absence of RNaseH2 (black).

Figure 12B:
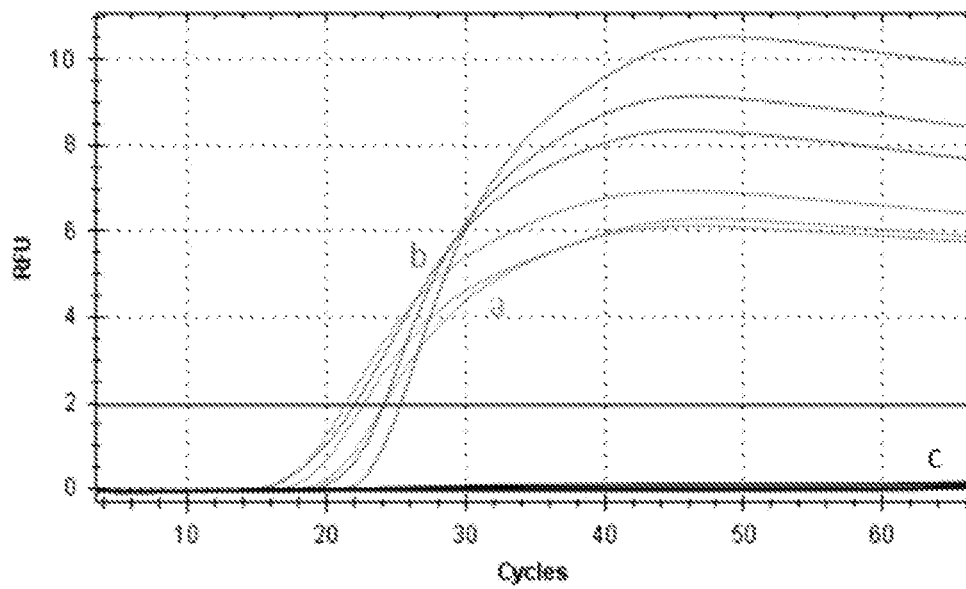
FIG. 12B shows RNase H2 is not required to activate ERiN primers in ERiN-SDA.
Figure 13:
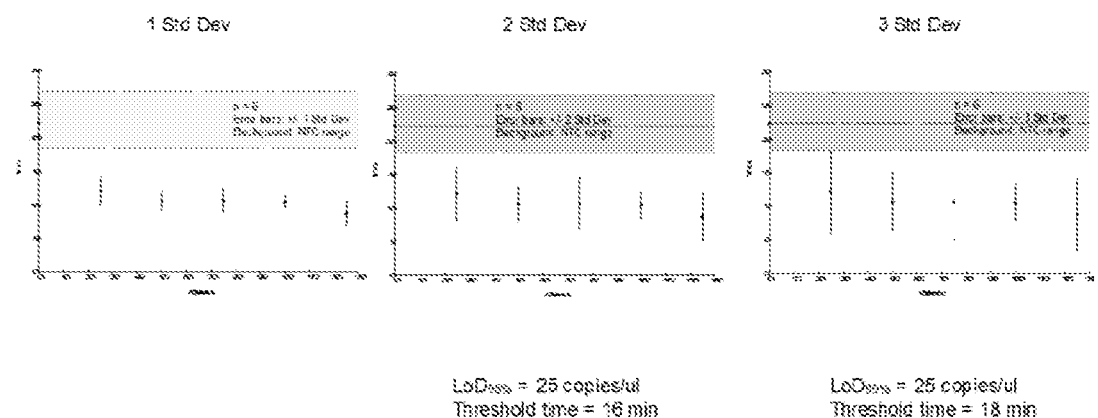
FIG. 13 shows background amplification places bounds on the limit of detection (LoD) by impacting the confidence of detecting a target within a given time (threshold time).

In contrast, ERiN primers did not require RNase H2 under any tested conditions (FIG. 12B). SDA kinetics were measured at a single temperature on a Bio-Rad Mini-Opticon thermocycler using SYTO-9 as a fluorescent reporter. ERiN primers: oligos SDA F(inner), R (inner), F(outer), R (outer). Reactions contained RNase H2: 32 mU/ul (a), no RNase H2 (b), and No Template Controls (NTC, black) (c). Reaction kinetics are reported as normalized relative fluorescent units (RFU). The kinetic curves overlap, and if anything the samples with RNase H2 have reduced RFU$_{max}$, possibly because of elements (e.g. glycerol) contributed by the RNase H2 buffer. Note that SDA has 15 second cycles and 10× the RFU intensity compared to PCR (b), which has 145 second cycles. The lack of a need for RNase H2 was unexpected, and in stark contrast to the requirement for RNase H2 for PCR (FIG. 12A). It is conceivable that an RNase H2-independent mechanism would not decrease background, but FIG. 11 conclusively demonstrated that this is not the case: ERiN primers decreased background when used as internal primers, external primers, and further reduced background when used as both internal and external primers. FIG. 9 shows that ERiN SDA resolves the background present in SDA. Although the molecular mechanism has not yet been elucidated, this discovery can be used to solve two primary challenges. First, RNase H2-dependent assays (e.g. RNase H2-dependent PCR, rhPCR, (Dobosy et al., 2011)) require high concentrations of RNase H2 with high activity. High concentrations of RNase H2 with high activity are expensive, and cost prohibitive for many applications, including resource-limited settings for which isothermal amplifications are ideally suited. Second, RNase H2 has specific buffer and temperature requirements, which limit the range of reaction conditions under which RNase-dependent methods can be performed, and may inhibit the $RFU_{max}$ in SDA (FIG. 12B). A major disadvantage of assays that require RNase (e.g. RNase H-dependent PCR (rhPCR) and RNase H-dependent LAMP (rhLAMP)) is that primers for cDNA synthesis form targets for RNase when they hybridize to the template RNA. RNase-dependent assays are therefore not suitable for analysis of RNA because they degrade the template RNA. This is particularly problematic for applications that require cDNA synthesis and amplification in the same tube. For example, performing cDNA synthesis and clean-up as separate steps before cDNA amplification introduces errors that complicate the accurate quantification of RNA. Applications for rhPCR were therefore primarily limited to discriminating single nucleotide variations (e.g. SNPs) and other sequences with high similarity. Thus these results indicate RNA can be directly amplified if the DNA polymerase contains reverse-transcriptase activity, allowing for cDNA synthesis and cDNA amplification to be performed in the same tube. The discovery that RNase is not necessary to activate ERiN primers can therefore be used to reduce the cost of performing a rapid, specific assay, and increases the range of conditions where ERiN primers can be utilized (e.g. single-tube cDNA synthesis and amplification), while increasing sensitivity/accuracy by decreasing background.

Clinical screening tests require a detection time that is 2 standard deviations greater than the mean detection in order to confidently detect 95% of the analytes at the limit of detection ($LoD_{95\%}$). Many clinical tests require greater confidence (e.g. the test must detect 99.7% of analytes). On average, no template controls (NTC) in SDA amplify within 12 min (FIG. 12B), which constrains the LoD. FIG. 13 illustrates the importance of reducing background amplification. The maximum reaction time of an assay is defined by the earliest time that a NTC replicate ever amplifies, which in this case is just greater than 18 min. The time required to detect 25 targets at a concentration of 25 copies/pi with a standard deviation of 2 is 16 min. The time required to detect 25 targets at a concentration of 25 copies/pi with a standard deviation of 3 is 18 min. ERiN primers reduced background and therefore raised the $LoD_{99\%}$ to 25 copies per microliter. This is the statistical mechanism through which ERiN primers increased assay sensitivity. FIG. 13 shows that the $LoD_{99\%}$ for SDA would be greater than any of the tested concentrations. Since the LoD of SDA without ERiN primers is greater than 125 copies/µl, ERiN primers increased the sensitivity of SDA by at least 5-fold.

ERiN SDA primers are also used for loop-mediated isothermal amplification (LAMP) without the requirement for the RNase H2 enzyme.

ERiN SDA primers used in an isothermal amplification is also combined with a reverse transcriptase step. A controlled system is developed with purified RNA from human breast cancer cell lines. Human genes are used as targets. Crude samples are titrated from an animal model that does not contain the target genes; otherwise the addition of target material would mask inhibition by the crude lysate. The assay detects the equivalent of 10 malignant cells within 15 min based on expression of 3 genes, in the presence of lysis buffer and cell lysate.

Table 7 shows an example calculation of sensitivity and specificity for SDA. In this case, confidence bounds were calculated using the 15 min SDA threshold of detecting 50 copies/ml. Confidence bounds for the target were derived using 3 standard deviations (99%) from the target and 2 standard deviations (95%) from the NTC.

TABLE 7

Model of ERiN SDA assay performance using confidence bounds from target amplification and background (NTC) amplification.

|  |  | True | |
| --- | --- | --- | --- |
|  |  | Positive | Negative |
| Test | Positive | 99 [a] | 5 [b] |
|  | Negative | 1 [c] | 95 [c] |
|  | Total | 100 | 100 |

Figure 14:
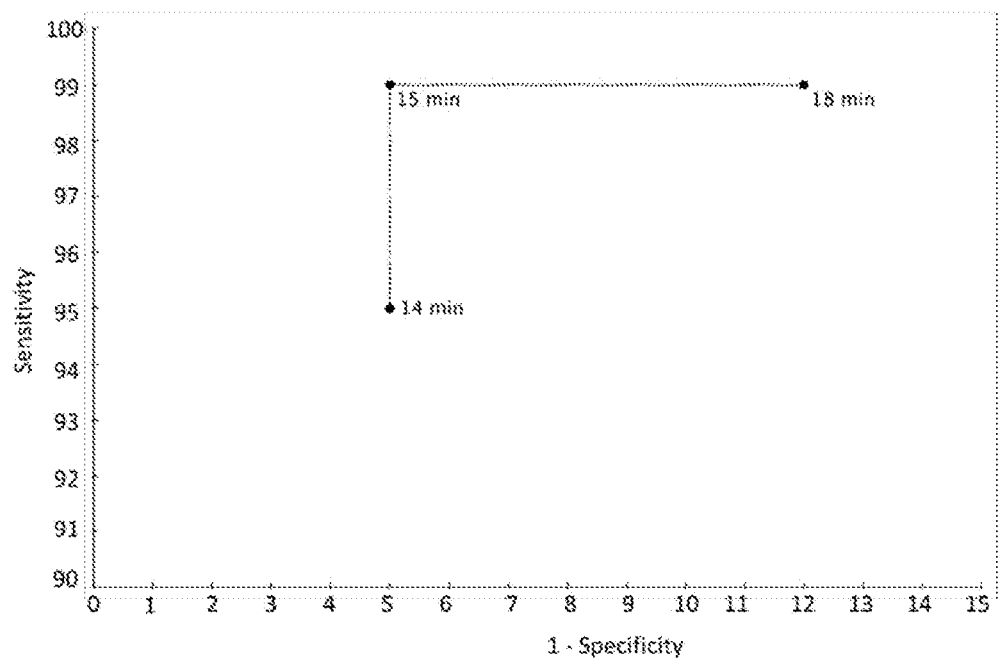
FIG. 14 shows Receiver Operator Characteristic (ROC) showing detection of 50 copies/ml of NBR1 from human genomic DNA using ERiN SDA.

FIG. 14 shows Receiver Operator Characteristic (ROC) for SDA showing relationship of sensitivity and specificity to threshold detection times. Table 7 builds on the relationship between background amplification and target amplification (FIG. 13) to calculate the sensitivity and specificity for the 15 min time point. This figure underscores the importance of limiting background amplification by demonstrating that background amplification broadly impacts assay performance.

Example 17. Target Nucleic Acid Amplification Protocols

Protocols for 3 isothermal methods are provided. The isothermal methods include LAMP, SDA, and ERiN SDA. These protocols were used to compare LAMP and SDA for FIG. 8 (Beeswarm plot).

LAMP: Amplification of the NBR1 Locus from Human Genomic DNA.

Exemplary Primer Sequences (custom synthesized oligonucleotides from IDT (listed 5' to 3')):

CG011 (F3):
(SEQ ID NO. 19)
TCCTTGAACTTTGGTCTCC

CG012 (B3):
(SEQ ID NO. 20)
CAGTTCATAAAGGAATTGATAGC

CG013 (FTP):
(SEQ ID NO. 21)
ATCCCCAGTCTGTGAAATTGGGCAAAATGCTGGGATTATAGATGT

-continued

CG014 (BIP):
(SEQ ID NO. 22)
GCAGCAGAAAGATTATTAACTTGGGCAGTTGGTAAGTAAATGGAAGA

CG015 (Loop F):
(SEQ ID NO. 23)
AGAACCAGAGGCCAGGCGAG

CG016 (Loop B):
(SEQ ID NO. 24)
AGGCAGATAGGCTTAGACTCAA

Reaction concentrations of component reagents:
20 mM Tris, pH 8.8 (@25° C.)
10 mM (NH4)2SO4
8 mM MgSO4
50 mM KCl
1.4 mM each dNTPs
0.1% (v/v) Tween-20
2 μM SYTO-9 (Life, Cat #S-34854)
0.04 U/μl Bst 2.0* (NEB, Cat #M0537S)
10 ng/ul Purified HeLa genomic DNA** (NEB, Cat #N4006S)

| Primers (reaction concentration) | |
|---|---|
| CG011: | 0.2 μM |
| CG012: | 0.2 μM |
| CG013: | 1.6 μM |
| CG014: | 1.6 μM |
| CG015: | 0.4 μM |
| CG016: | 0.4 μM |

* Polymerase concentration varies in some experiments
** Some reactions contain less DNA template and negative control reactions use water instead of DNA.
** Assuming 3.3 pg of DNA per haploid human genome, each reaction contains 3,000 templates per microliter of the reaction.

Components of 2× Lamp Reaction Buffer (LRB):
10× Thermopol buffer (NEB, Cat #B9004S)
10 mM Each dNTPs (NEB, Cat #N04475)
100 mM MgSO$_4$ (NEB, Cat #B1003S)

SYTO-9 Preparation: Life, Cat #S-34854 is 5 nM in DMSO stock. Dilute with water to 50 μM solution. Prepare the final 2 μM reaction concentration using water dilution.

LAMP Reaction conditions: Samples were prepared on ice and loaded into a preheated 71° C. block (with a 98° C. heated lid).

SDA: Amplification of the NBR1 locus from human genomic DNA.

Exemplary primer sequences: (custom synthesized oligonucleotides from IDT (listed 5' to 3')):

CG019 (F):
(SEQ ID NO. 25)
ACCGCATCGAATGCATGTCTCGGGAAATGCTGGGATTATAGATGT

CG021 (R):
(SEQ ID NO. 26)
GGATTCCGCTCCAGACTTCTCGGGGTTGGTAAGTAAATGGAAGA

CG020 (F $_{bump}$):
(SEQ ID NO. 27)
TCCTTGAACTTTGGTCTCC

CG022 (R $_{bump}$):
(SEQ ID NO. 28)
CAGTTCATAAAGGAATTGATAGC

Reagent reaction concentrations:
1× Isothermal Amplification Buffer (NEB, Cat #B0537S)
6 mM MgSO$_4$ (NEB B10038; mM total, 2 mM from 1× Buffer)
0.4 mM dATP, dGTP, dTTP (Nucleoside Triphosphates [unmodified] from Trilink)
0.8 mM dCTP-αS (Trilink, N-8002)
1.7 U/μL BsoBI* (NEB R0586)
0.04 U Bst 2.0* (NEB, Cat #M0537)
2 μM SYTO-9 (Life Technologies, Cat #S-34854)
10 ng/μL template HeLa Genomic DNA** (NEB, Cat #N4006S)

| Primers (reaction concentrations)***: | |
|---|---|
| CG019: | 0.5 μM |
| CG020: | 0.5 μM |
| CG021: | 0.5 μM |
| CG022: | 0.5 μM |

*Enzyme concentrations vary in some experiments
**Some reactions contain less DNA template. Some negative control reactions use water instead of DNA.
**Each reaction contains an estimated 3,000 templates/μl, assuming 3.3 pg/haploid human genome.
***In this example, the ratios of outer (bump) primers to inner primers is 1:1, although this ratio can vary.

SYTO-9 Preparation: Life, Cat #S-34854 is 5 nM in DMSO stock. Dilute with water to 50 μM solution. Prepare the final 2 μM reaction concentration using water dilution.

SDA Reaction conditions: Samples were prepared on ice and loaded into a preheated 71° C. block (with a 98° C. heated lid).

ERiN SDA: Amplification of the NBR1 Locus from Human Genomic DNA.

Structure of ERiN Primers:

Modifications to the 3' end of an oligonucleotide, where the modification includes at least one ribonucleotide, at least one deoxyribonucleotide, and at least one blocking group(s) that prevent or retard the 3' strand extension activity of a DNA polymerase. Modifications could take the form:

GEN1: (5') R-rDDDDMx (3'), or

GEN2: (5') R-rDxxDM (3')

Where,

R=original primer r=ribonucleotide base

D=deoxyribonucleotide base (Complementary to the target sequence)

M=deoxyribonucleotide base (Mismatch to the target sequence)

x=blocking group, which in this case is phosphoramidite (also known as a C3 Spacer)

xx=two internal modifications that are not naturally occurring DNA or RNA, and in this case are two phosphoramidites.

Exemplary primer sequences: (custom synthesized oligonucleotides from IDT (listed 5' to 3')):

CG028:
(SEQ ID NO. 29)
ACCGCATCGAATGCATGT<u>CTCGGG</u>AAATGCTGGGATTATAGATGT<u>r</u>CA
GCCG/3SpC3/

Derived from CG019
Added rDDDMx to 3' end
Template binding sequence italicized
BsoBI site underlined CG029:
(SEQ ID NO. 30)
GGATTCCGCTCCAGACTT<u>CTCGGGG</u>TTGGTAAGTAAATGGAAGArATA GG<u>A</u>/3SpC3/

Derived from CG021
Added rDDDMx to 3' end
Template binding sequence italicized
BsoBI site underlined (SEQ ID NO. 31)
CG044: *TCCTTGAACTTTGGTCTCC*rCAAAA<u>C</u>/3SpC3/

Derived from CG011 (aka CG020)
Added rDDDMx to 3' end (SEQ ID NO. 32)
CG045: *CAGTTCATAAAGGAATTGATAGC*rACAGT<u>C</u>/3SpC3/

Derived from CG012 (aka CG022)
Added rDDDMx to 3' end
Reagent reaction concentrations:
1× Isothermal Amplification Buffer (NEB, Cat #B0537S)
6 mM MgSO$_4$ (NEB B10038; mM total, 2 mM from 1× Buffer)
0.4 mM dATP, dGTP, dTTP (Nucleoside Triphosphates [unmodified] from Trilink)
0.8 mM dCTP-αS (Trilink, N-8002)
1.7 U/μL BsoBI* (NEB R0586)
0.04 U Bst 2.0* (NEB, Cat #M0537)
2 μM SYTO-9 (Life Technologies, Cat #S-34854)
10 ng/μL template HeLa Genomic DNA** (NEB, Cat #N4006S)

| Primers (reaction concentrations)***: | |
|---|---|
| CG028: | 0.5 μM |
| CG029: | 0.5 μM |
| CG044: | 0.5 μM |
| CG045: | 0.5 μM |

*Enzyme concentrations vary in some experiments
**Some reactions contain less DNA template. Some negative control reactions use water instead of DNA.
**Each reaction contains an estimated 3,000 templates/μL, assuming 3.3 pg/haploid human genome.
***In this example, the ratios of outer primers to inner primers is 1:1, although this ratio can vary.

SYTO-9 Preparation: Life, Cat #S-34854 is 5 nM in DMSO stock. Dilute with water to 50 μM solution. Prepare the final 2 μM reaction concentration using water dilution. ERiN SDA Reaction conditions: Samples were prepared on ice and loaded into a preheated 71° C. block (with a 98° C. heated lid).

Example 18. Breast Cancer Disease Classifier Development

Inclusion and exclusion criteria were selected to limit the analysis to early-stage, focal lesions that would be candidates for breast conservation surgery. Breast cancer continues to evolve as it progresses and including later-stage tumors in the analysis may detect global expression changes that do not provide the strongest signal for tumors removed during the indicated surgical procedure. Inclusion and exclusion criteria were defined according to the 7th Edition AJCC TNM protocol and shown in Table 8.

Table 8 shows inclusion and exclusion criteria for developing an early-stage classifier for breast cancer. The classifiers presented here are focused on invasive adenocarcinoma of the breast. The classifier is designed to detect positive margins during breast conservation surgeries (lumpectomies, BCS). Since the genomics of breast cancer change as tumors progress to later stages, the focus is on early-stage tumors that are candidates for BCS, as opposed to a classifier globally developed from all breast cancer tumors. For a similar reason, pTis (ductal carcinoma in situ, DCIS) were excluded from this analysis, and a separate classifier is developed for DCIS.

TABLE 8

Inclusion/exclusion criteria for Breast Cancer Disease Classifier

| | TNM Stage | Description |
|---|---|---|
| Primary tumor (Include) | T1-T2 | Primary tumor ≤5 cm |
| Primary tumor (Exclude) | T0 | No evidence of primary tumor |
| | T3 | Primary tumor >5 cm |
| | T4a-T4d | Tumor of any size with involvement of the skin or chest wall |
| | T is | DCIS |
| Multifocal (Exclude) | T m | Multifocal primary tumor |
| Lymph Node (Include) | N0 | No node involvement |
| | NX | Node status unknown |
| Lymph Node (Exclude) | N1-N3 | Node involvement characterized by metastasis or micrometastasis |
| | N0 (i+) | Malignant cells in regional lymph node(s) <0.2 mm and <200 cells |
| Metastasis (Include) | M0 | No detectable metastasis |
| | MX | Metastasis unknown |
| Metastasis (Exclude) | M1 | Distant metastasis (clinical, radiographic detection and/or histologically >0.2 mm) |

A combination of statistics and machine learning identified a panel of genes that distinguish breast cancer from adjacent healthy tissue. Cross-validation was used to evaluate the performance of multiple machine learning methods trained using the 200 most differentially expressed genes (see FIG. 15A) and description of cross validation in Example 10). 10-fold cross validation predicts that a 200-gene classifier developed with a multilayer perceptron neural network machine learning method can correctly classify 100% of samples as invasive breast cancer or healthy breast tissue with a root mean squared error (RMSE) of 0.01702. To determine the minimum number of genes required for a BCDC, feature selection methods were used to identify the most informative probes. Three feature selection methods were used to rank the 200 most differentially expressed probes before training machine learning methods with the top probes from each feature selection method. The top 100, 50, 20, 10, 5, 4, 3, 2 and 1 probes were tested. 10-fold cross-validation predicts that classifiers based on 3 genes can have an accuracy of 100% and a predicted error of 0.0000 (root mean squared error) (see, e.g., Example 12).

Five lines of evidence were established demonstrating that gene expression can be used to classify samples as healthy or tumor. First, principal component analysis (PCA)

was used to demonstrate that gene expression can separate tumor samples from healthy tissue using 90,000 microarray probes (see FIG. 6) and Example 6). Second, it was found that over 200 probes were differentially expressed more than 3 standard deviations from the mean, further validating that there are candidate biomarkers from which to build a classifier. Third, hierarchical cluster analysis (HCA) was used to demonstrate that the top 200 differentially expressed probes can be used to cluster samples as tumor or healthy, and that the top 200 probes generate a larger clustering distance between tumor and healthy samples than all 90,000 probes (See Examples 7 & 9 and FIG. 5). Fourth, it was found that machine learning methods trained on the 200 most differentially expressed probes can accurately classify samples as healthy or tumor (See Example 11). Fifth, it was found that machine learning methods can maintain high classification accuracy and low error when the number of probes are reduced from 200 to 3 (see Example 12). Sixth, the predicted accuracy and error was estimated for individual probes that were determined to be the most informative by correlation-based feature selection, among 200 probes selected by p-value from a linear model (see Example 8). Individual probes alone could correctly classify 98% of samples as healthy or tumor. These lines of evidence are further strengthened by three negative controls (see Example 13). First, the prevalence-based machine learning method NoRule has a higher error than other machine learning methods, which is expected because NoRule is exclusively based on class prevalence. Second, randomly selected probes have a high predicted error rate when tested by the same cross-validation methods used to evaluate the most informative probes. Finally, the highest error is seen when samples are assigned to random classes (Example 13). Taken together, these make a compelling case that breast cancer is a single disease that can be detected by a limited panel of biomarkers.

The results of these analyses were quite surprising given what is known or thought about breast cancer biology. Breast cancer is thought of as a constellation of distinct molecular phenotypes that happen to present as a mass in the same anatomic location. In 2007, Jeffrey Rosen and Tracy Vargo-Gogola summarized the current understanding of breast cancer by declaring "breast cancer is not a single disease." Wang, et al. wrote that "breast tumor subtypes represent biologically distinct disease entities, and may require different therapeutic strategies," (*BMC Genomics* 2006 volume 7, page 127). In contrast, strong evidence was present that three genes can be used to classify all breast cancers with 100% accuracy, and a single gene can have an accuracy of 98%.

To investigate why this may be the case, the biologic function of the genes selected was examined by our analysis. Some of the identified genes were involved in the extracellular matrix, which may reflect the tumor microenvironment. One candidate gene was COL10A1, a collagen deposited in hyalinated cartilage during ossification. Tumor tissue is not exclusively composed of malignant cells; it's plausible that the stromal response to breast cancer generates a more consistent gene expression signature for malignancy than genes within the malignant cells themselves.

Principal Component Analysis (PCA) provides another explanation for the unexpectedly strong performance of the disease classifiers. PCA was performed using over 90,000 microarrray probes, which correspond to approximately 19,000 genes across all TCGA samples. The genome-wide analysis provided a somewhat unbiased method to investigate the similarity between these two classes (healthy and malignant breast tissue), see FIG. 6. Tumor tissue and healthy tissue form distinct clusters with well demarcated space between them (this separation is almost without precedent for gene expression data). The BCDC performed well because it distinguishes two well-defined, clearly separated clusters. This contrasts with the goal of at least 9 published breast cancer classifiers, which require 12-800 genes to separate tumors that are shown as highly similar in the PCA cluster. The BCDC outperforms published breast cancer classifiers because it separates two distinct classes, rather than very similar classes.

TABLE 9

Target Nucleic Acid mRNA Sequences

| NAME | NCBI or UCSC Identifier SEQUENCE |
|---|---|
| ABCA10 (ATP-binding cassette, sub-family A (ABC1), member 10) | NM_080282.3 |
| ABCA9 (ATP-binding cassette, sub-family A (ABC1), member 9) | NM_080283.3 |
| ADAM33 (ADAM metallopeptidase domain 33) | NM_001282447.1, NM_025220.3, NM_153202.2 |
| ADAMTS5 (ADAM metallopeptidase with thrombospondin type 1 motif, 5) | NM_007038.3 |
| ANGPT1 (angiopoietin 1) | NM_001199859.1, uc003ymp.2 |
| ANKRD29 (ankyrin repeat domain 29) | NM_173505.3 |
| ARHGAP20 (Rho GTPase activating protein 20) | NM_001258415.1, NM_001258416.1, NM_001258417.1, NM_001258418.1, NM_020809.3 |
| ARMCX5-GPRASP2 | NM_001199818.1 |
| ASB1 (ankyrin repeat and SOCS box containing 1) | NM_001040445.1 |
| CA4 (carbonic anhydrase IV) | NM_000717.3, uc010wou.2 |
| CACHD1 (cache domain containing 1) | NM_020925.2 |
| CAPN11 (calpain 11) | NM_007058.3 |
| CAV1 (caveolin-1) | NM_001753.4, NM_001172895.1, NM_001172896.1, uc010lkd.1 |
| CAV2 (caveolin-2) | NM_001206747.1, NM_001233.4, NM_198212.2 |
| CAV3 (caveolin-3) | NM_033337.2 |
| CBX7 (chromobox homolog 7) | NM_175709.3 |
| CCNE2 (cyclin E2) | NM_057749.2, uc003yhd.1 |

TABLE 9-continued

Target Nucleic Acid mRNA Sequences

| NAME | NCBI or UCSC Identifier SEQUENCE |
|---|---|
| CD300LG (CD300 molecule-like family member g) | NM_001168322.1, NM_001168323.1, NM_001168324.1, NM_145273.3 |
| CDC14B (cell division cycle 14B) | NM_001077181.1, NM_003671.3, NM_033331.2 |
| CDC42SE1 (CDC42 small effector 1) | NM_001038707.1 |
| CENPF (centromere protein F, 350/400 kDa) | NM_016343.3 |
| CEP68 (centrosomal protein 68 kDa) | NM_015147.2 |
| CFL2 (cofilin 2 (muscle)) | NM_021914.7, NM_001243645.1, NM_138638.4 |
| CHL1 (cell adhesion molecule L1-like) | NM_001253387.1, NM_001253388.1, NM_006614.3 |
| CLIP4 (CAP-GLY domain containing linker protein family, member 4) | NM_001287527.1, NM_001287528.1, NM_024692.5 |
| CNTNAP3 (contactin associated protein-like 3) | NM_033655.3 |
| COL10A1 | NM_000493.3 |
| COL11A1 | NM_080629.2, NM_001854.3, uc001duk.3 |
| CRIM1 (cysteine rich transmembrane BMP regulator 1 (chordin-like)) | NM_016441.2 |
| CXCL3 (chemokine (C-X-C motif) ligand 3) | NM_002090.2 |
| DAB2IP (DAB2 interacting protein) | NM_032552.3, NM_138709.2 |
| DMD (dystrophin) | NM_000109.3, NM_004006.2, NM_004009.3, NM_004010.3, NM_004013.2, NM_004014.2, NM_004015.2, NM_004016.2, NM_004017.2, NM_004018.2, NM_004020.3, NM_004021.2, NM_004022.2, NM_004023.2, NM_004019.2, uc004ddf.2, NM_000109.3 |
| DPYSL2 (dihydropyrimidinase-like 2) | NM_001197293.2, NM_001244604.1, NM_001386.5 |
| DST (dystonin) | NM_001144769.2, NM_001144770.1, NM_001723.5, NM_015548.4, NM_183380.3 |
| EEPD1 (endonuclease/exonuclease/phosphatase family domain containing 1) | NM_030636.2 |
| ENTPD7 (ectonucleoside triphosphate diphosphohydrolase 7) | NM_020354.3, uc009xwl.1 |
| ERCC6L (excision repair cross-complementation group 6-like) | NM_017669.2, uc004eap.1 |
| EZH1 (enhancer of zeste 1 polycomb repressive complex 2 subunit) | NM_001991.3 |
| F10 (coagulation factor X) | NM_000504.3, uc010agq.1 |
| FAM126A (family with sequence similarity 126, member A) | NM_032581.3 |
| FBXO31 (F-box protein 31) | NM_001282683.1, NM_024735.4 |
| FGF1 (fibroblast growth factor 1 (acidic)) | NM_000800.4, NM_001144892.2, NM_001144934.1, NM_001144935.1, NM_001257205.1, NM_001257206.1, NM_001257207.1, NM_001257208.1, NM_001257209.1, NM_001257210.1, NM_001257211.1, NM_001257212.1, NM_033136.3, NM_033137.2 |
| FIGF (c-fos induced growth factor (vascular endothelial growth factor D)) | NM 004469.4, uc004cwt.1 |
| FM02 (flavin containing monooxygenase 2) | NM_001460.4 |
| FXYD1 (FXYD domain containing ion transport regulator 1) | NM_001278717.1, NM_001278718.1, NM_005031.4, NM_021902.3 |
| GIPC2 (GIPC PDZ domain containing family, member 2) | NM_017655.5 |
| GLYAT (glycine-N-acyltransferase) | NM_201648.2, NM_005838.3 |
| GPR17 (G protein-coupled receptor 17) | NM_001161415.1, NM_005291.2 |
| GPRASP1 (G protein-coupled receptor associated sorting protein 1) | NM_001099410.1, NM_001099411.1, NM_001184727.1, NM_014710.4 |
| GPRASP2 (G protein-coupled receptor associated sorting protein 2) | NM_001004051.3, NM_001184874.2, NM_001184875.2, NM_001184876.2, NM_138437.5 |

TABLE 9-continued

Target Nucleic Acid mRNA Sequences

| NAME | NCBI or UCSC Identifier SEQUENCE |
|---|---|
| HAND2-AS1 (HAND2 antisense RNA 1 (head to head)) | NR_003679.1 |
| HAGHL (hydroxyacylglutathione hydrolase-like) | NM_001290137.1, NM_032304.3, uc002cjn.1 |
| HLF (hepatic leukemia factor) | NM_002126.4, uc010dce.1, uc002iuh.1 |
| HMMR (hyaluronan-mediated motility receptor (RHAMM)) | NM_001142556.1 |
| HOXA2 (homeobox A2) | NM_006735.3 |
| HOXA4 (homeobox A4) | NM_002141.4 |
| HOXA5 (homeobox A5) | NM_019102.3 |
| IGSF10 (immunoglobulin superfamily, member 10) | NM_178822.4, NM_001178145.1, NM_178822.4 |
| IL11RA (interleukin 11 receptor, alpha) | NM_001142784.2 |
| INHBA (inhibin, beta A) | NM_002192.2, uc003thq.1 |
| ITM2A (integral membrane protein 2A) | NM_001171581.1, NM_004867.4 |
| JADE1 (jade family PHD finger 1) | NM_024900.4, NM_001287437.1 |
| JUN (jun proto-oncogene) | NM_002228.3 |
| KIAA0101 | NM_014736.5, NR_109934.1 |
| KIF4A (kinase family member 4A) | NM_012310.4, uc010nkw.1, uc004dyf.1 |
| KLHL29 (kelch-like family member 29) | NM_052920.1 |
| LCAT (lecithin-cholesterol acyltransferase) | NM_000229.1 |
| LGI4 (leucine-rich repeat LGI family, member 4) | NM_139284.2, uc002nxz.1, uc002nya.2, uc002nxy.1 |
| LIFR (leukemia inhibitory factor receptor alpha) | NM_001127671.1, NM_002310.5 |
| LIMS2 (LIM and senescent cell antigen-like domains 2) | NM_001136037.2, NM_001161403.1, NM_001161404.1, NM_001256542.1, NM_017980.4 |
| LRIG3 (leucine-rich repeats and immunoglobulin-like domains 3) | NM_001136051.2, NM_153377.4 |
| LRRC2 (leucine rich repeat containing 2) | NM_024512.4 |
| LRRC3B (leucine rich repeat containing 3B) | NM_052953.2, uc003cdq.1 |
| MAMDC2 (MAM domain containing 2) | NM_153267.4 |
| MATN2 (matrilin 2) | NM_002380.3 |
| MICU3 (mitochondrial calcium uptake family, member 3) | NM_181723.2 |
| MIR99AHG (mir-99a-let-7c cluster host gene) | NR_027790.2 |
| MME (membrane metallo-endopeptidase) | NM_000902.3, NM_007287.2, NM_007288.2, NM_007289.2 |
| MMP11 (matrix metallopeptidase 11) | NM_005940.3, uc002zxz.1 |
| NECAB1 (N-terminal EF-hand calcium binding protein 1) | NM_022351.4 |
| NEK2 (NIMA-related kinase 2) | NM_001204182.1, NM_002497.3, NM_001204183.1 |
| NKAPL (NFKB activating protein-like) | NM_001007531.2 |
| NPHP3 (nephronophthisis 3 (adolescent)) | NM_153240.4 |
| NR3C1 (glucocorticoid receptor) | NM_001018074.1, NM_001018075.1, NM_001018076.1, NM_001018077.1, NM_001020825.1, NM_001024094.1, NM_001204258.1, NM_001204259.1, NM_001204260.1, NM_001204261.1, NM_001204262.1, NM_001204263.1, NM_001204264.1 |
| NR3C2 (nuclear receptor subfamily 3, group C, member 2) | NM_000901.4, NM_001166104.1 |
| NUF2 (NDC80 kinetochore complex component) | NM_145697.2, uc001gcp.1 |
| PAFAH1B3 (platelet-activating factor acetylhydrolase 1b, catalytic subunit 3 (29 kDa)) | NM_001145939.1, NM_002573.3, NM_001145940.1 |
| PAMR1 | NM_001001991.2, NM_001282675.1, NM_001282676.1, NM_015430.3 |
| PAQR4 (progestin and adipoQ receptor family member IV) | NM_152341.4 |
| PARK2 (parkin RBR E3 ubiquitin protein ligase) | NM_004562.2, NM_013987.2, NM_013988.2 |
| PEAR1 (platelet endothelial aggregation receptor 1) | NM_001080471.1 |

TABLE 9-continued

Target Nucleic Acid mRNA Sequences

| NAME | NCBI or UCSC Identifier SEQUENCE |
|---|---|
| PGM5 (phosphoglucomutase 5) | NM_021965.3 |
| PLEKHM3 (pleckstrin homology domain containing, family M, member 3) | NM_001080475.2 |
| PLSCR4 (phospholipid scramblase 4) | NM_001128304.1, NM_001128305.1, NM_001128306.1, NM_001177304.1, NM_020353.2 |
| PKMYT1 (protein kinase, membrane associated tyrosine/threonine 1) | NM_182687.2, NM_001258451.1, uc010bsy.1 |
| POU6F1 (POU class 6 homeobox 1) | NM_002702.3 |
| PPAP2B (phosphatidic acid phosphatase type 2B) | NM_003713.4 |
| PPP1R12B (protein phosphatase 1, regulatory subunit 12B) | NM_001167857.1, NM_001167858.1, NM_001197131.1, NM_002481.3, NM_032103.2, NM_032104.2 |
| PRCD (progressive rod-cone degeneration) | NM_001077620.2 |
| PRX (periaxin) | NM_020956.2, NM_181882.2 |
| PYCR1 (pyrroline-5-carboxylate reductase 1) | NM_006907.3, NM_001282279.1 |
| RAPGEF3 (Rap guanine nucleotide exchange factor (GEF) 3) | NM_001098531.2, NM_001098532.2, NM_006105.5 |
| RBMS2 (RNA binding motif, single stranded interacting protein 2) | NM_002898.3 |
| SCN4B (sodium channel, voltage gated, type IV beta subunit) | NM_001142348.1, NM_001142349.1, NM_174934.3 |
| SDPR (serum deprivation response) | NM_004657.5 |
| SH3BGRL2 (SH3 domain binding glutamate-rich protein like 2) | NM_031469.2 |
| SLC35A2 (solute carrier family 35 (UDP-galactose transporter), member A2) | NM_005660.2, NM_001282651.1 |
| SPRY2 (sprouty homolog 2 (Drosophila)) | NM_005842.2, uc001vli.1 |
| STAT5B (signal transducer and activator of transcription 5B) | NM_012448.3 |
| SYN2 (synapsin II) | NM_003178.5, NM_133625.4 |
| TK1 (thymidine kinase 1, soluble) | NM_003258.4, uc002jux.2 |
| TMEM220 (transmembrane protein 220) | NM_001004313.1, NM_173485.5 |
| TMEM255A (transmembrane protein 255A) | NM_017938.3 |
| TMOD1 (tropomodulin 1) | NM_001166116.1, NM_003275.3 |
| TPM3 (tropomyosin 3) | NM_001043352.1, NM_001278191.1, NM_152263.3, uc001fdx.1, NR_103460.1 |
| TPX2 (microtubule associated) | NM_012112.4, uc010gdv.1 |
| TSHZ2 (teashirt zinc finger homeobox 2) | NM_001193421.1 |
| TSLP (thymic stromal lymphopoietin) | NM_033035.4, NM_138551.4, NR_045089.1 |
| TSTA3 (tissue specific transplantation antigen P35B) | NM_003313.3, uc003yza.1 |
| TTC28 (tetratricopeptide repeat domain 28) | NM_001145418.1 |
| USHBP1 (Usher syndrome 1C binding protein 1) | NM_001297703.1, NM_031941.3 |
| USP44 (ubiquitin specific peptidase 44) | NM_001042403.2, NM_001278393.1, NM_032147.4 |
| WISP1 (WNT1 inducible signaling pathway protein 1) | NM_003882.384 |
| ZWINT (ZW10 interacting kinetochore protein) | NM_032997.2, uc001jjz.1 |

Example 19. Postoperative Test of a Surgical Specimen

To evaluate the success of removing surgical tissue and/or to detect the presence of residual surgical tissues, a method was developed with the following steps.
1. Post-operative strategy
   a. Collect only surface cells from the surgical specimen:
      i. Analyzing at least 50% of the surface of the specimen
      ii. Surface (e.g. glass slide) with functionalized coating (e.g. poly-lysine)
      iii. Preferential selection of cells of epithelial origin (which preferentially adhere to, for example, poly-lysine)
   b. Cell lysis
   c. Optional step: convert RNA to cDNA
   d. Quantify target nucleotide (DNA, RNA or cDNA) sequence
      i. qPCR
      ii. ERiN-SDA, other isothermal methods
   e. Dedicated instrument, or leverage existing equipment
      i. Real-time Thermocycler
      ii. nanoString Technologies nCounter® Analysis System
   f Normalize to reference gene
   g. Internal and external controls
   h. Computer program product that combines quantity of targets and references to calculate a score.
2. Indication: presence of positive surgical margins from specimens/patient with invasive adenocarcinoma of the breast diagnosed by pathology
   a. Detect positive margins/determine success of the surgical procedure/infer residual disease.
   b. This unique combination of genes may be used for other indications:
      i. Screening (e.g. analysis of ductal lavage aspirates)
      ii. Diagnosis (e.g. needle or core biopsy)
   c. This test may be performed in a certified clinical laboratory.
3. Directing step: direct a physician to excise additional tissue in order to obtain clear margins.
4. Kit: touch-prep slide (surface with a functionalized coating)+reagents (buffers, enzymes, oligo primers)

Example 20. Identification of Biomarkers for Invasive Breast Cancer

To identify biomarkers of invasive breast cancer, candidate genes that were the most different between two classes (healthy and tumor) were selected, based on a two-step filtering process. First, genes with the strongest statistical difference (adjusted p-value, also known as False Discovery Rate, FDR) were first selected. Second, genes with the greatest increase in fold-change in tumor samples relative to healthy samples were selected. Table 10 describes the 200 genes selected by this two-step filtering process. These genes may be considered the genes with the greatest increase in activity (overexpression) in invasive adenocarcinoma of the breast, relative to healthy mammary tissue, as assessed using RNA Seq of 995 human tissue samples.

TABLE 10

Overexpressed genes from RNA Seq of 995 human tissue samples.

| logFC | AveExpr | t | P. Value | adj. P. Val | B | gene |
|---|---|---|---|---|---|---|
| 7.10357550375563 | 5.70705962119113 | 15.6954063563090 | 8.98E-50 | 1.47E-48 | 102.3141703493590 | COL10A1\|1300 |
| 6.60795936987975 | 1.69159504280020 | 23.1191334195911 | 5.23E-95 | 3.15E-93 | 205.8992468153580 | CST1\|1469 |
| 6.49006789003355 | 2.75259119087522 | 20.7439492718104 | 9.94E-80 | 4.09E-78 | 170.8747699848070 | MMP13\|4322 |
| 6.19948239594579 | 5.92744348742959 | 11.5144146581761 | 6.86E-29 | 4.79E-28 | 54.6029412806980 | COL11A1\|1301 |
| 5.99929993077064 | 7.55064397826498 | 18.7495519678398 | 2.06E-67 | 6.14E-66 | 142.6434131232910 | MMP11\|4320 |
| 5.57530627297406 | 2.18103196591693 | 16.9091400434933 | 1.40E-56 | 3.00E-55 | 117.8290746406150 | MMP1\|4312 |
| 5.45906318734330 | 1.64359441397574 | 28.5549862941174 | 1.66E-131 | 2.86E-129 | 289.6394509575700 | PPAPDC1A\|196051 |
| 5.16909299160928 | -0.21375994050490 | 36.1129794599416 | 3.23E-183 | 4.08E-180 | 408.4681078239120 | IBSP\|3381 |
| 5.04386567537180 | 5.62702762090422 | 11.5512854926637 | 4.70E-29 | 3.30E-28 | 54.9396651775396 | COMP\|1311 |
| 4.77113400805529 | 3.98858491919436 | 20.1966806223049 | 2.69E-76 | 1.02E-74 | 162.9924147902070 | NEK2\|4751 |
| 4.68566242405961 | 3.52086822533478 | 19.4415868458483 | 1.27E-71 | 4.27E-70 | 152.2952068597050 | PKMYT1\|9088 |
| 4.62145116719516 | 2.17036072695330 | 11.4958591955951 | 8.29E-29 | 5.78E-28 | 54.3792748355781 | TNNT1\|7138 |
| 4.61379398085491 | 3.42315334627692 | 9.3211465395113 | 7.20E-20 | 3.25E-19 | 34.1051633063824 | S100P\|6286 |
| 4.49753324627688 | -0.37332136727024 | 23.9045910901992 | 3.56E-100 | 2.46E-98 | 217.7624393497790 | EPYC\|1833 |
| 4.44153155328081 | 4.07127664754380 | 17.9208755271345 | 1.83E-62 | 4.70E-61 | 131.3401789833460 | KIF4A\|24137 |
| 4.33603326894979 | 4.33360097612435 | 15.3577754432118 | 6.22E-48 | 9.50E-47 | 98.0954149639670 | UBE2C\|11065 |
| 4.32303285656302 | 3.61182088194122 | 10.8560516093520 | 5.01E-26 | 3.10E-25 | 48.1004195430912 | PITX1\|5307 |
| 4.25833189100631 | 0.64637884018970 | 18.9440143537725 | 1.37E-68 | 4.23E-67 | 145.3380062852170 | GRM4\|2914 |
| 4.23657353868279 | -1.05700412410022 | 23.1099270352545 | 6.01E-95 | 3.61E-93 | 205.7477539238850 | CST4\|1472 |
| 4.12214383305142 | 4.46707109450876 | 16.7140671688332 | 1.82E-55 | 3.72E-54 | 115.3239442014080 | IQGAP3\|128239 |
| 4.05556819334484 | 3.32795369078249 | 17.8889592784267 | 2.82E-62 | 7.22E-61 | 130.9085138789850 | NUF2\|83540 |
| 4.04773535691257 | 1.80696733696766 | 25.1771218786964 | 1.22E-108 | 1.08E-106 | 237.0886841624100 | CDC25C\|995 |
| 4.03008208455454 | 0.71651739041728 | 23.4560019980254 | 3.23E-97 | 2.07E-95 | 210.9755494613400 | TDO2\|6999 |
| 4.01070000394128 | -0.82736201921445 | 18.5859687267653 | 1.99E-66 | 5.77E-65 | 140.3180500308560 | MS4A15\|219995 |
| 3.99081639477529 | 3.53224649793893 | 16.1340830115485 | 3.36E-52 | 6.07E-51 | 107.8602826270690 | MELK\|9833 |
| 3.99015622495437 | 4.36541115720163 | 11.6039581314847 | 2.74E-29 | 1.94E-28 | 55.4959381335833 | GJB2\|2706 |
| 3.91966947897418 | 4.20958798398178 | 15.9785574172072 | 2.46E-51 | 4.27E-50 | 105.8721753880180 | KIF20A\|10112 |
| 3.91789765440569 | 2.99137570439302 | 17.6635942606106 | 5.96E-61 | 1.45E-59 | 127.8771489690870 | TROAP\|10024 |
| 3.90995248723642 | 4.26901913327292 | 15.0310711529116 | 3.56E-46 | 5.09E-45 | 94.0689338452881 | ASPM\|259266 |
| 3.89502075183299 | 3.65636089236833 | 14.7613768855808 | 9.65E-45 | 1.31E-43 | 90.8067830954259 | BIRC5\|332 |
| 3.89437778701755 | 2.73121679706417 | 18.0918366722817 | 1.78E-63 | 4.73E-62 | 133.6519940765000 | KIF18B\|146909 |
| 3.88733103004565 | 3.44502349088937 | 17.2875741137627 | 9.25E-59 | 2.14E-57 | 122.8649604709970 | DLGAP5\|9787 |
| 3.87018946833039 | 3.61023820992416 | 14.7720523367522 | 8.47E-45 | 1.16E-43 | 90.9361819123229 | EPR1\|8475 |
| 3.84878810607463 | -0.66545350446872 | 21.7265746458053 | 5.58E-86 | 2.69E-84 | 185.1944855678210 | CST2\|1470 |
| 3.82907762611426 | 2.73012681219918 | 16.5642015348304 | 1.29E-54 | 2.57E-53 | 113.3895720509220 | KIF14\|9928 |

TABLE 10-continued

Overexpressed genes from RNA Seq of 995 human tissue samples.

| logFC | AveExpr | t | P. Value | adj. P. Val | B | gene |
|---|---|---|---|---|---|---|
| 3.82575612220082 | 6.55002283988513 | 17.5124892131277 | 4.56E-60 | 1.09E-58 | 125.7462531229920 | TOP2A\|7153 |
| 3.80517964335423 | -0.575344135339766 | 29.3430286677647 | 6.84E-137 | 1.51E-134 | 302.0356712307810 | CCL11\|6356 |
| 3.80034606343923 | 3.83707475294049 | 18.1752892026888 | 5.68E-64 | 1.53E-62 | 134.7896085508930 | UHRF1\|29128 |
| 3.79042021551971 | 4.76220889825209 | 11.8780068410004 | 1.59E-30 | 1.18E-29 | 58.2821624044399 | MYBL2\|4605 |
| 3.75234978235862 | 3.19567932738096 | 17.4057161480895 | 1.91E-59 | 4.48E-58 | 124.4338639918390 | PBK\|55872 |
| 3.71338053670073 | 2.36152250000946 | 16.6815195387656 | 2.78E-55 | 5.67E-54 | 114.9114058387670 | HAGHL\|84264 |
| 3.71232667412564 | 3.02150044360705 | 16.4664004484846 | 4.60E-54 | 8.94E-53 | 112.1246375002600 | EXO1\|9156 |
| 3.70150549966311 | 3.28597109744459 | 17.3880337830384 | 2.42E-59 | 5.66E-58 | 124.1986149982220 | HJURP\|55355 |
| 3.67456013527384 | 3.56064800110614 | 19.2701734481637 | 1.42E-70 | 4.63E-69 | 149.9007284310450 | KIAA0101\|9768 |
| 3.67343013959562 | 6.19280836399469 | 12.3517108499942 | 1.03E-32 | 8.48E-32 | 63.1220963592686 | LRRC15\|131578 |
| 3.66918246975984 | 0.96196497194637 | 24.6700831621615 | 2.97E-105 | 2.34E-103 | 229.3693513550260 | NEIL3\|55247 |
| 3.65892826457086 | -1.43518883705419 | 26.0223910809411 | 2.58E-114 | 2.66E-112 | 250.2238532585800 | SLC24A2\|25769 |
| 3.65883668984314 | -0.99683150906210 | 27.2385049918106 | 1.53E-122 | 2.06E-120 | 269.1082705661880 | PLAC1\|10761 |
| 3.64429323637660 | 4.03281655550737 | 15.7551305612968 | 4.22E-50 | 7.01E-49 | 103.0487188470350 | BUB1\|699 |
| 3.63461373813721 | 1.82294643781782 | 7.7057193707612 | 3.14E-14 | 1.03E-13 | 21.3007050734338 | CEACAM5\|1048 |
| 3.63122566260892 | 5.08667851523713 | 15.3684305417293 | 5.44E-48 | 8.34E-47 | 98.1756277028129 | RRM2\|6241 |
| 3.61068733928450 | 3.40238821413642 | 7.8592845451049 | 9.99E-15 | 3.38E-14 | 22.4238865578998 | NKAIN1\|79570 |
| 3.60893268558051 | 2.74667858261540 | 16.0047220173314 | 1.76E-51 | 3.09E-50 | 106.2179343768000 | AURKB\|9212 |
| 3.59680388069667 | 1.97160337410452 | 19.6312014494610 | 8.63E-73 | 3.00E-71 | 154.9653187626140 | ADAMTS14\|140766 |
| 3.57597299078218 | 2.57081200806757 | 16.4889269706455 | 3.43E-54 | 6.72E-53 | 112.4165092058430 | CDC45\|8318 |
| 3.56019817346748 | -0.10075214693166 | 17.0096934104647 | 3.71E-57 | 8.09E-56 | 119.1379178826980 | HAPLN1\|1404 |
| 3.55750272498706 | 3.15165655865317 | 11.9705474799204 | 6.01E-31 | 4.56E-30 | 59.3132234971635 | KIAA1199\|57214 |
| 3.55617687435855 | 1.80223379810443 | 17.8768520218973 | 3.32E-62 | 8.48E-61 | 130.7457226786770 | E2F8\|79733 |
| 3.54502292190614 | 4.23702341333167 | 15.0862917890171 | 1.80E-46 | 2.62E-45 | 94.7353491915676 | PLK1\|5347 |
| 3.54273894783901 | 4.08884447775921 | 15.0671507192176 | 2.28E-46 | 3.30E-45 | 94.5062159917732 | KIF2C\|11004 |
| 3.53759724252077 | 5.03148574173731 | 14.1717500826949 | 1.15E-41 | 1.37E-40 | 83.7039039605795 | FOXM1\|2305 |
| 3.53583922407015 | 4.46958024039039 | 13.8495315431080 | 5.08E-40 | 5.71E-39 | 79.9757029329386 | CDC20\|991 |
| 3.53483899435158 | 5.66394399960341 | 16.5069409275880 | 2.71E-54 | 5.35E-53 | 112.5615792506160 | TPX2\|22974 |
| 3.52690318054456 | 3.86258886704004 | 15.8209395533662 | 1.83E-50 | 3.09E-49 | 103.8791489065382730 | CEP55\|55165 |
| 3.51198847776444 | 3.34428425848266 | 18.1449959898438 | 8.60E-64 | 2.31E-62 | 134.3772063018340 | HMMR\|3161 |
| 3.49207234658994 | 3.30331161372436 | 16.4935966365594 | 3.23E-54 | 6.33E-53 | 112.4729459742530 | NDC80\|10403 |
| 3.46348543486029 | 1.12705258316479 | 25.1769389279483 | 1.23E-108 | 1.08E-106 | 237.0966583536890 | GABRD\|2563 |
| 3.45854001180299 | 4.77362046279071 | 14.5985728629287 | 6.94E-44 | 9.07E-43 | 88.7905765768961 | ANLN\|54443 |
| 3.45516807906727 | 3.13905263767668 | 15.2784246385918 | 1.67E-47 | 2.52E-46 | 97.1222842127765 | WISP1\|8840 |
| 3.43506325886700 | 2.54243051157208 | 17.6094346640824 | 1.24E-60 | 3.00E-59 | 127.1515649214830 | CKAP2L\|150468 |
| 3.43240757240713 | 4.15476183390027 | 8.5966635592373 | 3.14E-17 | 1.22E-16 | 28.0349524313759 | C19orf21\|126353 |
| 3.38910407228757 | 1.56243446170537 | 19.5442260677762 | 2.96E-72 | 1.01E-70 | 153.7462566166430 | SGOL1\|151648 |
| 3.38702229339408 | 0.22921476717308 | 19.0408656739218 | 3.55E-69 | 1.12E-67 | 146.6974890335890 | HIST1H3D\|8351 |
| 3.38278735162296 | 3.96605389593563 | 15.4111197345737 | 3.19E-48 | 4.93E-47 | 98.7458125262724 | CCNB2\|9133 |
| 3.37509596421206 | 2.88615244562035 | 7.1623201494804 | 1.54E-12 | 4.56E-12 | 17.4974447338731 | CNTNAP2\|26047 |
| 3.36412043737814 | 0.66925470166521 | 22.1098447685218 | 1.91E-88 | 9.77E-87 | 190.8528181731180 | PPEF1\|5475 |
| 3.35381125379753 | -0.39577822504817 | 27.7141196416418 | 8.97E-126 | 1.28E-123 | 276.4867934950840 | SPC24\|147841 |
| 3.34415787203959 | 2.32956034718016 | 21.7343532606475 | 4.97E-86 | 2.41E-84 | 185.2567625418560 | SPC25\|57405 |
| 3.31725464739382 | 1.37404526052613 | 15.0633214890312 | 2.39E-46 | 3.45E-45 | 94.4728473877340 | CCDC78\|124093 |
| 3.30284166514933 | 6.09943791103801 | 16.2737828571835 | 5.57E-53 | 1.04E-51 | 109.4983613450580 | MKI67\|4288 |
| 3.30040650511341 | 1.22867834737017 | 19.0753080479330 | 2.19E-69 | 6.93E-68 | 147.1836853784710 | CNIH2\|254263 |
| 3.30015602188775 | -1.40529559529268 | 26.6366695963010 | 1.84E-118 | 2.19E-116 | 259.7467121694340 | LOC283867\|283867 |
| 3.28935700831291 | 3.01241275229717 | 18.8047943229823 | 9.57E-68 | 2.88E-66 | 143.4244669174970 | WDR62\|284403 |
| 3.28870124858540 | 3.84048723536198 | 16.2205197363354 | 1.11E-52 | 2.04E-51 | 108.9515847472950 | BUB1B\|701 |
| 3.28604891086538 | 3.51546846838805 | 13.8480015622388 | 5.17E-40 | 5.81E-39 | 79.9899295628285 | FAM83D\|81610 |
| 3.28054414468737 | -1.43413958122496 | 12.3227134249007 | 1.41E-32 | 1.15E-31 | 62.7755088938265 | HOXB13\|10481 |
| 3.27564704122365 | 0.15647218559844 | 17.3709822882918 | 3.04E-59 | 7.09E-58 | 123.9435221762150 | KREMEN2\|79412 |
| 3.27214377902507 | 3.48403760059624 | 13.4636119964282 | 4.40E-38 | 4.55E-37 | 75.5803374383909 | INHBA\|3624 |
| 3.26460262051162 | -0.34399563034178 | 20.0759305421001 | 1.52E-75 | 5.69E-74 | 161.2830692355220 | HIST1H3H\|8357 |
| 3.26178592336470 | 6.29614296853982 | 17.7668327448939 | 1.48E-61 | 3.67E-60 | 129.1373051373670 | CENPF\|1063 |
| 3.26163154881692 | -0.58400509676785 | 15.4264358527562 | 2.64E-48 | 4.10E-47 | 98.8515091976672 | WT1\|7490 |
| 3.25985654685875 | 3.96120648756722 | 16.8314978711550 | 3.89E-56 | 8.21E-55 | 116.8515111246670 | UBE2T\|29089 |
| 3.22424638508395 | 4.97704839715688 | 16.9532593559418 | 7.82E-57 | 1.70E-55 | 118.4083323484060 | NUSAP1\|51203 |
| 3.21766281309089 | 2.34629673004066 | 16.6480410414811 | 4.31E-54 | 8.73E-53 | 114.4761801575570 | SKA1\|220134 |
| 3.21720990650700 | 2.14654632913465 | 16.0885874838663 | 6.02E-52 | 1.08E-50 | 107.2852489447370 | CENPA\|1058 |
| 3.20880413120166 | -0.52140739947501 | 21.6894446709108 | 9.65E-86 | 4.62E-84 | 184.6641689154950 | AIM1L\|55057 |
| 3.20167908208392 | 3.08787031400009 | 14.4116418848489 | 6.58E-43 | 8.22E-42 | 86.6157352024586 | DEPDC1\|55635 |
| 3.19472529042443 | 2.76069961184907 | 17.1427800475646 | 6.36E-58 | 1.42E-56 | 120.9504323746110 | SKA3\|221150 |
| 3.19240360926438 | 4.50280871380875 | 15.2878088609356 | 1.49E-47 | 2.25E-46 | 97.1893217768941 | KIFC1\|3833 |
| 3.18337142700308 | 4.37428488699899 | 16.2875526511739 | 4.66E-53 | 8.73E-52 | 109.7910694259770 | DTL\|51514 |
| 3.17083533327371 | 2.02166849633187 | 17.7653244217211 | 1.51E-61 | 3.74E-60 | 129.2413632945450 | DEPDC1B\|55789 |
| 3.16870583856373 | 2.02492465169192 | 16.4856036335283 | 3.58E-54 | 7.00E-53 | 112.3742796328370 | FAM64A\|54478 |
| 3.15882104651272 | 2.46906072987058 | 16.7674007917499 | 9.03E-56 | 1.88E-54 | 116.0282901676260 | RAD54L\|8438 |
| 3.15061185364743 | 1.16268416865113 | 9.8133849068322 | 9.21E-22 | 4.61E-21 | 38.3692915662344 | HOXC11\|3227 |
| 3.15013926390870 | 3.89357515472997 | 15.2988238009577 | 1.30E-47 | 1.96E-46 | 97.3507666936237 | PTTG1\|9232 |
| 3.14504239523493 | 2.45970604674012 | 10.6792968218618 | 2.79E-25 | 1.67E-24 | 46.4077923029061 | CXCL11\|6373 |
| 3.14259992673961 | 2.50488969144285 | 18.6867502942661 | 4.93E-67 | 1.45E-65 | 141.7913402214910 | CENPM\|79019 |
| 3.11233530401959 | -1.14177624324419 | 26.5371766852135 | 8.65E-118 | 1.00E-115 | 258.1928368661810 | HIST1H2AM\|8336 |
| 3.11061672036822 | 5.01553715565834 | 16.3570677575714 | 1.90E-53 | 3.61E-52 | 110.6463644776110 | CDK1\|983 |
| 3.09715365790969 | 1.97173660780117 | 15.4857753716997 | 1.25E-48 | 1.98E-47 | 99.6996996253860 | CLEC5A\|23601 |
| 3.09702089234182 | 1.59119045603801 | 10.5227231051813 | 1.26E-24 | 7.28E-24 | 44.9260737048488 | ADAMDEC1\|27299 |

TABLE 10-continued

Overexpressed genes from RNA Seq of 995 human tissue samples.

| logFC | AveExpr | t | P. Value | adj. P. Val | B | gene |
|---|---|---|---|---|---|---|
| 3.09664229140160 | 2.65402797979451 | 18.5283461757107 | 4.42E-66 | 1.27E-64 | 139.6130625639650 | CDKN3\|1033 |
| 3.09309664104312 | 5.39756475031269 | 16.8163392719968 | 4.75E-56 | 9.98E-55 | 116.5782552219110 | TK1\|7083 |
| 3.09275157176292 | -1.07267182125050 | 19.3542304771866 | 4.34E-71 | 1.43E-69 | 151.0471536929040 | IGFL2\|147920 |
| 3.08662067803667 | -1.60926194231309 | 24.7611320301334 | 7.35E-106 | 5.93E-104 | 230.8156717021270 | CHRNA6\|8973 |
| 3.08386357566675 | 2.97511582855039 | 16.0864356207685 | 6.19E-52 | 1.11E-50 | 107.2517584369270 | GTSE1\|51512 |
| 3.08317980193265 | 4.01330067850542 | 15.4325969484564 | 2.44E-48 | 3.80E-47 | 99.0018427925333 | NCAPG\|64151 |
| 3.07754131539837 | 4.32334057249122 | 17.5591315272604 | 2.43E-60 | 5.86E-59 | 126.4624141068720 | ASF1B\|55723 |
| 3.07356623345742 | 5.53110355194487 | 10.1858354003419 | 3.02E-23 | 1.62E-22 | 41.5312650024876 | MMP9\|4318 |
| 3.07309383909270 | 2.04617307401355 | 14.4625032854429 | 3.58E-43 | 4.53E-42 | 87.2347665245982 | CLSPN\|63967 |
| 3.06705303711114 | 1.88400164991430 | 21.5421930594587 | 8.46E-85 | 3.94E-83 | 182.4338601973170 | HSD17B6\|8630 |
| 3.06422826943826 | 3.46959236312794 | 13.7339850850681 | 1.95E-39 | 2.14E-38 | 78.6679159380488 | KIF26B\|55083 |
| 3.06366048470735 | 2.21132403333251 | 13.1427681039658 | 1.69E-36 | 1.62E-35 | 71.9932002331888 | RAB26\|25837 |
| 3.04386550304661 | -2.11304646307715 | 24.6055839190447 | 7.99E-105 | 6.20E-103 | 228.4205643663950 | SCT\|6343 |
| 3.03977162874757 | 3.98789653473688 | 17.3425661450916 | 4.44E-59 | 1.03E-57 | 123.5827551325040 | CCDC64\|92558 |
| 3.03476857377114 | 3.15916570416905 | 13.2090800971352 | 7.97E-37 | 7.76E-36 | 72.7122855158812 | CILP2\|148113 |
| 3.03353974898614 | 3.00786978582372 | 11.4556458363995 | 1.25E-28 | 8.64E-28 | 54.0174528924635 | C20orf103\|24141 |
| 3.02809843821817 | 2.88068662431889 | 13.0268756633026 | 6.19E-36 | 5.78E-35 | 70.6887489379367 | MCM10\|55388 |
| 3.02091182458610 | -0.48653966996455 | 15.5806321326336 | 3.81E-49 | 6.13E-48 | 100.7966825588850 | TMEM145\|284339 |
| 3.01736454165061 | 3.07863635360655 | 15.3004596627175 | 1.27E-47 | 1.92E-46 | 97.3900398263046 | CDCA3\|83461 |
| 3.01455625411674 | 0.16280117366366 | 12.2845521554171 | 2.13E-32 | 1.72E-31 | 62.5443612818304 | MMP10\|4319 |
| 3.00816866737099 | -1.44637819226635 | 17.6017658487837 | 1.37E-60 | 3.32E-59 | 126.9517972787020 | CAMP\|820 |
| 3.00006794512026 | -1.09202031241088 | 25.4323429842117 | 2.39E-110 | 2.26E-108 | 241.1142312690820 | RDM1\|201299 |
| 2.99630746604533 | 1.06694158606185 | 17.2080483400991 | 2.67E-58 | 6.04E-57 | 121.8104459958740 | MND1\|84057 |
| 2.99087198524396 | -2.12397064584061 | 13.9175513688545 | 2.29E-40 | 2.61E-39 | 80.5295002721492 | ACTL8\|81569 |
| 2.98918556435894 | 3.55805729376481 | 14.8530387215670 | 3.16E-45 | 4.38E-44 | 91.8995898366439 | ESPL1\|9700 |
| 2.98887375352747 | 2.95454661364176 | 16.2741438561814 | 5.54E-53 | 1.04E-51 | 109.6488803433740 | SDS\|10993 |
| 2.98578896199484 | -1.19045998680063 | 17.2218722750379 | 2.22E-58 | 5.06E-57 | 121.9091219739230 | DQX1\|165545 |
| 2.98553217571216 | 2.25992626937363 | 17.9379411280002 | 1.45E-62 | 3.75E-61 | 131.5689428791370 | ESCO2\|157570 |
| 2.97738921835308 | 3.27802220989092 | 13.9905343066499 | 9.74E-41 | 1.12E-39 | 81.6461811186890 | TTK\|7272 |
| 2.97138557352863 | 4.33224795408322 | 9.2280058776390 | 1.61E-19 | 7.06E-19 | 33.1826934566495 | CXCL10\|3627 |
| 2.96955744727619 | 4.01760567177760 | 13.4430643971148 | 5.57E-38 | 5.73E-37 | 75.3109869467696 | FAM111B\|374393 |
| 2.95226531724626 | 4.23931794892952 | 14.4418891107635 | 4.58E-43 | 5.78E-42 | 86.9226886827617 | CDCA5\|113130 |
| 2.94071306439969 | 2.30636290254372 | 19.3229176922416 | 6.75E-71 | 2.22E-69 | 150.6312521206650 | C16orf59\|80178 |
| 2.92812469621062 | 1.69783020752769 | 16.2922668459404 | 4.38E-53 | 8.24E-52 | 109.8876367958530 | E2F7\|144455 |
| 2.92631848786436 | 4.11700591472716 | 14.8677301048742 | 2.64E-45 | 3.67E-44 | 92.0512358189309 | AURKA\|6790 |
| 2.92547667663891 | 3.49236010007419 | 15.3634878289410 | 5.79E-48 | 8.86E-47 | 98.1578846857073 | NCAPH\|23397 |
| 2.92347306302607 | 2.62502480122406 | 14.6081592430529 | 6.18E-44 | 8.10E-43 | 88.9673300811885 | P4HA3\|283208 |
| 2.92206963135702 | -2.42515563763657 | 17.6666565258230 | 5.72E-61 | 1.40E-59 | 127.7221486786970 | GNG13\|51764 |
| 2.91834271526104 | 2.82209506898921 | 15.7410153231348 | 5.04E-50 | 8.35E-49 | 102.8827235547410 | ESM1\|11082 |
| 2.91408334647240 | 2.92867992398670 | 15.0535755519545 | 2.70E-46 | 3.88E-45 | 94.3568400738851 | KIF15\|56992 |
| 2.91205653017259 | 2.61378094146455 | 13.2409709070756 | 5.56E-37 | 5.44E-36 | 73.0834715834426 | CASC5\|57082 |
| 2.90417444571163 | 2.91085725136654 | 5.5040680749272 | 4.72E-08 | 1.04E-07 | 7.4123103574425 | SYT13\|57586 |
| 2.90311154439339 | -1.41193598712845 | 18.1331695710494 | 1.01E-63 | 2.71E-62 | 134.1429443615670 | C6orf126\|389383 |
| 2.89499849538721 | 2.48400531561932 | 14.4430104140366 | 4.52E-43 | 5.71E-42 | 86.9959275128881 | CDCA2\|157313 |
| 2.89262955929058 | 11.62883412789860 | 19.6636848523962 | 5.44E-73 | 1.90E-71 | 155.1504302090440 | FN1\|2335 |
| 2.87779831345934 | 3.99299004593291 | 14.1745934038075 | 1.11E-41 | 1.33E-40 | 83.7672306935263 | CTXN1\|404217 |
| 2.87111372570394 | 4.04723320328039 | 14.6497644228814 | 3.74E-44 | 4.94E-43 | 89.4186821033206 | RECQL4\|9401 |
| 2.86249509102005 | 4.00480769378108 | 15.0474497566360 | 2.91E-46 | 4.18E-45 | 94.2448182245337 | CDCA8\|55143 |
| 2.85285566944565 | 4.31152246573386 | 5.0475716221707 | 5.32E-07 | 1.08E-06 | 4.9426109563040 | CEACAM6\|4680 |
| 2.84806493843500 | 1.61559588332260 | 20.1009158414838 | 1.06E-75 | 4.00E-74 | 161.6127645696820 | OIP5\|11339 |
| 2.83180733921213 | -1.95862894999899 | 21.9400354633181 | 2.37E-87 | 1.18E-85 | 188.3221599684720 | MARCH4\|57574 |
| 2.81015003604678 | -0.91733921658230 | 20.2006609115731 | 2.54E-76 | 9.65E-75 | 163.0613661202460 | HTR1D\|3352 |
| 2.80018568789894 | -1.33036379423720 | 10.6897319856615 | 2.53E-25 | 1.51E-24 | 46.2769532253175 | CA9\|768 |
| 2.79482419793122 | -1.06940218944513 | 13.1772844279523 | 1.14E-36 | 1.10E-35 | 72.2178693083265 | MYT1\|4661 |
| 2.78521330408706 | -1.20467752268194 | 26.5934551155386 | 3.60E-118 | 4.24E-116 | 259.0577412358110 | PROC\|5624 |
| 2.78221082962521 | -0.86885871449056 | 20.0972121574332 | 1.12E-75 | 4.21E-74 | 161.5849930092550 | HCN2\|610 |
| 2.78135785870307 | 2.20616510115234 | 13.5537577685631 | 1.57E-38 | 1.65E-37 | 76.6299650727768 | F12\|2161 |
| 2.77912643715574 | 4.75398913888223 | 10.7754639892220 | 1.10E-25 | 6.70E-25 | 47.1561154103842 | TUBB3\|10381 |
| 2.77249612720691 | 4.30010665926822 | 5.4018277754523 | 8.25E-08 | 1.78E-07 | 6.7345236419249 | EEF1A2\|1917 |
| 2.77111854105647 | -2.18219839434507 | 13.8117070287517 | 7.90E-40 | 8.80E-39 | 79.3150861950224 | NMU\|10874 |
| 2.76967673471972 | 0.37043745211164 | 14.7315364848075 | 1.39E-44 | 1.87E-43 | 90.4205896491139 | TFR2\|7036 |
| 2.76517440204087 | 5.59648186966318 | 10.3289398506946 | 7.91E-24 | 4.39E-23 | 42.8095519006224 | ISG15\|9636 |
| 2.76414484554176 | 3.05343598040411 | 15.4832983805651 | 1.29E-48 | 2.04E-47 | 99.6534315309210 | SHCBP1\|79801 |
| 2.76288302837646 | 3.26500755533911 | 14.3156038872765 | 2.07E-42 | 2.55E-41 | 85.4609280394793 | CCNE2\|9134 |
| 2.76153757657954 | 4.32430854545612 | 15.5635886304059 | 4.73E-49 | 7.56E-48 | 100.6050954331410 | KIF23\|9493 |
| 2.76122116573997 | 1.36890635527163 | 17.1971116801894 | 3.09E-58 | 6.97E-57 | 121.6678819186060 | FAM54A\|113115 |
| 2.76057273284446 | 0.22942648847589 | 19.1450534138059 | 8.24E-70 | 2.63E-68 | 148.1574610762890 | FAM72A\|729533 |
| 2.75349181279248 | 2.38415452298358 | 17.2446347480731 | 1.64E-58 | 3.76E-57 | 122.2964979631440 | ERCC6L\|54821 |
| 2.75005596045228 | 1.59289400399816 | 14.0521979901037 | 4.72E-41 | 5.49E-40 | 82.3947637748202 | CCDC19\|25790 |
| 2.74275408376458 | -2.32817889808744 | 23.7025530205507 | 7.68E-99 | 5.12E-97 | 214.6812447965070 | HIST1H2BO\|8348 |
| 2.73941167637823 | 4.11244666791688 | 13.7032829724132 | 2.78E-39 | 3.03E-38 | 78.2663034464255 | CCNA2\|890 |
| 2.73301155465735 | 2.36644307365881 | 8.3064392852976 | 3.20E-16 | 1.17E-15 | 25.8237958731802 | HOXC13\|3229 |
| 2.73158096267509 | -1.85971792048778 | 16.8590911293724 | 2.71E-56 | 5.74E-55 | 117.0845465922190 | VGF\|7425 |
| 2.71853193329988 | -1.11233111967325 | 18.9846147228529 | 7.79E-69 | 2.42E-67 | 145.8926427223630 | ITPKA\|3706 |
| 2.71191581795560 | 4.05994368959496 | 12.5709415902681 | 9.58E-34 | 8.15E-33 | 65.6162154096058 | CDC6\|990 |
| 2.71110417484442 | 2.10575080447627 | 10.9955585382791 | 1.27E-26 | 8.05E-26 | 49.4667325375149 | FBN2\|2201 |

TABLE 10-continued

Overexpressed genes from RNA Seq of 995 human tissue samples.

| logFC | AveExpr | t | P. Value | adj. P. Val | B | gene |
|---|---|---|---|---|---|---|
| 2.71053869360937 | 2.58274774827020 | 12.7454626397043 | 1.41E−34 | 1.24E−33 | 67.5906423944744 | KIAA1211\|57482 |
| 2.70709780062589 | 4.76439521439953 | 14.7803948535066 | 7.65E−45 | 1.05E−43 | 90.9341145084476 | SPAG5\|110615 |
| 2.70222035950262 | 2.39348828497869 | 15.2694735112891 | 1.87E−47 | 2.81E−46 | 97.0145007297289 | POLQ\|10721 |
| 2.69181611381364 | 1.85883612391051 | 11.3301473298095 | 4.47E−28 | 3.02E−27 | 52.7818569259874 | TMEM90B\|79953 |
| 2.69130540821567 | −1.36721087923066 | 24.9745865776202 | 2.76E−107 | 2.30E−105 | 234.0842402867810 | GRM8\|2918 |
| 2.67578318489118 | 6.75149276672458 | 10.1871603207817 | 2.98E−23 | 1.61E−22 | 41.3181114926880 | S100A14\|57402 |
| 2.65862155733904 | 0.12875172967432 | 6.5388792756013 | 9.89E−11 | 2.62E−10 | 13.3354297728883 | PRAME\|23532 |
| 2.65599660438260 | 3.69833544541446 | 13.0556138219468 | 4.49E−36 | 4.21E−35 | 70.9586907769516 | OLR1\|4973 |
| 2.65389265837385 | 2.86341812848488 | 16.6312539934799 | 5.37E−55 | 1.09E−53 | 114.2529789231820 | GPRIN1\|114787 |
| 2.65286110117351 | 3.76982183002898 | 13.4836962904382 | 3.50E−38 | 3.63E−37 | 75.7708802189542 | CENPE\|1062 |
| 2.65235793922212 | 1.42026742593978 | 12.1956751094551 | 5.51E−32 | 4.38E−31 | 61.7007847223653 | ACAN\|176 |
| 2.65188806104411 | 6.15208489828679 | 15.7118207769148 | 7.29E−50 | 1.20E−48 | 102.2769367282590 | CTHRC1\|115908 |
| 2.64868673031372 | 0.75918447726173 | 14.3479294711156 | 1.41E−42 | 1.75E−41 | 85.8548863095983 | ZNF695\|57116 |

To analyze the expression profile of biomarkers, a RNAseq was performed to sequence the biomarkers in a collected surgical specimen. Briefly, the RNAseq data was imported for analysis, using steps as the following Table 11:

TABLE 11

Analysis of RNAseq data of collected biomarkers.

1. RNAseq data import
2. RNAseq data initial exploration and cleaning
   checking for missing data and filtering
   evaluating genes' entries whose sum of count across all the samples is 0
3. Metadata import and content overview
4. Differential expression: linear modelling w.r.t the Sample Type attribute
   Collecting the 200 gene entries whose quantities is higher in tumor vs. normal
5. Collecting the 200 gene entries differentially expressed (either up or down)
6. Additional filtering (noise)

A concordance study was performed using steps as the following Table 12:

TABLE 12

Concordance study

1. Collecting the 200 RNA-Seq gene entries differentially expressed in this
2. Collecting the 200 RNA-Seq gene entries over expressed in tissue vs. healthy
3. Agilent Reporter_ID mapped to Gene_Symbol
4. Agilent level3 data analyses
5. RNA-Seq top 200 overexpressed vs. Agilent array top 200 overexpressed.
6. Distribution of the 130 genes overexpressed in tumor vs. normal Example 21. Machine Learning to Eliminate Highly Correlated Breast Cancer Biomarkers Tests with an unnecessarily large number of genes often increases complexity, increases the difficulty performing the test, requires more skill to implement, and increases the opportunity for errors. Most clinical tests require technical replicates. For tests that detect rare malignant cells in a population of healthy cells, aliquoting the precious sample across an unnecessary number of reactions decreases the signal and therefore decreases the sensitivity of the test for detecting rare cells. To optimize the number of genes in a test, a correlation-based feature selection (CFS) is performed to identify genes that independently add information.

Genes can be correlated for multiple reasons. They may be co-regulated, where both genes respond to the same stimulus. One gene may be dependent on the other gene, for example they may be in the same signaling pathway, where one gene product affects the activity of another gene. Or they may share a mathematical relationship independently of known biological mechanisms. The advantage of an unbiased, genomic approach is that tests for diseases may be developed with little understanding of the molecular mechanisms or relationships underlying those diseases. The test may comprise genes that provide independent information, or they are independently correlated.

For example, a list of three hypothetical genes: A, B, C, D, E, F contains three genes that are overexpressed (A, B, C) and three genes that are underexpressed (D, E, F). A test that includes all 3 overexpressed genes is not necessarily more informative than a test that only includes one of the overexpressed genes. Since clinical tests require technical replicates (often 3-5), and since the sample may be diluted and aliquoted across all reactions, a hypothetical test with 195 unnecessary genes could potentially reduce specificity for rare cells by 975-fold (195 unnecessary genes*5 technical replicates=975-fold dilution) over a test that only included informative genes. While it may appear favorable to build a test with the greatest number of genes, and thus increase the amount of available information, inclusion of unnecessary genes actually risks decreasing the ability to detect rare target cells, like malignant cells on the surface of a surgical specimen.

Table 13 lists genes that were selected by the algorithm Correlation-based Feature Selection (CFS), implemented in the Weka environment. The 200 overexpressed genes listed in Table 10 were used as input for CFS.

"Instances: 995" indicates the number of human tissue samples.

"Attributes: 201" indicates the number of overexpressed genes (200), plus the tissue class (tumor or healthy). CFS relies on a model that distinguishes two classes of samples (tumor and healthy). The CFS algorithm identified multiple genes that were highly correlated, and that did not provide independent data to a model that distinguished the two classes. Table 13 was based on an evaluation mode that simultaneously evaluated all 995 instances. A test selected from genes in Table 13 may provide more information while eliminating redundancy.

TABLE 13

Overexpressed genes selected by correlation-based feature selection (CFS)

```
=== Run information ===
Evaluator: weka.attributeSelection.CfsSubsetEval
Search:weka.attributeSelection.GreedyStepwise -T -1.7976931348623157E308 -N -1
Relation: RNASeq_995_OE200
Instances: 995
Attributes: 201
[list of attributes omitted]
=== Attribute Selection on all input data ===
Search Method:
    Greedy Stepwise (forwards).
    Start set: no attributes
    Merit of best subset found: 0.792
Attribute Subset Evaluator (supervised, Class (nominal): 201 sample_type):
    CFS Subset Evaluator
    Including locally predictive attributes
Selected attributes:
1,5,8,12,13,17,18,24,41,48,54,56,57,71,73,76,81,86,91,96,110,121,123,125,126,129,132,135,13
7,138,144,149,150,153,154,157,163,164,165,166,167,172,173,180,181,183,185,188,189,193,19
6,198 : 52
    COL10A1.1300
    MMP11.4320
    IBSP.3381
    TNNT1.7138
    S100P.6286
    PITX1.5307
    GRM4.2914
    MS4A15.219995
    HAGHL.84264
    PLAC1.10761
    ADAMTS14.140766
    HAPLN1.1404
    KIAA1199.57214
    C19orf21.126353
    HIST1H3D.8351
    PPEF1.5475
    CNIH2.254263
    HOXB13.10481
    WT1.7490
    AIM1L.55057
    CLEC5A.23601
    HSD17B6.8630
    RAB26.25837
    CCDC64.92558
    CILP2.148113
    TMEM145.284339
    CAMP.820
    ACTL8.81569
    SDS.10993
    DQX1.165545
    C16orf59.80178
    GNG13.51764
    ESM1.11082
    SYT13.57586
    C6orf126.389383
    CTXN1.404217
    HTR1D.3352
    CA9.768
    MYT1.4661
    PROC.5624
    HCN2.610
    TFR2.7036
    ISG15.9636
    CCDC19.25790
    HIST1H2BO.8348
    HOXC13.3229
    ITPKA.3706
    KIAA1211.57482
    SPAG5.10615
    S100A14.57402
    GPRIN1.114787
    ACAN.176
```

In contrast to Table 13, the results of Table 14 were based on 10-fold cross validation, where performance estimates ("scores") were obtained from 10 iterations of test-validations. Table 14 provides useful information by adding a score for each of the 200 input genes from Table 10. Scores are useful in the event that the most desirable gene is not suitable, for example if the most promising gene contains repeat elements that are challenging to detect with an amplification or hybridization assay. In this case, the most desirable replacement may have activity that is perfectly correlated with the unsuitable gene. The scores in Table 14 may be used to select replacement genes.

In general, CFS excluded genes in Table 14 from Table 13 if they had a score less than 50%, although there are some discrepancies. Some genes with a score of 50% in Table 14 were excluded from Table 13 (e.g. CCL11), while other genes with a 50% score in Table 14 were included in Table 13 (e.g. ADAMTS14, C19orf21, and DQX1). Two genes with a score of 60% (GABRD and GRM8) were excluded from Table 13. One gene with a 40% score (HOXB13) was included in Table 13, even though other genes with 40% score (for example, SCT and FBN2) were excluded. One gene with a score of 20% (CNIH2) was included in Table 13. One gene with a score of 10% (CA9) was included in Table 13. These discrepancies could relate to the different evaluation modes used to estimate correlation for Table 13 and Table 14.

TABLE 14

Overexpressed genes selected by correlation-based feature selection (CFS) based on 10-fold cross validation.

```
=== Run information ===
Evaluator: weka.attributeSelection.CfsSubsetEval
Search:weka.attributeSelection.GreedyStepwise -T -1.7976931348623157E308 -N -1
Relation: RNASeq_995_OE200
Instances: 995
Attributes: 201
[list of attributes omitted]
Evaluation mode: 10-fold cross-validation
=== Attribute selection 10 fold cross-validation (stratified), seed: 1 ===
number of folds (%) attribute
      10(100 %)     1 COL10A1.1300
       0(  0 %)     2 CST1.1469
       0(  0 %)     3 MMP13.4322
       2( 20 %)     4 COL11A1.1301
      10(100 %)     5 MMP11.4320
       2( 20 %)     6 MMP1.4312
       0(  0 %)     7 PPAPDC1A.196051
      10(100 %)     8 IBSP.3381
       0(  0 %)     9 COMP.1311
       1( 10 %)    10 NEK2.4751
       0(  0 %)    11 PKMYT1.9088
       9( 90 %)    12 TNNT1.7138
      10(100 %)    13 S100P.6286
       0(  0 %)    14 EPYC.1833
       0(  0 %)    15 KIF4A.24137
       0(  0 %)    16 UBE2C.11065
      10(100 %)    17 PITX1.5307
      10(100 %)    18 GRM4.2914
       2( 20 %)    19 CST4.1472
       1( 10 %)    20 IQGAP3.128239
       0(  0 %)    21 NUF2.83540
       0(  0 %)    22 CDC25C.995
       1( 10 %)    23 TDO2.6999
      10(100 %)    24 MS4A15.219995
       0(  0 %)    25 MELK.9833
       1( 10 %)    26 GJB2.2706
       0(  0 %)    27 KIF20A.10112
       0(  0 %)    28 TROAP.10024
       0(  0 %)    29 ASPM.259266
       0(  0 %)    30 BIRC5.332
       0(  0 %)    31 KIF18B.146909
       0(  0 %)    32 DLGAP5.9787
       0(  0 %)    33 EPR1.8475
       0(  0 %)    34 CST2.1470
       0(  0 %)    35 KIF14.9928
       0(  0 %)    36 TOP2A.7153
       5( 50 %)    37 CCL11.6356
       2( 20 %)    38 UHRF1.29128
       0(  0 %)    39 MYBL2.4605
       0(  0 %)    40 PBK.55872
       9( 90 %)    41 HAGHL.84264
       0(  0 %)    42 EXO1.9156
       0(  0 %)    43 HJURP.55355
       1( 10 %)    44 KIAA0101.9768
       0(  0 %)    45 LRRC15.131578
       0(  0 %)    46 NEIL3.55247
       0(  0 %)    47 SLC24A2.25769
      10(100 %)    48 PLAC1.10761
       0(  0 %)    49 BUB 1.699
       0(  0 %)    50 CEACAM5.1048
       0(  0 %)    51 RRM2.6241
       3( 30 %)    52 NKAIN1.79570
       0(  0 %)    53 AURKB.9212
       5( 50 %)    54 ADAMTS14.140766
```

TABLE 14-continued

Overexpressed genes selected by correlation-based feature selection (CFS) based on 10-fold cross validation.

0( 0 %)   55 CDC45.8318
10(100 %)  56 HAPLN1.1404
9( 90 %)   57 KIAA1199.57214
0( 0 %)   58 E2F8.79733
0( 0 %)   59 PLK1.5347
0( 0 %)   60 KIF2C.11004
0( 0 %)   61 FOXM1.2305
0( 0 %)   62 CDC20.991
0( 0 %)   63 TPX2.22974
0( 0 %)   64 CEP55.55165
0( 0 %)   65 HMMR.3161
0( 0 %)   66 NDC80.10403
6( 60 %)   67 GABRD.2563
0( 0 %)   68 ANLN.54443
0( 0 %)   69 WISP1.8840
0( 0 %)   70 CKAP2L.150468
5( 50 %)   71 C19orf21.126353
0( 0 %)   72 SGOL1.151648
9( 90 %)   73 HIST1H3D.8351
0( 0 %)   74 CCNB2.9133
0( 0 %)   75 CNTNAP2.26047
6( 60 %)   76 PPEF1.5475
0( 0 %)   77 SPC24.147841
0( 0 %)   78 SPC25.57405
1( 10 %)   79 CCDC78.124093
0( 0 %)   80 MKI67.4288
2( 20 %)   81 CNIH2.254263
0( 0 %)   82 LOC283867.283867
2( 20 %)   83 WDR62.284403
0( 0 %)   84 BUB1B.701
0( 0 %)   85 FAM83D.81610
4( 40 %)   86 HOXB13.10481
1( 10 %)   87 KREMEN2.79412
4( 40 %)   88 INHBA.3624
3( 30 %)   89 HIST1H3H.8357
0( 0 %)   90 CENPF.1063
9( 90 %)   91 WT1.7490
0( 0 %)   92 UBE2T.29089
0( 0 %)   93 NUSAP1.51203
0( 0 %)   94 SKA1.220134
0( 0 %)   95 CENPA.1058
10(100 %)  96 AIM1L.55057
0( 0 %)   97 DEPDC1.55635
0( 0 %)   98 SKA3.221150
0( 0 %)   99 KIFC1.3833
0( 0 %)   100 DTL.51514
0( 0 %)   101 DEPDC1B.55789
0( 0 %)   102 FAM64A.54478
0( 0 %)   103 RAD54L.8438
0( 0 %)   104 HOXC11.3227
0( 0 %)   105 PTTG1.9232
1( 10 %)   106 CXCL11.6373
0( 0 %)   107 CENPM.79019
2( 20 %)   108 HIST1H2AM.8336
0( 0 %)   109 CDK1.983
10(100 %)  110 CLEC5A.23601
0( 0 %)   111 ADAMDEC1.27299
0( 0 %)   112 CDKN3.1033
0( 0 %)   113 TK1.7083
0( 0 %)   114 IGFL2.147920
2( 20 %)   115 CHRNA6.8973
0( 0 %)   116 GTSE1.51512
0( 0 %)   117 NCAPG.64151
1( 10 %)   118 ASF1B.55723
2( 20 %)   119 MMP9.4318
0( 0 %)   120 CLSPN.63967
10(100 %)  121 HSD17B6.8630
0( 0 %)   122 KIF26B.55083
10(100 %)  123 RAB26.25837
4( 40 %)   124 SCT.6343
10(100 %)  125 CCDC64.92558
10(100 %)  126 CILP2.148113
0( 0 %)   127 C20orf103.24141
0( 0 %)   128 MCM10.55388
10(100 %)  129 TMEM145.284339
0( 0 %)   130 CDCA3.83461
0( 0 %)   131 MMP10.4319

TABLE 14-continued

Overexpressed genes selected by correlation-based feature selection (CFS) based on 10-fold cross validation.

| | | |
|---|---|---|
| 9( 90 %) | 132 | CAMP.820 |
| 3( 30 %) | 133 | RDM1.201299 |
| 0( 0 %) | 134 | MND1.84057 |
| 10(100 %) | 135 | ACTL8.81569 |
| 0( 0 %) | 136 | ESPL1.9700 |
| 6( 60 %) | 137 | SDS.10993 |
| 5( 50 %) | 138 | DQX1.165545 |
| 0( 0 %) | 139 | ESCO2.157570 |
| 0( 0 %) | 140 | TTK.7272 |
| 2( 20 %) | 141 | CXCL10.3627 |
| 0( 0 %) | 142 | FAM111B.374393 |
| 0( 0 %) | 143 | CDCA5.113130 |
| 9( 90 %) | 144 | C16orf59.80178 |
| 0( 0 %) | 145 | E2F7.144455 |
| 1( 10 %) | 146 | AURKA.6790 |
| 0( 0 %) | 147 | NCAPH.23397 |
| 0( 0 %) | 148 | P4HA3.283208 |
| 10(100 %) | 149 | GNG13.51764 |
| 10(100 %) | 150 | ESM1.11082 |
| 0( 0 %) | 151 | KIF15.56992 |
| 0( 0 %) | 152 | CASC5.57082 |
| 10(100 %) | 153 | SYT13.57586 |
| 10(100 %) | 154 | C6orf126.389383 |
| 0( 0 %) | 155 | CDCA2.157313 |
| 0( 0 %) | 156 | FN1.2335 |
| 10(100 %) | 157 | CTXN1.404217 |
| 0( 0 %) | 158 | RECQL4.9401 |
| 3( 30 %) | 159 | CDCA8.55143 |
| 2( 20 %) | 160 | CEACAM6.4680 |
| 0( 0 %) | 161 | OIP5.11339 |
| 1( 10 %) | 162 | MARCH4.57574 |
| 10(100 %) | 163 | HTR1D.3352 |
| 1( 10 %) | 164 | CA9.768 |
| 7( 70 %) | 165 | MYT1.4661 |
| 10(100 %) | 166 | PROC.5624 |
| 9( 90 %) | 167 | HCN2.610 |
| 3( 30 %) | 168 | F12.2161 |
| 0( 0 %) | 169 | TUBB3.10381 |
| 0( 0 %) | 170 | EEF1A2.1917 |
| 0( 0 %) | 171 | NMU.10874 |
| 10(100 %) | 172 | TFR2.7036 |
| 7( 70 %) | 173 | ISG15.9636 |
| 0( 0 %) | 174 | SHCBP1.79801 |
| 0( 0 %) | 175 | CCNE2.9134 |
| 0( 0 %) | 176 | KIF23.9493 |
| 0( 0 %) | 177 | FAM54A.113115 |
| 0( 0 %) | 178 | FAM72A.729533 |
| 0( 0 %) | 179 | ERCC6L.54821 |
| 9( 90 %) | 180 | CCDC19.25790 |
| 8( 80 %) | 181 | HIST1H2BO.8348 |
| 0( 0 %) | 182 | CCNA2.890 |
| 10(100 %) | 183 | HOXC13.3229 |
| 1( 10 %) | 184 | VGF.7425 |
| 10(100 %) | 185 | ITPKA.3706 |
| 0( 0 %) | 186 | CDC6.990 |
| 4( 40 %) | 187 | FBN2.2201 |
| 10(100 %) | 188 | KIAA1211.57482 |
| 5( 50 %) | 189 | SPAG5.10615 |
| 0( 0 %) | 190 | POLQ.10721 |
| 0( 0 %) | 191 | TMEM90B.79953 |
| 6( 60 %) | 192 | GRM8.2918 |
| 10(100 %) | 193 | S100A14.57402 |
| 0( 0 %) | 194 | PRAME.23532 |
| 0( 0 %) | 195 | OLR1.4973 |
| 10(100 %) | 196 | GPRIN1.114787 |
| 0( 0 %) | 197 | CENPE.1062 |
| 9( 90 %) | 198 | ACAN.176 |
| 0( 0 %) | 199 | CTHRC1.115908 |
| 0( 0 %) | 200 | ZNF695.57116 |

Figure 17:
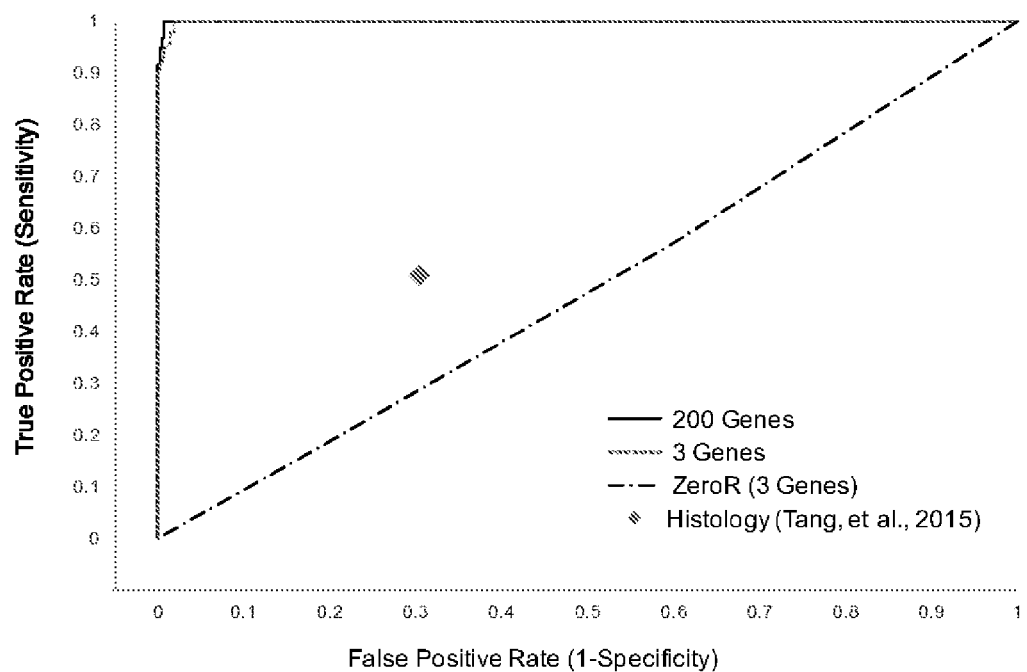
FIG. 17 shows that a panel of 3 genes has similar performance to a panel of 200 genes when used to classify samples as invasive breast cancer or adjacent healthy tissue.

Example 22. Comparison of Prediction Between a Panel of 3 Overexpressed Genes and a Panel of 200 Genes To identify the number of genes that could accurately distinguish two classes (tumor and healthy) without compromising sensitivity by diluting the sample across replicates in order to measure an unnecessary number of genes, an analysis of an 10-fold cross validation using the top-ranked genes from CFS for each of 10 training subsets was performed. FIG. 17 shows that a panel of 3 genes has similar performance to a panel of 200 genes when used to classify samples as invasive breast cancer or adjacent healthy tissue. This figure also shows the performance of the conventional method, as recently reported by Tang, et al. The gene panels provide a major performance advantage. ZeroR is a negative control (see FIG. 16) that shows the performance when you consistently guess that every sample is a member of the most prevalent class. This is similar to an approach adopted by some surgeons who are frustrated with the performance of histopathology. These surgeons routinely remove additional tissue from all patients. FIG. 17 shows that a panel of three genes developed using Random Forest is accurate, has an ROC AUC of 0.994, and RMSE of 0.83. FIG. 17 shows an ROC plot comparing the performance of a 200-gene classifier developed using Random Forest to a 3-gene classifier developed using Random Forest. The solid black line in the ROC Plot (FIG. 17) shows that a panel of 200 overexpressed genes can distinguish cancer from healthy tissue with an accuracy >99%, corresponding to the area under the ROC curve (ROC AUC) of 0.999 in Table 15 using the classifier developed using the Random Forest algorithm. Analysis of 996 human tissues by RNA Seq confirms findings from 132 microarray samples. Five machine learning methods can achieve >98% accuracy using a panel of only 3 genes (Table 15). FIG. 17 shows a developed method that used a panel of 3 genes to correctly classify 996 human tissue samples as either healthy or malignant. FIG. 17 shows that the 3-gene classifier (green line or dotted line) performs comparably to the 200-gene classifier (black line or solid line). Moreover, FIG. 17 demonstrates the performance advantage of a nucleic acid test over existing microscopy methods (blue diamond or diamond). The dashed diagonal line was a negative control that demonstrates the performance of a classifier that guesses between healthy and tumor based on class prevalence (it consistently guesses that each sample is a member of the most prevalent class; for example, if the majority of the samples processed by a pathology lab are malignant, then the control demonstrates the performance of a pathologist who guesses that every sample is positive). This is similar to an approach adopted by some surgeons who are frustrated with the performance of histopathology. These surgeons routinely remove additional tissue from all patients. The results of this analysis show that existing histopathology methods are only marginally better than guessing based on class prevalence. In contrast, a panel of only 3 genes provides an extremely accurate analysis.

Figure 18:
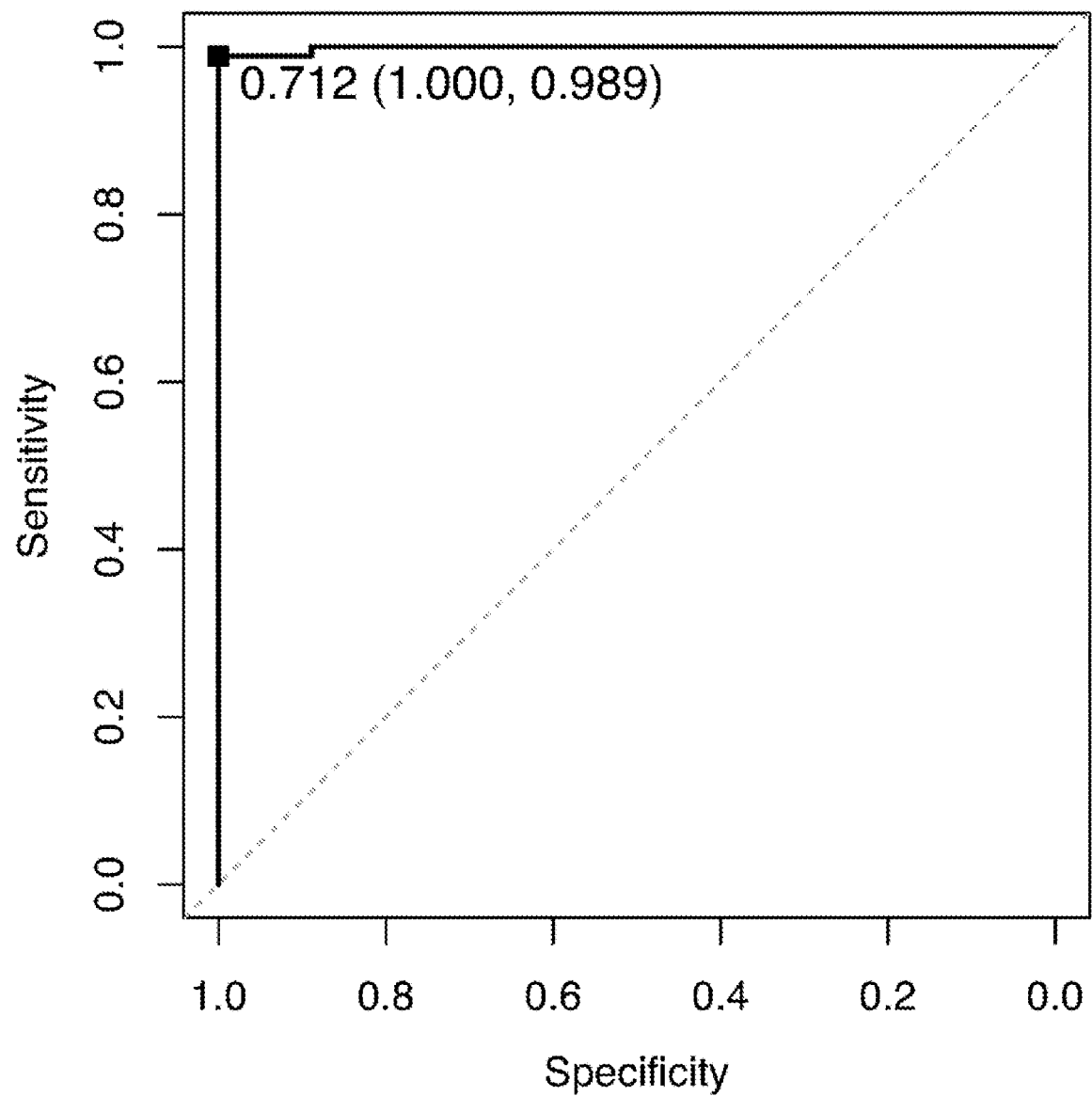
FIG. 18 shows a receiver operator characteristic (ROC) curve of a 3-gene test performed on hold-out samples. In contrast to FIG. 17, where performance was estimated using cross-validation, independent samples conclusively demonstrate that the workflow and classifier did not overfit the data.

To further validate the accuracy of the prediction, a hold-out group comprising 99 samples were analyzed using RNA Seq on an Illumina platform. The hold-out samples were not involved in selecting the biomarkers or building the Random Forest model. Although it can be mathematically proven that cross-validation method accurately predicts performance on future samples, the genomics literature provides abundant examples of mistakes that biased the cross-validation analysis (such as performing feature selection outside of resampling). For these reasons, results from this separate holdout dataset confirm that the model did not overfit the data. In fact, performance on naïve samples was slightly higher than predicted from 10-fold cross validation of the training dataset. An ideal test has sensitivity of 1 and specificity of 1. In this model, a threshold of 0.712 is the closest point on the ROC curve to idealized performance. FIG. 18 shows a receiver operator characteristic (ROC) curve of a 3-gene test performed on the 99 hold-out samples.

In some embodiments, the 3 genes are selected from any combinations of biomarkers disclosed herein. In some embodiments, the 3 genes are selected from a group of biomarkers consisting of COL10A1, MMP11, IBSP, CST1, and combinations thereof. In some cases, the panel may have more than 3 genes, for example, up to 4 genes that provides accurate analysis (Table 16). In some cases, a panel of less than 3 genes, for example, 2 genes, or 1 gene, is sufficient to provide accurate analysis.

Example 23. Performance of Gene Panels for Distinguishing Tumor and Healthy Tissues is Platform Independent This example shows a panel of three genes distinguishing tumor from adjacent healthy tissue and the expression is not platform specific. 995 human tissue samples were analyzed by whole-exome RNA Seq, and a subset of 110 samples were analyzed by custom Agilent microarray as part of TCGA. Expression is on a scale of log base 10. FIG. 20A shows expression of COL10A1, MMP11, and IBSP for 995 RNA Seq samples. Gene expression is presented as cumulative frequency plots. FIG. 20B shows expression of COL10A1, MMP11, and IBSP for 110 microarray samples. Gene expression is presented as cumulative frequency plots. Comparison of RNA Seq (FIG. 20A) and microarray results show that these results are not platform specific. FIG. 20D shows a non-limiting example, where Density Maps were used to show the combination of COL10A1 with either MMP11 or IBSP. Expression is based on 995 RNA Seq samples. 2D Density Maps illustrate the advantage of a multi-analyte test over a single analyte. Combinations are not limited to these particular analytes, or to only two analytes. Density Maps are useful to illustrate how data points cluster without over-plotting a large number of samples in a small space, but should not be used to draw thresholds because they do not show every data point, some of which cross class boundaries. FIG. 20C displays 2D Density Maps that show the combination of COL10A1 with either MMP11 or IBSP. Here expression is based on 110 microarray samples. Here expression is based on 110 microarray samples. Comparison to RNA Seq (FIG. 20D) confirms that the results are not platform specific. These results explain why multiple machine learning methods have high performance using these genes to classify samples as tumor or healthy: these biomarkers provide abundant biologic information to distinguish biologic samples.

TABLE 15

Disease classifier performance on 132 microarray samples and 996 whole exome RNA Seq samples.

| Machine Learning Method | RNA Seq (996 Samples) | | | Microarray (132 Samples) | | | Randomized Samples (Control) | | |
|---|---|---|---|---|---|---|---|---|---|
| | Correctly Classified | ROC AUC | RMSE | Correctly Classified | ROC AUC | RMSE | Correctly Classified | ROC AUC | RMSE |
| Panel of 20 genes (or microarray probes) | | | | | | | | | |
| k-Nearest Neighbor (IBk) | 98.8% | 0.964 | 0.088 | 99.2% | 0.992 | 0.035 | 49.7% | 0.501 | 0.695 |
| Naïve Bayes | 97.1% | 0.991 | 0.153 | 99.2% | 0.992 | 0.028 | 40.8% | 0.420 | 0.745 |
| Support Vector (SMO) | 99.3% | 0.986 | 0.070 | 99.2% | 0.992 | 0.028 | 49.9% | 0.522 | 0.705 |
| Multilayer Perceptron (Neural Network) | 99.2% | 0.998 | 0.070 | 100.0% | 1.000 | 0.017 | 49.1% | 0.512 | 0.642 |
| Random Forest | 99.4% | 0.999 | 0.071 | 99.2% | 1.000 | 0.087 | 45.4% | 0.472 | 0.525 |
| J48 Decision Tree | 98.3% | 0.962 | 0.108 | 97.7% | 0.975 | 0.075 | 47.7% | 0.478 | 0.714 |
| Rule ZeroR (Internal Control) | 90.6% | 0.500 | 0.289 | 74.8% | 0.500 | 0.433 | 38.6% | 0.500 | 0.504 |
| Panel of 5 genes (or microarray probes) | | | | | | | | | |
| k-Nearest Neighbor (IBk) | 98.7% | 0.954 | 0.091 | 97.7% | 0.975 | 0.073 | 39.3% | 0.407 | 0.766 |
| Naïve Bayes | 97.0% | 0.999 | 0.168 | 97.7% | 0.985 | 0.065 | 56.3% | 0.593 | 0.538 |
| Support Vector (SMO) | 98.7% | 0.952 | 0.099 | 97.7% | 0.975 | 0.067 | 55.4% | 0.585 | 0.661 |
| Multilayer Perceptron (Neural Network) | 99.0% | 0.999 | 0.077 | 98.5% | 0.995 | 0.051 | 56.0% | 0.605 | 0.568 |
| Random Forest | 99.0% | 0.999 | 0.078 | 97.7% | 0.988 | 0.089 | 46.2% | 0.524 | 0.560 |
| J48 Decision tree | 98.3% | 0.961 | 0.110 | 97.7% | 0.975 | 0.075 | 52.7% | 0.542 | 0.610 |
| Rule ZeroR (Internal Control) | 90.6% | 0.500 | 0.289 | 74.8% | 0.500 | 0.433 | 38.6% | 0.500 | 0.504 |
| Panel of 3 genes (or microarray probes) | | | | | | | | | |
| k-Nearest Neighbor (IBk) | 98.5% | 0.953 | 0.101 | 98.5% | 0.982 | 0.062 | 45.6% | 0.462 | 0.727 |
| Naïve Bayes | 97.2% | 0.998 | 0.147 | 98.5% | 0.979 | 0.067 | 60.0% | 0.605 | 0.526 |
| Support Vector (SMO) | 98.4% | 0.937 | 0.100 | 98.5% | 0.982 | 0.055 | 57.7% | 0.608 | 0.642 |
| Multilayer Perceptron (Neural Network) | 98.9% | 0.999 | 0.082 | 96.9% | 0.990 | 0.092 | 56.9% | 0.633 | 0.516 |
| Random Forest | 98.7% | 0.994 | 0.083 | 97.7% | 0.984 | 0.087 | 51.6% | 0.511 | 0.563 |
| J48 Decision Tree | 98.5% | 0.964 | 0.098 | 97.7% | 0.975 | 0.075 | 53.6% | 0.566 | 0.556 |
| Rule ZeroR (Internal Control) | 90.6% | 0.500 | 0.289 | 74.8% | 0.500 | 0.433 | 38.6% | 0.500 | 0.504 |
| Single gene (or microarray probe) | | | | | | | | | |
| k-Nearest Neighbor (IBk) | 97.5% | 0.920 | 0.152 | 96.2% | 0.966 | 0.125 | 42.1% | 0.446 | 0.749 |
| Naïve Bayes | 98.0% | 0.996 | 0.137 | 97.7% | 0.993 | 0.081 | 51.5% | 0.494 | 0.531 |
| Support Vector (SMO) | 97.8% | 0.889 | 0.136 | 98.5% | 0.982 | 0.055 | 44.0% | 0.494 | 0.743 |
| Multilayer Perceptron (Neural Network) | 98.1% | 0.996 | 0.116 | 98.5% | 0.993 | 0.070 | 47.7% | 0.492 | 0.544 |
| Random Forest | 97.6% | 0.975 | 0.138 | 96.2% | 0.985 | 0.103 | 42.1% | 0.455 | 0.653 |
| J48 Decision Tree | 97.9% | 0.973 | 0.128 | 97.7% | 0.973 | 0.074 | 51.5% | 0.495 | 0.543 |
| Rule ZeroR (Internal Control) | 90.6% | 0.500 | 0.289 | 74.8% | 0.500 | 0.433 | 38.6% | 0.500 | 0.504 |

TABLE 16

Exemplary gene panels for distinguishing tumor and healthy cells in a biological sample.

Target genes 4-gene panel: COL10A1, MMP11, IBSP, CST1
3-gene panel (version 1): COL10A1, MMP11, IBSP
3-gene panel (version 2): COL10A1, MMP11, CST1
2-gene panel: COL10A1, MMP11
1-gene panel (version 1): COL10A1
1-gene panel (version 2): MMP11
Reference genes (aka endogenous reference genes, aka normalization genes)

C2orf22, EXOC7, RWDD4A, CTDNEP1

Figure 21A:
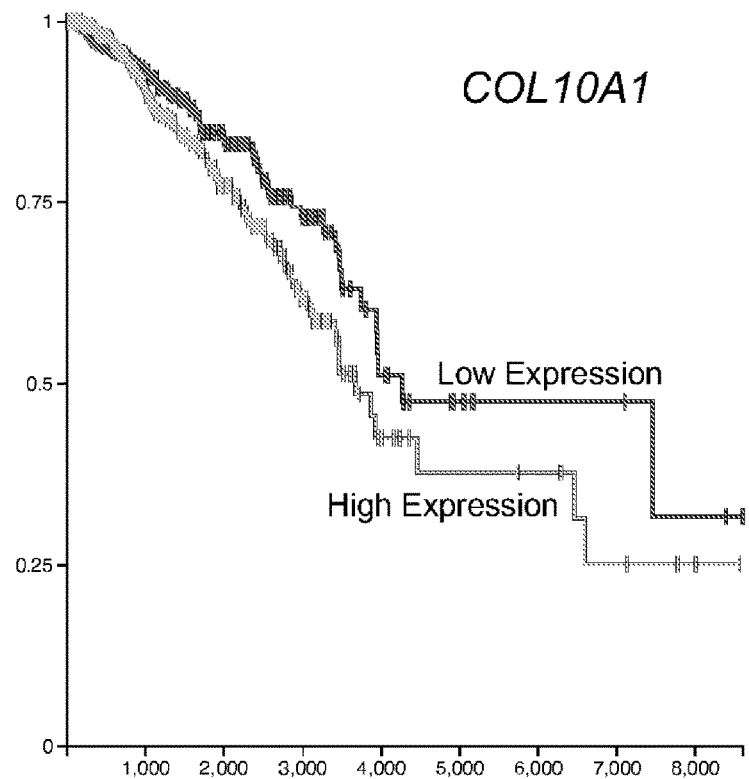
FIG. 21A shows a correlation between COL10A1 expression and survival. Kaplan-Meier Survival Curves for survival times of 916 patients with high COL10A1 expression (above the mean of all tumors) and low COL10A1 expression (below the mean of all tumors). Survival data further support the role of the selected genes in breast cancer.
Figure 21B:
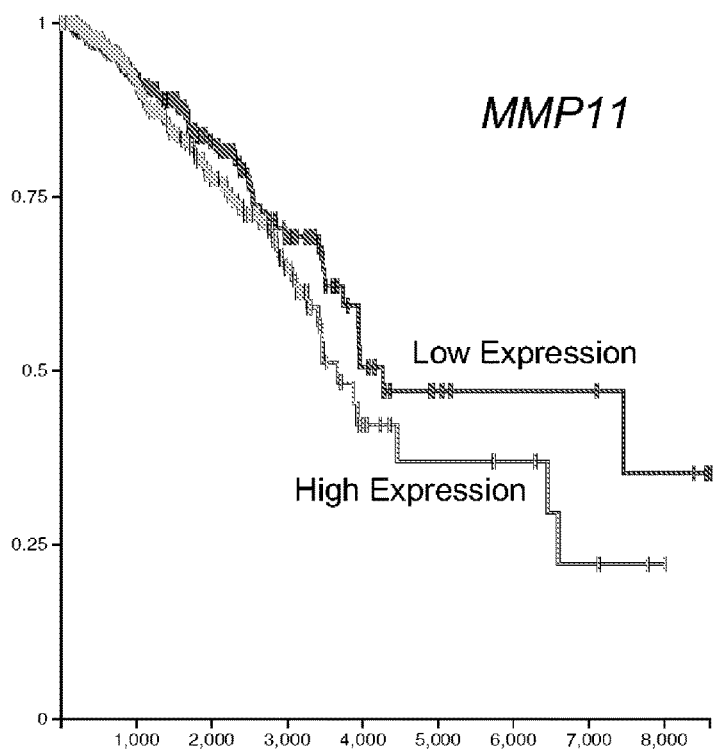
FIG. 21B shows correlation between MMP11 expression and survival. Kaplan-Meier Survival Curves for survival times of 916 patients with high MMP11 expression (above the mean of all tumors) and low MMP11 expression (below the mean of all tumors).

Example 24. Correlation of Biomarker Expression Level and Patient Survival Time This example shows the correlation of biomarker expression level and patient survival time. FIGS. 21A-21B show Kaplan-Meier Survival Curves for patients with invasive adenocarcinoma of the breast. For each gene, patients were grouped based on whether their tumor expressed that gene more or less than the mean expression of all primary tumors. Patients with higher expression levels, e.g., higher than mean expression level, had shorter survival than patients with lower expression levels, e.g., lower than mean expression level. All test genes are more significant than the estrogen receptor (ESR1). Estrogen receptor expression is one of the most well characterized clinical biomarkers for classification and one of the most important biomarkers for prognosis. Identifying biomarkers that are more significant than ESR1 provides strong confirmation that the biomarkers are relevant to the disease.

Figure 24:
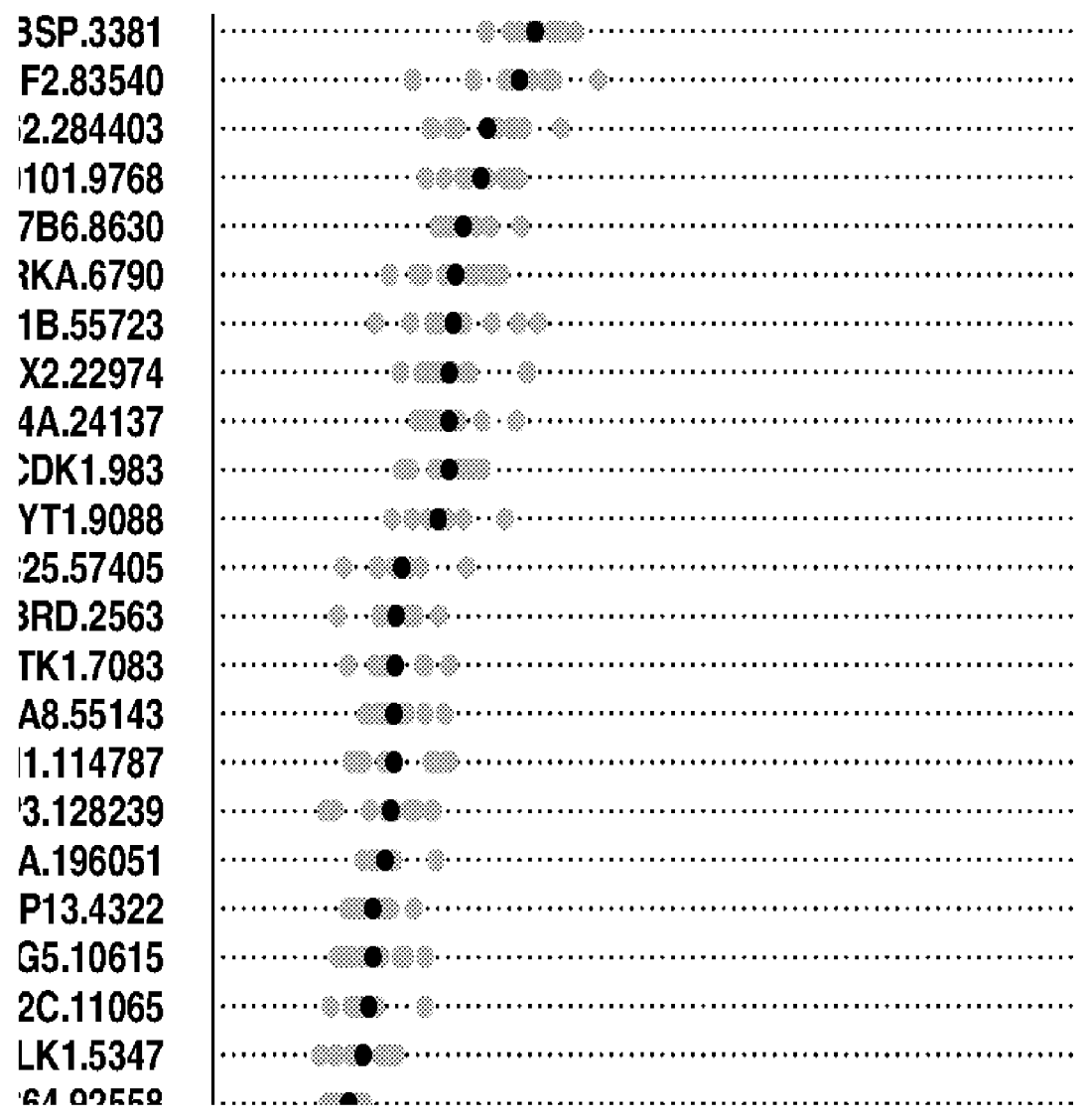

Example 25. Relative Contribution of Individual Gene for Prediction Tumor Cells in a Surgical Sample FIG. 24 is a variable importance plot. It shows the importance of the top variables (genes) based on their relative contribution (mean decrease Gini coefficient) to a Random Forest model that classifies samples as tumor or healthy. Genes are displayed by their gene symbol, followed by their NCBI Gene ID. This plot shows the top 30 genes using the Random Forest machine learning method.

Since Random Forest involves randomization steps, we observed subtle variations when we repeat the analysis multiple times (gray dots). We used a process called "setting seeds" to lock in a reproducible, pseudo-random variable. This allows us to repeat the experiment using a different randomization setting each time. We calculated the Decrease Gini Coefficient 10 times for each gene. By examining multiple randomization seeds, we get a stable rank of gene importance The mean of 10 randomizations provides greater confidence in the average value of each gene (solid black dots). The amount of unique information decreases exponentially as we moved down the biomarker ranking. After the top few biomarkers, adding additional biomarkers only adds a small amount of additional information. The number of biomarkers in a panel is therefore highly customizable based on the particular needs of the end user. It is noted that the end user may not simply require the top 3 genes in this list. In many cases it is desirable to select biomarkers that are not correlated with other biomarkers in the panel. Our analysis typically performs an additional filter step, although the final gene panel is typically composed of 3-4 genes selected from the top 10 genes in this list.

Table 20 shows the most informative 200 biomarkers. The 200 most informative biomarkers provide a customizable breast cancer panel. These biomarkers may be used for detecting and/or monitoring breast cancer. Based on the needs of the end user, a selection of these biomarkers may be used to detect and or monitor breast cancer. The panel may consist of 2, 3, 4, 5, 6, 7, 8, 9, and/or 10 biomarkers from this list. The test may consist of 10-20, 20-30, 30-40, 40-50, 50-60, 60-70, 70-80, 80-90, and/or 90-100 biomarkers from this list. The test may consist of 1-50, 50-100, 100-150, and/or 150-200 biomarkers from this list. Any or all of these 200 biomarkers may be used to detect or monitor breast cancer. The test may consist of 1 biomarker from this list. One of the biomarkers may be selected from MMP11, COL10,41, NEK2, UBE2T, IBSP, NUF2, WDR62, KIAA0101, HSD17B6, AURKA, ASF1B, TPX2, KIF4A, CDK1, or PKMYT1. One of these selected biomarkers may be combined with any of the other biomarkers from Table 20.

TABLE 20

The most informative 200 biomarkers for analyzing a presence of breast cancer cell.

| Gene Symbol | Gene ID | Seed 1 | Seed 23 | Seed 39 | Seed 118 | Seed 512 | Seed 19 | Seed 17 | Seed 10 | Seed 15 | Seed 5 | Mean |
|---|---|---|---|---|---|---|---|---|---|---|---|---|
| MMP11 | 4320 | 11.405 | 11.225 | 10.306 | 11.699 | 11.865 | 11.747 | 10.553 | 14.430 | 12.606 | 11.056 | 11.689 |
| COL10A1 | 1300 | 10.864 | 10.876 | 11.769 | 11.495 | 11.177 | 11.396 | 11.812 | 9.564 | 9.526 | 11.453 | 10.993 |
| NEK2 | 4751 | 8.012 | 6.271 | 7.463 | 6.686 | 6.019 | 6.697 | 7.727 | 6.428 | 7.139 | 7.329 | 6.977 |
| UBE2T | 29089 | 6.252 | 5.494 | 4.933 | 4.249 | 5.434 | 5.584 | 5.084 | 6.984 | 5.799 | 4.860 | 5.467 |
| IBSP | 3381 | 5.169 | 4.535 | 3.752 | 4.801 | 4.456 | 4.456 | 4.129 | 4.954 | 4.593 | 4.274 | 4.512 |
| NUF2 | 83540 | 2.581 | 4.683 | 3.541 | 5.528 | 4.035 | 4.809 | 4.177 | 4.162 | 4.791 | 4.458 | 4.276 |
| WDR62 | 284403 | 2.849 | 3.275 | 4.939 | 3.810 | 4.192 | 3.182 | 3.927 | 4.147 | 4.314 | 2.912 | 3.755 |
| KIAA0101 | 9768 | 2.782 | 3.473 | 4.152 | 4.025 | 3.362 | 4.260 | 4.113 | 3.615 | 3.754 | 3.078 | 3.662 |
| HSD17B6 | 8630 | 4.286 | 3.303 | 3.574 | 3.154 | 3.075 | 3.064 | 2.976 | 3.806 | 3.383 | 3.111 | 3.373 |
| AURKA | 6790 | 3.254 | 3.767 | 3.865 | 3.564 | 3.981 | 2.632 | 2.747 | 2.212 | 3.082 | 3.482 | 3.259 |
| ASF1B | 55723 | 4.564 | 2.883 | 3.827 | 3.373 | 3.252 | 4.254 | 2.539 | 1.987 | 2.984 | 2.534 | 3.220 |
| TPX2 | 22974 | 2.378 | 2.850 | 4.396 | 3.438 | 3.217 | 2.716 | 2.869 | 3.010 | 3.479 | 3.211 | 3.156 |
| KIF4A | 24137 | 2.890 | 3.137 | 2.997 | 2.824 | 3.297 | 2.707 | 2.646 | 4.216 | 3.162 | 3.668 | 3.154 |
| CDK1 | 983 | 3.655 | 3.517 | 2.529 | 3.290 | 2.479 | 2.406 | 2.934 | 3.684 | 3.405 | 3.546 | 3.144 |
| PKMYT1 | 9088 | 3.118 | 2.987 | 2.560 | 3.373 | 4.045 | 3.051 | 2.242 | 2.580 | 2.817 | 2.975 | 2.975 |
| SPC25 | 57405 | 2.507 | 3.432 | 2.012 | 2.359 | 2.405 | 2.283 | 2.353 | 2.460 | 1.480 | 2.690 | 2.398 |
| GABRD | 2563 | 2.993 | 2.345 | 1.377 | 2.522 | 2.253 | 2.046 | 2.481 | 2.282 | 2.229 | 2.603 | 2.313 |
| TK1 | 7083 | 2.224 | 3.155 | 2.151 | 2.150 | 1.974 | 1.533 | 2.117 | 2.197 | 2.733 | 2.759 | 2.299 |
| CDCA8 | 55143 | 2.077 | 2.769 | 3.083 | 2.019 | 2.124 | 2.470 | 1.858 | 2.411 | 2.197 | 1.829 | 2.284 |
| GPRIN1 | 114787 | 1.588 | 1.756 | 3.101 | 1.789 | 2.877 | 1.784 | 1.691 | 2.130 | 2.934 | 3.144 | 2.279 |
| IQGAP3 | 128239 | 2.523 | 1.325 | 1.890 | 1.186 | 2.625 | 2.880 | 2.533 | 2.865 | 2.168 | 2.280 | 2.227 |
| PPAPDC1A | 196051 | 1.949 | 2.943 | 1.990 | 2.145 | 1.923 | 2.277 | 1.791 | 1.972 | 2.159 | 2.233 | 2.138 |
| MMP13 | 4322 | 1.576 | 1.621 | 2.002 | 1.810 | 2.138 | 2.594 | 2.231 | 1.542 | 1.721 | 2.197 | 1.943 |
| SPAG5 | 10615 | 1.389 | 1.788 | 1.541 | 2.763 | 1.953 | 2.450 | 2.375 | 1.452 | 1.624 | 2.066 | 1.940 |
| UBE2C | 11065 | 1.269 | 2.773 | 2.005 | 1.842 | 1.600 | 1.960 | 1.990 | 1.794 | 1.722 | 1.861 | 1.882 |
| PLK1 | 5347 | 2.064 | 1.788 | 1.610 | 2.149 | 1.674 | 1.713 | 1.352 | 1.104 | 2.317 | 2.177 | 1.795 |
| CCDC64 | 92558 | 1.616 | 1.789 | 1.667 | 1.673 | 1.504 | 1.227 | 1.702 | 1.377 | 1.271 | 1.745 | 1.557 |
| KIF18B | 146909 | 2.001 | 1.536 | 1.075 | 1.671 | 1.232 | 1.087 | 1.683 | 1.561 | 1.679 | 1.574 | 1.510 |
| TROAP | 10024 | 1.662 | 1.041 | 1.477 | 1.389 | 1.381 | 0.978 | 1.900 | 1.205 | 1.064 | 1.836 | 1.393 |
| PPEF1 | 5475 | 1.940 | 1.245 | 1.263 | 1.992 | 1.239 | 1.000 | 1.213 | 1.334 | 1.167 | 0.854 | 1.325 |
| UHRF1 | 29128 | 1.152 | 1.122 | 1.189 | 1.157 | 1.316 | 1.106 | 1.641 | 1.387 | 1.015 | 1.876 | 1.296 |
| PROC | 5624 | 1.361 | 1.274 | 1.153 | 1.198 | 1.217 | 1.379 | 1.343 | 1.258 | 1.120 | 1.425 | 1.273 |
| CEP55 | 55165 | 1.140 | 0.940 | 1.316 | 1.195 | 1.392 | 1.089 | 0.678 | 1.311 | 0.748 | 1.228 | 1.104 |
| MELK | 9833 | 0.728 | 0.953 | 1.145 | 0.805 | 1.435 | 0.995 | 1.172 | 1.028 | 1.009 | 1.020 | 1.029 |
| COL11A1 | 1301 | 0.826 | 1.003 | 1.185 | 1.227 | 1.229 | 0.905 | 1.394 | 0.967 | 0.681 | 0.727 | 1.014 |
| CDC25C | 995 | 0.891 | 1.331 | 0.863 | 0.538 | 0.775 | 1.662 | 0.984 | 0.815 | 1.103 | 0.966 | 0.993 |
| CDKN3 | 1033 | 0.842 | 1.323 | 0.611 | 0.849 | 0.740 | 1.057 | 1.232 | 0.995 | 0.956 | 0.922 | 0.953 |
| LOC283867 | 283867 | 1.124 | 0.992 | 0.996 | 0.766 | 1.026 | 0.774 | 0.879 | 0.933 | 0.876 | 0.966 | 0.933 |
| CILP2 | 148113 | 0.748 | 0.852 | 0.806 | 1.158 | 0.811 | 0.806 | 0.960 | 1.162 | 0.903 | 0.920 | 0.913 |
| HJURP | 55355 | 0.411 | 0.992 | 0.700 | 0.918 | 0.468 | 0.551 | 0.994 | 0.699 | 0.950 | 0.927 | 0.761 |
| C19orf21 | 126353 | 0.880 | 0.952 | 0.662 | 0.765 | 0.719 | 0.713 | 0.624 | 0.807 | 0.615 | 0.773 | 0.751 |
| HAGHL | 84264 | 0.866 | 0.972 | 0.682 | 0.599 | 0.759 | 0.718 | 0.733 | 0.687 | 0.778 | 0.661 | 0.745 |
| CST1 | 1469 | 0.696 | 0.643 | 0.531 | 0.761 | 0.813 | 0.796 | 0.674 | 0.571 | 0.626 | 0.881 | 0.699 |
| KIFC1 | 3833 | 0.999 | 0.384 | 0.538 | 0.781 | 0.652 | 0.753 | 1.180 | 0.594 | 0.669 | 0.422 | 0.697 |
| ASPM | 259266 | 0.657 | 0.761 | 0.648 | 0.795 | 0.636 | 0.767 | 0.742 | 0.626 | 0.683 | 0.640 | 0.696 |
| COMP | 1311 | 0.743 | 0.578 | 0.633 | 0.657 | 0.750 | 0.609 | 0.631 | 0.701 | 0.811 | 0.739 | 0.685 |
| C16orf59 | 80178 | 0.561 | 0.692 | 0.751 | 0.662 | 0.376 | 0.783 | 0.711 | 0.551 | 0.974 | 0.656 | 0.672 |
| ESM1 | 11082 | 0.599 | 0.714 | 0.716 | 0.708 | 0.761 | 0.489 | 0.599 | 0.694 | 0.623 | 0.539 | 0.644 |
| CLEC5A | 23601 | 0.638 | 0.692 | 0.620 | 0.555 | 0.797 | 0.576 | 0.782 | 0.529 | 0.727 | 0.475 | 0.639 |
| RAB26 | 25837 | 0.549 | 0.535 | 0.629 | 0.598 | 0.700 | 0.567 | 0.648 | 0.645 | 0.507 | 0.963 | 0.634 |

TABLE 20-continued

The most informative 200 biomarkers for analyzing a presence of breast cancer cell.

| Gene Symbol | Gene ID | Seed 1 | Seed 23 | Seed 39 | Seed 118 | Seed 512 | Seed 19 | Seed 17 | Seed 10 | Seed 15 | Seed 5 | Mean |
|---|---|---|---|---|---|---|---|---|---|---|---|---|
| CENPF | 1063 | 0.544 | 0.846 | 0.927 | 0.519 | 0.503 | 0.986 | 0.649 | 0.354 | 0.414 | 0.521 | 0.626 |
| CCNE2 | 9134 | 0.674 | 0.595 | 0.728 | 0.475 | 0.632 | 0.585 | 0.796 | 0.511 | 0.547 | 0.672 | 0.622 |
| PBK | 55872 | 0.895 | 0.605 | 0.423 | 0.505 | 0.572 | 0.568 | 0.744 | 0.523 | 0.593 | 0.543 | 0.597 |
| INHBA | 3624 | 0.471 | 0.524 | 0.521 | 0.486 | 0.757 | 0.718 | 0.579 | 0.474 | 0.593 | 0.798 | 0.592 |
| KIF2C | 11004 | 0.304 | 0.376 | 0.484 | 0.517 | 1.312 | 0.913 | 0.679 | 0.510 | 0.442 | 0.248 | 0.578 |
| ADAMTS14 | 140766 | 0.574 | 0.654 | 0.448 | 0.724 | 0.366 | 0.748 | 0.463 | 0.598 | 0.657 | 0.505 | 0.574 |
| TOP2A | 7153 | 0.752 | 0.287 | 0.579 | 0.356 | 0.645 | 0.433 | 0.724 | 0.651 | 0.754 | 0.500 | 0.568 |
| TMEM145 | 284339 | 0.684 | 0.707 | 0.567 | 0.578 | 0.405 | 0.538 | 0.547 | 0.567 | 0.459 | 0.622 | 0.567 |
| SLC24A2 | 25769 | 0.489 | 0.534 | 0.577 | 0.470 | 0.496 | 0.699 | 0.468 | 0.562 | 0.700 | 0.569 | 0.556 |
| CCL11 | 6356 | 0.638 | 0.419 | 0.422 | 0.471 | 0.495 | 0.703 | 0.742 | 0.374 | 0.577 | 0.513 | 0.535 |
| PTTG1 | 9232 | 0.684 | 0.758 | 0.473 | 0.347 | 0.770 | 0.690 | 0.282 | 0.199 | 0.617 | 0.530 | 0.535 |
| WISP1 | 8840 | 0.489 | 0.668 | 0.562 | 0.503 | 0.494 | 0.544 | 0.422 | 0.405 | 0.646 | 0.550 | 0.528 |
| GRM4 | 2914 | 0.490 | 0.511 | 0.581 | 0.555 | 0.497 | 0.432 | 0.418 | 0.600 | 0.665 | 0.496 | 0.525 |
| BUB1 | 699 | 0.345 | 0.472 | 0.512 | 0.342 | 0.453 | 0.478 | 0.537 | 0.588 | 0.759 | 0.574 | 0.506 |
| K1F26B | 55083 | 0.513 | 0.543 | 0.622 | 0.495 | 0.457 | 0.506 | 0.335 | 0.534 | 0.572 | 0.476 | 0.505 |
| CCDC78 | 124093 | 0.337 | 0.553 | 0.490 | 0.589 | 0.460 | 0.465 | 0.506 | 0.439 | 0.692 | 0.463 | 0.499 |
| FOXM1 | 2305 | 0.358 | 0.479 | 0.354 | 0.980 | 0.375 | 0.264 | 0.655 | 0.377 | 0.276 | 0.742 | 0.486 |
| HTR1D | 3352 | 0.433 | 0.383 | 0.541 | 0.430 | 0.456 | 0.467 | 0.545 | 0.525 | 0.528 | 0.471 | 0.478 |
| RRM2 | 6241 | 0.620 | 0.656 | 0.358 | 0.144 | 0.325 | 0.562 | 0.573 | 0.640 | 0.468 | 0.327 | 0.467 |
| CTXN1 | 404217 | 0.422 | 0.670 | 0.450 | 0.356 | 0.420 | 0.489 | 0.426 | 0.576 | 0.419 | 0.389 | 0.462 |
| RECQL4 | 9401 | 0.473 | 0.446 | 0.499 | 0.410 | 0.564 | 0.505 | 0.559 | 0.343 | 0.392 | 0.406 | 0.460 |
| GJB2 | 2706 | 0.368 | 0.448 | 0.413 | 0.592 | 0.484 | 0.594 | 0.324 | 0.461 | 0.416 | 0.328 | 0.443 |
| CST4 | 1472 | 0.442 | 0.487 | 0.411 | 0.304 | 0.339 | 0.483 | 0.652 | 0.468 | 0.319 | 0.473 | 0.438 |
| PLAC1 | 10761 | 0.352 | 0.528 | 0.445 | 0.453 | 0.451 | 0.430 | 0.453 | 0.387 | 0.379 | 0.461 | 0.434 |
| LRRC15 | 131578 | 0.428 | 0.525 | 0.462 | 0.377 | 0.312 | 0.530 | 0.424 | 0.379 | 0.494 | 0.383 | 0.431 |
| HOXC13 | 3229 | 0.386 | 0.342 | 0.348 | 0.441 | 0.349 | 0.484 | 0.343 | 0.371 | 0.315 | 0.494 | 0.387 |
| NCAPG | 64151 | 0.447 | 0.169 | 0.496 | 0.395 | 0.138 | 0.129 | 0.894 | 0.588 | 0.285 | 0.290 | 0.383 |
| CDCA5 | 113130 | 0.134 | 0.308 | 0.611 | 0.256 | 0.510 | 0.843 | 0.532 | 0.139 | 0.059 | 0.381 | 0.377 |
| HMMR | 3161 | 0.290 | 0.194 | 0.335 | 0.276 | 0.520 | 0.367 | 0.692 | 0.310 | 0.284 | 0.427 | 0.370 |
| DTL | 51514 | 0.384 | 0.239 | 0.313 | 0.248 | 0.241 | 0.708 | 0.283 | 0.321 | 0.416 | 0.389 | 0.354 |
| F12 | 2161 | 0.321 | 0.305 | 0.502 | 0.412 | 0.409 | 0.401 | 0.364 | 0.281 | 0.296 | 0.209 | 0.350 |
| C20orf103 | 24141 | 0.284 | 0.364 | 0.412 | 0.416 | 0.424 | 0.386 | 0.393 | 0.246 | 0.337 | 0.231 | 0.349 |
| NDC80 | 10403 | 0.202 | 0.193 | 0.493 | 0.483 | 0.499 | 0.285 | 0.212 | 0.385 | 0.297 | 0.360 | 0.341 |
| CENPM | 79019 | 0.309 | 0.460 | 0.281 | 0.433 | 0.284 | 0.196 | 0.163 | 0.432 | 0.206 | 0.465 | 0.323 |
| HCN2 | 610 | 0.257 | 0.311 | 0.433 | 0.360 | 0.291 | 0.314 | 0.343 | 0.321 | 0.228 | 0.314 | 0.317 |
| CCDC19 | 25790 | 0.237 | 0.374 | 0.279 | 0.353 | 0.249 | 0.360 | 0.294 | 0.291 | 0.366 | 0.367 | 0.317 |
| PITX1 | 5307 | 0.291 | 0.304 | 0.348 | 0.300 | 0.248 | 0.264 | 0.443 | 0.302 | 0.298 | 0.276 | 0.307 |
| HIST1H2AM | 8336 | 0.262 | 0.352 | 0.247 | 0.290 | 0.333 | 0.301 | 0.255 | 0.224 | 0.366 | 0.390 | 0.302 |
| BIRC5 | 332 | 0.227 | 0.212 | 0.137 | 0.068 | 0.404 | 0.282 | 0.291 | 0.353 | 0.548 | 0.447 | 0.297 |
| CCNB2 | 9133 | 0.296 | 0.185 | 0.218 | 0.446 | 0.462 | 0.294 | 0.181 | 0.293 | 0.254 | 0.327 | 0.296 |
| HIST1H3H | 8357 | 0.311 | 0.227 | 0.269 | 0.319 | 0.296 | 0.332 | 0.199 | 0.226 | 0.325 | 0.312 | 0.282 |
| OIP5 | 11339 | 0.218 | 0.495 | 0.222 | 0.271 | 0.282 | 0.293 | 0.224 | 0.259 | 0.213 | 0.212 | 0.269 |
| FN1 | 2335 | 0.205 | 0.232 | 0.241 | 0.235 | 0.352 | 0.238 | 0.263 | 0.309 | 0.347 | 0.252 | 0.267 |
| P4HA3 | 283208 | 0.201 | 0.238 | 0.263 | 0.235 | 0.300 | 0.324 | 0.238 | 0.279 | 0.247 | 0.342 | 0.267 |
| EPR1 | 8475 | 0.476 | 0.176 | 0.416 | 0.304 | 0.387 | 0.124 | 0.189 | 0.230 | 0.248 | 0.045 | 0.260 |
| KIF14 | 9928 | 0.174 | 0.110 | 0.257 | 0.344 | 0.337 | 0.359 | 0.078 | 0.479 | 0.172 | 0.220 | 0.253 |
| DLGAP5 | 9787 | 0.217 | 0.147 | 0.150 | 0.388 | 0.270 | 0.310 | 0.275 | 0.187 | 0.308 | 0.279 | 0.253 |
| EPYC | 1833 | 0.305 | 0.169 | 0.334 | 0.226 | 0.268 | 0.232 | 0.262 | 0.232 | 0.302 | 0.177 | 0.251 |
| GNG13 | 51764 | 0.261 | 0.235 | 0.286 | 0.331 | 0.199 | 0.150 | 0.267 | 0.257 | 0.251 | 0.219 | 0.246 |
| SDS | 10993 | 0.225 | 0.216 | 0.323 | 0.236 | 0.276 | 0.225 | 0.306 | 0.200 | 0.258 | 0.191 | 0.246 |
| CST2 | 1470 | 0.320 | 0.306 | 0.153 | 0.188 | 0.210 | 0.335 | 0.258 | 0.164 | 0.299 | 0.215 | 0.245 |
| SCT | 6343 | 0.257 | 0.266 | 0.165 | 0.275 | 0.377 | 0.234 | 0.211 | 0.177 | 0.279 | 0.179 | 0.242 |
| TMEM90B | 79953 | 0.315 | 0.278 | 0.145 | 0.308 | 0.262 | 0.180 | 0.206 | 0.248 | 0.231 | 0.245 | 0.242 |
| CDCA3 | 83461 | 0.302 | 0.156 | 0.159 | 0.247 | 0.131 | 0.174 | 0.195 | 0.285 | 0.184 | 0.526 | 0.236 |
| C6orf126 | 389383 | 0.167 | 0.235 | 0.214 | 0.303 | 0.215 | 0.227 | 0.261 | 0.238 | 0.152 | 0.329 | 0.234 |
| SPC24 | 147841 | 0.151 | 0.258 | 0.160 | 0.164 | 0.224 | 0.194 | 0.351 | 0.240 | 0.253 | 0.312 | 0.231 |
| EEF1A2 | 1917 | 0.231 | 0.235 | 0.197 | 0.193 | 0.213 | 0.137 | 0.335 | 0.275 | 0.221 | 0.185 | 0.222 |
| MMP1 | 4312 | 0.231 | 0.235 | 0.176 | 0.314 | 0.218 | 0.251 | 0.203 | 0.163 | 0.168 | 0.227 | 0.218 |
| TFR2 | 7036 | 0.267 | 0.203 | 0.206 | 0.202 | 0.226 | 0.218 | 0.200 | 0.182 | 0.229 | 0.228 | 0.216 |
| HIST1H3D | 8351 | 0.341 | 0.232 | 0.150 | 0.097 | 0.258 | 0.216 | 0.256 | 0.238 | 0.145 | 0.227 | 0.216 |
| CHRNA6 | 8973 | 0.166 | 0.101 | 0.275 | 0.221 | 0.305 | 0.280 | 0.202 | 0.254 | 0.128 | 0.208 | 0.214 |
| HOXC11 | 3227 | 0.186 | 0.165 | 0.258 | 0.195 | 0.208 | 0.206 | 0.212 | 0.191 | 0.262 | 0.234 | 0.212 |
| KIF20A | 10112 | 0.346 | 0.167 | 0.047 | 0.166 | 0.276 | 0.309 | 0.275 | 0.265 | 0.142 | 0.125 | 0.212 |
| NUSAP1 | 51203 | 0.199 | 0.169 | 0.360 | 0.302 | 0.275 | 0.219 | 0.167 | 0.122 | 0.125 | 0.173 | 0.211 |
| ANLN | 54443 | 0.212 | 0.144 | 0.060 | 0.195 | 0.046 | 0.397 | 0.147 | 0.251 | 0.312 | 0.339 | 0.210 |
| SBK1 | 388228 | 0.243 | 0.202 | 0.245 | 0.129 | 0.129 | 0.236 | 0.278 | 0.245 | 0.191 | 0.197 | 0.210 |
| ACAN | 176 | 0.224 | 0.154 | 0.259 | 0.261 | 0.187 | 0.250 | 0.199 | 0.187 | 0.170 | 0.179 | 0.207 |
| SKA1 | 220134 | 0.201 | 0.321 | 0.150 | 0.204 | 0.157 | 0.065 | 0.328 | 0.315 | 0.191 | 0.096 | 0.203 |
| TUBB3 | 10381 | 0.159 | 0.192 | 0.264 | 0.163 | 0.184 | 0.206 | 0.239 | 0.216 | 0.198 | 0.169 | 0.199 |
| KIAA1199 | 57214 | 0.217 | 0.143 | 0.170 | 0.153 | 0.176 | 0.178 | 0.242 | 0.172 | 0.188 | 0.267 | 0.191 |
| CTHRC1 | 115908 | 0.164 | 0.241 | 0.250 | 0.137 | 0.211 | 0.161 | 0.175 | 0.123 | 0.196 | 0.117 | 0.178 |
| SKA3 | 221150 | 0.154 | 0.209 | 0.054 | 0.207 | 0.084 | 0.183 | 0.153 | 0.393 | 0.069 | 0.268 | 0.177 |
| CDC20 | 991 | 0.045 | 0.183 | 0.191 | 0.105 | 0.340 | 0.153 | 0.158 | 0.366 | 0.136 | 0.046 | 0.172 |
| VGF | 7425 | 0.216 | 0.152 | 0.179 | 0.147 | 0.111 | 0.184 | 0.126 | 0.188 | 0.219 | 0.148 | 0.167 |
| GTSE1 | 51512 | 0.124 | 0.048 | 0.250 | 0.268 | 0.156 | 0.066 | 0.291 | 0.225 | 0.055 | 0.155 | 0.164 |

TABLE 20-continued

The most informative 200 biomarkers for analyzing a presence of breast cancer cell.

| Gene Symbol | Gene ID | Seed 1 | Seed 23 | Seed 39 | Seed 118 | Seed 512 | Seed 19 | Seed 17 | Seed 10 | Seed 15 | Seed 5 | Mean |
|---|---|---|---|---|---|---|---|---|---|---|---|---|
| NKAIN1 | 79570 | 0.127 | 0.177 | 0.180 | 0.137 | 0.154 | 0.184 | 0.204 | 0.121 | 0.170 | 0.148 | 0.160 |
| CNIH2 | 254263 | 0.191 | 0.203 | 0.186 | 0.090 | 0.086 | 0.109 | 0.144 | 0.209 | 0.273 | 0.096 | 0.159 |
| TDO2 | 6999 | 0.213 | 0.133 | 0.271 | 0.140 | 0.169 | 0.088 | 0.286 | 0.075 | 0.080 | 0.127 | 0.158 |
| S100A14 | 57402 | 0.093 | 0.115 | 0.150 | 0.166 | 0.208 | 0.202 | 0.139 | 0.181 | 0.168 | 0.133 | 0.155 |
| ITPKA | 3706 | 0.120 | 0.149 | 0.179 | 0.152 | 0.148 | 0.105 | 0.209 | 0.158 | 0.139 | 0.169 | 0.153 |
| CKAP2L | 150468 | 0.104 | 0.247 | 0.238 | 0.178 | 0.088 | 0.162 | 0.106 | 0.029 | 0.229 | 0.133 | 0.151 |
| AURKB | 9212 | 0.193 | 0.159 | 0.110 | 0.221 | 0.088 | 0.212 | 0.126 | 0.119 | 0.125 | 0.157 | 0.151 |
| MS4A15 | 219995 | 0.135 | 0.094 | 0.175 | 0.193 | 0.143 | 0.128 | 0.137 | 0.111 | 0.198 | 0.136 | 0.145 |
| HIST1H2BO | 8348 | 0.104 | 0.195 | 0.141 | 0.175 | 0.111 | 0.135 | 0.089 | 0.167 | 0.159 | 0.158 | 0.143 |
| AIM1L | 55057 | 0.178 | 0.106 | 0.147 | 0.125 | 0.108 | 0.095 | 0.131 | 0.184 | 0.211 | 0.137 | 0.142 |
| TNNT1 | 7138 | 0.148 | 0.110 | 0.131 | 0.223 | 0.102 | 0.128 | 0.186 | 0.171 | 0.111 | 0.107 | 0.142 |
| HAPLN1 | 1404 | 0.149 | 0.131 | 0.165 | 0.162 | 0.128 | 0.122 | 0.163 | 0.182 | 0.119 | 0.091 | 0.141 |
| MMP10 | 4319 | 0.159 | 0.154 | 0.168 | 0.092 | 0.152 | 0.146 | 0.157 | 0.105 | 0.112 | 0.155 | 0.140 |
| ERCC6L | 54821 | 0.084 | 0.144 | 0.158 | 0.142 | 0.146 | 0.197 | 0.191 | 0.091 | 0.096 | 0.140 | 0.139 |
| MYT1 | 4661 | 0.126 | 0.140 | 0.112 | 0.090 | 0.067 | 0.142 | 0.209 | 0.165 | 0.183 | 0.118 | 0.135 |
| ISG15 | 9636 | 0.124 | 0.099 | 0.149 | 0.155 | 0.110 | 0.083 | 0.147 | 0.132 | 0.132 | 0.114 | 0.124 |
| KIF23 | 9493 | 0.075 | 0.062 | 0.123 | 0.078 | 0.148 | 0.144 | 0.194 | 0.114 | 0.182 | 0.113 | 0.123 |
| WT1 | 7490 | 0.130 | 0.104 | 0.165 | 0.121 | 0.151 | 0.125 | 0.097 | 0.106 | 0.116 | 0.113 | 0.123 |
| GRM8 | 2918 | 0.130 | 0.148 | 0.081 | 0.118 | 0.074 | 0.144 | 0.144 | 0.130 | 0.125 | 0.128 | 0.122 |
| 4-Mar | 57574 | 0.072 | 0.217 | 0.082 | 0.113 | 0.068 | 0.122 | 0.155 | 0.113 | 0.094 | 0.130 | 0.116 |
| FAM54A | 113115 | 0.103 | 0.036 | 0.061 | 0.239 | 0.139 | 0.133 | 0.139 | 0.094 | 0.066 | 0.142 | 0.115 |
| BUB1B | 701 | 0.196 | 0.075 | 0.106 | 0.208 | 0.139 | 0.081 | 0.071 | 0.160 | 0.068 | 0.034 | 0.114 |
| EXO1 | 9156 | 0.142 | 0.058 | 0.050 | 0.111 | 0.233 | 0.179 | 0.034 | 0.159 | 0.064 | 0.093 | 0.112 |
| NCAPH | 23397 | 0.068 | 0.310 | 0.033 | 0.118 | 0.173 | 0.036 | 0.118 | 0.041 | 0.112 | 0.032 | 0.104 |
| S100P | 6286 | 0.134 | 0.098 | 0.091 | 0.068 | 0.105 | 0.102 | 0.126 | 0.043 | 0.121 | 0.106 | 0.099 |
| CDC20B | 166979 | 0.109 | 0.082 | 0.102 | 0.077 | 0.092 | 0.094 | 0.114 | 0.091 | 0.109 | 0.113 | 0.098 |
| DEPDC1 | 55635 | 0.039 | 0.251 | 0.047 | 0.068 | 0.059 | 0.050 | 0.145 | 0.048 | 0.166 | 0.091 | 0.096 |
| KIAA1211 | 57482 | 0.120 | 0.073 | 0.093 | 0.104 | 0.085 | 0.089 | 0.117 | 0.077 | 0.085 | 0.116 | 0.096 |
| FBN2 | 2201 | 0.085 | 0.118 | 0.073 | 0.050 | 0.122 | 0.083 | 0.111 | 0.104 | 0.092 | 0.086 | 0.093 |
| OLR1 | 4973 | 0.066 | 0.061 | 0.093 | 0.097 | 0.077 | 0.116 | 0.106 | 0.128 | 0.083 | 0.097 | 0.092 |
| RAD54L | 8438 | 0.043 | 0.088 | 0.173 | 0.053 | 0.107 | 0.129 | 0.083 | 0.072 | 0.031 | 0.131 | 0.091 |
| FAM83D | 81610 | 0.055 | 0.082 | 0.148 | 0.032 | 0.182 | 0.080 | 0.058 | 0.045 | 0.194 | 0.027 | 0.090 |
| RDM1 | 201299 | 0.153 | 0.047 | 0.088 | 0.051 | 0.078 | 0.074 | 0.075 | 0.138 | 0.117 | 0.060 | 0.088 |
| KREMEN2 | 79412 | 0.074 | 0.114 | 0.089 | 0.098 | 0.088 | 0.113 | 0.050 | 0.081 | 0.097 | 0.077 | 0.088 |
| MND1 | 84057 | 0.065 | 0.102 | 0.106 | 0.123 | 0.082 | 0.062 | 0.107 | 0.033 | 0.096 | 0.102 | 0.088 |
| ESPL1 | 9700 | 0.101 | 0.037 | 0.167 | 0.051 | 0.111 | 0.058 | 0.096 | 0.098 | 0.070 | 0.083 | 0.087 |
| CDC45 | 8318 | 0.106 | 0.040 | 0.095 | 0.038 | 0.074 | 0.100 | 0.117 | 0.083 | 0.093 | 0.126 | 0.087 |
| FAM64A | 54478 | 0.058 | 0.074 | 0.078 | 0.257 | 0.069 | 0.049 | 0.065 | 0.076 | 0.061 | 0.077 | 0.086 |
| KIF15 | 56992 | 0.112 | 0.053 | 0.043 | 0.069 | 0.067 | 0.093 | 0.118 | 0.109 | 0.095 | 0.097 | 0.086 |
| MMP9 | 4318 | 0.077 | 0.107 | 0.070 | 0.114 | 0.073 | 0.119 | 0.058 | 0.090 | 0.054 | 0.069 | 0.083 |
| NEIL3 | 55247 | 0.107 | 0.071 | 0.075 | 0.130 | 0.083 | 0.062 | 0.035 | 0.060 | 0.077 | 0.121 | 0.082 |
| DQX1 | 165545 | 0.088 | 0.071 | 0.103 | 0.075 | 0.079 | 0.060 | 0.050 | 0.061 | 0.110 | 0.100 | 0.080 |
| CDC6 | 990 | 0.085 | 0.076 | 0.075 | 0.067 | 0.113 | 0.132 | 0.109 | 0.024 | 0.032 | 0.084 | 0.080 |
| CDCA2 | 157313 | 0.113 | 0.102 | 0.049 | 0.113 | 0.074 | 0.082 | 0.063 | 0.081 | 0.060 | 0.057 | 0.079 |
| CENPA | 1058 | 0.099 | 0.099 | 0.084 | 0.061 | 0.071 | 0.095 | 0.062 | 0.036 | 0.084 | 0.079 | 0.077 |
| CENPE | 1062 | 0.058 | 0.077 | 0.054 | 0.140 | 0.046 | 0.115 | 0.054 | 0.113 | 0.045 | 0.051 | 0.075 |
| TTK | 7272 | 0.051 | 0.057 | 0.080 | 0.072 | 0.100 | 0.065 | 0.065 | 0.101 | 0.075 | 0.062 | 0.073 |
| ESCO2 | 157570 | 0.083 | 0.071 | 0.048 | 0.058 | 0.064 | 0.051 | 0.070 | 0.102 | 0.062 | 0.069 | 0.068 |
| DSCR6 | 53820 | 0.038 | 0.058 | 0.080 | 0.105 | 0.060 | 0.078 | 0.041 | 0.090 | 0.054 | 0.063 | 0.067 |
| IGFL2 | 147920 | 0.054 | 0.053 | 0.066 | 0.065 | 0.089 | 0.051 | 0.038 | 0.076 | 0.086 | 0.077 | 0.065 |
| CXCL11 | 6373 | 0.082 | 0.075 | 0.051 | 0.068 | 0.070 | 0.050 | 0.053 | 0.079 | 0.051 | 0.052 | 0.063 |
| KLK4 | 9622 | 0.100 | 0.085 | 0.042 | 0.024 | 0.089 | 0.055 | 0.056 | 0.055 | 0.052 | 0.068 | 0.063 |
| SYT13 | 57586 | 0.055 | 0.068 | 0.042 | 0.048 | 0.024 | 0.059 | 0.081 | 0.051 | 0.088 | 0.100 | 0.062 |
| SGOL1 | 151648 | 0.032 | 0.097 | 0.055 | 0.050 | 0.073 | 0.044 | 0.051 | 0.040 | 0.095 | 0.068 | 0.061 |
| MCM10 | 55388 | 0.031 | 0.068 | 0.044 | 0.050 | 0.084 | 0.096 | 0.070 | 0.070 | 0.044 | 0.044 | 0.060 |
| CAMP | 820 | 0.063 | 0.075 | 0.045 | 0.071 | 0.051 | 0.050 | 0.086 | 0.062 | 0.061 | 0.037 | 0.060 |
| SHCBP1 | 79801 | 0.122 | 0.051 | 0.083 | 0.024 | 0.039 | 0.032 | 0.031 | 0.088 | 0.076 | 0.052 | 0.060 |
| POLQ | 10721 | 0.076 | 0.054 | 0.078 | 0.013 | 0.038 | 0.062 | 0.073 | 0.079 | 0.031 | 0.061 | 0.056 |
| E2F8 | 79733 | 0.048 | 0.033 | 0.067 | 0.083 | 0.047 | 0.045 | 0.031 | 0.063 | 0.053 | 0.071 | 0.054 |
| CEACAM6 | 4680 | 0.054 | 0.056 | 0.045 | 0.104 | 0.052 | 0.053 | 0.037 | 0.055 | 0.043 | 0.041 | 0.054 |
| FAM72A | 729533 | 0.070 | 0.080 | 0.036 | 0.052 | 0.044 | 0.029 | 0.102 | 0.040 | 0.032 | 0.054 | 0.054 |
| DEPDC1B | 55789 | 0.055 | 0.068 | 0.029 | 0.052 | 0.029 | 0.049 | 0.063 | 0.056 | 0.054 | 0.079 | 0.053 |
| CCNA2 | 890 | 0.035 | 0.076 | 0.055 | 0.094 | 0.038 | 0.062 | 0.031 | 0.053 | 0.041 | 0.041 | 0.053 |
| CLSPN | 63967 | 0.051 | 0.081 | 0.028 | 0.041 | 0.028 | 0.050 | 0.061 | 0.050 | 0.052 | 0.084 | 0.053 |
| MKI67 | 4288 | 0.054 | 0.077 | 0.048 | 0.075 | 0.077 | 0.019 | 0.025 | 0.051 | 0.044 | 0.056 | 0.053 |
| MYBL2 | 4605 | 0.050 | 0.053 | 0.045 | 0.067 | 0.055 | 0.063 | 0.050 | 0.043 | 0.050 | 0.035 | 0.051 |
| CXCL10 | 3627 | 0.027 | 0.040 | 0.031 | 0.036 | 0.037 | 0.074 | 0.062 | 0.078 | 0.046 | 0.075 | 0.051 |
| CEACAM5 | 1048 | 0.032 | 0.031 | 0.053 | 0.074 | 0.045 | 0.042 | 0.074 | 0.066 | 0.053 | 0.035 | 0.050 |
| ARTN | 9048 | 0.021 | 0.027 | 0.049 | 0.023 | 0.060 | 0.078 | 0.091 | 0.052 | 0.065 | 0.037 | 0.050 |
| FAM111B | 374393 | 0.072 | 0.051 | 0.037 | 0.047 | 0.032 | 0.066 | 0.056 | 0.041 | 0.053 | 0.027 | 0.048 |
| RAD51 | 5888 | 0.035 | 0.025 | 0.024 | 0.012 | 0.016 | 0.011 | 0.018 | 0.098 | 0.119 | 0.115 | 0.047 |
| CNTNAP2 | 26047 | 0.024 | 0.039 | 0.038 | 0.041 | 0.058 | 0.032 | 0.037 | 0.049 | 0.106 | 0.041 | 0.047 |
| ACTL8 | 81569 | 0.050 | 0.051 | 0.027 | 0.038 | 0.037 | 0.040 | 0.050 | 0.032 | 0.047 | 0.032 | 0.040 |
| ADAMDEC1 | 27299 | 0.030 | 0.064 | 0.035 | 0.033 | 0.011 | 0.076 | 0.059 | 0.024 | 0.034 | 0.030 | 0.040 |
| ZNF695 | 57116 | 0.045 | 0.036 | 0.047 | 0.026 | 0.017 | 0.034 | 0.032 | 0.055 | 0.033 | 0.053 | 0.038 |

TABLE 20-continued

The most informative 200 biomarkers for analyzing a presence of breast cancer cell.

| Gene Symbol | Gene ID | Seed 1 | Seed 23 | Seed 39 | Seed 118 | Seed 512 | Seed 19 | Seed 17 | Seed 10 | Seed 15 | Seed 5 | Mean |
|---|---|---|---|---|---|---|---|---|---|---|---|---|
| CA9 | 768 | 0.040 | 0.071 | 0.044 | 0.040 | 0.027 | 0.029 | 0.050 | 0.022 | 0.020 | 0.028 | 0.037 |
| CASC5 | 57082 | 0.035 | 0.049 | 0.031 | 0.048 | 0.035 | 0.029 | 0.037 | 0.036 | 0.036 | 0.026 | 0.036 |
| CAPN9 | 10753 | 0.033 | 0.017 | 0.055 | 0.012 | 0.056 | 0.044 | 0.028 | 0.025 | 0.066 | 0.020 | 0.036 |
| E2F7 | 144455 | 0.036 | 0.032 | 0.035 | 0.023 | 0.044 | 0.046 | 0.017 | 0.035 | 0.029 | 0.038 | 0.033 |
| PRAME | 23532 | 0.027 | 0.017 | 0.031 | 0.033 | 0.034 | 0.013 | 0.058 | 0.042 | 0.025 | 0.034 | 0.031 |
| NMU | 10874 | 0.034 | 0.029 | 0.012 | 0.043 | 0.028 | 0.035 | 0.018 | 0.035 | 0.043 | 0.037 | 0.031 |
| IL21R | 50615 | 0.016 | 0.024 | 0.042 | 0.031 | 0.055 | 0.031 | 0.015 | 0.024 | 0.037 | 0.017 | 0.029 |
| COL1A1 | 1277 | 0.067 | 0.054 | 0.011 | 0.006 | 0.020 | 0.007 | 0.025 | 0.017 | 0.015 | 0.015 | 0.024 |
| HOXB13 | 10481 | 0.015 | 0.015 | 0.006 | 0.011 | 0.031 | 0.017 | 0.023 | 0.027 | 0.025 | 0.007 | 0.018 |
| RAMP1 | 10267 | 0.004 | 0.013 | 0.002 | 0.016 | 0.000 | 0.012 | 0.010 | 0.019 | 0.019 | 0.005 | 0.010 |
| SYNGR3 | 9143 | 0.008 | 0.007 | 0.015 | 0.007 | 0.011 | 0.004 | 0.004 | 0.011 | 0.011 | 0.012 | 0.009 |
| TRPA1 | 8989 | 0.004 | 0.019 | 0.007 | 0.006 | 0.006 | 0.008 | 0.004 | 0.012 | 0.007 | 0.014 | 0.009 |
| NEURL | 9148 | 0.000 | 0.019 | 0.006 | 0.000 | 0.003 | 0.023 | 0.002 | 0.002 | 0.020 | 0.004 | 0.008 |
| CDT1 | 81620 | 0.010 | 0.012 | 0.016 | 0.000 | 0.005 | 0.006 | 0.006 | 0.005 | 0.005 | 0.004 | 0.007 |
| CGA | 1081 | 0.007 | 0.005 | 0.007 | 0.005 | 0.007 | 0.007 | 0.007 | 0.005 | 0.015 | 0.003 | 0.007 |
| ARMC3 | 219681 | 0.003 | 0.005 | 0.004 | 0.001 | 0.005 | 0.001 | 0.007 | 0.012 | 0.000 | 0.011 | 0.005 |
| FAM72D | 728833 | 0.000 | 0.002 | 0.000 | 0.005 | 0.014 | 0.000 | 0.000 | 0.008 | 0.007 | 0.003 | 0.004 |

Example 26. Reaction Kinetics of Primers for Detecting Tumor Cells by QPCR

Figure 19:
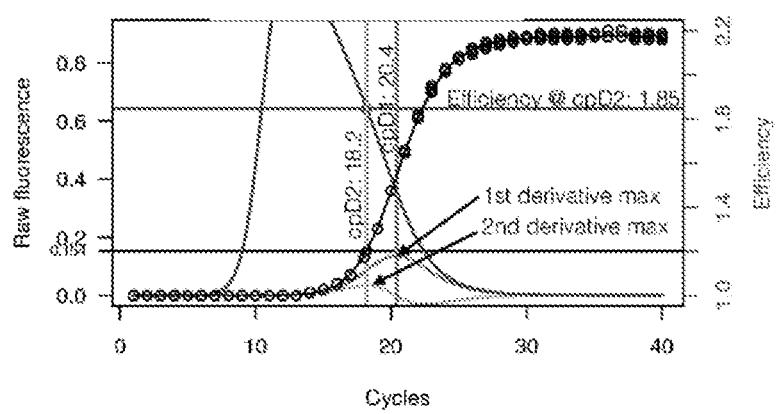
FIG. 19A shows the kinetics of three technical amplification reactions, indicating the efficiency calculated at the second derivative maximum.
FIG. 19B shows that the melting curve corresponds to the size of the expected amplicon.
FIG. 19C shows a dilution curve of PCR primers.
FIG. 19D shows the relationship between primer concentration and Ct, the time to detection.
Figure 19:
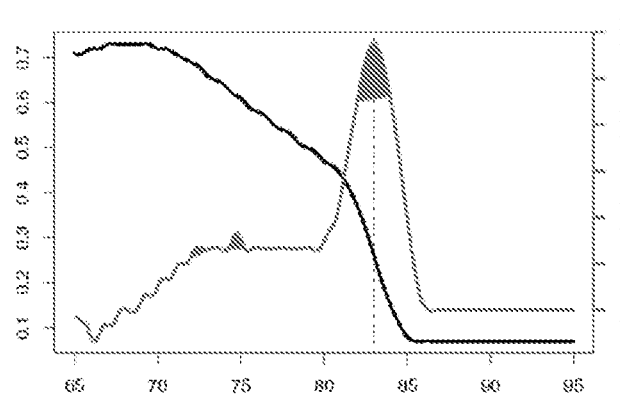
Figure 19:
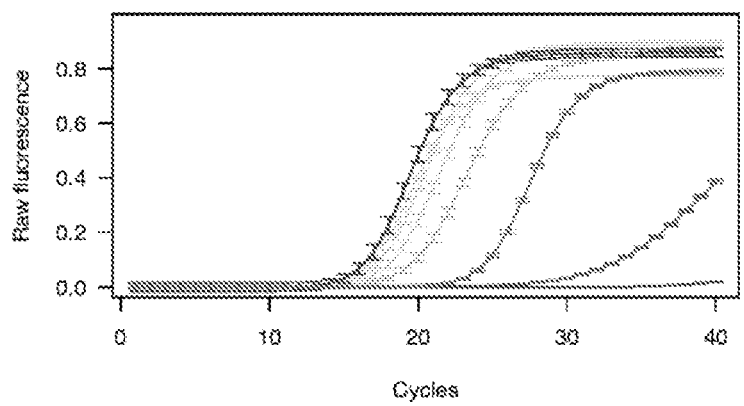
Figure 19:
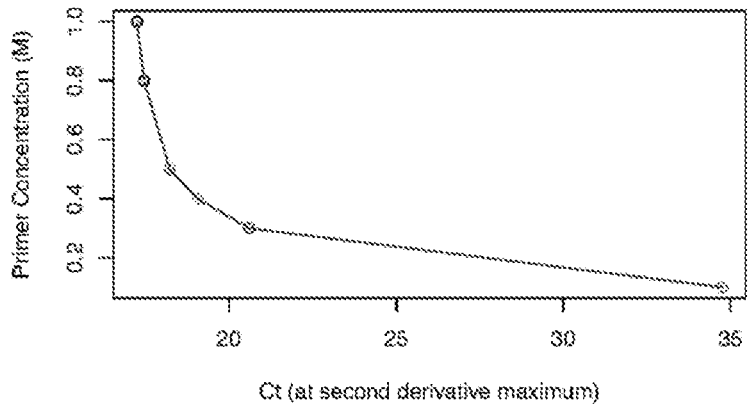

FIGS. 19A-19D illustrate reaction kinetics of primers for detecting tumor cells by QPCR. FIG. 19A shows amplification of 1M concentration of primers CG068+CG069 with 250 fg/ul of synthetic template. Triplicate reactions are shown (circles). Reaction kinetics are well fit by an 14 linear model (R-squared=0.9998 and Root Mean Squared Error=0.0058). Taking the first and second derivative of the 14 model allows us to determine the Ct at the first derivative maximum (cpD1=20.4) and the Ct at the second derivative maximum (cpD2=18.22). From this we see that the Efficiency of the reaction at cpD2 is 1.846. Reporter: double-stranded intercalating dye SYBR, without a passive reference dye. Template: Synthetic double-stranded cDNA cassette of primer binding sites at a concentration of 4.83*10^5 copies per microliter. FIG. 19B shows the melt curve of 1M concentration of primers CG068+CG069 with 250 fg/ul of synthetic template. The dark line shows raw fluorescence curve. The lighter line shows the first derivative curve and the identified melting peak. The largest peak is at 84 C, which corresponds to the expected melting temperature of the amplicon, confirming that the reaction shown in (a) is the specific amplification of the target sequence. FIG. 19C shows dilution of Primers CG068+CG069. Amplification curves with error bars representing the 95% confidence intervals of triplicate technical replicates. Concentrations: 0.1, 0.3, 0.4, 0.5, 0.8, and 1.0 M primers with 250 fg/ul template; 0.1 and 1.0 M primers with no template (No Template Control, NTC). Reporter: double-stranded intercalating dye SYBR, without a passive reference dye. Template: Synthetic double-stranded cDNA cassette of primer binding sites at a concentration of 4.83*10A5 copies per microliter. FIG. 19D shows the relationship between primer concentration and the number of cycles to reach a cutoff threshold (Ct).

Example 27. Comparison of Reaction Kinetics of Multiple Primer Pairs

Figure 23:
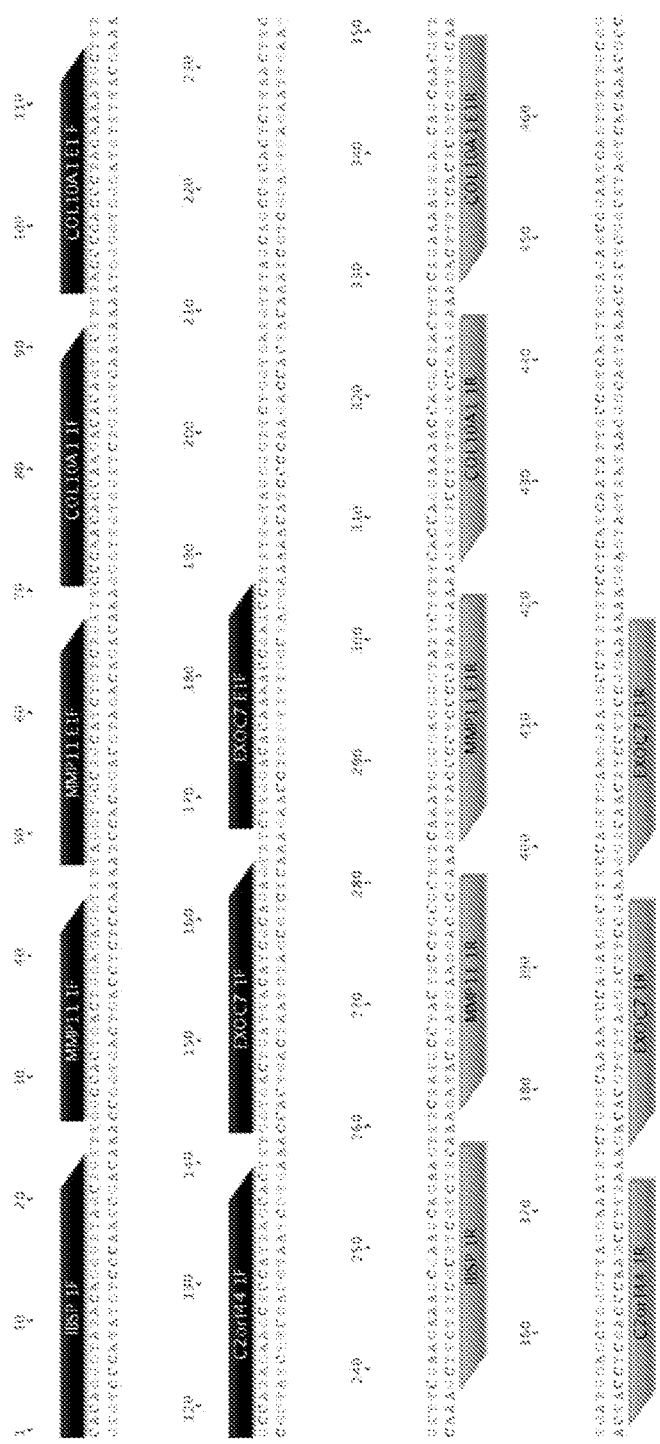
FIG. 23 illustrates a schematic synthetic cDNA cassette that contains binding sites for multiple primer pairs.

A single synthetic cDNA cassette contains binding sites for multiple primer pairs, thereby allowing the direct comparison of reaction kinetics from the same concentration of the same template. This cassette was synthesized as a doubles-stranded block of DNA (FIG. 23).

Example 28. The Inclusion/Exclusion Filtering Method is not Bias Toward Race or Ethnicity Table 17 shows the racial and ethnic breakdown of those samples that were available for analysis, and those samples that met our inclusion and exclusion criteria. The available samples slightly over-represent are African American and Asian patients, relative to U.S. census data. Available samples slightly underrepresent White patients compared to the 2010 census, but represent the average of the 2000 census. American Indian/Alaska Native (AI/AN) are poorly represented in the available samples. Moreover, our inclusion/exclusion criteria eliminated the only AI/AN patient. Other than the AI/AN sample, our inclusion/exclusion criteria did not substantially impact the racial representation of the available samples. Although the available data under-represent Hispanic or Latino ethnicity, analysis of Hispanic or Latino ethnicity was not impacted by inclusion/exclusion filtering. In this analysis, Fisher's Exact test indicates that performance of breast cancer disease classifier is not significantly different between ethnicity groups, e.g., a p-value higher than 0.2. Taken together, these data show that the U.S. population is well represented by the samples in our dataset.

TABLE 17

Representative age and racial sampling of U.S. breast cancer patients, with the exception of American Indians/Native Alaskans.

| | Available | Included | 2010 U.S. Census | 2000 U.S. Census |
|---|---|---|---|---|
| Race | | | | |
| AI/AN | 1 (0.1%) | 0 (0.0%) | 0.7% | 0.9% |
| Asian | 62 (5.1%) | 52 (5.2%) | 4.7% | 3.6% |
| African American | 187 (15.5%) | 157 (15.8%) | 12.2% | 12.3% |
| White | 861 (71.2%) | 708 (71.2%) | 63.7% | 75.1% |
| Not Available | 99 (8.2%) | 78 (7.8%) | 18.7% | 8.1% |

TABLE 17-continued

Representative age and racial sampling of U.S. breast cancer patients, with the exception of American Indians/Native Alaskans.

|  | Available | Included | 2010 U.S. Census | 2000 U.S. Census |
|---|---|---|---|---|
| Ethnicity |  |  |  |  |
| Hispanic or Latino | 39 (3.2%) | 33 (3.3%) | 16.3% | 12.5% |
| Not Hispanic or Latino | 970 (80.2%) | 793 (79.7%) | 83.7% | 87.5% |
| Not Available | 201 (16.6%) | 169 (17.0%) |  |  |

Example 29. The Breast Cancer Classifier does not have a Performance Bias for Clinical Breast Cancer Subtypes or Demographic Criteria There are 4 major clinical subtypes of breast cancer, based on whether the tumor expresses the estrogen receptor, progesterone receptor, Her2/neu, or whether the tumor is negative for all 3 biomarkers (triple negative tumors). Estrogen receptor, progesterone receptor, and Her2 status is routinely determined by clinical immunohistochemistry. While overall accuracy is important it is also important to specifically evaluate the performance of a breast cancer test for individual breast cancer subtypes. For example, some breast cancer prognostic disease classifiers are only indicated for tumors that are estrogen receptor positive.

Example 30. Cloud-Based Analysis

Table 18 shows the results of Fisher's Exact Test for performance of a 3-gene classifier based on Random Forest. There is no significant difference in performance of the 3-gene disease classifier regardless of clinical subtype (estrogen receptor status, progesterone receptor status, Her2/neu status, and triple negative status), age at diagnosis, ethnicity, or race. Data were collected from 995 RNAseq samples, age at diagnosis, ethnicity, or race. Table 18 shows that the inclusion/exclusion criteria successfully excluded metastatic samples, and only included early-stage samples from female patients. Analysis of the samples that were incorrectly classified shows that there was not a statistically significant difference in performance of the 3-gene classifier based on age at initial diagnosis ($p=0.4107$), race ($p=0.4763$), ethnicity ($p=0.2793$), tumor stage ($p=0.4179$), estrogen receptor status ($p=1.0000$), progesterone receptor status ($p=1.0000$), Her2/neu status ($p=0.4706$), or triple negative status ($p=1.0000$) where triple negative tumors are those that lack estrogen receptors, progesterone receptors, and Her2. Estrogen receptor, progesterone receptor, and Her2 status were determined by clinical immunohistochemistry. In contrast to some breast cancer disease classifiers (e.g. OncoTypeDX), which is only indicated for tumors that are positive for the estrogen receptor, these results demonstrate that the disclosed 3-gene classifier performs well on all clinical breast cancer subtypes, regardless of patient age or race.

TABLE 18

The 3-gene test performs well regardless of the patient's age or race, or tumor subtype

|  |  | Available | Included | Correctly Classified | Incorrectly Classified | p-value |
|---|---|---|---|---|---|---|
| Total |  | 1210 | 995 | 986 (99.09%) | 9 (0.90%) |  |
| Gender | FEMALE | 1197 (98.92%) | 995 (100.00%) | 986 (99.09%) | 9 (0.90%) | NA |
|  | MALE | 13 (1.07%) | — | — | — |  |
| Tissue (sample_type) | Metastatic | 7 (0.57%) | — | — | — | NA |
|  | Primary Solid Tumor | 1089 (90.00%) | 901 (90.55%) | 897 (99.55%) | 4 (0.44%) |  |
|  | Solid Tissue Normal | 114 (9.42%) | 94 (9.44%) | 89 (94.68%) | 5 (5.31%) |  |
| Age at initial pathologic diagnosis | <41 | 114 (9.42%) | 87 (8.74%) | 85 (97.70%) | 2 (2.29%) | 0.4107 |
|  | 41-50 | 265 (21.90%) | 223 (22.41%) | 221 (99.10%) | 2 (0.89%) |  |
|  | 51-60 | 302 (24.95%) | 246 (24.72%) | 245 (99.59%) | 1 (0.40%) |  |
|  | >60 | 529 (43.71%) | 439 (44.12%) | 435 (99.08%) | 4 (0.91%) |  |
| Race | [Not Available] | 96 (7.93%) | 75 (7.53%) | 74 (98.66%) | 1 (1.33%) | 0.4763 |
|  | [Not Evaluated] | 3 (0.24%) | 3 (0.30%) | 3 (100.00%) | — |  |
|  | AI/AN * | 1 (0.08%) | — | — | — |  |
|  | ASIAN | 62 (5.12%) | 52 (5.22%) | 51 (98.07%) | 1 (1.92%) |  |
|  | BLACK OR AFRICAN AMERICAN | 187 (15.45%) | 157 (15.77%) | 156 (99.36%) | 1 (0.63%) |  |
|  | WHITE | 861 (71.15%) | 708 (71.15%) | 702 (99.15%) | 6 (0.84%) |  |
| Ethnicity | [Not Available] | 190 (15.70%) | 158 (15.87%) | 157 (99.36%) | 1 (0.63%) | 0.2793 |
|  | [Not Evaluated] | 3 (0.24%) | 3 (0.30%) | 3 (100.00%) | — |  |
|  | [Unknown] | 8 (0.66%) | 8 (0.80%) | 8 (100.00%) | — |  |
|  | HISPANIC OR LATINO | 39 (3.22%) | 33 (3.31%) | 32 (96.96%) | 1 (3.03%) |  |
|  | NOT HISPANIC OR LATINO | 970 (80.16%) | 793 (79.69%) | 786 (99.11%) | 7 (0.88%) |  |
| Tumor stage (AJCC) | T1 | 45 (3.71%) | 45 (4.52%) | 44 (97.77%) | 1 (2.22%) | 0.4179 |
|  | T1a | 5 (0.41%) | 5 (0.50%) | 5 (100.00%) | — |  |
|  | T1b | 17 (1.40%) | 17 (1.70%) | 17 (100.00%) | — |  |
|  | T1c | 245 (20.24%) | 243 (24.42%) | 240 (98.76%) | 3 (1.23%) |  |
|  | T2 | 700 (57.85%) | 682 (68.54%) | 677 (99.26%) | 5 (0.73%) |  |
|  | T2a | 1 (0.08%) | 1 (0.10%) | 1 (100.00%) | — |  |
|  | T2b | 2 (0.16%) | 2 (0.20%) | 2 (100.00%) | — |  |
|  | T3 | 143 (11.81%) | — | — | — |  |
|  | T3a | 1 (0.08%) | — | — | — |  |
|  | T4 | 9 (0.74%) | — | — | — |  |

TABLE 18-continued

The 3-gene test performs well regardless of the patient's age or race, or tumor subtype

|  |  | Available | Included | Correctly Classified | Incorrectly Classified | p-value |
|---|---|---|---|---|---|---|
|  | T4b | 34 (2.80%) | — | — | — |  |
|  | T4d | 4 (0.33%) | — | — | — |  |
|  | TX | 4 (0.33%) | — | — | — |  |
| Estrogen Receptor Status | [Not Evaluated] | 60 (4.95%) | 52 (5.22%) | 52 (100.00%) | — | 1.0000 |
|  | Indeterminate | 3 (0.24%) | 2 (0.20%) | 2 (100.00%) | — |  |
|  | Negative | 260 (21.48%) | 221 (22.21%) | 219 (99.09%) | 2 (0.90%) |  |
|  | Positive | 887 (73.30%) | 720 (72.36%) | 713 (99.02%) | 7 (0.97%) |  |
| Progesterone Receptor Status | [Not Evaluated] | 61 (5.04%) | 53 (5.32%) | 53 (100.00%) | — | 1.0000 |
|  | Indeterminate | 5 (0.41%) | 5 (0.50%) | 5 (100.00%) | — |  |
|  | Negative | 374 (30.90%) | 311 (31.25%) | 308 (99.03%) | 3 (0.96%) |  |
|  | Positive | 770 (63.63%) | 626 (62.91%) | 620 (99.04%) | 6 (0.95%) |  |
| Her2/neu Status | [Not Available] | 12 (0.99%) | 10 (1.00%) | 9 (90.00%) | 1 (10.00%) | 0.4706 |
|  | [Not Evaluated] | 193 (15.95%) | 147 (14.77%) | 145 (98.63%) | 2 (1.36%) |  |
|  | Equivocal | 188 (15.53%) | 163 (16.38%) | 161 (98.77%) | 2 (1.22%) |  |
|  | Indeterminate | 12 (0.99%) | 9 (0.90%) | 9 (100.00%) | — |  |
|  | Negative | 620 (51.23%) | 512 (51.45%) | 508 (99.21%) | 4 (0.78%) |  |
|  | Positive | 185 (15.28%) | 154 (15.47%) | 154 (100.00%) | — |  |
| Triple Negative Status | Triple Negative | 128 (10.57%) | 108 (10.85%) | 107 (99.07%) | 1 (0.92%) | 1.0000 |
|  | Not Triple Negative | 1,082 (89.42%) | 887 (89.14%) | 879 (99.09%) | 8 (0.90%) |  |

Example 30. Cloud-Based Analysis

This example shows a system for cloud-based analysis (FIG. 25). The system may be used to detect problems in real time, improve algorithms over time, and provide novel and live evaluation of clinical performance. The systems provides quantitative signals for predictive outcome, e.g., the presence of tumor cells on the surface of a surgical specimen, the presence of residual tumor cells on a surgical site in a patient. Briefly, the system involves collecting a biological sample comprising cells from the surface of a surgical specimen. The collected cells are subjected for nucleic acid extraction and/or isolation. For example, RNA or mRNA is extracted from the collected cells followed by synthesis of cDNA. The cDNA may be used for subsequent molecular assays. In some cases, the collected cells are immersed in a reagent for nucleic acid extraction. The reagent may be a buffer comprising lysing buffer. In some cases, the collected cells may be fixed or frozen before subsequent molecular assays. For predicting the presence of a tumor cell in the surgical specimen, nipple aspirate fluid, or biopsy sample, quantitative signal of a combination of biomarkers is collected. The combination of biomarkers may comprise at least one biomarker. The combination of biomarkers may comprise at least two biomarkers. The combination of biomarkers may comprise at least three biomarkers. The combination of biomarkers may comprise at least four biomarkers. The combination of biomarkers may comprise at least one of COL10A1, MMP1, IBSP, and CST1. The molecular assays may involve amplifying nucleic acids using at least one pair of primer sets comprising sequences selected from SEQ ID No. 33-SEQ ID No. 52 (Table 19). Although molecular assays of the nucleic acids may be conducted in a variety of platforms, the system is not limited to a particular platform. Molecular assays of the nucleic acids may be conducted by performing quantitative PCR, microarray, RNAseq, next generation sequencing, digital PCR (dPCR), digital droplet PCR (ddPCR), isothermal amplification, ERiN SDA, or combinations thereof.

TABLE 19

Primers amplifying nucleic acid molecules for molecular assays

| Gene | Target/ Reference | Oligo Sequence (5' to 3') | SEQ ID NO. |
|---|---|---|---|
| TBSP | Target | CACAGGGTATACAGGGTTAGCTG | SEQ ID NO. 33 |
| TBSP |  | CTTCTGCTTCGCTTTCTTCG | SEQ ID NO. 34 |
| MMP11 | Target | GGCCACTGACTGGAGAGG | SEQ ID NO. 35 |
| MMP11 |  | GCGCAGGAAGTAGGCATAG | SEQ ID NO. 36 |
| MMP11 | Target | TAGGTGCCTGCATCTGTCTG | SEQ ID NO. 37 |
| MMP11 |  | AGAATACCCCTCCCCATTTG | SEQ ID NO. 38 |
| COL10A1 | Target | CCCAACACCAAGACACAGTTC | SEQ ID NO. 39 |
| COL10A1 |  | GTAGCCTGGTTTTCCTGGTG | SEQ ID NO. 40 |
| COL10A1 | Target | TACCCCACCCTACAAAATGC | SEQ ID NO. 41 |
| COL10A1 |  | CGTTGCTGCTCACTTTTCAG | SEQ ID NO. 42 |
| C2orf44 | Reference | GCCATAGAAGCTCCATTAGCAC | SEQ ID NO. 43 |
| C2orf44 | rence | TTTCCTAACCCAGCTCCATC | SEQ ID NO. 44 |
| EXOC7 | Reference | GGTGACTGATTACATCGCAGAG | SEQ ID NO. 45 |
| EXOC7 | rence | GCCTTCTGGATTTTGCACAG | SEQ ID NO. 46 |
| EXOC7 | Reference | CTTGGACACAAAACCGATCC | SEQ ID NO. 47 |
| EXOC7 | rence | AAAGGCCTTCCTTCAACTGG | SEQ ID NO. 48 |

TABLE 19 -continued

Primers amplifying nucleic acid molecules for molecular assays

| Gene | Target/ Reference | Oligo Sequence (5' to 3') | SEQ ID NO. |
|---|---|---|---|
| RWDD4A | Reference | TTGTAGGGGTTCTGGTGATG | SEQ ID NO. 49 |
| RWDD4A | rence | TGACGGCAATATTGATGAGG | SEQ ID NO. 50 |
| CTDNEP1 | Reference | AGCAGCCTCACTCTTAACTTCG | SEQ ID NO. 51 |
| CTDNEP1 | rence | AAACACTGATTCGGCTCTCC | SEQ ID NO. 52 |

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for determining success of a surgical procedure for removing a tumor from a subject, said system comprising:
   a) a kit comprising
      a sample acquisition device comprising a sample collection unit comprising a coated surface suitable for an imprint cytology method for collecting a biological sample from said subject, wherein said biological sample is collected from the surface of a surgical specimen;
      a set of reagents for processing said biological sample, and
      a set of instructions for performing said imprint cytology method and for detecting a pattern of expression of at least three biomarkers associated with a cancer in said biological sample from said sample collection unit; and
   b) a platform for analyzing said biological sample for detecting a presence or absence of a positive surgical margin in said biological sample;
   wherein said platform determines a presence or absence of a positive surgical margin in said biological sample, thereby determining a likelihood of success of said surgical procedure for removing said tumor, wherein said platform comprises a computer system comprising a cancer disease classifier that interprets the expression levels of said at least three biomarker genes.

2. The system of claim 1, wherein said sample collection unit comprises a poly-lysine coated surface.

3. The system of claim 2, wherein said coated surface is selected from a slide, a plate, tube, a chip and a paper.

4. The system of claim 1, wherein said sample collection unit comprises a nitrocellulose membrane.

5. The system of claim 1, wherein said sample collection unit comprises a receptacle containing a reagent for collecting said biological sample.

6. The system of claim 1, wherein said collecting comprises an imprint cytology method.

7. The system of claim 1, wherein said collecting comprises a touch-prep method.

8. The system of claim 1, wherein said analyzing said biological sample is performed after said surgical procedure.

9. The system of claim 1, wherein said analyzing said biological sample is performed during said surgical procedure.

10. The system of claim 1, wherein said likelihood of success of said surgical procedure for removing said tumor is determined by an absence of a cancer remission in said subject within 5 years of said surgical procedure.

11. The system of claim 1, wherein said likelihood of success of said surgical procedure for removing said tumor is determined by reduction of a risk of a cancer remission in said subject within 5 years of said surgical procedure by at least 70%.

12. The system of claim 1, wherein if no positive surgical margin is detected, said subject has a 70% likelihood of no cancer remission within 5 years of said surgical procedure.

13. The system of claim 1, wherein said biological sample comprises at least 20% of the surface of a surgical specimen.

14. The system of claim 1, wherein said kit further comprising a set of reagents for extracting nucleic acid molecules from said biological sample.

15. The system of claim 14, wherein said nucleic acid molecules comprise RNA, mRNA, spliced RNA, non-spliced RNA, DNA, or combinations thereof.

16. The system of claim 1, wherein said kit further comprising a set of reagents for synthesizing cDNA from said biological sample.

17. The system of claim 1, wherein said reagents are for preserving or storing said biological sample.

18. The system of claim 1, wherein said reagents are for shipping said biological sample.

19. The system of claim 1, wherein said kit further comprising at least one pair of primers for amplifying said at least one biomarker.

20. The system of claim 1, wherein said instructions for detecting a pattern of expression of at least one biomarker associated with a cancer in said biological sample comprise instructions for detecting a pattern of expression of said at least one biomarker associate with a cancer in said biological sample.

21. The system of claim 1, further comprising detecting a pattern of expression of a second biomarker associated with a cancer in said biological sample, wherein a combination of an increase of said at least one biomarker and said second biomarker indicates a presence or absence of positive surgical margin in said biological sample.

22. The system of claim 1, wherein said at least three biomarkers associated with a cancer in said biological sample are biomarkers associated with a gene selected from the group consisting of ACTR3B, ALK, ANLN, AURKA, BAG1, Bcl2, BCL2, BCR-Abl, BIRC5, BLVRA, BRAF, c-KIT Cathepsin L2, CCNB1, CCNE1, CD20 antigen, CD30, CD68, $CDCl_20$, $CDCl_6$, CDH3, CENPF, CEP55, CXXC5, Cyclin B1, EGFR, ER, ERBB2, ESR1, EXO1, FGFR4, FIP1L-PDGFRalpha, FOXA1, FOXC1, GPR160, GRB7, GSTM1, HOXB13, IL17BR, Ki-67, KIF2C, KRAS, KRT14, KRT17, KRT5, MAPT, MDM2, MELK, MIA, MKI67, MLPH, MMP11, MYBL2, MYC, NAT1, NDC80, NUF2, ORC6L, PDGFR, PGR, PHGDH, PML/RAR alpha, PR, PTTG1, RRM2, SCUBE2, SFRP1, SLC39A6, STK15, Stromelysin 3 (MMP11), Survivin, TMEM45B, TPMT, TYMS, UBE2C, UBE2T, UGT1A1, ABCA10, ABCA9, ADAM33, ADAMTS5, ANGPT1, ANKRD29, ARHGAP20, ARMCX5GPRASP2, ASB1, CA4, CACHD1, CAPN11, CAV1, CAV2, CAV3, CBX7, CCNE2, CD300LG, CDC14B, $CDCl_42SE1$, CENPF, CEP68, CFL2, CHL1, CLIP4, CNTNAP3, COL10A1, COL11A1, CRIM1, CXCL3, DAB2IP, DMD, DPYSL2, DST, EEPD1, ENTPD7, ERCC6L, EZH1, F10, FAM126A, FBXO31, FGF1, FIGF, FMO2, FXYD1, GIPC2, GLYAT, GPR17, GPRASP1, GPRASP2, HAGL, HAND2-AS1, HLF, HMMR, HOXA2, HOXA4, HOXA5, IGSF10, INHBA, IL11RA, ITM2A, JADE1, JUN, KIAA0101, KIF4A, KLHL29, LCAT, LGI4, LIFR, LIMS2, LRIG3, LRRC2, LRRC3B, MAMDC2, MATN2, MICU3, MIR99AHG, MME, MMP11, NECAB1, NEK2, NKAPL, NPHP3, NR3C1, NR3C2, NUF2, PAMR1, PAFAH1B3, PAQR4, PARK2, PEAR1, PGM5, PKMYT1, PLEKHM3, PLSCR4, POU6F1, PPAP2B, PPP1R12B, PRCD, PRX, PYCR1, RAPGEF3, RBMS2, SCN4B, SDPR, SLC35A2, SH3BGRL2, SPRY2, STAT5B, SYN2, TK1, TMEM220, TMEM255A, TMOD1, TPM3, TPX2, TSHZ2, TSLP, TSTA3, TTC28, WISP1, USHBP1, USP44, IBSP, CST1, ZWINT, and combinations thereof.

23. The system of claim 1, wherein said at least three biomarkers associated with a cancer in said biological sample are biomarkers associated with a gene selected from the group consisting of COL10A1, MMP11, IBSP, CST1, and combinations thereof.

24. The system of claim 1, wherein said biomarker associated with a cancer is a biomarker associated with a cancer selected from the group consisting of breast cancer, prostate cancer, colon cancer, lung cancer, liver cancer, brain cancer, skin cancer, testicular cancer, oral cancer, pancreatic cancer, stomach cancer, cervical cancer, uterine cancer, endometrial cancer, and ovarian cancer.

25. The system of claim 1, wherein said biomarker associated with a cancer is a biomarker associated with breast cancer.

26. The system of claim 1, wherein said platform for analyzing said biological sample is selected from the group consisting of a device for performing polymerase chain reaction (PCR), quantitative PCR (QPCR), next generation sequencing, RNAseq, digital PCR (dPCR), digital droplet PCR (ddPCR), isothermal amplification, endoribonucleotide strand displacement assay (ERiN SDA), microarray, and combinations thereof.

27. The system of claim 1, wherein said platform for analyzing said biological sample comprises a device for performing RNAseq.

28. The system of claim 1, wherein said platform for analyzing said biological sample comprises a device for performing quantitative (QPCR).

29. The system of claim 1, wherein a presence of said positive surgical margins in said biological sample indicates incomplete removal of said tumor from said subject.

30. The system of claim 1, wherein an absence of positive surgical margin in said biological sample indicates complete removal of said tumor from said subject.

31. The system of claim 1, wherein said pattern of expression of said at least one biomarker has at least 60% sensitivity for determining success of said surgical procedure for removing said tumor.

32. The system of claim 1, further comprising communicating with a physician or surgeon for additional surgical procedures.

33. The system of claim 1, further comprising communicating with a physician or surgeon for prescription of chemotherapy, radiotherapy, trastuzumab, endocrine therapy, or combinations thereof.

34. The system of claim 1, wherein said tissue sample is a breast tissue sample.

35. The system of claim 1, wherein said breast tissue sample is a lumpectomy sample.

36. The system of claim 1, wherein said tumor is an invasive adenocarcinoma of the breast.

37. The system of claim 1, wherein said cancer disease classifier is developed using a machine learning algorithm.

38. The system of claim 1, wherein the machine learning algorithm comprises a k-nearest neighbor (IBk), Naive Bayes, support vector machine (SVM), Random Forest, Decision Tree, ZeroR, or neural network (multilayer perceptron, MLP) algorithm, or a combination thereof.

39. The system of claim 1, wherein the at least three biomarker genes are IBSP, COL10A1 and MMP11.

* * * * *

UNITED STATES PATENT AND TRADEMARK OFFICE
CERTIFICATE OF CORRECTION

PATENT NO. : 11,401,558 B2
APPLICATION NO. : 16/061517
DATED : August 2, 2022
INVENTOR(S) : Brandon Steelman It is certified that error appears in the above-identified patent and that said Letters Patent is hereby corrected as shown below:

In the Claims

Column 186, Line 29: "$CDC1_20, CDC1_6$" should read --CDC20, CDC6--

Column 186, Line 42: "$CDC1_42SE1$" should read --CDC42SE1--

Signed and Sealed this
Eighteenth Day of October, 2022

Katherine Kelly Vidal
*Director of the United States Patent and Trademark Office*